US012240887B2

(12) United States Patent
Kumar et al.

(10) Patent No.: US 12,240,887 B2
(45) Date of Patent: **\*Mar. 4, 2025**

(54) VARIANT ACTRIIB PROTEINS AND USES THEREOF

(71) Applicant: Acceleron Pharma Inc., Cambridge, MA (US)

(72) Inventors: Ravindra Kumar, Cambridge, MA (US); Asya Grinberg, Cambridge, MA (US); Erik M. Vogan, Cambridge, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 319 days.

This patent is subject to a terminal disclaimer.

(21) Appl. No.: 17/687,934

(22) Filed: Mar. 7, 2022

(65) Prior Publication Data

US 2022/0306724 A1  Sep. 29, 2022

Related U.S. Application Data

(63) Continuation of application No. 16/340,048, filed as application No. PCT/US2017/055421 on Oct. 5, 2017, now Pat. No. 11,267,865.

(60) Provisional application No. 62/404,718, filed on Oct. 5, 2016.

(51) Int. Cl.
| C07K 14/71 | (2006.01) |
| A61K 38/00 | (2006.01) |
| A61P 21/00 | (2006.01) |

(52) U.S. Cl.
CPC .............. *C07K 14/71* (2013.01); *A61P 21/00* (2018.01); *A61K 38/00* (2013.01); *C07K 2319/30* (2013.01)

(58) Field of Classification Search
None
See application file for complete search history.

(56) References Cited

U.S. PATENT DOCUMENTS

| 5,932,448 | A | 8/1999 | Tso et al. |
| 7,893,213 | B2 | 2/2011 | Mathews et al. |
| 8,343,933 | B2 | 1/2013 | Knopf et al. |
| 2003/0078385 | A1 | 4/2003 | Arathoon et al. |
| 2006/0068468 | A1 | 3/2006 | Knopf et al. |
| 2010/0286374 | A1 | 11/2010 | Kannan et al. |
| 2011/0092670 | A1 | 4/2011 | Knopf et al. |
| 2012/0015877 | A1 | 1/2012 | Seehra et al. |
| 2012/0302737 | A1 | 11/2012 | Christensen et al. |
| 2013/0177559 | A1 | 7/2013 | Seehra et al. |
| 2015/0361163 | A1 | 12/2015 | Kumar et al. |
| 2016/0289292 | A1 | 10/2016 | Kumar et al. |
| 2016/0289298 | A1 | 10/2016 | Kumar et al. |
| 2016/0297867 | A1 | 10/2016 | Kumar et al. |
| 2016/0298093 | A1 | 10/2016 | Kumar et al. |
| 2017/0306027 | A1 | 10/2017 | Knopf et al. |
| 2018/0009872 | A1 | 1/2018 | Sherman et al. |
| 2018/0148491 | A1 | 5/2018 | Han et al. |
| 2018/0163187 | A1 | 6/2018 | Kumar et al. |
| 2019/0100570 | A1 | 4/2019 | Kumar et al. |
| 2019/0263876 | A1 | 8/2019 | Seehra et al. |

FOREIGN PATENT DOCUMENTS

| JP | 2014530253 | A | 11/2014 |
| JP | 7280182 | B2 | 5/2023 |
| WO | 1993011162 | A1 | 6/1993 |
| WO | 2000043781 | A2 | 7/2000 |
| WO | 2005084699 | A1 | 9/2005 |
| WO | 2006012627 | A2 | 2/2006 |
| WO | 2007147901 | A1 | 12/2007 |
| WO | 2008076437 | A3 | 6/2008 |
| WO | 2008097541 | A2 | 8/2008 |
| WO | 2009089004 | A1 | 7/2009 |
| WO | 2009134428 | A2 | 11/2009 |
| WO | 2009158015 | A2 | 12/2009 |
| WO | 2010019261 | A1 | 2/2010 |
| WO | 2010083034 | A1 | 7/2010 |
| WO | 2010151426 | A1 | 12/2010 |
| WO | 2011020045 | A | 2/2011 |
| WO | 2011031901 | A1 | 3/2011 |
| WO | 2011034605 | A2 | 3/2011 |
| WO | 2012027065 | A2 | 3/2012 |
| WO | 2013000234 | A1 | 1/2013 |
| WO | 2013059347 | A1 | 4/2013 |
| WO | 2013063536 | A1 | 5/2013 |
| WO | 2015027082 | A1 | 2/2015 |
| WO | 2015143403 | A1 | 9/2015 |
| WO | 2015161220 | A1 | 10/2015 |

(Continued)

OTHER PUBLICATIONS

Amthor, Helge et al., The Regulation and Action of Myostatin as a Negative Regulator of Muscle Development during Avian Embryogenesis, Developmental Biology, 2002, 241-257, 251.

Ashmore, C.R. et al., Comparative aspects of muscle fiber types in fetuses of the normal and "double-muscled" cattle, Growth, 1974, 501-506, 38(4).

Attisano, Liiana et al., Novel Activin Receptors: Distinct Genes and Alternative mRNA Splicing Generate a Repertoire of Serine/Threonine Kinase Receptors, Cell, 1992, 97-108, 68.

Database Accession No. AYN43338 "Human activin type-IIB receptor (20-134)-IgGI Fe fusion protein." (Mar. 3, 2011), 2 pages.

(Continued)

*Primary Examiner* — Ruixiang Li
(74) *Attorney, Agent, or Firm* — Eric Greenwald; John C. Todaro

(57) ABSTRACT

In certain aspects, the present invention provides compositions and methods for modulating (promoting or inhibiting) growth of red blood cells or a tissue, such as bone, cartilage, muscle, fat, and/or neuronal tissue. The present invention also provides methods of screening compounds that modulate activity of an ActRIIB protein and/or an ActRIIB ligand. The compositions and methods provided herein are useful in treating diseases associated with abnormal activity of an ActRIIB protein and/or an ActRIIB ligand.

19 Claims, 14 Drawing Sheets

Specification includes a Sequence Listing.

(56) References Cited

FOREIGN PATENT DOCUMENTS

| WO | 2015192111 A1 | 12/2015 |
|---|---|---|
| WO | 2016090077 A1 | 6/2016 |
| WO | 2016164089 A2 | 10/2016 |
| WO | 2016164497 A1 | 10/2016 |
| WO | 2016205370 A1 | 12/2016 |
| WO | 2017037634 A1 | 3/2017 |
| WO | 2018009624 A1 | 1/2018 |
| WO | 2018067873 A2 | 4/2018 |
| WO | 2018067874 A1 | 4/2018 |
| WO | 2018075747 A1 | 4/2018 |
| WO | 2018089706 A2 | 5/2018 |
| WO | 2018089715 A1 | 5/2018 |

OTHER PUBLICATIONS

Database Accession No. BDB79662 "Human ActRIIB-Fc mature fusion protein SEQ ID No. 8." (Aug. 25, 2016), 1 page.

Database Geneseq [Online] brJul. 28, 2016 (Jul. 28, 2016), br"Human actRIIB extracellular domain—IgGI Fe domain fusion protein, SEQ 31.", XP002797641, brretrieved from EBI accession No. bra href="GSP:BDB17016" target="_blank"GSP:BDB17016/a brDatabase accession No. BDB17016, 1 page.

Davis, Jonathan H. et al., SEEDbodies: fusion proteins based on strand-exchange engineered domain (SEED) CH3 heterodimers in an Fc analogue platform for asymmetric binders or immunofusions and bispecific antibodies, rotein Engineering, Design & Selection, 2010, 195-202, 23:4.

Gamer, Laura W. et al., A Novel BMP Expressed in Developing Mouse Limb, Spinal Cord, and Tail Bud Is a Potent Mesoderm Inducer in Xenopus Embryos, Developmental Biology, 1999, 222-232, 208.

Gonzalez-Cadavid, Nestor F. et al., Organization of the human myostatin gene and expression in healthy men and HIV-infected men with muscle wasting, Proc. Natl. Acad. Sci. USA, 1998, 14938-14943, 95.

Gray, Peter C. et al., Identification of a Binding Site on the Type II Activin Receptor for Activin and Inhibin, The Journal of Biological Chemistry, 2000, 3206-3212, 275(5).

Grobet, Luc et al., A deletion in the bovine myostatin gene causes the double-muscled phenotype in cattle, nature genetics, 1997, 71-74, 17.

Groopman, Jerome E. et al., Chemotherapy-Induced Anemia in Adults: Incidence and Treatment, J Natl Cancer Inst, 1999, 1616-1634, 91.

Gunasekaran, Kannan et al., Enhancing Antibody Fc Heterodimer Formation through Electrostatic Steering Effects, The Journal of Biological Chemistry, 2010, 19637-19646, 285(25).

Hilden, Kristiina et al., Expression of Type II Activin Receptor Genes During Differentiation of Human K562 Cells and cDNA Cloning of the Human Type IIB Activin Receptor, Blood, 1994, 2163-2170, 83(8).

Hossler, Optimal and Consistent Protein Glycosylation in Mammalian Cell Culture, Glycobiology, 2009, pp. 936-949, 19.

Jacobs, Claude et al., European Best Practice Guidelines 5 Target haemoglobin, Nephrology Dialysis Transplantation, 2000, 15-19, 15 [Suppl 4].

Kambadur, Ravi et al., Mutations in myostatin (GDF8) in Double-Muscled Belgian Blue and Piedmontese Cattle, Genome Research, 1997, 910-915, 7.

Konrad, Lutz et al., Alternative splicing of TGF-betas and their high-affinity receptors TβRI, TβRII and TβRIII (betaglycan) reveal new variants in human prostatic cells, BMC Genomics, 2007, 1-13, 8:318.

Laurent, Michael R. et al., Muscle-bone interactions: From experimental models to the clinic? A critical update, Molecular and Cellular Endocrinology, 2016, 14-36, 432.

Lee, Se-Jin et al., Regulation of Myostatin Activity and Muscle Growth, PNAS, 2001, 9306-9311, 98(16).

Levin, Adeera et al., Prevalent Left Ventricular Hypertrophy in the Predialysis Population: Identifying Opportunities for Intervention, American Journal of Kidney Diseases, 1996, 347-354, 27(3).

Mcpherron, Alexandra C. et al., Double muscling in cattle due to mutations in the myostatin gene, Proc. Natl. Acad. Sci. USA, 1997, 12457-1246, 94.

Mcpherron, Alexandra C. et al., Regulation of skeletal muscle mass in mice by a new TGF-β superfamily member, Nature, 1997, 83-90, 387.

Merchant, A. Margaret et al., An efficient route to human bispecific IgG, Nature Biotechnology, 1998, 677-681, 16.

Oh, S. Paul et al., Activin type IIA and IIB receptors mediate Gdf11 signaling in axial vertebral patterning, Genes & Development, 2002, 2749-2754, 16.

Qin, Tai et al., A novel highly potent trivalent TGF-β receptor trap inhibits early-stage tumorigenesis and tumor cell invasion in murine Pten-deficient prostate glands, Oncotarget, 2016, 86087-86102, 7(52).

Relizani, Karima et al., Blockade of ActRIIB Signaling Triggers Muscle Fatigability and Metabolic Myopathy, The American Society of Gene & Cell Therapy, 2014, 1423-1433, 22(8).

Ridgway, John B.B. et al., 'Knobs-into-holes' engineering of antibody CH3 domains for heavy chain heterodimerization, Protein Engineering, 1996, 617-621, 9(7).

Roberts, Heather J. et al., Identification of Novel Isoforms of Activin Receptor-Like Kinase 7 (ALK7) Generated by Alternative Splicing and Expression of ALK7 and Its Ligand, Nodal, in Human Placenta, Biology of Reproduction, 2003, 1719-1726, 68.

Sako, Dianne et al., Characterization of the Ligand Binding Functionality of the Extracellular Domain of Activin Receptor Type IIB, Journal of Biological Chemistry, 2010, 21037-21048, 285(27).

Schuelke, Markus et al., Myostatin Mutation Associated with Gross Muscle Hypertrophy in a Child, N Engl J Med, 2004, 2682-2688, 350.

Spiess, Christoph et al., Alternative molecular formats and therapeutic applications for bispecific antibodies, Molecular Immunology, 2015, 95-106, 67.

Swatland, H. J. et al., Fetal development of the double muscled condition in cattle, Journal of Animal Science, 1974, 752-757, 38(4).

Whittemore, Lisa-Anne et al., Inhibition of myostatin in adult mice increases skeletal muscle mass and strength, Biochemical and Biophysical Research Communications, 2003, 965-971, 300.

Wranik, Bernd J. et al., LUZ-Y, a Novel Platform for the Mammalian Cell Production of Full-length IgG-bispecific Antibodies, The Journal of Biological Chemistry, 2012, 43331-43339, vol. 287, No. 52.

Wu, Hsiao-Huei et al., Autoregulation of Neurogenesis by GDF11, Neuron, 2003, 197-207, 37.

Yamashita, Hidetoshi et al., Osteogenic Protein-1 Binds to Activin Type II Receptors and Induces Certain Activin-like Effects, The Journal of Cell Biology, 1995, 217-226, 130(1).

Yeo, Chang-Yeol et al., Nodal Signals to Smads through Cripto-Dependent and Cripto-Independent Mechanisms, Molecular Cell, 2001, 949-957, 7.

Zhou, Xiaolan et al., Reversal of Cancer Cachexia and Muscle Wasting by ActRIIB Antagonism Leads to Prolonged Survival, Cell, 2010, 531-543, 4(142).

U.S. Appl. No. 16/340,048, filed Apr. 5, 2019.

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPPT
           GGPEVTYEPP PTAPT
```

FIGURE 2

|           | 10                          | 20                          | 30                          | 40                          | 50                          |
|-----------|-----------------------------|-----------------------------|-----------------------------|-----------------------------|-----------------------------|
| Rat IIb   | MTAPWAA-LALLWGSLCAGSGRGEAETRECIYYNANWELERTNQSGLER-CEGEQDKR |
| Pig IIb   | MTAPWAA-LALLWGSLCVGSGRGEAETRECIYYNANWELERTNQSGLER-CEGEQDKR |
| Mouse IIb | MTAPWAA-LALLWGSLCAGSGRGEAETRECIYYNANWELERTNQSGLER-CEGEQDKR |
| Human IIb | MTAPWVA-LALLWGSLCAGSGRGEAETRECIYYNANWELERTNQSGLER-CEGEQDKR |
| Bovine IIb| MTAPWAA-LALLWGSLCAGSGRGEAETRECIYYNANWELERTNQSGLER-CEGERDKR |
| Xenopus IIb| MGASVALTFLLLLATFRAGSGHDEVETRECIYYNANWELEKTNQSGVERLVEGKKDKR |
| Human IIA | MGAAKLAFAVFLISCSSGAILGRSETQECLFFNANWEKDRTNQTGVEP-CYGDKDKR |
| Consensus | MtApwaaXlalllwgslcaGsgrgeaETrECryyNANWEllerTNQsGlErLceGeqDKR |

|           | 60                          | 70                          | 80                          | 90                          | 100                         | 110                         |
|-----------|-----------------------------|-----------------------------|-----------------------------|-----------------------------|-----------------------------|-----------------------------|
| Rat IIb   | LHCYASWPNSSGTIELVKKGCWLDDFNCYDRQECVATEENPQVYFCCCEGNFCNERFT |
| Pig IIb   | LHCYASWRNSSGTIELVKKGCWLDDFNCYDRQECVATEENPQVYFCCCEGNFCNERFT |
| Mouse IIb | LHCYASWRNSSGTIELVKKGCWLDDFNCYDRQECVATEENPQVYFCCCEGNFCNERFT |
| Human IIb | LHCYASWRNSSGTIELVKKGCWLDDFNCYDRQECVATEENPQVYFCCCEGNFCNERFT |
| Bovine IIb| LHCYASWRNSSGTIELVKKGCWLDDFNCYDRQECVATEENPQVYFCCCEGNFCNERFT |
| Xenopus IIb| LHCYASWRNNSGFIELVKKGCWLDDFNCYDRQECIAKEENPQVFFCCCEGNYCNKKFT |
| Human IIA | RHCFATWKNISGSIEIVKQGCWLDDINCYDRTDCVEKKDSPEVYFCCCEGNMCNEKFS |
| Consensus | lHCyAsWrNsSGtIElVKkGCWLDDfNCYDRqeCvateenPqVyFCCCEGNfCNerFt |

|           | 120                         | 130                         | 140                         | 150                         |
|-----------|-----------------------------|-----------------------------|-----------------------------|-----------------------------|
| Rat IIb   | HLPEPGGPEVTYEP-PPTAPTLLTVLAYSLLPIGGLS- |
| Pig IIb   | HLPEAGGPEVTYEP-PPTAPTLLTVLAYSLLPIGGLS- |
| Mouse IIb | HLPEPGGPEVTYEP-PPTAPTLLTVLAYSLLPIGGLS- |
| Human IIb | HLPEAGGPEVTYEP-PPTAPTLLTVLAYSLLPIGGLS- |
| Bovine IIb| HLPEAGGPEVTYEP-PPTAPTLLTVLAYSLLPVGGLS- |
| Xenopus IIb| HLPEV---ETFDPKPQPSASVLNILIYSLLPIVGLSM |
| Human IIA | YFPEMEVTQPTSNP-VTPKPPYYNILLYSLVPLMLII-- |
| Consensus | hlPEXggpevTyePKpptapllltvLaYSLlPiggISM |

FIGURE 3

```
IgG1  ------THTCPPCPAPELLGGPSVFLFPPKPKDTLMISRTPEVTCVVVDVSHEDPEVKF   53
IgG4  ---ESKYGPPCPSCPAPEFLGGPSVFLFPPKPKDTLMISRTPEVTCVVVDVSQEDPEVQF   57
IgG2  --------VECPPCPAPPVAG-PSVFLFPPKPKDTLMISRTPEVTCVVVDVSHEDPEVQF   51
IgG3  EPKSCDTPPPCPRCPAPELLGGPSVFLFPPKPKDTLMISRTPEVTCVVVDVSHEDPEVQF   60
           ** ****  .  * ************************************;****;*

IgG1  NWYVDGVEVHNAKTKPREEQYNSTYRVVSVLTVLHQDWLNGKEYKCKVSNKALPAPIEKT  113
IgG4  NWYVDGVEVHNAKTKPREEQFNSTYRVVSVLTVLHQDWLNGKEYKCKVSNKGLPSSIEKT  117
IgG2  NWYVDGVEVHNAKTKPREEQFNSTFRVVSVLTVVHQDWLNGKEYKCKVSNKGLPAPIEKT  111
IgG3  KWYVDGVEVHNAKTKPREEQYNSTFRVVSVLTVLHQDWLNGKEYKCKVSNKALPAPIEKT  120
      ;****************** ** *;*** ***.*********************;****

IgG1  ISKAKGQPREPQVYTLPPSREEMTKNQVSLTCLVKGFYPSDIAVEWESNGQPENNYKTTP  173
IgG4  ISKAKGQPREPQVYTLPPSQEEMTKNQVSLTCLVKGFYPSDIAVEWESNGQPENNYKTTP  177
IgG2  ISKTKGQPREPQVYTLPPSREEMTKNQVSLTCLVKGFYPSDIAVEWESNGQPENNYKTTP  171
IgG3  ISKTKGQPREPQVYTLPPSREEMTKNQVSLTCLVKGFYPSDIAVEWESSGQPENNYNTTP  180
      ***;**************;*****************************;*******;***

IgG1  PVLDSDGSFFLYSKLTVDKSRWQQGNVFSCSVMHEALHNHYTQKSLSLSPGK  225
IgG4  PVLDSDGSFFLYSRLTVDKSRWQEGNVFSCSVMHEALHNHYTQKSLSLSLGK  229
IgG2  PMLDSDGSFFLYSKLTVDKSRWQQGNVFSCSVMHEALHNHYTQKSLSLSPGK  223
IgG3  PMLDSDGSFFLYSKLTVDKSRWQQGNIFSCSVMHEALHNRFTQKSLSLSPGK  232
      *;***********;*********;**;************.;*********  **
```

FIGURE 4

```
 20    GRGEAETREC IYYNANWELE RTNQSGLERC EGEQDKRLHC YASWRNSSGT
 70    IELVKKGCWL DDFNCYDRQE CVATEENPQV YFCCCEGNFC NERFTHLPEA
120    GGPEVTYEPP PTAPT      (SEQ ID NO: 1)
```

FIGURE 5

```
  1  MTAPWVALAL  LWGSLCAGSG  RGEAETRECI  YYNANWELER  TNQSGLERCE
 51  GEQDKRLHCY  ASWRNSSGTI  ELVKKGCWLD  DFNCYDRQEC  VATEENPQVY
101  FCCCEGNFCN  ERFTHLPEAG  GPEVTYEPPP  TAPTLLTVLA  YSLLPIGGLS
151  LIVLLAFWMY  RHRKPPYGHV  DIHEDPGPPP  PSPLVGLKPL  QLLEIKARGR
201  FGCVWKAQLM  NDFVAVKIFP  LQDKQSWQSE  REIFSTPGMK  HENLLQFIAA
251  EKRGSNLEVE  LWLITAFHDK  GSLTDYLKGN  IITWNELCHV  AETMSRGLSY
301  LHEDVPWCRG  EGHKPSIAHR  DFKSKNVLLK  SDLTAVLADF  GLAVRFEPGK
351  PPGDTHGQVG  TRRYMAPEVL  EGAINFQRDA  FLRIDMYAMG  LVLWELVSRC
401  KAADGPVDEY  MLPFEEEIGQ  HPSLEELQEV  VVHKKMRPTI  KDHWLKHPGL
451  AQLCVTIEEC  WDHDAEARLS  AGCVEERVSL  IRRSVNGTTS  DCLVSLVTSV
501  TNVDLPPKES  SI       (SEQ ID NO: 2)
```

FIGURE 6

GGGCGTGGGGAGGCTGAGACACGGGAGTGCATCTACTACAACGCCAACTGGGAGCTGGAGCGCACCAAGC
AGAGCGGCCTGGAGCGCTGCGAAGGCGAGCAGGACAAGCGGCTGCACTGCTACGCCTCCTGGCGCAACAG
CTCTGGCACCATCGAGCTCGTGAAGAAGGGCTGCTGGCTAGATGACTTCAACTGCTACGATAGGCAGGAG
TGTGTGGCCACTGAGGAGAACCCCCAGGTGTACTTCTGCTGCTGTGAAGGCAACTTCTGCAACGAGCGCT
TCACTCATTGCCAGAGGCTGGGGGCCCGGAAGTCACGTACGAGCCACCCCGACAGCCCCCACC
(SEQ ID NO: 3)

FIGURE 7

ATGACGGCGCCCTGGGTGGCCCTCGCCCTCCTCTGGGGATCGCTGTGGCCCGGCTCTGGGCGTGGGGAGG
CTGAGACACGGGAGTGCATCTACTACAACGCCAACTGGGAGCTGGAGCGCACCAACCAGAGCGGCCTGGA
GCGCTGCGAAGGCGAGCAGGACAAGCGGCTGCACTGCTACGCCTCCTGGCGCAACAGCTCTGGCACCATC
GAGCTCGTGAAGAAGGGCTGCTGGCTAGATGACTTCAACTGCTACGATAGGCAGGAGTGTGTGGCCACTG
AGGAGAACCCCCAGGTGTACTTCTGCTGCTGTGAAGGCAACTTCTGCAACGAGCGCTTCACTCATTTGCC
AGAGGCTGGGGGCCCGGAAGTCACGTACGAGCCACCCCCGACAGCCCCACCCTGCTCACGGTGCTGGCC
TACTCACTGCTGCCCATCGGGGGCCTTTCCCTCATCGTCCTGCTGGCCTTTTGGATGTACCGGCATCGCA
AGCCCCCCTACGGTCATGTGGACATCCATGAGGACCCTGGGCCTCCACCACCATCCCCTCTGGTGGGCCT
GAAGCCACTGCAGCTGCTGGAGATCAAGGCTCGGGGGCGCTTTGGCTGTGTCTGGAAGGCCCAGCTCATG
AATGACTTTGTAGCTGTCAAGATCTTCCCACTCCAGGACAAGCAGTCGTGGCAGAGTGAACGGGAGATCT
TCAGCACACCTGGCATGAAGCACGAGAACCTGCTACAGTTCATTGCTGCCGAGAAGCGAGGCTCCAACCT
CGAAGTAGAGCTGTGGCTCATCACGGCCTTCCATGACAAGGGCTCCCTCACGGATTACCTCAAGGGGAAC
ATCATCACATGGAACGAACTGTGTCATGTAGCAGAGACGATGTCACGAGGCCTCTCATACCTGCATGAGG
ATGTGCCCTGGTGCCGTGGCGAGGGCCACAAGCCGTCTATTGCCCACAGGGACTTTAAAAGTAAGAATGT
ATTGCTGAAGAGCGACCTCACAGCCGTGCTGGCTGACTTTGGCTTGGCTGTTCGATTTGAGCCAGGGAAA
CCTCCAGGGGACACCCACGGACACGTAGGCACGAGACGGTACATGGCTCCTGAGGTGCTCGAGGGAGCCA
TCAACTTCCAGAGAGATGCCTTCCTGCGCATTGACATGTATGCCATGGGGTTGGTGCTGTGGGAGCTTGT
GTCTCGCTGCAAGGCTGCAGACGGACCCGTGGATGAGTACATGCTGCCCTTTGAGGAAGAGATTGGCCAG
CACCCTTCGTTGGAGGAGCTGCAGGAGGTGGTGGTGCACAAGAAGATGAGGCCCACCATTAAAGATCACT
GGTTGAAACACCCGGGCCTGGCCCAGCTTTGTGTGACCATCGAGGAGTGCTGGGACCATGATGCAGAGCC
TCGCTTGTCCGCGGGCTGTGTGGAGGAGCGGGTGTCCCTGATTCGGAGGTCGGTCAACGGCACTACCTCG
GACTGTCTCGTTTCCCTGGTGACCTCTGTCACCAATGTGGACCTGCCCCCTAAAGAGTCAAGCATCTAA
(SEQ ID NO: 4)

FIGURE 8

| Ligand Binding by Homodimeric ActRIIB-Fc Proteins at 37°C | | | | | | | | | | | | |
|---|---|---|---|---|---|---|---|---|---|---|---|---|
| ActRIIB protein | Activin A | | | GDF11 | | | BMP9 | | | BMP10 | | |
|  | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Wild-type | $2.3 \times 10^6$ | $1.1 \times 10^{-4}$ | 47 | $1.0 \times 10^7$ | $1.2 \times 10^{-4}$ | 12 | $3.0 \times 10^7$ | $1.1 \times 10^{-3}$ | 37 | $3.6 \times 10^7$ | $1.6 \times 10^{-4}$ | 4 |
| K55A | $3.0 \times 10^6$ | $1.4 \times 10^{-4}$ | 46 | $1.6 \times 10^7$ | $4.0 \times 10^{-4}$ | 26 | $4.9 \times 10^7$ | $7.0 \times 10^{-3}$ | 142 | $3.2 \times 10^7$ | $7.4 \times 10^{-4}$ | 23 |
| K55A/F82I | $5.7 \times 10^6$ | $2.7 \times 10^{-4}$ | 47 | $2.2 \times 10^7$ | $2.0 \times 10^{-3}$ | 90 | $1.6 \times 10^7$ | $2.1 \times 10^{-3}$ | 134 | $1.3 \times 10^8$ | $8.6 \times 10^{-4}$ | 7 |
| K55E | $2.5 \times 10^6$ | $1.6 \times 10^{-4}$ | 64 | $1.2 \times 10^7$ | $6.3 \times 10^{-4}$ | 52 | $1.1 \times 10^8$ | $3.0 \times 10^{-2}$ | 270 | $3.4 \times 10^7$ | $4.7 \times 10^{-4}$ | 14 |
| K74A | $3.2 \times 10^7$ | $1.1 \times 10^{-3}$ | 34 | $1.9 \times 10^6$ | $8.1 \times 10^{-4}$ | 430 | $1.7 \times 10^8$ | $6.2 \times 10^{-2}$ | 360 | $7.5 \times 10^7$ | $2.5 \times 10^{-3}$ | 33 |
| L79H | $1.9 \times 10^6$ | $5.6 \times 10^{-4}$ | 300 | $2.0 \times 10^7$ | $7.5 \times 10^{-4}$ | 37 | $2.4 \times 10^6$ | $1.8 \times 10^{-3}$ | 760 | $1.9 \times 10^7$ | $2.1 \times 10^{-3}$ | 120 |
| L79H/F82I | $1.2 \times 10^6$ | $6.7 \times 10^{-4}$ | 580 | $2.6 \times 10^7$ | $1.7 \times 10^{-3}$ | 64 | $1.3 \times 10^7$ | $2.8 \times 10^{-3}$ | 220 | $2.7 \times 10^7$ | $3.0 \times 10^{-3}$ | 110 |
| L79K | $4.0 \times 10^6$ | $5.1 \times 10^{-4}$ | 130 | $1.2 \times 10^7$ | $1.7 \times 10^{-3}$ | 140 | $1.6 \times 10^7$ | $1.7 \times 10^{-2}$ | 1100 | $4.7 \times 10^6$ | $6.5 \times 10^{-3}$ | 1480 |
| L79K/F82K | $1.4 \times 10^6$ | $8.6 \times 10^{-4}$ | 640 | $4.5 \times 10^7$ | $6.7 \times 10^{-2}$ | 1600 | No binding | | | $2.2 \times 10^7$ | $1.5 \times 10^{-4}$ | 68 |
| F82I | $1.9 \times 10^6$ | $1.5 \times 10^{-4}$ | 78 | $8.2 \times 10^6$ | $8.4 \times 10^{-5}$ | 10 | $9.2 \times 10^7$ | $2.5 \times 10^{-2}$ | 275 | $2.4 \times 10^7$ | $1.5 \times 10^{-4}$ | 8 |
| F82K | $1.8 \times 10^6$ | $1.7 \times 10^{-4}$ | 93 | $1.6 \times 10^7$ | $9.1 \times 10^{-4}$ | 57 | Transient binding* | | | $3.1 \times 10^7$ | $2.6 \times 10^{-4}$ | 8 |

* Indeterminate due to transient nature of interaction

FIGURE 9

| Ligand Binding by Homodimeric ActRIIB-Fc Proteins at 25°C | | | | | | | | | | | | |
|---|---|---|---|---|---|---|---|---|---|---|---|---|
| ActRIIB protein | Activin A | | | GDF11 | | | BMP9 | | | BMP10 | | |
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Wild-type | $2.3 \times 10^6$ | $5.2 \times 10^{-4}$ | 250 | $9.1 \times 10^6$ | $9.8 \times 10^{-5}$ | 11 | $7.4 \times 10^6$ | $4.4 \times 10^{-4}$ | 59 | $3.3 \times 10^6$ | $5.0 \times 10^{-4}$ | 169 |
| N35E | $1.3 \times 10^6$ | $1.0 \times 10^{-3}$ | 800 | $6.7 \times 10^6$ | $1.9 \times 10^{-4}$ | 28 | No binding | | | $4.3 \times 10^6$ | $1.2 \times 10^{-3}$ | 280 |
| N35F | $1.6 \times 10^6$ | $4.7 \times 10^{-4}$ | 290 | $8.2 \times 10^6$ | $1.4 \times 10^{-4}$ | 17 | Reduced binding | | | $2.6 \times 10^6$ | $5.8 \times 10^{-4}$ | 220 |
| N35Q | $2.0 \times 10^6$ | $6.5 \times 10^{-4}$ | 320 | $7.7 \times 10^6$ | $1.6 \times 10^{-4}$ | 20 | Little binding | | | $2.7 \times 10^6$ | $7.1 \times 10^{-4}$ | 270 |
| L38D | $1.7 \times 10^6$ | $4.0 \times 10^{-4}$ | 230 | $5.8 \times 10^6$ | $1.8 \times 10^{-4}$ | 30 | $6.6 \times 10^6$ | $4.2 \times 10^{-4}$ | 63 | $3.3 \times 10^6$ | $4.9 \times 10^{-4}$ | 150 |
| L38Q | $1.8 \times 10^6$ | $3.5 \times 10^{-4}$ | 200 | $7.0 \times 10^6$ | $1.5 \times 10^{-4}$ | 21 | $7.4 \times 10^6$ | $2.5 \times 10^{-4}$ | 33 | $3.9 \times 10^6$ | $3.5 \times 10^{-4}$ | 89 |
| L38R | $1.9 \times 10^6$ | $4.5 \times 10^{-4}$ | 230 | $6.4 \times 10^6$ | $4.6 \times 10^{-5}$ | 7 | $1.4 \times 10^7$ | $5.5 \times 10^{-4}$ | 50 | $1.6 \times 10^6$ | $1.7 \times 10^{-4}$ | 110 |
| K74M | No binding | | | No binding | | | No binding | | | No binding | | |
| K74T | No binding | | | No binding | | | No binding | | | No binding | | |
| L79W | $1.3 \times 10^6$ | $3.2 \times 10^{-4}$ | 260 | $1.2 \times 10^7$ | $5.2 \times 10^{-4}$ | 44 | $9.2 \times 10^6$ | $1.1 \times 10^{-3}$ | 110 | $2.9 \times 10^6$ | $4.7 \times 10^{-4}$ | 160 |
| F82Y | $2.3 \times 10^6$ | $3.9 \times 10^{-4}$ | 170 | $7.1 \times 10^6$ | $1.3 \times 10^{-4}$ | 18 | $8.4 \times 10^6$ | $6.9 \times 10^{-4}$ | 82 | $3.7 \times 10^6$ | $5.2 \times 10^{-4}$ | 140 |
| Q98A | $3.4 \times 10^6$ | $5.3 \times 10^{-4}$ | 155 | $4.7 \times 10^6$ | $1.8 \times 10^{-4}$ | 37 | $1.2 \times 10^7$ | $5.3 \times 10^{-4}$ | 43 | $2.6 \times 10^6$ | $5.4 \times 10^{-4}$ | 210 |
| Q98I | $4.1 \times 10^6$ | $6.4 \times 10^{-4}$ | 157 | $3.9 \times 10^6$ | $1.9 \times 10^{-4}$ | 49 | $1.6 \times 10^7$ | $9.4 \times 10^{-4}$ | 59 | $2.6 \times 10^6$ | $5.6 \times 10^{-4}$ | 210 |
| Q98K | $3.3 \times 10^6$ | $4.8 \times 10^{-4}$ | 145 | $4.6 \times 10^6$ | $1.7 \times 10^{-4}$ | 37 | $1.1 \times 10^7$ | $7.4 \times 10^{-4}$ | 69 | $7.4 \times 10^6$ | $5.0 \times 10^{-4}$ | 68 |
| Q98L | $3.8 \times 10^6$ | $8.2 \times 10^{-4}$ | 220 | $4.0 \times 10^6$ | $1.7 \times 10^{-4}$ | 43 | $1.6 \times 10^7$ | $1.2 \times 10^{-3}$ | 71 | $1.1 \times 10^7$ | $7.2 \times 10^{-4}$ | 65 |
| Q98R | $3.4 \times 10^6$ | $1.0 \times 10^{-3}$ | 300 | $5.5 \times 10^6$ | $1.1 \times 10^{-4}$ | 20 | $9.7 \times 10^7$ | $7.2 \times 10^{-3}$ | 74 | $2.5 \times 10^6$ | $8.1 \times 10^{-4}$ | 320 |
| Q98V | $3.6 \times 10^6$ | $6.0 \times 10^{-4}$ | 160 | $5.0 \times 10^6$ | $1.6 \times 10^{-4}$ | 33 | $1.1 \times 10^7$ | $5.0 \times 10^{-4}$ | 47 | $1.0 \times 10^7$ | $5.0 \times 10^{-4}$ | 48 |

SEQUENCE LISTING

<160> NUMBER OF SEQ ID NOS: 280

<210> SEQ ID NO 1
<211> LENGTH: 115
<212> TYPE: PRT
<213> ORGANISM: Homo sapiens

<400> SEQUENCE: 1

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115
```

<210> SEQ ID NO 2
<211> LENGTH: 512
<212> TYPE: PRT
<213> ORGANISM: Homo sapiens

<400> SEQUENCE: 2

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
```

```
            20                  25                  30
Asn Ala Asn Trp Glu Leu Glu Arg Thr Asn Gln Ser Gly Leu Glu Arg
         35                  40                  45
Cys Glu Gly Glu Gln Asp Lys Arg Leu His Cys Tyr Ala Ser Trp Arg
     50                  55                  60
Asn Ser Ser Gly Thr Ile Glu Leu Val Lys Lys Gly Cys Trp Leu Asp
 65                  70                  75                  80
Asp Phe Asn Cys Tyr Asp Arg Gln Glu Cys Val Ala Thr Glu Glu Asn
                 85                  90                  95
Pro Gln Val Tyr Phe Cys Cys Glu Gly Asn Phe Cys Asn Glu Arg
                100                 105                 110
Phe Thr His Leu Pro Glu Ala Gly Pro Glu Val Thr Tyr Glu Pro
             115                 120                 125
Pro Pro Thr Ala Pro Thr Leu Leu Thr Val Leu Ala Tyr Ser Leu Leu
         130                 135                 140
Pro Ile Gly Gly Leu Ser Leu Ile Val Leu Leu Ala Phe Trp Met Tyr
145                 150                 155                 160
Arg His Arg Lys Pro Pro Tyr Gly His Val Asp Ile His Glu Asp Pro
                165                 170                 175
Gly Pro Pro Pro Pro Ser Pro Leu Val Gly Leu Lys Pro Leu Gln Leu
             180                 185                 190
Leu Glu Ile Lys Ala Arg Gly Arg Phe Gly Cys Val Trp Lys Ala Gln
         195                 200                 205
Leu Met Asn Asp Phe Val Ala Val Lys Ile Phe Pro Leu Gln Asp Lys
         210                 215                 220
Gln Ser Trp Gln Ser Glu Arg Glu Ile Phe Ser Thr Pro Gly Met Lys
225                 230                 235                 240
His Glu Asn Leu Leu Gln Phe Ile Ala Ala Glu Lys Arg Gly Ser Asn
                245                 250                 255
Leu Glu Val Glu Leu Trp Leu Ile Thr Ala Phe His Asp Lys Gly Ser
             260                 265                 270
Leu Thr Asp Tyr Leu Lys Gly Asn Ile Ile Thr Trp Asn Glu Leu Cys
         275                 280                 285
His Val Ala Glu Thr Met Ser Arg Gly Leu Ser Tyr Leu His Glu Asp
         290                 295                 300
Val Pro Trp Cys Arg Gly Glu Gly His Lys Pro Ser Ile Ala His Arg
305                 310                 315                 320
Asp Phe Lys Ser Lys Asn Val Leu Leu Lys Ser Asp Leu Thr Ala Val
                325                 330                 335
Leu Ala Asp Phe Gly Leu Ala Val Arg Phe Glu Pro Gly Lys Pro Pro
             340                 345                 350
Gly Asp Thr His Gly Gln Val Gly Thr Arg Arg Tyr Met Ala Pro Glu
         355                 360                 365
Val Leu Glu Gly Ala Ile Asn Phe Gln Arg Asp Ala Phe Leu Arg Ile
     370                 375                 380
Asp Met Tyr Ala Met Gly Leu Val Leu Trp Glu Leu Val Ser Arg Cys
385                 390                 395                 400
Lys Ala Ala Asp Gly Pro Val Asp Glu Tyr Met Leu Pro Phe Glu Glu
                405                 410                 415
Glu Ile Gly Gln His Pro Ser Leu Glu Glu Leu Gln Glu Val Val Val
             420                 425                 430
His Lys Lys Met Arg Pro Thr Ile Lys Asp His Trp Leu Lys His Pro
         435                 440                 445
```

```
Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 3
<211> LENGTH: 345
<212> TYPE: DNA
<213> ORGANISM: Homo sapiens

<400> SEQUENCE: 3
gggcgtgggg aggctgagac acgggagtgc atctactaca acgccaactg ggagctggag      60
cgcaccaacc agagcggcct ggagcgctgc gaaggcgagc aggacaagcg gctgcactgc     120
tacgcctcct ggcgcaacag ctctggcacc atcgagctcg tgaagaaggg ctgctggcta     180
gatgacttca actgctacga taggcaggag tgtgtggcca ctgaggagaa cccccaggtg     240
tacttctgct gctgtgaagg caacttctgc aacgagcgct tcactcattt gccagaggct     300
gggggcccgg aagtcacgta cgagccaccc ccgacagccc ccacc                     345

<210> SEQ ID NO 4
<211> LENGTH: 1539
<212> TYPE: DNA
<213> ORGANISM: Homo sapiens

<400> SEQUENCE: 4
atgacggcgc cctgggtggc cctcgccctc ctctggggat cgctgtggcc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gagcgcttca ctcatttgcc agaggctggg     360
ggcccggaag tcacgtacga gccaccccg acagccccca cctgctcac ggtgctggcc     420 tactcactgc tgcccatcgg ggccttttcc ctcatcgtcc tgctggcctt ttggatgtac     480
cggcatcgca gccccccta cggtcatgtg acatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca     660
ctccaggaca gcagtcgtg gcagagtgaa cgggagatct cagcacacc tggcatgaag     720 cacgagaacc tgctacagtt cattgctgcc gagaagcgag gctccaacct cgaagtagag     780
ctgtggctca tcacggcctt ccatgacaag ggctccctca cggattacct caaggggaac     840
atcatcacat ggaacgaact gtgtcatgta gcagagacga tgtcacgagg cctctcatac     900
ctgcatgagg atgtgccctg gtgccgtggc gagggccaca gccgtctat tgcccacagg     960 gactttaaaa gtaagaatgt attgctgaag agcgacctca cagccgtgct ggctgacttt    1020
ggcttggctg ttcgatttga gccagggaaa cctccagggg acacccacgg acaggtaggc    1080
acgagacggt acatggctcc tgaggtgctc gagggagcca tcaacttcca gagagatgcc    1140
```

-continued

```
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260 caccttcgt tggaggagct gcaggaggtg gtggtgcaca agaagatgag gcccaccatt     1320
aaagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgccccc taaagagtca agcatctaa                          1539
```

<210> SEQ ID NO 5
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285
```

```
Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 6
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300
```

```
Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 7
<211> LENGTH: 21
<212> TYPE: PRT
<213> ORGANISM: Apis mellifera

<400> SEQUENCE: 7

Met Lys Phe Leu Val Asn Val Ala Leu Val Phe Met Val Val Tyr Ile
1               5                   10                  15

Ser Tyr Ile Tyr Ala
            20

<210> SEQ ID NO 8
<211> LENGTH: 22
<212> TYPE: PRT
<213> ORGANISM: Unknown
<220> FEATURE:
<223> OTHER INFORMATION: Description of Unknown:
      Tissue plasminogen activator

<400> SEQUENCE: 8

Met Asp Ala Met Lys Arg Gly Leu Cys Cys Val Leu Leu Leu Cys Gly
1               5                   10                  15

Ala Val Phe Val Ser Pro
            20

<210> SEQ ID NO 9
<211> LENGTH: 18
<212> TYPE: PRT
<213> ORGANISM: Unknown
<220> FEATURE:
<223> OTHER INFORMATION: Description of Unknown:
      Native sequence

<400> SEQUENCE: 9

Met Thr Ala Pro Trp Val Ala Leu Ala Leu Leu Trp Gly Ser Leu Cys
1               5                   10                  15

Ala Gly

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggatgcaa tgaagagagg gctctgctgt gtgctgctgc tgtgtggagc agtcttcgtt      60
tcgcccggcg cctctgggcg tgggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
```

```
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc caccccgac agcccccacc     420 ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Gly Glu Ala Glu
1               5

<210> SEQ ID NO 12
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
        115                 120                 125

```
Phe Leu Phe Pro Pro Lys Pro Lys Asp Thr Leu Met Ile Ser Arg Thr
    130                 135                 140

Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 13
<211> LENGTH: 225
<212> TYPE: PRT
<213> ORGANISM: Homo sapiens

<400> SEQUENCE: 13

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175
```

```
Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 14
<211> LENGTH: 223
<212> TYPE: PRT
<213> ORGANISM: Homo sapiens

<400> SEQUENCE: 14

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 15
<211> LENGTH: 232
<212> TYPE: PRT
<213> ORGANISM: Homo sapiens

<400> SEQUENCE: 15

Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

Val Asp Val Ser His Glu Asp Pro Glu Val Gln Phe Lys Trp Tyr Val
50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230

<210> SEQ ID NO 16
<211> LENGTH: 279
<212> TYPE: PRT
<213> ORGANISM: Homo sapiens

<400> SEQUENCE: 16

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys

```
                    180                 185                 190
Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
            210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
                260                 265                 270

Leu Ser Leu Ser Pro Gly Lys
            275

<210> SEQ ID NO 17
<211> LENGTH: 229
<212> TYPE: PRT
<213> ORGANISM: Homo sapiens

<400> SEQUENCE: 17

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
        210                 215                 220

Leu Ser Leu Gly Lys
225

<210> SEQ ID NO 18
<211> LENGTH: 225
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 18

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Lys Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 19
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

```
Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 20
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Tyr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220
```

Lys
225

<210> SEQ ID NO 21
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

<210> SEQ ID NO 22
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45
```

```
Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Cys Arg Glu Glu Met Thr Lys Asn Gln Val Ser Leu Trp
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
210                 215                 220

Lys
225

<210> SEQ ID NO 23
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr His Thr Cys Pro Pro Cys Pro Ala Pro Glu Leu Leu Gly Gly Pro
1               5                  10                  15

Ser Val Phe Leu Phe Pro Pro Lys Pro Lys Asp Thr Leu Met Ile Ser
                 20                  25                  30

Arg Thr Pro Glu Val Thr Cys Val Val Val Asp Val Ser His Glu Asp
             35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Cys Thr
            115                 120                 125

Leu Pro Pro Ser Arg Glu Glu Met Thr Lys Asn Gln Val Ser Leu Ser
130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
```

```
                    165                 170                 175

Asp Ser Asp Gly Ser Phe Phe Leu Val Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys
225

<210> SEQ ID NO 24
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Phe Arg Pro Glu Val His Leu
        115                 120                 125

Leu Pro Pro Ser Arg Glu Glu Met Thr Lys Asn Gln Val Ser Leu Thr
    130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225

<210> SEQ ID NO 25
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 25

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Glu Glu Leu Ala Leu Asn Glu Leu Val Thr Leu
    130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190

Val Ala Ala Glu Asp Trp Lys Lys Gly Asp Thr Phe Ser Cys Ser Val
        195                 200                 205

Met His Glu Ala Leu His Asn His Tyr Thr Gln Lys Ser Leu Asp Arg
    210                 215                 220

Ser Pro Gly Lys
225

<210> SEQ ID NO 26
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110
```

-continued

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260

<210> SEQ ID NO 27
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

```
Ala Leu His Asn His Tyr Thr Gln Lys Ser Leu Ser Leu Ser Pro Gly
    210                 215                 220

Lys Gly Gly Ser Ala Gln Leu Lys Lys Lys Leu Gln Ala Leu Lys Lys
225                 230                 235                 240

Lys Asn Ala Gln Leu Lys Trp Lys Leu Gln Ala Leu Lys Lys Lys Leu
                245                 250                 255

Ala Gln Gly Ala Thr
            260

<210> SEQ ID NO 28
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Glu Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Asp Ser Leu Ser Leu Ser Pro Gly
    210                 215                 220

Lys
225

<210> SEQ ID NO 29
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29
```

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
            115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Arg Gly Gln Pro Glu Asn Asn Tyr Lys Thr Thr Pro Pro Val Leu
            165                 170                 175

Asp Ser Arg Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

Lys
225

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr

```
                115                 120                 125
Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn Arg Tyr Thr Gln Lys Ser Leu Ser Leu Ser Pro Gly
    210                 215                 220

Lys
225

<210> SEQ ID NO 31
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Ala Arg Leu His
        50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
                180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
        210                 215                 220

Ser Val Leu Thr Val Leu His Gln Asp Trp Leu Asn Gly Lys Glu Tyr
225                 230                 235                 240
```

```
Lys Cys Lys Val Ser Asn Lys Ala Leu Pro Ala Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 32
<211> LENGTH: 1104
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
gcccggctgc actgctacgc ctcctggcgc aacagctctg gcaccatcga gctcgtgaag   240
aagggctgct ggctagatga cttcaactgc tacgataggc aggagtgtgt ggccactgag   300
gagaaccccc aggtgtactt ctgctgctgt gaaggcaact tctgcaacga cgcttcact   360
catttgccag aggctggggg cccggaagtc acgtacgagc accccccgac agcccccacc   420
ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaaccat ctccaaagcc   780
aaagggcagc cccgagaacc acaggtgtac accctgcccc catcccggga ggagatgacc   840
aagaaccagg tcagcctgac ctgcctggtc aaaggcttct atcccagcga catcgccgtg   900
gagtgggaga gcaatgggca gccggagaac aactacaaga ccacgcctcc cgtgctggac   960
tccgacggct ccttcttcct ctatagcaag ctcaccgtgg acaagagcag gtggcagcag  1020
gggaacgtct tctcatgctc cgtgatgcat gaggctctgc acaaccacta cacgcagaag  1080
agcctctccc tgtccccggg taaa                                         1104
```

<210> SEQ ID NO 33
<211> LENGTH: 343
<212> TYPE: PRT
<213> ORGANISM: Artificial Sequence
<220> FEATURE:

-continued

<223> OTHER INFORMATION: Description of Artificial Sequence: Synthetic
polypeptide

<400> SEQUENCE: 33

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Ala Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340
```

<210> SEQ ID NO 34
<211> LENGTH: 368
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Glu Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 35
<211> LENGTH: 1104
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 35

```
atggatgcaa tgaagagagg gctctgctgt gtgctgctgc tgtgtggagc agtcttcgtt        60
tcgcccggcg cctctgggcg tggggaggct gagacacggg agtgcatcta ctacaacgcc       120
aactgggagc tggagcgcac caaccagagc ggcctggagc gctgcgaagg cgagcaggac       180
gagcggctgc actgctacgc ctcctggcgc aacagtctg gcaccatcga gctcgtgaag        240
aagggctgct ggctagatga cttcaactgc tacgataggc aggagtgtgt ggccactgag       300
gagaaccccc aggtgtactt ctgctgctgt gaaggcaact tctgcaacga gcgcttcact       360
catttgccag aggctggggg cccggaagtc acgtacgagc cacccccgac agcccccacc       420
ggtggtggaa ctcacacatg cccaccgtgc ccagcacctg aactcctggg gggaccgtca       480
gtcttcctct tccccccaaa acccaaggac accctcatga tctcccggac ccctgaggtc       540
acatgcgtgg tggtggacgt gagccacgaa gaccctgagg tcaagttcaa ctggtacgtg       600
gacggcgtgg aggtgcataa tgccaagaca aagccgcggg aggagcagta caacagcacg       660
taccgtgtgg tcagcgtcct caccgtcctg caccaggact ggctgaatgg caaggagtac       720
aagtgcaagg tctccaacaa agccctccca gcccccatcg agaaaaccat ctccaaagcc       780
aaagggcagc cccgagaacc acaggtgtac accctgcccc catcccggga ggagatgacc       840
aagaaccagg tcagcctgac ctgcctggtc aaaggcttct atcccagcga catcgccgtg       900
gagtgggaga gcaatgggca gccggagaac aactacaaga ccacgcctcc cgtgctggac       960
tccgacggct ccttcttcct ctatagcaag ctcaccgtgg acaagagcag gtggcagcag      1020
gggaacgtct tctcatgctc cgtgatgcat gaggctctgc acaaccacta cacgcagaag      1080
agcctctccc tgtccccggg taaa                                             1104
```

<210> SEQ ID NO 36
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Glu Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140
```

```
Asp Thr Leu Met Ile Ser Arg Thr Pro Glu Val Thr Cys Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
        290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 37
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Ile Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
```

```
                145                 150                 155                 160
Val Phe Leu Phe Pro Pro Lys Pro Lys Asp Thr Leu Met Ile Ser Arg
                    165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 38
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct ggctagatga catcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc acccccgac agcccccacc      420 ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gcccccatcg agaaaaccat ctccaaagcc     780
aaagggcagc ccgagaacc acaggtgtac accctgcccc catcccggga ggagatgacc      840
```

-continued

```
aagaaccagg tcagcctgac ctgcctggtc aaaggcttct atcccagcga catcgccgtg      900
gagtgggaga gcaatgggca gccggagaac aactacaaga ccacgcctcc cgtgctggac      960
tccgacggct ccttcttcct ctatagcaag ctcaccgtgg acaagagcag gtggcagcag     1020
gggaacgtct tctcatgctc cgtgatgcat gaggctctgc acaaccacta cacgcagaag     1080
agcctctccc tgtctccggg taaa                                            1104
```

<210> SEQ ID NO 39
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Ile Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300
```

```
Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
            325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Lys Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320
```

```
Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
        340                 345                 350

Leu His Asn His Tyr Thr Gln Lys Ser Leu Ser Leu Ser Pro Gly Lys
        355                 360                 365

<210> SEQ ID NO 41
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atggatgcaa tgaagagagg ctctgctgt gtgctgctgc tgtgtggagc agtcttcgtt      60
tcgcccggcg cctctgggcg tggggaggct gagacacggg agtgcatcta ctacaacgcc    120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct ggctagatga caagaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc acccccgac agcccccacc     420 ggtggtggaa ctcacacatg cccaccgtgc ccagcacctg aactcctggg gggaccgtca    480
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaa                                          1104

<210> SEQ ID NO 42
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45
```

```
Gly Thr Ile Glu Leu Val Lys Lys Gly Cys Trp Leu Asp Asp Lys Asn
    50                  55                  60

Cys Tyr Asp Arg Gln Glu Cys Val Ala Thr Glu Asn Pro Gln Val
 65              70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Thr
            100                 105                 110

Ala Pro Thr Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
    195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
    275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 43
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60
```

| | | | | | | | | | | | | | | | |
|---|---|---|---|---|---|---|---|---|---|---|---|---|---|---|---|
|Cys|Tyr|Ala|Ser|Trp|Arg|Asn|Ser|Gly|Thr|Ile|Glu|Leu|Val|Lys| |
|65| | | |70| | | |75| | | |80| | | |

Cys Tyr Ala Ser Trp Arg Asn Ser Gly Thr Ile Glu Leu Val Lys
65                  70              75              80

Lys Gly Cys Trp Glu Asp Asp Phe Asn Cys Tyr Asp Arg Gln Glu Cys
                85              90              95

Val Ala Thr Glu Glu Asn Pro Gln Val Tyr Phe Cys Cys Glu Gly
            100             105             110

Asn Phe Cys Asn Glu Arg Phe Thr His Leu Pro Glu Ala Gly Gly Pro
            115             120             125

Glu Val Thr Tyr Glu Pro Pro Thr Ala Pro Thr Gly Gly Gly Thr
            130             135             140

His Thr Cys Pro Pro Cys Pro Ala Pro Glu Leu Leu Gly Gly Pro Ser
145             150             155             160

Val Phe Leu Phe Pro Pro Lys Pro Lys Asp Thr Leu Met Ile Ser Arg
            165             170             175

Thr Pro Glu Val Thr Cys Val Val Val Asp Val Ser His Glu Asp Pro
            180             185             190

Glu Val Lys Phe Asn Trp Tyr Val Asp Gly Val Glu Val His Asn Ala
            195             200             205

Lys Thr Lys Pro Arg Glu Glu Gln Tyr Asn Ser Thr Tyr Arg Val Val
            210             215             220

Ser Val Leu Thr Val Leu His Gln Asp Trp Leu Asn Gly Lys Glu Tyr
225             230             235             240

Lys Cys Lys Val Ser Asn Lys Ala Leu Pro Ala Pro Ile Glu Lys Thr
            245             250             255

Ile Ser Lys Ala Lys Gly Gln Pro Arg Glu Pro Gln Val Tyr Thr Leu
            260             265             270

Pro Pro Ser Arg Glu Glu Met Thr Lys Asn Gln Val Ser Leu Thr Cys
            275             280             285

Leu Val Lys Gly Phe Tyr Pro Ser Asp Ile Ala Val Glu Trp Glu Ser
290             295             300

Asn Gly Gln Pro Glu Asn Asn Tyr Asp Thr Thr Pro Pro Val Leu Asp
305             310             315             320

Ser Asp Gly Ser Phe Phe Leu Tyr Ser Asp Leu Thr Val Asp Lys Ser
            325             330             335

Arg Trp Gln Gln Gly Asn Val Phe Ser Cys Ser Val Met His Glu Ala
            340             345             350

Leu His Asn His Tyr Thr Gln Lys Ser Leu Ser Leu Ser Pro Gly
            355             360             365

<210> SEQ ID NO 44
<211> LENGTH: 1101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atggatgcaa tgaagagagg gctctgctgt gtgctgctgc tgtgtggagc agtcttcgtt    60
tcgcccggcg cctctgggcg tgggaggct gagacacggg agtgcatcta ctacaacgcc    120
aactgggagc tggagcgcac caaccagagc ggcctggagc gctgcgaagg cgagcaggac    180
aagcggctgc actgctacgc ctcctggcgc aacagtctg gcaccatcga gctcgtgaag    240
aagggctgct gggaagatga cttcaactgc tacgataggc aggagtgtgt ggccactgag    300

-continued

```
gagaacccccc aggtgtactt ctgctgctgt gaaggcaact tctgcaacga gcgcttcact    360
catttgccag aggctggggg cccggaagtc acgtacgagc caccccgac agcccccacc     420
ggtggtggaa ctcacacatg cccaccgtgc ccagcacctg aactcctggg gggaccgtca    480
gtcttcctct ccccccaaa acccaaggac accctcatga tctcccggac ccctgaggtc     540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacgaca ccacgcctcc cgtgctggac    960
tccgacggct ccttcttcct ctatagcgac ctcaccgtgg acaagagcag gtggcagcag   1020
gggaacgtct tctcatgctc cgtgatgcat gaggctctgc acaaccacta cacgcagaag   1080
agcctctccc tgtctccggg t                                             1101
```

<210> SEQ ID NO 45
<211> LENGTH: 342
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Glu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
```

```
                   210                 215                 220
Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Met Thr Lys
                245                 250                 255

Asn Gln Val Ser Leu Thr Cys Leu Val Lys Gly Phe Tyr Pro Ser Asp
                260                 265                 270

Ile Ala Val Glu Trp Glu Ser Asn Gly Gln Pro Glu Asn Asn Tyr Asp
                275                 280                 285

Thr Thr Pro Pro Val Leu Asp Ser Asp Gly Ser Phe Phe Leu Tyr Ser
                290                 295                 300

Asp Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly
                340

<210> SEQ ID NO 46
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
                180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
        210                 215                 220
```

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
            245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 47
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct ggctagatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc accccccgac agcccccacc     420
ggtggtggaa ctcacacatg cccaccgtgc ccagcacctg aactcctggg gggaccgtca     480
gtcttcctct tccccccaaa acccaaggac accctcatga tctcccggac ccctgaggtc     540
acatgcgtgg tggtggacgt gagccacgaa gaccctgagg tcaagttcaa ctggtacgtg     600
gacggcgtgg aggtgcataa tgccaagaca aagccgcggg aggagcagta caacagcacg     660
taccgtgtgg tcagcgtcct caccgtcctg caccaggact ggctgaatgg caaggagtac     720
aagtgcaagg tctccaacaa agccctccca gcccccatcg agaaaaccat ctccaaagcc     780
aaagggcagc cccgagaacc acaggtgtac accctgcccc catcccggaa ggagatgacc     840
aagaaccagg tcagcctgac ctgcctggtc aaaggcttct atcccagcga catcgccgtg     900
gagtgggaga gcaatgggca gccggagaac aactacaaga ccacgcctcc cgtgctgaag     960
tccgacggct ccttcttcct ctatagcaag ctcaccgtgg acaagagcag gtggcagcag    1020
gggaacgtct tctcatgctc cgtgatgcat gaggctctgc acaaccacta cacgcagaag    1080
agcctctccc tgtctccggg taaa                                          1104

<210> SEQ ID NO 48
<211> LENGTH: 343

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Lys Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 49
<211> LENGTH: 367
<212> TYPE: PRT
<213> ORGANISM: Artificial Sequence
```

<220> FEATURE:
<223> OTHER INFORMATION: Description of Artificial Sequence: Synthetic
    polypeptide

<400> SEQUENCE: 49

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Glu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Cys Arg Glu Glu Met Thr Lys Asn Gln Val Ser Leu Trp Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly
        355                 360                 365

<210> SEQ ID NO 50
<211> LENGTH: 342
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 50

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Glu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly
            340

<210> SEQ ID NO 51
<211> LENGTH: 368
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 51

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Cys Thr Leu
            260                 265                 270

Pro Pro Ser Arg Glu Glu Met Thr Lys Asn Gln Val Ser Leu Ser Cys
        275                 280                 285

Ala Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Val Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365
```

<210> SEQ ID NO 52
<211> LENGTH: 343
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 52

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Cys Thr Leu Pro Pro Ser Arg Glu Glu Met Thr Lys
                245                 250                 255

Asn Gln Val Ser Leu Ser Cys Ala Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Val Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 53

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr
            100                 105

<210> SEQ ID NO 54

<400> SEQUENCE: 54

000

<210> SEQ ID NO 55

<400> SEQUENCE: 55

000

<210> SEQ ID NO 56
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

```
Thr Pro Glu Val Thr Cys Val Val Asp Val Ser His Glu Asp Pro
            165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Asp Thr Thr Pro Pro Val Leu Asp
            290                 295                 300

Ser Asp Gly Ser Phe Phe Leu Tyr Ser Asp Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 57
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
            35                  40                  45

Gly Asn Leu His Arg Glu Leu Cys Arg Gly Arg Pro Thr Glu Phe Val
50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
            115                 120                 125

Lys Asp Thr Leu Met Ile Ser Arg Thr Pro Glu Val Thr Cys Val Val
            130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
```

```
                165                 170                 175
Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Asp Thr Thr Pro Pro Val Leu Asp Ser Asp Gly Ser Phe Phe Leu Tyr
        275                 280                 285

Ser Asp Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly
                325

<210> SEQ ID NO 58

<400> SEQUENCE: 58

000

<210> SEQ ID NO 59

<400> SEQUENCE: 59

000

<210> SEQ ID NO 60
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
```

```
            115                 120                 125
His Thr Cys Pro Pro Cys Pro Ala Pro Glu Leu Leu Gly Pro Ser
        130                 135                 140

Val Phe Leu Phe Pro Lys Pro Lys Asp Thr Leu Met Ile Ser Arg
145                 150                 155                 160

Thr Pro Glu Val Thr Cys Val Val Val Asp Val Ser His Glu Asp Pro
                    165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Arg Glu Glu Met Thr Lys Asn Gln Val Ser Leu Ser Cys
            260                 265                 270

Ala Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Val Leu Asp
        290                 295                 300

Ser Asp Gly Ser Phe Phe Leu Val Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 61
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
                20                  25                  30

Val Leu Val Arg Glu Glu Gly Arg His Pro Gln Glu His Arg Gly Cys
            35                  40                  45

Gly Asn Leu His Arg Glu Leu Cys Arg Gly Arg Pro Thr Glu Phe Val
        50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125
```

-continued

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Cys Thr Leu Pro Pro Ser Arg Glu Glu Met Thr
225                 230                 235                 240

Lys Asn Gln Val Ser Leu Ser Cys Ala Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Val
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 62

<400> SEQUENCE: 62

000

<210> SEQ ID NO 63

<400> SEQUENCE: 63

000

<210> SEQ ID NO 64
<211> LENGTH: 509
<212> TYPE: PRT
<213> ORGANISM: Homo sapiens

<400> SEQUENCE: 64

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

```
Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
        500                 505
```

```
<210> SEQ ID NO 65
<211> LENGTH: 103
<212> TYPE: PRT
<213> ORGANISM: Homo sapiens

<400> SEQUENCE: 65

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu
            100

<210> SEQ ID NO 66
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
        35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
```

```
                210                 215                 220
Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Met Thr Lys Asn Gln Val
                260                 265                 270

Ser Leu Thr Cys Leu Val Lys Gly Phe Tyr Pro Ser Asp Ile Ala Val
                275                 280                 285

Glu Trp Glu Ser Asn Gly Gln Pro Glu Asn Asn Tyr Asp Thr Thr Pro
290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly
        355

<210> SEQ ID NO 67
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
                20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
        50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205
```

```
Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Val Leu Asp Ser Asp Gly Ser
        275                 280                 285

Phe Phe Leu Tyr Ser Asp Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330
```

<210> SEQ ID NO 68

<400> SEQUENCE: 68

000

<210> SEQ ID NO 69

<400> SEQUENCE: 69

000

<210> SEQ ID NO 70
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
                20                  25                  30

Asn Pro Lys Leu Tyr Met Cys Val Cys Glu Gly Leu Ser Cys Gly Asn
            35                  40                  45

Glu Asp His Cys Glu Gly Gln Gln Cys Phe Ser Ser Leu Ser Ile Asn
50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160
```

```
Met Ile Ser Arg Thr Pro Glu Val Thr Cys Val Val Asp Val Ser
            165                 170                 175

His Glu Asp Pro Glu Val Lys Phe Asn Trp Tyr Val Asp Gly Val Glu
        180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 71
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160
```

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 72

<400> SEQUENCE: 72

000

<210> SEQ ID NO 73

<400> SEQUENCE: 73

000

<210> SEQ ID NO 74
<211> LENGTH: 532
<212> TYPE: PRT
<213> ORGANISM: Homo sapiens

<400> SEQUENCE: 74

Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

```
Leu Cys Asn Gln Tyr Leu Gln Pro Thr Leu Pro Pro Val Ile Gly
        130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                    165                 170                 175

Lys His Tyr Cys Lys Ser Ile Ser Ser Arg Arg Tyr Asn Arg Asp
                180                 185                 190

Leu Glu Gln Asp Glu Ala Phe Ile Pro Val Gly Glu Ser Leu Lys Asp
            195                 200                 205

Leu Ile Asp Gln Ser Gln Ser Ser Gly Ser Gly Ser Gly Leu Pro Leu
        210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                    245                 250                 255

Lys Val Ala Val Lys Val Phe Phe Thr Thr Glu Glu Ala Ser Trp Phe
                260                 265                 270

Arg Glu Thr Glu Ile Tyr Gln Thr Val Leu Met Arg His Glu Asn Ile
            275                 280                 285

Leu Gly Phe Ile Ala Ala Asp Ile Lys Gly Thr Gly Ser Trp Thr Gln
        290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                    325                 330                 335

Ser Ala Ala Cys Gly Leu Cys His Leu His Thr Glu Ile Tyr Gly Thr
                340                 345                 350

Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
        370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                    405                 410                 415

Leu Asn Lys Asn His Phe Gln Pro Tyr Ile Met Ala Asp Ile Tyr Ser
                420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
        450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                    485                 490                 495

Leu Lys Leu Met Ser Glu Cys Trp Ala His Asn Pro Ala Ser Arg Leu
                500                 505                 510

Thr Ala Leu Arg Ile Lys Lys Thr Leu Ala Lys Met Val Glu Ser Gln
            515                 520                 525

Asp Val Lys Ile
            530
```

<210> SEQ ID NO 75
<211> LENGTH: 129
<212> TYPE: PRT
<213> ORGANISM: Homo sapiens

<400> SEQUENCE: 75

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
        35                  40                  45

Ile Asn Asn Thr Cys Ile Thr Asn Gly His Cys Phe Ala Ile Ile Glu
50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg

<210> SEQ ID NO 76
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro

```
            180                 185                 190
Glu Val Thr Cys Val Val Asp Val Ser His Glu Asp Pro Glu Val
                195                 200                 205

Lys Phe Asn Trp Tyr Val Asp Gly Val Glu Val His Asn Ala Lys Thr
210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Tyr Thr Leu Pro Pro
                275                 280                 285

Ser Arg Glu Glu Met Thr Lys Asn Gln Val Ser Leu Thr Cys Leu Val
                290                 295                 300

Lys Gly Phe Tyr Pro Ser Asp Ile Ala Val Glu Trp Glu Ser Asn Gly
305                 310                 315                 320

Gln Pro Glu Asn Asn Tyr Asp Thr Thr Pro Pro Val Leu Asp Ser Asp
                325                 330                 335

Gly Ser Phe Phe Leu Tyr Ser Asp Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly
                370                 375                 380

<210> SEQ ID NO 77
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
                20                  25                  30

Asp Thr Leu Pro Phe Leu Lys Cys Tyr Cys Ser Gly His Cys Pro Asp
                35                  40                  45

Asp Ala Ile Asn Asn Thr Cys Ile Thr Asn Gly His Cys Phe Ala Ile
                50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
                100                 105                 110

Leu Gln Pro Thr Leu Pro Pro Val Val Ile Gly Pro Phe Phe Asp Gly
                115                 120                 125

Ser Ile Arg Thr Gly Gly Gly Thr His Thr Cys Pro Pro Cys Pro Ala
                130                 135                 140

Pro Glu Leu Leu Gly Gly Pro Ser Val Phe Leu Phe Pro Pro Lys Pro
145                 150                 155                 160
```

```
Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Asp Thr Thr Pro Pro Val Leu Asp Ser Asp Gly Ser Phe Phe Leu Tyr
305                 310                 315                 320

Ser Asp Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
        355

<210> SEQ ID NO 78

<400> SEQUENCE: 78

000

<210> SEQ ID NO 79

<400> SEQUENCE: 79

000

<210> SEQ ID NO 80
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
            20                  25                  30

Gly Thr Gly Met Lys Ser Asp Ser Asp Gln Lys Lys Ser Glu Asn Gly
        35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80
```

```
Gly His Cys Phe Ala Ile Ile Glu Glu Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Cys Thr Leu Pro Pro
        275                 280                 285

Ser Arg Glu Glu Met Thr Lys Asn Gln Val Ser Leu Ser Cys Ala Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Val Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 81
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60
```

Ile Glu Glu Asp Asp Gln Gly Glu Thr Thr Leu Ala Ser Gly Cys Met
 65                  70                  75                  80

Lys Tyr Glu Gly Ser Asp Phe Gln Cys Lys Asp Ser Pro Lys Ala Gln
             85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Cys Thr Leu Pro Pro Ser Arg Glu Glu Met Thr
            260                 265                 270

Lys Asn Gln Val Ser Leu Ser Cys Ala Val Lys Gly Phe Tyr Pro Ser
        275                 280                 285

Asp Ile Ala Val Glu Trp Glu Ser Asn Gly Gln Pro Glu Asn Asn Tyr
290                 295                 300

Lys Thr Thr Pro Pro Val Leu Asp Ser Asp Gly Ser Phe Phe Leu Val
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 82

<400> SEQUENCE: 82

000

<210> SEQ ID NO 83

<400> SEQUENCE: 83

000

<210> SEQ ID NO 84
<211> LENGTH: 505
<212> TYPE: PRT
<213> ORGANISM: Homo sapiens

<400> SEQUENCE: 84

```
Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20                  25                  30

Leu Cys Ala Cys Thr Ser Cys Leu Gln Ala Asn Tyr Thr Cys Glu Thr
            35                  40                  45

Asp Gly Ala Cys Met Val Ser Ile Phe Asn Leu Asp Gly Met Glu His
            50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
                100                 105                 110

Leu Lys Glu Pro Glu His Pro Ser Met Trp Gly Pro Val Glu Leu Val
            115                 120                 125

Gly Ile Ile Ala Gly Pro Val Phe Leu Leu Phe Leu Ile Ile Ile Ile
            130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
                180                 185                 190

Ser Gly Leu Pro Leu Phe Val Gln Arg Thr Val Ala Arg Thr Ile Val
            195                 200                 205

Leu Gln Glu Ile Ile Gly Lys Gly Arg Phe Gly Glu Val Trp Arg Gly
210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
                260                 265                 270

Gly Thr Trp Thr Gln Leu Trp Leu Val Ser Asp Tyr His Glu His Gly
                275                 280                 285

Ser Leu Phe Asp Tyr Leu Asn Arg Tyr Thr Val Thr Ile Glu Gly Met
            290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
            355                 360                 365

Ile Ala Pro Asn Gln Arg Val Gly Thr Lys Arg Tyr Met Ala Pro Glu
            370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415
```

Cys Asn Ser Gly Gly Val His Glu Glu Tyr Gln Leu Pro Tyr Tyr Asp
                420                 425                 430

Leu Val Pro Ser Asp Pro Ser Ile Glu Glu Met Arg Lys Val Val Cys
            435                 440                 445

Asp Gln Lys Leu Arg Pro Asn Ile Pro Asn Trp Trp Gln Ser Tyr Glu
        450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505

<210> SEQ ID NO 85
<211> LENGTH: 546
<212> TYPE: PRT
<213> ORGANISM: Homo sapiens

<400> SEQUENCE: 85

Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Ala Asp
            260                 265                 270

Cys Ser Phe Leu Thr Leu Pro Trp Glu Val Val Met Val Ser Ala Ala
        275                 280                 285

```
Pro Lys Leu Arg Ser Leu Arg Leu Gln Tyr Lys Gly Gly Arg Gly Arg
    290                 295                 300

Ala Arg Phe Leu Phe Pro Leu Asn Asn Gly Thr Trp Thr Gln Leu Trp
305                 310                 315                 320

Leu Val Ser Asp Tyr His Glu His Gly Ser Leu Phe Asp Tyr Leu Asn
                325                 330                 335

Arg Tyr Thr Val Thr Ile Glu Gly Met Ile Lys Leu Ala Leu Ser Ala
                340                 345                 350

Ala Ser Gly Leu Ala His Leu His Met Glu Ile Val Gly Thr Gln Gly
                355                 360                 365

Lys Pro Gly Ile Ala His Arg Asp Leu Lys Ser Lys Asn Ile Leu Val
    370                 375                 380

Lys Lys Asn Gly Met Cys Ala Ile Ala Asp Leu Gly Leu Ala Val Arg
385                 390                 395                 400

His Asp Ala Val Thr Asp Thr Ile Asp Ile Ala Pro Asn Gln Arg Val
                405                 410                 415

Gly Thr Lys Arg Tyr Met Ala Pro Glu Val Leu Asp Glu Thr Ile Asn
                420                 425                 430

Met Lys His Phe Asp Ser Phe Lys Cys Ala Asp Ile Tyr Ala Leu Gly
                435                 440                 445

Leu Val Tyr Trp Glu Ile Ala Arg Arg Cys Asn Ser Gly Gly Val His
    450                 455                 460

Glu Glu Tyr Gln Leu Pro Tyr Tyr Asp Leu Val Pro Ser Asp Pro Ser
465                 470                 475                 480

Ile Glu Glu Met Arg Lys Val Val Cys Asp Gln Lys Leu Arg Pro Asn
                485                 490                 495

Ile Pro Asn Trp Trp Gln Ser Tyr Glu Ala Leu Arg Val Met Gly Lys
                500                 505                 510

Met Met Arg Glu Cys Trp Tyr Ala Asn Gly Ala Ala Arg Leu Thr Ala
                515                 520                 525

Leu Arg Ile Lys Lys Thr Leu Ser Gln Leu Ser Val Gln Glu Asp Val
    530                 535                 540

Lys Ile
545

<210> SEQ ID NO 86
<211> LENGTH: 103
<212> TYPE: PRT
<213> ORGANISM: Homo sapiens

<400> SEQUENCE: 86

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
                20                  25                  30

Ile Phe Asn Leu Asp Gly Met Glu His His Val Arg Thr Cys Ile Pro
                35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
```

```
                100

<210> SEQ ID NO 87
<211> LENGTH: 103
<212> TYPE: PRT
<213> ORGANISM: Homo sapiens

<400> SEQUENCE: 87

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 88
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
```

```
            195                 200                 205
Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355

<210> SEQ ID NO 89
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Gly Thr Thr Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190
```

```
Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
        210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Asp Thr Thr Pro Pro Val Leu Asp Ser Asp Gly Ser
        275                 280                 285

Phe Phe Leu Tyr Ser Asp Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330

<210> SEQ ID NO 90

<400> SEQUENCE: 90

000

<210> SEQ ID NO 91

<400> SEQUENCE: 91

000

<210> SEQ ID NO 92
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
                20                  25                  30

Leu Leu Cys Ala Cys Thr Ser Cys Leu Gln Ala Asn Tyr Thr Cys Glu
            35                  40                  45

Thr Asp Gly Ala Cys Met Val Ser Ile Phe Asn Leu Asp Gly Met Glu
        50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
                100                 105                 110

His Leu Lys Glu Pro Glu His Pro Ser Met Trp Gly Pro Val Glu Thr
            115                 120                 125

Gly Gly Gly Thr His Thr Cys Pro Pro Cys Pro Ala Pro Glu Leu Leu
        130                 135                 140
```

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 93
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

```
Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 94

<400> SEQUENCE: 94

000

<210> SEQ ID NO 95

<400> SEQUENCE: 95

000

<210> SEQ ID NO 96
<211> LENGTH: 503
<212> TYPE: PRT
<213> ORGANISM: Homo sapiens

<400> SEQUENCE: 96

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110
```

Thr Thr Val Lys Ser Ser Pro Gly Leu Gly Pro Val Glu Leu Ala Ala
            115                 120                 125

Val Ile Ala Gly Pro Val Cys Phe Val Cys Ile Ser Leu Met Leu Met
        130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
                180                 185                 190

Leu Pro Leu Leu Val Gln Arg Thr Ile Ala Arg Thr Ile Val Leu Gln
                195                 200                 205

Glu Ser Ile Gly Lys Gly Arg Phe Gly Glu Val Trp Arg Gly Lys Trp
            210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
                340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
                500

<210> SEQ ID NO 97
<211> LENGTH: 507

<212> TYPE: PRT
<213> ORGANISM: Homo sapiens

<400> SEQUENCE: 97

```
Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
            115                 120                 125

Glu Leu Ala Ala Val Ile Ala Gly Pro Val Cys Phe Val Cys Ile Ser
130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
            195                 200                 205

Ile Val Leu Gln Glu Ser Ile Gly Lys Gly Arg Phe Gly Glu Val Trp
210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
            275                 280                 285

His Gly Ser Leu Phe Asp Tyr Leu Asn Arg Tyr Thr Val Thr Val Glu
290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
            355                 360                 365

Ile Asp Ile Ala Pro Asn His Arg Val Gly Thr Lys Arg Tyr Met Ala
370                 375                 380

Pro Glu Val Leu Asp Asp Ser Ile Asn Met Lys His Phe Glu Ser Phe
385                 390                 395                 400
```

```
Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
        435                 440                 445

Val Cys Glu Gln Lys Leu Arg Pro Asn Ile Pro Asn Arg Trp Gln Ser
    450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
                485                 490                 495

Ser Gln Leu Ser Gln Gln Glu Gly Ile Lys Met
            500                 505

<210> SEQ ID NO 98
<211> LENGTH: 102
<212> TYPE: PRT
<213> ORGANISM: Homo sapiens

<400> SEQUENCE: 98

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Leu
            100

<210> SEQ ID NO 99
<211> LENGTH: 106
<212> TYPE: PRT
<213> ORGANISM: Homo sapiens

<400> SEQUENCE: 99

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Gly Pro Phe Ser Val Lys
                85                  90                  95

Ser Ser Pro Gly Leu Gly Pro Val Glu Leu
            100                 105
```

<210> SEQ ID NO 100
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
            20                  25                  30

Leu Gln Cys Phe Cys His Leu Cys Thr Lys Asp Asn Phe Thr Cys Val
        35                  40                  45

Thr Asp Gly Leu Cys Phe Val Ser Val Thr Glu Thr Thr Asp Lys Val
    50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Asp Thr Thr Pro Pro Val Leu
    290                 295                 300

Asp Ser Asp Gly Ser Phe Phe Leu Tyr Ser Asp Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350
```

```
<210> SEQ ID NO 101
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
            20                  25                  30

Val Thr Glu Thr Thr Asp Lys Val Ile His Asn Ser Met Cys Ile Ala
        35                  40                  45

Glu Ile Asp Leu Ile Pro Arg Asp Arg Pro Phe Val Cys Ala Pro Ser
    50                  55                  60

Ser Lys Thr Gly Ser Val Thr Thr Tyr Cys Cys Asn Gln Asp His
65                  70                  75                  80

Cys Asn Lys Ile Glu Leu Pro Thr Thr Val Lys Ser Ser Pro Gly Leu
                85                  90                  95

Gly Pro Val Glu Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Asp Thr Thr Pro Pro Val Leu Asp Ser Asp Gly Ser Phe Phe Leu
        275                 280                 285

Tyr Ser Asp Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 102

<400> SEQUENCE: 102

000
```

<210> SEQ ID NO 103

<400> SEQUENCE: 103

000

<210> SEQ ID NO 104
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Asp Ala Met Lys Arg Gly Leu Cys Cys Val Leu Leu Cys Gly
1               5                   10                  15

Ala Val Phe Val Ser Pro Gly Ala Ala Leu Leu Pro Gly Ala Thr Ala
                20                  25                  30

Leu Gln Cys Phe Cys His Leu Cys Thr Lys Asp Asn Phe Thr Cys Val
                35                  40                  45

Thr Asp Gly Leu Cys Phe Val Ser Val Thr Glu Thr Thr Asp Lys Val
            50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
                100                 105                 110

Thr Val Lys Ser Ser Pro Gly Leu Gly Pro Val Glu Thr Gly Gly Gly
            115                 120                 125

Thr His Thr Cys Pro Pro Cys Pro Ala Pro Glu Leu Leu Gly Gly Pro
130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
            195                 200                 205

Val Ser Val Leu Thr Val Leu His Gln Asp Trp Leu Asn Gly Lys Glu
        210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Cys Thr
                245                 250                 255

Leu Pro Pro Ser Arg Glu Glu Met Thr Lys Asn Gln Val Ser Leu Ser
            260                 265                 270

Cys Ala Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Val Ser Lys Leu Thr Val Asp Lys
305                 310                 315                 320
```

```
Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 105
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
            20                  25                  30

Val Thr Glu Thr Thr Asp Lys Val Ile His Asn Ser Met Cys Ile Ala
        35                  40                  45

Glu Ile Asp Leu Ile Pro Arg Asp Arg Pro Phe Val Cys Ala Pro Ser
50                  55                  60

Ser Lys Thr Gly Ser Val Thr Thr Thr Tyr Cys Cys Asn Gln Asp His
65                  70                  75                  80

Cys Asn Lys Ile Glu Leu Pro Thr Thr Val Lys Ser Ser Pro Gly Leu
                85                  90                  95

Gly Pro Val Glu Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Cys Thr Leu Pro Pro Ser Arg Glu Glu Met
225                 230                 235                 240

Thr Lys Asn Gln Val Ser Leu Ser Cys Ala Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Val Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320
```

Lys Ser Leu Ser Leu Ser Pro Gly Lys
            325

<210> SEQ ID NO 106

<400> SEQUENCE: 106

000

<210> SEQ ID NO 107

<400> SEQUENCE: 107

000

<210> SEQ ID NO 108
<211> LENGTH: 502
<212> TYPE: PRT
<213> ORGANISM: Homo sapiens

<400> SEQUENCE: 108

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Ser Gly Leu
    50                  55                  60

Pro Val Val Thr Ser Gly Cys Leu Gly Leu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

```
Asp Tyr Leu Lys Ser Thr Thr Leu Asp Ala Lys Ser Met Leu Lys Leu
290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
                340                 345                 350

Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 109
<211> LENGTH: 113
<212> TYPE: PRT
<213> ORGANISM: Homo sapiens

<400> SEQUENCE: 109

Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
                20                  25                  30

Ile Cys Ser Thr Asp Gly Tyr Cys Phe Thr Met Ile Glu Glu Asp Asp
                35                  40                  45

Ser Gly Leu Pro Val Val Thr Ser Gly Cys Leu Gly Leu Glu Gly Ser
50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
                100                 105                 110

Arg

<210> SEQ ID NO 110
<211> LENGTH: 532
<212> TYPE: PRT
<213> ORGANISM: Homo sapiens
```

<400> SEQUENCE: 110

```
Met Gly Trp Leu Glu Glu Leu Asn Trp Gln Leu His Ile Phe Leu Leu
1               5                   10                  15

Ile Leu Leu Ser Met His Thr Arg Ala Asn Phe Leu Asp Asn Met Leu
            20                  25                  30

Leu Arg Ser Ala Gly Lys Leu Asn Val Gly Thr Lys Lys Glu Asp Gly
        35                  40                  45

Glu Ser Thr Ala Pro Thr Pro Arg Pro Lys Val Leu Arg Cys Lys Cys
    50                  55                  60

His His His Cys Pro Glu Asp Ser Val Asn Asn Ile Cys Ser Thr Asp
65                  70                  75                  80

Gly Tyr Cys Phe Thr Met Ile Glu Glu Asp Asp Ser Gly Leu Pro Val
                85                  90                  95

Val Thr Ser Gly Cys Leu Gly Leu Glu Gly Ser Asp Phe Gln Cys Arg
            100                 105                 110

Asp Thr Pro Ile Pro His Gln Arg Arg Ser Ile Glu Cys Cys Thr Glu
        115                 120                 125

Arg Asn Glu Cys Asn Lys Asp Leu His Pro Thr Leu Pro Pro Leu Lys
    130                 135                 140

Asn Arg Asp Phe Val Asp Gly Pro Ile His His Arg Ala Leu Leu Ile
145                 150                 155                 160

Ser Val Thr Val Cys Ser Leu Leu Leu Val Leu Ile Ile Leu Phe Cys
                165                 170                 175

Tyr Phe Arg Tyr Lys Arg Gln Glu Thr Arg Pro Arg Tyr Ser Ile Gly
            180                 185                 190

Leu Glu Gln Asp Glu Thr Tyr Ile Pro Pro Gly Glu Ser Leu Arg Asp
        195                 200                 205

Leu Ile Glu Gln Ser Gln Ser Ser Gly Ser Gly Ser Gly Leu Pro Leu
    210                 215                 220

Leu Val Gln Arg Thr Ile Ala Lys Gln Ile Gln Met Val Lys Gln Ile
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
    290                 295                 300

Leu Tyr Leu Ile Thr Asp Tyr His Glu Asn Gly Ser Leu Tyr Asp Tyr
305                 310                 315                 320

Leu Lys Ser Thr Thr Leu Asp Ala Lys Ser Met Leu Lys Leu Ala Tyr
                325                 330                 335

Ser Ser Val Ser Gly Leu Cys His Leu His Thr Glu Ile Phe Ser Thr
            340                 345                 350

Gln Gly Lys Pro Ala Ile Ala His Arg Asp Leu Lys Ser Lys Asn Ile
        355                 360                 365

Leu Val Lys Lys Asn Gly Thr Cys Cys Ile Ala Asp Leu Gly Leu Ala
    370                 375                 380

Val Lys Phe Ile Ser Asp Thr Asn Glu Val Asp Ile Pro Pro Asn Thr
385                 390                 395                 400

Arg Val Gly Thr Lys Arg Tyr Met Pro Pro Glu Val Leu Asp Glu Ser
                405                 410                 415
```

```
Leu Asn Arg Asn His Phe Gln Ser Tyr Ile Met Ala Asp Met Tyr Ser
            420                 425                 430

Phe Gly Leu Ile Leu Trp Glu Val Ala Arg Arg Cys Val Ser Gly Gly
        435                 440                 445

Ile Val Glu Glu Tyr Gln Leu Pro Tyr His Asp Leu Val Pro Ser Asp
    450                 455                 460

Pro Ser Tyr Glu Asp Met Arg Glu Ile Val Cys Ile Lys Lys Leu Arg
465                 470                 475                 480

Pro Ser Phe Pro Asn Arg Trp Ser Ser Asp Glu Cys Leu Arg Gln Met
                485                 490                 495

Gly Lys Leu Met Thr Glu Cys Trp Ala His Asn Pro Ala Ser Arg Leu
            500                 505                 510

Thr Ala Leu Arg Val Lys Lys Thr Leu Ala Lys Met Ser Glu Ser Gln
        515                 520                 525

Asp Ile Lys Leu
    530

<210> SEQ ID NO 111
<211> LENGTH: 131
<212> TYPE: PRT
<213> ORGANISM: Homo sapiens

<400> SEQUENCE: 111

Asn Phe Leu Asp Asn Met Leu Leu Arg Ser Ala Gly Lys Leu Asn Val
1               5                   10                  15

Gly Thr Lys Lys Glu Asp Gly Glu Ser Thr Ala Pro Thr Pro Arg Pro
            20                  25                  30

Lys Val Leu Arg Cys Lys Cys His His His Cys Pro Glu Asp Ser Val
        35                  40                  45

Asn Asn Ile Cys Ser Thr Asp Gly Tyr Cys Phe Thr Met Ile Glu Glu
    50                  55                  60

Asp Asp Ser Gly Leu Pro Val Val Thr Ser Gly Cys Leu Gly Leu Glu
65                  70                  75                  80

Gly Ser Asp Phe Gln Cys Arg Asp Thr Pro Ile Pro His Gln Arg Arg
                85                  90                  95

Ser Ile Glu Cys Cys Thr Glu Arg Asn Glu Cys Asn Lys Asp Leu His
            100                 105                 110

Pro Thr Leu Pro Pro Leu Lys Asn Arg Asp Phe Val Asp Gly Pro Ile
        115                 120                 125

His His Arg
    130

<210> SEQ ID NO 112
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45
```

```
Cys Pro Glu Asp Ser Val Asn Asn Ile Cys Ser Thr Asp Gly Tyr Cys
         50                  55                  60

Phe Thr Met Ile Glu Glu Asp Asp Ser Gly Leu Pro Val Val Thr Ser
 65                  70                  75                  80

Gly Cys Leu Gly Leu Glu Gly Ser Asp Phe Gln Cys Arg Asp Thr Pro
                 85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
                180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
                260                 265                 270

Ser Arg Glu Glu Met Thr Lys Asn Gln Val Ser Leu Thr Cys Leu Val
            275                 280                 285

Lys Gly Phe Tyr Pro Ser Asp Ile Ala Val Glu Trp Glu Ser Asn Gly
        290                 295                 300

Gln Pro Glu Asn Asn Tyr Asp Thr Thr Pro Pro Val Leu Asp Ser Asp
305                 310                 315                 320

Gly Ser Phe Phe Leu Tyr Ser Asp Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
            355                 360                 365

<210> SEQ ID NO 113
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Lys Lys Glu Asp Gly Glu Ser Thr Ala Pro Thr Pro Arg Pro Lys Val
  1               5                  10                  15

Leu Arg Cys Lys Cys His His His Cys Pro Glu Asp Ser Val Asn Asn
                 20                  25                  30

Ile Cys Ser Thr Asp Gly Tyr Cys Phe Thr Met Ile Glu Glu Asp Asp
```

```
                35                  40                  45
Ser Gly Leu Pro Val Val Thr Ser Gly Cys Leu Gly Leu Glu Gly Ser
 50                  55                  60

Asp Phe Gln Cys Arg Asp Thr Pro Ile Pro His Gln Arg Arg Ser Ile
 65                  70                  75                  80

Glu Cys Cys Thr Glu Arg Asn Glu Cys Asn Lys Asp Leu His Pro Thr
                 85                  90                  95

Leu Pro Pro Leu Lys Asn Arg Asp Phe Val Asp Gly Pro Ile His His
                100                 105                 110

Arg Thr Gly Gly Gly Thr His Thr Cys Pro Pro Cys Pro Ala Pro Glu
                115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
                180                 185                 190

Ser Thr Tyr Arg Val Val Ser Val Leu Thr Val Leu His Gln Asp Trp
                195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
                260                 265                 270

Ala Val Glu Trp Glu Ser Asn Gly Gln Pro Glu Asn Asn Tyr Asp Thr
                275                 280                 285

Thr Pro Pro Val Leu Asp Ser Asp Gly Ser Phe Phe Leu Tyr Ser Asp
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
                340

<210> SEQ ID NO 114

<400> SEQUENCE: 114

000

<210> SEQ ID NO 115

<400> SEQUENCE: 115

000

<210> SEQ ID NO 116
<211> LENGTH: 366
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 116

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Asp Ser Gly Leu Pro Val Val Thr Ser
65                  70                  75                  80

Gly Cys Leu Gly Leu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Cys Thr Leu Pro Pro
            260                 265                 270

Ser Arg Glu Glu Met Thr Lys Asn Gln Val Ser Leu Ser Cys Ala Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Val Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 117
<211> LENGTH: 342
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 117

Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
            20                  25                  30

Ile Cys Ser Thr Asp Gly Tyr Cys Phe Thr Met Ile Glu Glu Asp Asp
        35                  40                  45

Ser Gly Leu Pro Val Val Thr Ser Gly Cys Leu Gly Leu Glu Gly Ser
    50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Cys Thr Leu Pro Pro Ser Arg Glu Glu Met Thr Lys Asn
                245                 250                 255

Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 118

<400> SEQUENCE: 118

000
```

<210> SEQ ID NO 119

<400> SEQUENCE: 119

000

<210> SEQ ID NO 120
<211> LENGTH: 493
<212> TYPE: PRT
<213> ORGANISM: Homo sapiens

<400> SEQUENCE: 120

```
Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
                20                  25                  30

Cys Asp Ser Ser Asn Phe Thr Cys Gln Thr Glu Gly Ala Cys Trp Ala
            35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
    115                 120                 125

Ala Met Leu Thr Val Trp Ala Cys Gln Gly Arg Gln Cys Ser Tyr Arg
130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
            180                 185                 190

Arg Thr Ile Val Leu Gln Glu Ile Val Gly Lys Gly Arg Phe Gly Glu
    195                 200                 205

Val Trp His Gly Arg Trp Cys Gly Glu Asp Val Ala Val Lys Ile Phe
210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
            260                 265                 270

His Glu Gln Gly Ser Leu Tyr Asp Tyr Leu Asn Arg Asn Ile Val Thr
    275                 280                 285

Val Ala Gly Met Ile Lys Leu Ala Leu Ser Ile Ala Ser Gly Leu Ala
290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
```

```
                340                 345                 350
Asn Thr Ile Asp Ile Pro Gln Asn Pro Lys Val Gly Thr Lys Arg Tyr
            355                 360                 365

Met Ala Pro Glu Met Leu Asp Asp Thr Met Asn Val Asn Ile Phe Glu
        370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
            420                 425                 430

Lys Val Val Cys Asp Gln Lys Phe Arg Pro Ser Ile Pro Asn Gln Trp
        435                 440                 445

Gln Ser Cys Glu Ala Leu Arg Val Met Gly Arg Ile Met Arg Glu Cys
    450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490

<210> SEQ ID NO 121
<211> LENGTH: 413
<212> TYPE: PRT
<213> ORGANISM: Homo sapiens

<400> SEQUENCE: 121

Met Thr Arg Ala Leu Cys Ser Ala Leu Arg Gln Ala Leu Leu Leu Leu
1               5                   10                  15

Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
            100                 105                 110

Arg Thr Ile Val Leu Gln Glu Ile Val Gly Lys Gly Arg Phe Gly Glu
        115                 120                 125

Val Trp His Gly Arg Trp Cys Gly Glu Asp Val Ala Val Lys Ile Phe
    130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175

Asn Lys Asp Asn Gly Thr Trp Thr Gln Leu Trp Leu Val Ser Glu Tyr
            180                 185                 190

His Glu Gln Gly Ser Leu Tyr Asp Tyr Leu Asn Arg Asn Ile Val Thr
        195                 200                 205

Val Ala Gly Met Ile Lys Leu Ala Leu Ser Ile Ala Ser Gly Leu Ala
    210                 215                 220
```

His Leu His Met Glu Ile Val Gly Thr Gln Gly Lys Pro Ala Ile Ala
225                 230                 235                 240

His Arg Asp Ile Lys Ser Lys Asn Ile Leu Val Lys Lys Cys Glu Thr
            245                 250                 255

Cys Ala Ile Ala Asp Leu Gly Leu Ala Val Lys His Asp Ser Ile Leu
        260                 265                 270

Asn Thr Ile Asp Ile Pro Gln Asn Pro Lys Val Gly Thr Lys Arg Tyr
    275                 280                 285

Met Ala Pro Glu Met Leu Asp Asp Thr Met Asn Val Asn Ile Phe Glu
290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335

Pro Tyr Tyr Asp Met Val Pro Ser Asp Pro Ser Ile Glu Glu Met Arg
            340                 345                 350

Lys Val Val Cys Asp Gln Lys Phe Arg Pro Ser Ile Pro Asn Gln Trp
        355                 360                 365

Gln Ser Cys Glu Ala Leu Arg Val Met Gly Arg Ile Met Arg Glu Cys
    370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
                405                 410

<210> SEQ ID NO 122
<211> LENGTH: 336
<212> TYPE: PRT
<213> ORGANISM: Homo sapiens

<400> SEQUENCE: 122

Met Thr Arg Ala Leu Cys Ser Ala Leu Arg Gln Ala Leu Leu Leu Leu
1               5                   10                  15

Ala Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Asp Asn Gly Thr Trp Thr Gln Leu Trp Leu Val
            100                 105                 110

Ser Glu Tyr His Glu Gln Gly Ser Leu Tyr Asp Tyr Leu Asn Arg Asn
        115                 120                 125

Ile Val Thr Val Ala Gly Met Ile Lys Leu Ala Leu Ser Ile Ala Ser
    130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
                165                 170                 175

Cys Glu Thr Cys Ala Ile Ala Asp Leu Gly Leu Ala Val Lys His Asp
            180                 185                 190

Ser Ile Leu Asn Thr Ile Asp Ile Pro Gln Asn Pro Lys Val Gly Thr
        195                 200                 205

Lys Arg Tyr Met Ala Pro Glu Met Leu Asp Asp Thr Met Asn Val Asn
        210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Gly Ile Val Glu Glu
                245                 250                 255

Tyr Gln Leu Pro Tyr Tyr Asp Met Val Pro Ser Asp Pro Ser Ile Glu
            260                 265                 270

Glu Met Arg Lys Val Val Cys Asp Gln Lys Phe Arg Pro Ser Ile Pro
        275                 280                 285

Asn Gln Trp Gln Ser Cys Glu Ala Leu Arg Val Met Gly Arg Ile Met
        290                 295                 300

Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335

<210> SEQ ID NO 123
<211> LENGTH: 93
<212> TYPE: PRT
<213> ORGANISM: Homo sapiens

<400> SEQUENCE: 123

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Ala Ser Pro Asn Ala Pro Lys Leu Gly Pro Met Glu
                85                  90

<210> SEQ ID NO 124
<211> LENGTH: 443
<212> TYPE: PRT
<213> ORGANISM: Homo sapiens

<400> SEQUENCE: 124

Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu Leu
    50                  55                  60

Ala Ile Ile Ile Thr Val Pro Val Cys Leu Leu Ser Ile Ala Ala Met
65                  70                  75                  80

Leu Thr Val Trp Ala Cys Gln Gly Arg Gln Cys Ser Tyr Arg Lys Lys
                85                  90                  95

```
Lys Arg Pro Asn Val Glu Pro Leu Ser Glu Cys Asn Leu Val Asn
                100                 105                 110

Ala Gly Lys Thr Leu Lys Asp Leu Ile Tyr Asp Val Thr Ala Ser Gly
            115                 120                 125

Ser Gly Ser Gly Leu Pro Leu Leu Val Gln Arg Thr Ile Ala Arg Thr
130                 135                 140

Ile Val Leu Gln Glu Ile Val Gly Lys Gly Arg Phe Gly Glu Val Trp
145                 150                 155                 160

His Gly Arg Trp Cys Gly Glu Asp Val Ala Val Lys Ile Phe Ser Ser
                165                 170                 175

Arg Asp Glu Arg Ser Trp Phe Arg Glu Ala Ile Tyr Gln Thr Val
            180                 185                 190

Met Leu Arg His Glu Asn Ile Leu Gly Phe Ile Ala Ala Asp Asn Lys
        195                 200                 205

Asp Asn Gly Thr Trp Thr Gln Leu Trp Leu Val Ser Glu Tyr His Glu
    210                 215                 220

Gln Gly Ser Leu Tyr Asp Tyr Leu Asn Arg Asn Ile Val Thr Val Ala
225                 230                 235                 240

Gly Met Ile Lys Leu Ala Leu Ser Ile Ala Ser Gly Leu Ala His Leu
                245                 250                 255

His Met Glu Ile Val Gly Thr Gln Gly Lys Pro Ala Ile Ala His Arg
            260                 265                 270

Asp Ile Lys Ser Lys Asn Ile Leu Val Lys Lys Cys Glu Thr Cys Ala
        275                 280                 285

Ile Ala Asp Leu Gly Leu Ala Val Lys His Asp Ser Ile Leu Asn Thr
    290                 295                 300

Ile Asp Ile Pro Gln Asn Pro Lys Val Gly Thr Lys Arg Tyr Met Ala
305                 310                 315                 320

Pro Glu Met Leu Asp Asp Thr Met Asn Val Asn Ile Phe Glu Ser Phe
                325                 330                 335

Lys Arg Ala Asp Ile Tyr Ser Val Gly Leu Val Tyr Trp Glu Ile Ala
            340                 345                 350

Arg Arg Cys Ser Val Gly Gly Ile Val Glu Glu Tyr Gln Leu Pro Tyr
        355                 360                 365

Tyr Asp Met Val Pro Ser Asp Pro Ser Ile Glu Glu Met Arg Lys Val
    370                 375                 380

Val Cys Asp Gln Lys Phe Arg Pro Ser Ile Pro Asn Gln Trp Gln Ser
385                 390                 395                 400

Cys Glu Ala Leu Arg Val Met Gly Arg Ile Met Arg Glu Cys Trp Tyr
                405                 410                 415

Ala Asn Gly Ala Ala Arg Leu Thr Ala Leu Arg Ile Lys Lys Thr Ile
            420                 425                 430

Ser Gln Leu Cys Val Lys Glu Asp Cys Lys Ala
        435                 440

<210> SEQ ID NO 125
<211> LENGTH: 63
<212> TYPE: PRT
<213> ORGANISM: Homo sapiens

<400> SEQUENCE: 125

Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
```

```
            20                  25                  30
Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu
    50                  55                  60

<210> SEQ ID NO 126
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Gly Leu Pro Leu Leu Val Gln Arg Thr Ile Ala Arg Thr Ile Val
                85                  90                  95

Leu Gln Glu Ile Val Gly Lys Gly Arg Phe Gly Glu Val Trp His Gly
            100                 105                 110

Arg Trp Cys Gly Glu Asp Val Ala Val Lys Ile Phe Ser Ser Arg Asp
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Glu Tyr His Glu Gln Gly
                165                 170                 175

Ser Leu Tyr Asp Tyr Leu Asn Arg Asn Ile Val Thr Val Ala Gly Met
            180                 185                 190

Ile Lys Leu Ala Leu Ser Ile Ala Ser Gly Leu Ala His Leu His Met
        195                 200                 205

Glu Ile Val Gly Thr Gln Gly Lys Pro Ala Ile Ala His Arg Asp Ile
    210                 215                 220

Lys Ser Lys Asn Ile Leu Val Lys Lys Cys Glu Thr Cys Ala Ile Ala
225                 230                 235                 240

Asp Leu Gly Leu Ala Val Lys His Asp Ser Ile Leu Asn Thr Ile Asp
                245                 250                 255

Ile Pro Gln Asn Pro Lys Val Gly Thr Lys Arg Tyr Met Ala Pro Glu
            260                 265                 270

Met Leu Asp Asp Thr Met Asn Val Asn Ile Phe Glu Ser Phe Lys Arg
        275                 280                 285

Ala Asp Ile Tyr Ser Val Gly Leu Val Tyr Trp Glu Ile Ala Arg Arg
    290                 295                 300

Cys Ser Val Gly Gly Ile Val Glu Glu Tyr Gln Leu Pro Tyr Tyr Asp
305                 310                 315                 320
```

```
Met Val Pro Ser Asp Pro Ser Ile Glu Glu Met Arg Lys Val Val Cys
                325                 330                 335

Asp Gln Lys Phe Arg Pro Ser Ile Pro Asn Gln Trp Gln Ser Cys Glu
            340                 345                 350

Ala Leu Arg Val Met Gly Arg Ile Met Arg Glu Cys Trp Tyr Ala Asn
        355                 360                 365

Gly Ala Ala Arg Leu Thr Ala Leu Arg Ile Lys Lys Thr Ile Ser Gln
370                 375                 380

Leu Cys Val Lys Glu Asp Cys Lys Ala
385                 390

<210> SEQ ID NO 127
<211> LENGTH: 316
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Asp Asn Gly Thr Trp Thr Gln Leu Trp Leu Val Ser Glu Tyr His
                85                  90                  95

Glu Gln Gly Ser Leu Tyr Asp Tyr Leu Asn Arg Asn Ile Val Thr Val
            100                 105                 110

Ala Gly Met Ile Lys Leu Ala Leu Ser Ile Ala Ser Gly Leu Ala His
        115                 120                 125

Leu His Met Glu Ile Val Gly Thr Gln Gly Lys Pro Ala Ile Ala His
    130                 135                 140

Arg Asp Ile Lys Ser Lys Asn Ile Leu Val Lys Lys Cys Glu Thr Cys
145                 150                 155                 160

Ala Ile Ala Asp Leu Gly Leu Ala Val Lys His Asp Ser Ile Leu Asn
                165                 170                 175

Thr Ile Asp Ile Pro Gln Asn Pro Lys Val Gly Thr Lys Arg Tyr Met
            180                 185                 190

Ala Pro Glu Met Leu Asp Asp Thr Met Asn Val Asn Ile Phe Glu Ser
        195                 200                 205

Phe Lys Arg Ala Asp Ile Tyr Ser Val Gly Leu Val Tyr Trp Glu Ile
    210                 215                 220

Ala Arg Arg Cys Ser Val Gly Gly Ile Val Glu Glu Tyr Gln Leu Pro
225                 230                 235                 240

Tyr Tyr Asp Met Val Pro Ser Asp Pro Ser Ile Glu Glu Met Arg Lys
                245                 250                 255

Val Val Cys Asp Gln Lys Phe Arg Pro Ser Ile Pro Asn Gln Trp Gln
            260                 265                 270

Ser Cys Glu Ala Leu Arg Val Met Gly Arg Ile Met Arg Glu Cys Trp
        275                 280                 285
```

Tyr Ala Asn Gly Ala Ala Arg Leu Thr Ala Leu Arg Ile Lys Lys Thr
            290                 295                 300

Ile Ser Gln Leu Cys Val Lys Glu Asp Cys Lys Ala
305                 310                 315

<210> SEQ ID NO 128
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85

<210> SEQ ID NO 129
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
            85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Gln Tyr Asn
            180                 185                 190

Ser Thr Tyr Arg Val Val Ser Val Leu Thr Val Leu His Gln Asp Trp
            195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Asp Thr
            275                 280                 285

Thr Pro Pro Val Leu Asp Ser Asp Gly Ser Phe Phe Leu Tyr Ser Asp
        290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340

<210> SEQ ID NO 130
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys

```
                    180                 185                 190
Lys Val Ser Asn Lys Ala Leu Pro Ala Pro Ile Glu Lys Thr Ile Ser
                195                 200                 205
Lys Ala Lys Gly Gln Pro Arg Glu Pro Gln Val Tyr Thr Leu Pro Pro
            210                 215                 220
Ser Arg Glu Glu Met Thr Lys Asn Gln Val Ser Leu Thr Cys Leu Val
225                 230                 235                 240
Lys Gly Phe Tyr Pro Ser Asp Ile Ala Val Glu Trp Glu Ser Asn Gly
                245                 250                 255
Gln Pro Glu Asn Asn Tyr Asp Thr Thr Pro Pro Val Leu Asp Ser Asp
            260                 265                 270
Gly Ser Phe Phe Leu Tyr Ser Asp Leu Thr Val Asp Lys Ser Arg Trp
            275                 280                 285
Gln Gln Gly Asn Val Phe Ser Cys Ser Val Met His Glu Ala Leu His
            290                 295                 300
Asn His Tyr Thr Gln Lys Ser Leu Ser Leu Ser Pro Gly
305                 310                 315

<210> SEQ ID NO 131

<400> SEQUENCE: 131

000

<210> SEQ ID NO 132

<400> SEQUENCE: 132

000

<210> SEQ ID NO 133
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Asp Ala Met Lys Arg Gly Leu Cys Cys Val Leu Leu Leu Cys Gly
1               5                   10                  15
Ala Val Phe Val Ser Pro Gly Ala Gly Leu Lys Cys Val Cys Leu Leu
                20                  25                  30
Cys Asp Ser Ser Asn Phe Thr Cys Gln Thr Glu Gly Ala Cys Trp Ala
            35                  40                  45
Ser Val Met Leu Thr Asn Gly Lys Glu Gln Val Ile Lys Ser Cys Val
        50                  55                  60
Ser Leu Pro Glu Leu Asn Ala Gln Val Phe Cys His Ser Ser Asn Asn
65                  70                  75                  80
Val Thr Lys Thr Glu Cys Cys Phe Thr Asp Phe Cys Asn Asn Ile Thr
                85                  90                  95
Leu His Leu Pro Thr Ala Ser Pro Asn Ala Pro Lys Leu Gly Pro Met
            100                 105                 110
Glu Thr Gly Gly Gly Thr His Thr Cys Pro Pro Cys Pro Ala Pro Glu
            115                 120                 125
Leu Leu Gly Gly Pro Ser Val Phe Leu Phe Pro Pro Lys Pro Lys Asp
        130                 135                 140
Thr Leu Met Ile Ser Arg Thr Pro Glu Val Thr Cys Val Val Val Asp
```

```
                145                 150                 155                 160
        Val Ser His Glu Asp Pro Glu Val Lys Phe Asn Trp Tyr Val Asp Gly
                        165                 170                 175

Val Glu Val His Asn Ala Lys Thr Lys Pro Arg Glu Glu Gln Tyr Asn
                        180                 185                 190

Ser Thr Tyr Arg Val Val Ser Val Leu Thr Val Leu His Gln Asp Trp
                        195                 200                 205

Leu Asn Gly Lys Glu Tyr Lys Cys Lys Val Ser Asn Lys Ala Leu Pro
                        210                 215                 220

Ala Pro Ile Glu Lys Thr Ile Ser Lys Ala Lys Gly Gln Pro Arg Glu
        225                 230                 235                 240

Pro Gln Val Cys Thr Leu Pro Pro Ser Arg Glu Glu Met Thr Lys Asn
                        245                 250                 255

Gln Val Ser Leu Ser Cys Ala Val Lys Gly Phe Tyr Pro Ser Asp Ile
                        260                 265                 270

Ala Val Glu Trp Glu Ser Asn Gly Gln Pro Glu Asn Asn Tyr Lys Thr
                        275                 280                 285

Thr Pro Pro Val Leu Asp Ser Asp Gly Ser Phe Phe Leu Val Ser Lys
                        290                 295                 300

Leu Thr Val Asp Lys Ser Arg Trp Gln Gln Gly Asn Val Phe Ser Cys
        305                 310                 315                 320

Ser Val Met His Glu Ala Leu His Asn His Tyr Thr Gln Lys Ser Leu
                        325                 330                 335

Ser Leu Ser Pro Gly Lys
                        340

<210> SEQ ID NO 134
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Leu Lys Cys Val Cys Leu Leu Cys Asp Ser Ser Asn Phe Thr Cys
        1               5                   10                  15

Gln Thr Glu Gly Ala Cys Trp Ala Ser Val Met Leu Thr Asn Gly Lys
                        20                  25                  30

Glu Gln Val Ile Lys Ser Cys Val Ser Leu Pro Glu Leu Asn Ala Gln
                        35                  40                  45

Val Phe Cys His Ser Ser Asn Asn Val Thr Lys Thr Glu Cys Cys Phe
                        50                  55                  60

Thr Asp Phe Cys Asn Asn Ile Thr Leu His Leu Pro Thr Ala Ser Pro
        65                  70                  75                  80

Asn Ala Pro Lys Leu Gly Pro Met Glu Thr Gly Gly Thr His Thr
                        85                  90                  95

Cys Pro Pro Cys Pro Ala Pro Glu Leu Leu Gly Gly Pro Ser Val Phe
                        100                 105                 110

Leu Phe Pro Pro Lys Pro Lys Asp Thr Leu Met Ile Ser Arg Thr Pro
                        115                 120                 125

Glu Val Thr Cys Val Val Val Asp Val Ser His Glu Asp Pro Glu Val
                        130                 135                 140

Lys Phe Asn Trp Tyr Val Asp Gly Val Glu Val His Asn Ala Lys Thr
        145                 150                 155                 160
```

```
Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Cys Thr Leu Pro Pro
    210                 215                 220

Ser Arg Glu Glu Met Thr Lys Asn Gln Val Ser Leu Ser Cys Ala Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270

Gly Ser Phe Phe Leu Val Ser Lys Leu Thr Val Asp Lys Ser Arg Trp
        275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly Lys
305                 310                 315

<210> SEQ ID NO 135

<400> SEQUENCE: 135

000

<210> SEQ ID NO 136

<400> SEQUENCE: 136

000

<210> SEQ ID NO 137
<211> LENGTH: 513
<212> TYPE: PRT
<213> ORGANISM: Homo sapiens

<400> SEQUENCE: 137

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140
```

```
Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
        210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
                260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
                355                 360                 365

Glu Val Leu Glu Gly Ala Ile Asn Phe Gln Arg Asp Ala Phe Leu Arg
                370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
                435                 440                 445

Ala Gly Met Ala Met Leu Cys Glu Thr Ile Glu Glu Cys Trp Asp His
                450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 138
<211> LENGTH: 115
<212> TYPE: PRT
<213> ORGANISM: Homo sapiens

<400> SEQUENCE: 138
```

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 139
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 140
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60
```

```
Cys Phe Ala Thr Trp Lys Asn Ile Ser Gly Ser Ile Glu Ile Val Lys
 65                  70                  75                  80

Gln Gly Cys Trp Leu Asp Asp Ile Asn Cys Tyr Asp Arg Thr Asp Cys
                 85                  90                  95

Val Glu Lys Lys Asp Ser Pro Glu Val Tyr Phe Cys Cys Glu Gly
            100                 105                 110

Asn Met Cys Asn Glu Lys Phe Ser Tyr Phe Pro Glu Met Glu Val Thr
            115                 120                 125

Gln Pro Thr Ser Asn Pro Val Thr Pro Lys Pro Thr Gly Gly Gly
        130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
                180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Lys Glu Met Thr Lys Asn Gln Val Ser Leu Thr
        275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Lys Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 141
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Leu Gly Arg Ser Glu Thr Gln Glu Cys Leu Phe Phe Asn Ala Asn
1               5                  10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45
```

```
Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
 65                 70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Thr His Thr Cys Pro Pro Cys Pro Ala
        115                 120                 125

Pro Glu Leu Leu Gly Gly Pro Ser Val Phe Leu Phe Pro Pro Lys Pro
130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Lys Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Lys Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 142

<400> SEQUENCE: 142

000

<210> SEQ ID NO 143

<400> SEQUENCE: 143

000

<210> SEQ ID NO 144
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 144

```
Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Cys Arg Glu Glu Met Thr Lys Asn Gln Val Ser Leu Trp
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys
```

<210> SEQ ID NO 145
<211> LENGTH: 344
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 145

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro Thr Gly Gly Thr His Thr Cys Pro Pro Cys Pro Ala
            115                 120                 125

Pro Glu Leu Leu Gly Gly Pro Ser Val Phe Leu Phe Pro Pro Lys Pro
            130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Cys Arg Glu Glu Met Thr
                245                 250                 255

Lys Asn Gln Val Ser Leu Trp Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 146

<400> SEQUENCE: 146

000
```

```
<210> SEQ ID NO 147

<400> SEQUENCE: 147

000

<210> SEQ ID NO 148
<211> LENGTH: 1038
<212> TYPE: PRT
<213> ORGANISM: Homo sapiens

<400> SEQUENCE: 148
```

| Met | Thr | Ser | Ser | Leu | Gln | Arg | Pro | Trp | Arg | Val | Pro | Trp | Leu | Pro | Trp |
|---|---|---|---|---|---|---|---|---|---|---|---|---|---|---|---|
| 1 | | | | 5 | | | | | 10 | | | | | 15 | |

| Thr | Ile | Leu | Leu | Val | Ser | Thr | Ala | Ala | Ser | Gln | Asn | Gln | Glu | Arg |
|---|---|---|---|---|---|---|---|---|---|---|---|---|---|---|
| | | | 20 | | | | | 25 | | | | | 30 | |

| Leu | Cys | Ala | Phe | Lys | Asp | Pro | Tyr | Gln | Gln | Asp | Leu | Gly | Ile | Gly | Glu |
|---|---|---|---|---|---|---|---|---|---|---|---|---|---|---|---|
| | | | 35 | | | | | 40 | | | | | 45 | | |

| Ser | Arg | Ile | Ser | His | Glu | Asn | Gly | Thr | Ile | Leu | Cys | Ser | Lys | Gly | Ser |
|---|---|---|---|---|---|---|---|---|---|---|---|---|---|---|---|
| | 50 | | | | | 55 | | | | | 60 | | | | |

| Thr | Cys | Tyr | Gly | Leu | Trp | Glu | Lys | Ser | Lys | Gly | Asp | Ile | Asn | Leu | Val |
|---|---|---|---|---|---|---|---|---|---|---|---|---|---|---|---|
| 65 | | | | | 70 | | | | | 75 | | | | | 80 |

| Lys | Gln | Gly | Cys | Trp | Ser | His | Ile | Gly | Asp | Pro | Gln | Glu | Cys | His | Tyr |
|---|---|---|---|---|---|---|---|---|---|---|---|---|---|---|---|
| | | | | 85 | | | | | 90 | | | | | 95 | |

| Glu | Glu | Cys | Val | Val | Thr | Thr | Thr | Pro | Pro | Ser | Ile | Gln | Asn | Gly | Thr |
|---|---|---|---|---|---|---|---|---|---|---|---|---|---|---|---|
| | | | 100 | | | | | 105 | | | | | 110 | | |

| Tyr | Arg | Phe | Cys | Cys | Cys | Ser | Thr | Asp | Leu | Cys | Asn | Val | Asn | Phe | Thr |
|---|---|---|---|---|---|---|---|---|---|---|---|---|---|---|---|
| | | | 115 | | | | | 120 | | | | | 125 | | |

| Glu | Asn | Phe | Pro | Pro | Pro | Asp | Thr | Thr | Pro | Leu | Ser | Pro | Pro | His | Ser |
|---|---|---|---|---|---|---|---|---|---|---|---|---|---|---|---|
| | 130 | | | | | 135 | | | | | 140 | | | | |

| Phe | Asn | Arg | Asp | Glu | Thr | Ile | Ile | Ile | Ala | Leu | Ala | Ser | Val | Ser | Val |
|---|---|---|---|---|---|---|---|---|---|---|---|---|---|---|---|
| 145 | | | | | 150 | | | | | 155 | | | | | 160 |

| Leu | Ala | Val | Leu | Ile | Val | Ala | Leu | Cys | Phe | Gly | Tyr | Arg | Met | Leu | Thr |
|---|---|---|---|---|---|---|---|---|---|---|---|---|---|---|---|
| | | | | 165 | | | | | 170 | | | | | 175 | |

| Gly | Asp | Arg | Lys | Gln | Gly | Leu | His | Ser | Met | Asn | Met | Met | Glu | Ala | Ala |
|---|---|---|---|---|---|---|---|---|---|---|---|---|---|---|---|
| | | | 180 | | | | | 185 | | | | | 190 | | |

| Ala | Ser | Glu | Pro | Ser | Leu | Asp | Leu | Asp | Asn | Leu | Lys | Leu | Leu | Glu | Leu |
|---|---|---|---|---|---|---|---|---|---|---|---|---|---|---|---|
| | | | 195 | | | | | 200 | | | | | 205 | | |

| Ile | Gly | Arg | Gly | Arg | Tyr | Gly | Ala | Val | Tyr | Lys | Gly | Ser | Leu | Asp | Glu |
|---|---|---|---|---|---|---|---|---|---|---|---|---|---|---|---|
| | 210 | | | | | 215 | | | | | 220 | | | | |

| Arg | Pro | Val | Ala | Val | Lys | Val | Phe | Ser | Phe | Ala | Asn | Arg | Gln | Asn | Phe |
|---|---|---|---|---|---|---|---|---|---|---|---|---|---|---|---|
| 225 | | | | | 230 | | | | | 235 | | | | | 240 |

| Ile | Asn | Glu | Lys | Asn | Ile | Tyr | Arg | Val | Pro | Leu | Met | Glu | His | Asp | Asn |
|---|---|---|---|---|---|---|---|---|---|---|---|---|---|---|---|
| | | | | 245 | | | | | 250 | | | | | 255 | |

| Ile | Ala | Arg | Phe | Ile | Val | Gly | Asp | Glu | Arg | Val | Thr | Ala | Asp | Gly | Arg |
|---|---|---|---|---|---|---|---|---|---|---|---|---|---|---|---|
| | | | 260 | | | | | 265 | | | | | 270 | | |

| Met | Glu | Tyr | Leu | Leu | Val | Met | Glu | Tyr | Tyr | Pro | Asn | Gly | Ser | Leu | Cys |
|---|---|---|---|---|---|---|---|---|---|---|---|---|---|---|---|
| | | 275 | | | | | 280 | | | | | 285 | | | |

| Lys | Tyr | Leu | Ser | Leu | His | Thr | Ser | Asp | Trp | Val | Ser | Ser | Cys | Arg | Leu |
|---|---|---|---|---|---|---|---|---|---|---|---|---|---|---|---|
| | 290 | | | | | 295 | | | | | 300 | | | | |

| Ala | His | Ser | Val | Thr | Arg | Gly | Leu | Ala | Tyr | Leu | His | Thr | Glu | Leu | Pro |
|---|---|---|---|---|---|---|---|---|---|---|---|---|---|---|---|
| 305 | | | | | 310 | | | | | 315 | | | | | 320 |

| Arg | Gly | Asp | His | Tyr | Lys | Pro | Ala | Ile | Ser | His | Arg | Asp | Leu | Asn | Ser |
|---|---|---|---|---|---|---|---|---|---|---|---|---|---|---|---|
| | | | | 325 | | | | | 330 | | | | | 335 | |

| Arg | Asn | Val | Leu | Val | Lys | Asn | Asp | Gly | Thr | Cys | Val | Ile | Ser | Asp | Phe |

```
                340             345             350
Gly Leu Ser Met Arg Leu Thr Gly Asn Arg Leu Val Arg Pro Gly Glu
                355             360             365
Glu Asp Asn Ala Ala Ile Ser Glu Val Gly Thr Ile Arg Tyr Met Ala
        370             375             380
Pro Glu Val Leu Glu Gly Ala Val Asn Leu Arg Asp Cys Glu Ser Ala
385             390             395             400
Leu Lys Gln Val Asp Met Tyr Ala Leu Gly Leu Ile Tyr Trp Glu Ile
                405             410             415
Phe Met Arg Cys Thr Asp Leu Phe Pro Gly Glu Ser Val Pro Glu Tyr
            420             425             430
Gln Met Ala Phe Gln Thr Glu Val Gly Asn His Pro Thr Phe Glu Asp
            435             440             445
Met Gln Val Leu Val Ser Arg Glu Lys Gln Arg Pro Lys Phe Pro Glu
        450             455             460
Ala Trp Lys Glu Asn Ser Leu Ala Val Arg Ser Leu Lys Glu Thr Ile
465             470             475             480
Glu Asp Cys Trp Asp Gln Asp Ala Glu Ala Arg Leu Thr Ala Gln Cys
                485             490             495
Ala Glu Glu Arg Met Ala Glu Leu Met Met Ile Trp Glu Arg Asn Lys
                500             505             510
Ser Val Ser Pro Thr Val Asn Pro Met Ser Thr Ala Met Gln Asn Glu
            515             520             525
Arg Asn Leu Ser His Asn Arg Arg Val Pro Lys Ile Gly Pro Tyr Pro
            530             535             540
Asp Tyr Ser Ser Ser Ser Tyr Ile Glu Asp Ser Ile His His Thr Asp
545             550             555             560
Ser Ile Val Lys Asn Ile Ser Ser Glu His Ser Met Ser Ser Thr Pro
                565             570             575
Leu Thr Ile Gly Glu Lys Asn Arg Asn Ser Ile Asn Tyr Glu Arg Gln
                580             585             590
Gln Ala Gln Ala Arg Ile Pro Ser Pro Glu Thr Ser Val Thr Ser Leu
            595             600             605
Ser Thr Asn Thr Thr Thr Thr Asn Thr Thr Gly Leu Thr Pro Ser Thr
        610             615             620
Gly Met Thr Thr Ile Ser Glu Met Pro Tyr Pro Asp Glu Thr Asn Leu
625             630             635             640
His Thr Thr Asn Val Ala Gln Ser Ile Gly Pro Thr Pro Val Cys Leu
                645             650             655
Gln Leu Thr Glu Glu Asp Leu Glu Thr Asn Lys Leu Asp Pro Lys Glu
            660             665             670
Val Asp Lys Asn Leu Lys Glu Ser Ser Asp Glu Asn Leu Met Glu His
            675             680             685
Ser Leu Lys Gln Phe Ser Gly Pro Asp Pro Leu Ser Ser Thr Ser Ser
            690             695             700
Ser Leu Leu Tyr Pro Leu Ile Lys Leu Ala Val Glu Ala Thr Gly Gln
705             710             715             720
Gln Asp Phe Thr Gln Thr Ala Asn Gly Gln Ala Cys Leu Ile Pro Asp
                725             730             735
Val Leu Pro Thr Gln Ile Tyr Pro Leu Pro Lys Gln Gln Asn Leu Pro
            740             745             750
Lys Arg Pro Thr Ser Leu Pro Leu Asn Thr Lys Asn Ser Thr Lys Glu
            755             760             765
```

```
Pro Arg Leu Lys Phe Gly Ser Lys His Lys Ser Asn Leu Lys Gln Val
    770             775             780

Glu Thr Gly Val Ala Lys Met Asn Thr Ile Asn Ala Ala Glu Pro His
785             790             795             800

Val Val Thr Val Thr Met Asn Gly Val Ala Gly Arg Asn His Ser Val
                805             810             815

Asn Ser His Ala Ala Thr Thr Gln Tyr Ala Asn Gly Thr Val Leu Ser
            820             825             830

Gly Gln Thr Thr Asn Ile Val Thr His Arg Ala Gln Glu Met Leu Gln
            835             840             845

Asn Gln Phe Ile Gly Glu Asp Thr Arg Leu Asn Ile Asn Ser Ser Pro
850             855             860

Asp Glu His Glu Pro Leu Leu Arg Arg Glu Gln Gln Ala Gly His Asp
865             870             875             880

Glu Gly Val Leu Asp Arg Leu Val Asp Arg Arg Glu Arg Pro Leu Glu
                885             890             895

Gly Gly Arg Thr Asn Ser Asn Asn Asn Ser Asn Pro Cys Ser Glu
                900             905             910

Gln Asp Val Leu Ala Gln Gly Val Pro Ser Thr Ala Ala Asp Pro Gly
            915             920             925

Pro Ser Lys Pro Arg Arg Ala Gln Arg Pro Asn Ser Leu Asp Leu Ser
    930             935             940

Ala Thr Asn Val Leu Asp Gly Ser Ser Ile Gln Ile Gly Glu Ser Thr
945             950             955             960

Gln Asp Gly Lys Ser Gly Ser Gly Glu Lys Ile Lys Lys Arg Val Lys
                965             970             975

Thr Pro Tyr Ser Leu Lys Arg Trp Arg Pro Ser Thr Trp Val Ile Ser
            980             985             990

Thr Glu Ser Leu Asp Cys Glu Val  Asn Asn Asn Gly Ser  Asn Arg Ala
            995             1000             1005

Val His  Ser Lys Ser Ser Thr  Ala Val Tyr Leu Ala  Glu Gly Gly
    1010             1015             1020

Thr Ala  Thr Thr Met Val Ser  Lys Asp Ile Gly Met  Asn Cys Leu
1025             1030             1035

<210> SEQ ID NO 149
<211> LENGTH: 530
<212> TYPE: PRT
<213> ORGANISM: Homo sapiens

<400> SEQUENCE: 149

Met Thr Ser Ser Leu Gln Arg Pro Trp Arg Val Pro Trp Leu Pro Trp
1               5               10              15

Thr Ile Leu Leu Val Ser Thr Ala Ala Ala Ser Gln Asn Gln Glu Arg
            20              25              30

Leu Cys Ala Phe Lys Asp Pro Tyr Gln Gln Asp Leu Gly Ile Gly Glu
        35              40              45

Ser Arg Ile Ser His Glu Asn Gly Thr Ile Leu Cys Ser Lys Gly Ser
    50              55              60

Thr Cys Tyr Gly Leu Trp Glu Lys Ser Lys Gly Asp Ile Asn Leu Val
65              70              75              80

Lys Gln Gly Cys Trp Ser His Ile Gly Asp Pro Gln Glu Cys His Tyr
            85              90              95

Glu Glu Cys Val Val Thr Thr Thr Pro Pro Ser Ile Gln Asn Gly Thr
```

```
            100                 105                 110
Tyr Arg Phe Cys Cys Cys Ser Thr Asp Leu Cys Asn Val Asn Phe Thr
            115                 120                 125
Glu Asn Phe Pro Pro Pro Asp Thr Thr Pro Leu Ser Pro Pro His Ser
            130                 135                 140
Phe Asn Arg Asp Glu Thr Ile Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
Gly Asp Arg Lys Gln Gly Leu His Ser Met Asn Met Met Glu Ala Ala
            180                 185                 190
Ala Ser Glu Pro Ser Leu Asp Leu Asp Asn Leu Lys Leu Leu Glu Leu
            195                 200                 205
Ile Gly Arg Gly Arg Tyr Gly Ala Val Tyr Lys Gly Ser Leu Asp Glu
            210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
            260                 265                 270
Met Glu Tyr Leu Leu Val Met Glu Tyr Tyr Pro Asn Gly Ser Leu Cys
            275                 280                 285
Lys Tyr Leu Ser Leu His Thr Ser Asp Trp Val Ser Ser Cys Arg Leu
            290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
            355                 360                 365
Glu Asp Asn Ala Ala Ile Ser Glu Val Gly Thr Ile Arg Tyr Met Ala
            370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
            420                 425                 430
Gln Met Ala Phe Gln Thr Glu Val Gly Asn His Pro Thr Phe Glu Asp
            435                 440                 445
Met Gln Val Leu Val Ser Arg Glu Lys Gln Arg Pro Lys Phe Pro Glu
            450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
            500                 505                 510
Ser Val Ser Pro Thr Val Asn Pro Met Ser Thr Ala Met Gln Asn Glu
            515                 520                 525
```

Arg Arg
    530

<210> SEQ ID NO 150
<211> LENGTH: 124
<212> TYPE: PRT
<213> ORGANISM: Homo sapiens

<400> SEQUENCE: 150

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
        115                 120

<210> SEQ ID NO 151
<211> LENGTH: 124
<212> TYPE: PRT
<213> ORGANISM: Homo sapiens

<400> SEQUENCE: 151

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
        115                 120

<210> SEQ ID NO 152
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30

Ala Phe Lys Asp Pro Tyr Gln Gln Asp Leu Gly Ile Gly Glu Ser Arg
        35                  40                  45

Ile Ser His Glu Asn Gly Thr Ile Leu Cys Ser Lys Gly Ser Thr Cys
    50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro His Ser Phe Asn
130                 135                 140

Arg Asp Glu Thr Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Lys Glu Met Thr
        275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Lys Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 153
<211> LENGTH: 352
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 153

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Ser Thr Asp Leu
                85                  90                  95

Cys Asn Val Asn Phe Thr Glu Asn Phe Pro Pro Asp Thr Thr Pro
            100                 105                 110

Leu Ser Pro Pro His Ser Phe Asn Arg Asp Glu Thr Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Lys Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Lys
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 154

<400> SEQUENCE: 154

000

<210> SEQ ID NO 155

-continued

<400> SEQUENCE: 155

000

<210> SEQ ID NO 156
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30

Ala Phe Lys Asp Pro Tyr Gln Gln Asp Leu Gly Ile Gly Glu Ser Arg
        35                  40                  45

Ile Ser His Glu Asn Gly Thr Ile Leu Cys Ser Lys Gly Ser Thr Cys
    50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro His Ser Phe Asn
    130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Cys Arg Glu Glu Met Thr
        275                 280                 285

Lys Asn Gln Val Ser Leu Trp Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

```
Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
            355                 360                 365

Ser Leu Ser Leu Ser Pro Gly Lys
        370                 375

<210> SEQ ID NO 157
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Arg Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320
```

```
Arg Trp Gln Gln Gly Asn Val Phe Ser Cys Ser Val Met His Glu Ala
            325                 330                 335

Leu His Asn His Tyr Thr Gln Lys Ser Leu Ser Leu Ser Pro Gly Lys
            340                 345                 350

<210> SEQ ID NO 158

<400> SEQUENCE: 158

000

<210> SEQ ID NO 159

<400> SEQUENCE: 159

000

<210> SEQ ID NO 160
<211> LENGTH: 592
<212> TYPE: PRT
<213> ORGANISM: Homo sapiens

<400> SEQUENCE: 160

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270
```

```
Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
        290                 295                 300

Pro Tyr Glu Glu Tyr Ala Ser Trp Lys Thr Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 161
<211> LENGTH: 567
<212> TYPE: PRT
<213> ORGANISM: Homo sapiens

<400> SEQUENCE: 161

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
```

```
           50                  55                  60
Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                     85                  90                  95

Leu Glu Thr Val Cys His Asp Pro Lys Leu Pro Tyr His Asp Phe Ile
                    100                 105                 110

Leu Glu Asp Ala Ala Ser Pro Lys Cys Ile Met Lys Glu Lys Lys Lys
                    115                 120                 125

Pro Gly Glu Thr Phe Phe Met Cys Ser Cys Ser Ser Asp Glu Cys Asn
            130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                    165                 170                 175

Gly Val Ala Ile Ser Val Ile Ile Ile Phe Tyr Cys Tyr Arg Val Asn
                180                 185                 190

Arg Gln Gln Lys Leu Ser Ser Thr Trp Glu Thr Gly Lys Thr Arg Lys
            195                 200                 205

Leu Met Glu Phe Ser Glu His Cys Ala Ile Ile Leu Glu Asp Asp Arg
210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                    245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                    325                 330                 335

Leu Thr Arg His Val Ile Ser Trp Glu Asp Leu Arg Lys Leu Gly Ser
                340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                    405                 410                 415

Gly Gln Val Gly Thr Ala Arg Tyr Met Ala Pro Glu Val Leu Glu Ser
                420                 425                 430

Arg Met Asn Leu Glu Asn Val Glu Ser Phe Lys Gln Thr Asp Val Tyr
            435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480
```

```
His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 162
<211> LENGTH: 144
<212> TYPE: PRT
<213> ORGANISM: Homo sapiens

<400> SEQUENCE: 162

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

<210> SEQ ID NO 163
<211> LENGTH: 169
<212> TYPE: PRT
<213> ORGANISM: Homo sapiens

<400> SEQUENCE: 163

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95
```

```
Asn Ile Thr Leu Glu Thr Val Cys His Asp Pro Lys Leu Pro Tyr His
                100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
                165

<210> SEQ ID NO 164
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
                100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
```

```
                275                 280                 285
Pro Gln Val Tyr Thr Leu Pro Pro Ser Arg Lys Glu Met Thr Lys Asn
290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Lys Ser Asp Gly Ser Phe Phe Leu Tyr Ser Lys
                340                 345                 350

Leu Thr Val Asp Lys Ser Arg Trp Gln Gln Gly Asn Val Phe Ser Cys
                355                 360                 365

Ser Val Met His Glu Ala Leu His Asn His Tyr Thr Gln Lys Ser Leu
370                 375                 380

Ser Leu Ser Pro Gly Lys
385                 390

<210> SEQ ID NO 165
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
                35                  40                  45

Cys Ser Ile Thr Ser Ile Cys Glu Lys Pro Gln Glu Val Cys Val Ala
                50                  55                  60

Val Trp Arg Lys Asn Asp Glu Asn Ile Thr Leu Glu Thr Val Cys His
65              70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
                100                 105                 110

Met Cys Ser Cys Ser Ser Asp Glu Cys Asn Asp Asn Ile Ile Phe Ser
                115                 120                 125

Glu Glu Tyr Asn Thr Ser Asn Pro Asp Thr Gly Gly Thr His Thr
                130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
                180                 185                 190

Lys Phe Asn Trp Tyr Val Asp Gly Val Glu Val His Asn Ala Lys Thr
                195                 200                 205

Lys Pro Arg Glu Glu Gln Tyr Asn Ser Thr Tyr Arg Val Val Ser Val
                210                 215                 220

Leu Thr Val Leu His Gln Asp Trp Leu Asn Gly Lys Glu Tyr Lys Cys
225                 230                 235                 240
```

Lys Val Ser Asn Lys Ala Leu Pro Ala Pro Ile Glu Lys Thr Ile Ser
            245                 250                 255

Lys Ala Lys Gly Gln Pro Arg Glu Pro Gln Val Tyr Thr Leu Pro Pro
            260                 265                 270

Ser Arg Lys Glu Met Thr Lys Asn Gln Val Ser Leu Thr Cys Leu Val
            275                 280                 285

Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Val Leu Lys Ser Asp
305                 310                 315                 320

Gly Ser Phe Phe Leu Tyr Ser Lys Leu Thr Val Asp Lys Ser Arg Trp
            325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 166
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
        50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
            85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
            115                 120                 125

His Asp Pro Lys Leu Pro Tyr His Asp Phe Ile Leu Glu Asp Ala Ala
        130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
            165                 170                 175

Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
            195                 200                 205

Phe Leu Phe Pro Pro Lys Pro Lys Asp Thr Leu Met Ile Ser Arg Thr
        210                 215                 220

Pro Glu Val Thr Cys Val Val Val Asp Val Ser His Glu Asp Pro Glu
225                 230                 235                 240

-continued

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
                260                 265                 270

Val Leu Thr Val Leu His Gln Asp Trp Leu Asn Gly Lys Glu Tyr Lys
            275                 280                 285

Cys Lys Val Ser Asn Lys Ala Leu Pro Ala Pro Ile Glu Lys Thr Ile
        290                 295                 300

Ser Lys Ala Lys Gly Gln Pro Arg Glu Pro Gln Val Tyr Thr Leu Pro
305                 310                 315                 320

Pro Ser Arg Lys Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
                340                 345                 350

Gly Gln Pro Glu Asn Asn Tyr Lys Thr Thr Pro Pro Val Leu Lys Ser
            355                 360                 365

Asp Gly Ser Phe Phe Leu Tyr Ser Lys Leu Thr Val Asp Lys Ser Arg
        370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 167
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
        50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
                100                 105                 110

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp Thr Gly Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys

```
                180                 185                 190
Asp Thr Leu Met Ile Ser Arg Thr Pro Glu Val Thr Cys Val Val Val
            195                 200                 205

Asp Val Ser His Glu Asp Pro Glu Val Lys Phe Asn Trp Tyr Val Asp
        210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Ser Arg Lys Glu Met Thr Lys
    290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Lys Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
    370                 375                 380

Leu Ser Leu Ser Pro Gly Lys
385                 390

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172
```

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
            165                 170                 175

Leu Leu Gly Gly Pro Ser Val Phe Leu Phe Pro Pro Lys Pro Lys Asp
        180                 185                 190

Thr Leu Met Ile Ser Arg Thr Pro Glu Val Thr Cys Val Val Val Asp
    195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
            245                 250                 255

Leu Asn Gly Lys Glu Tyr Lys Cys Lys Val Ser Asn Lys Ala Leu Pro
        260                 265                 270

Ala Pro Ile Glu Lys Thr Ile Ser Lys Ala Lys Gly Gln Pro Arg Glu
    275                 280                 285

Pro Gln Val Tyr Thr Leu Pro Pro Cys Arg Glu Glu Met Thr Lys Asn
290                 295                 300

Gln Val Ser Leu Trp Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
            325                 330                 335

Thr Pro Pro Val Leu Asp Ser Asp Gly Ser Phe Phe Leu Tyr Ser Lys
        340                 345                 350

Leu Thr Val Asp Lys Ser Arg Trp Gln Gln Gly Asn Val Phe Ser Cys
    355                 360                 365

Ser Val Met His Glu Ala Leu His Asn His Tyr Thr Gln Lys Ser Leu
370                 375                 380

Ser Leu Ser Pro Gly Lys
385             390

<210> SEQ ID NO 173
<211> LENGTH: 366
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Cys Arg Glu Glu Met Thr Lys Asn Gln Val Ser Leu Trp Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 174
```

```
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174
```

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
    195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Cys Arg Glu Glu Met Thr Lys Asn Gln Val Ser Leu Trp Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg

```
                370               375               380
Trp Gln Gln Gly Asn Val Phe Ser Cys Ser Val Met His Glu Ala Leu
385               390               395               400

His Asn His Tyr Thr Gln Lys Ser Leu Ser Leu Ser Pro Gly Lys
                405               410               415

<210> SEQ ID NO 175
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Thr Ile Pro Pro His Val Gln Lys Ser Asp Val Glu Met Glu Ala Gln
1               5                  10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Thr Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
        275                 280                 285

Glu Pro Gln Val Tyr Thr Leu Pro Pro Cys Arg Glu Glu Met Thr Lys
290                 295                 300

Asn Gln Val Ser Leu Trp Cys Leu Val Lys Gly Phe Tyr Pro Ser Asp
305                 310                 315                 320
```

```
Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
        340                 345                 350

Lys Leu Thr Val Asp Lys Ser Arg Trp Gln Gln Gly Asn Val Phe Ser
            355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180
<211> LENGTH: 573
<212> TYPE: PRT
<213> ORGANISM: Homo sapiens

<400> SEQUENCE: 180

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
        50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
                100                 105                 110

Thr Asp Phe Cys Asn Ala Asn Tyr Ser His Leu Pro Pro Pro Gly Ser
            115                 120                 125

Pro Gly Thr Pro Gly Ser Gln Gly Pro Gln Ala Ala Pro Gly Glu Ser
        130                 135                 140

Ile Trp Met Ala Leu Val Leu Leu Gly Leu Phe Leu Leu Leu Leu Leu
```

```
            145                 150                 155                 160
Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
                180                 185                 190

Trp Ser Val Glu Leu Gln Glu Leu Pro Glu Leu Cys Phe Ser Gln Val
                195                 200                 205

Ile Arg Glu Gly Gly His Ala Val Val Trp Ala Gly Gln Leu Gln Gly
                210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
                260                 265                 270

Ser Gly Pro Leu Leu Val Leu Glu Leu His Pro Lys Gly Ser Leu Cys
                275                 280                 285

His Tyr Leu Thr Gln Tyr Thr Ser Asp Trp Gly Ser Ser Leu Arg Met
                290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
                340                 345                 350

Gly Leu Ala Leu Val Leu Pro Gly Leu Thr Gln Pro Pro Ala Trp Thr
                355                 360                 365

Pro Thr Gln Pro Gln Gly Pro Ala Ala Ile Met Glu Ala Gly Thr Gln
                370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                405                 410                 415

Leu Trp Glu Ile Leu Ser Arg Cys Pro Asp Leu Arg Pro Asp Ser Ser
                420                 425                 430

Pro Pro Pro Phe Gln Leu Ala Tyr Glu Ala Glu Leu Gly Asn Thr Pro
                435                 440                 445

Thr Ser Asp Glu Leu Trp Ala Leu Ala Val Gln Glu Arg Arg Arg Pro
450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
                485                 490                 495

Thr Ala Glu Cys Val Gln Gln Arg Leu Ala Ala Leu Ala His Pro Gln
                500                 505                 510

Glu Ser His Pro Phe Pro Glu Ser Cys Pro Arg Gly Cys Pro Pro Leu
                515                 520                 525

Cys Pro Glu Asp Cys Thr Ser Ile Pro Ala Pro Thr Ile Leu Pro Cys
                530                 535                 540

Arg Pro Gln Arg Ser Ala Cys His Phe Ser Val Gln Gln Gly Pro Cys
545                 550                 555                 560

Ser Arg Asn Pro Gln Pro Ala Cys Thr Leu Ser Pro Val
                565                 570
```

```
<210> SEQ ID NO 181
<211> LENGTH: 478
<212> TYPE: PRT
<213> ORGANISM: Homo sapiens

<400> SEQUENCE: 181

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
                20                  25                  30

Arg Gly Ser Thr Lys Thr Leu Gly Glu Leu Leu Asp Thr Gly Thr Glu
            35                  40                  45

Leu Pro Arg Ala Ile Arg Cys Leu Tyr Ser Arg Cys Cys Phe Gly Ile
        50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
                100                 105                 110

Thr Asp Phe Cys Asn Ala Asn Tyr Ser His Leu Pro Pro Gly Ser
            115                 120                 125

Pro Gly Thr Pro Gly Ser Gln Gly Pro Gln Ala Ala Pro Gly Glu Ser
        130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
                180                 185                 190

Trp Ser Val Glu Leu Gln Glu Leu Pro Glu Leu Cys Phe Ser Gln Val
            195                 200                 205

Ile Arg Glu Gly Gly His Ala Val Val Trp Ala Gly Gln Leu Gln Gly
        210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
                260                 265                 270

Ser Gly Pro Leu Leu Val Leu Glu Leu His Pro Lys Gly Ser Leu Cys
            275                 280                 285

His Tyr Leu Thr Gln Tyr Thr Ser Asp Trp Gly Ser Ser Leu Arg Met
        290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
                340                 345                 350

Gly Leu Ala Leu Val Leu Pro Gly Leu Thr Gln Pro Pro Ala Trp Thr
            355                 360                 365

Pro Thr Gln Pro Gln Gly Pro Ala Ala Ile Met Glu Ala Gly Thr Gln
```

```
                    370                 375                 380
Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
                    405                 410                 415

Leu Trp Glu Ile Leu Ser Arg Cys Pro Asp Leu Arg Pro Ala Val His
                    420                 425                 430

His Pro Ser Asn Trp Pro Met Arg Gln Asn Trp Ala Ile Pro Leu Pro
                    435                 440                 445

Leu Met Ser Tyr Gly Pro Trp Gln Cys Arg Arg Gly Gly Val Pro Thr
450                 455                 460

Ser His Pro Pro Gly Ala Ala Leu Pro Gln Thr Leu Met Gly
465                 470                 475

<210> SEQ ID NO 182
<211> LENGTH: 478
<212> TYPE: PRT
<213> ORGANISM: Homo sapiens

<400> SEQUENCE: 182

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
                    20                  25                  30

Arg Gly Ser Thr Lys Thr Leu Gly Glu Leu Leu Asp Thr Gly Thr Glu
                    35                  40                  45

Leu Pro Arg Ala Ile Arg Cys Leu Tyr Ser Arg Cys Cys Phe Gly Ile
50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                    85                  90                  95

Arg Ala His Pro Ser Pro Gly Ser Thr Leu Phe Thr Cys Ser Cys Gly
                    100                 105                 110

Thr Asp Phe Cys Asn Ala Asn Tyr Ser His Leu Pro Pro Pro Gly Ser
                    115                 120                 125

Pro Gly Thr Pro Gly Ser Gln Gly Pro Gln Ala Ala Pro Gly Glu Ser
130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                    165                 170                 175

Val Arg Gly Glu Pro Val Pro Glu Pro Arg Pro Asp Ser Gly Arg Asp
                    180                 185                 190

Trp Ser Val Glu Leu Gln Glu Leu Pro Glu Leu Cys Phe Ser Gln Val
                    195                 200                 205

Ile Arg Glu Gly Gly His Ala Val Val Trp Ala Gly Gln Leu Gln Gly
                    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                    245                 250                 255

Ile Val Arg Phe Ile Thr Ala Ser Arg Gly Gly Pro Gly Arg Leu Leu
                    260                 265                 270
```

```
Ser Gly Pro Leu Leu Val Leu Glu Leu His Pro Lys Gly Ser Leu Cys
            275                 280                 285

His Tyr Leu Thr Gln Tyr Thr Ser Asp Trp Gly Ser Ser Leu Arg Met
290                     295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Asp Pro Asp Gly
    370                 375                 380

Leu Arg Glu Leu Leu Glu Asp Cys Trp Asp Ala Asp Pro Glu Ala Arg
385                 390                 395                 400

Leu Thr Ala Glu Cys Val Gln Gln Arg Leu Ala Ala Leu Ala His Pro
                405                 410                 415

Gln Glu Ser His Pro Phe Pro Glu Ser Cys Pro Arg Gly Cys Pro Pro
                420                 425                 430

Leu Cys Pro Glu Asp Cys Thr Ser Ile Pro Ala Pro Thr Ile Leu Pro
            435                 440                 445

Cys Arg Pro Gln Arg Ser Ala Cys His Phe Ser Val Gln Gln Gly Pro
        450                 455                 460

Cys Ser Arg Asn Pro Gln Pro Ala Cys Thr Leu Ser Pro Val
465                 470                 475

<210> SEQ ID NO 183
<211> LENGTH: 132
<212> TYPE: PRT
<213> ORGANISM: Homo sapiens

<400> SEQUENCE: 183

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
                100                 105                 110

Gly Thr Pro Gly Ser Gln Gly Pro Gln Ala Ala Pro Gly Glu Ser Ile
            115                 120                 125

Trp Met Ala Leu
    130

<210> SEQ ID NO 184
<211> LENGTH: 132
<212> TYPE: PRT
<213> ORGANISM: Homo sapiens
```

<400> SEQUENCE: 184

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Gly Ser Pro
                100                 105                 110

Gly Thr Pro Gly Ser Gln Gly Pro Gln Ala Ala Pro Gly Glu Ser Ile
            115                 120                 125

Trp Met Ala Leu
    130

<210> SEQ ID NO 185
<211> LENGTH: 132
<212> TYPE: PRT
<213> ORGANISM: Homo sapiens

<400> SEQUENCE: 185

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Gly Ser Pro
                100                 105                 110

Gly Thr Pro Gly Ser Gln Gly Pro Gln Ala Ala Pro Gly Glu Ser Ile
            115                 120                 125

Trp Met Ala Leu
    130

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194
<211> LENGTH: 567
<212> TYPE: PRT
<213> ORGANISM: Homo sapiens

<400> SEQUENCE: 194

```
Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
                35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                    85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
            115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160
```

```
Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
                195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
                260                 265                 270

Thr Val Ala Val Lys Ile Phe Pro Tyr Glu Glu Tyr Ala Ser Trp Lys
            275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
                355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
    435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
    515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565
```

<210> SEQ ID NO 195
<211> LENGTH: 144
<212> TYPE: PRT
<213> ORGANISM: Homo sapiens

<400> SEQUENCE: 195

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

<210> SEQ ID NO 196
<211> LENGTH: 1701
<212> TYPE: DNA
<213> ORGANISM: Homo sapiens

<400> SEQUENCE: 196
atgggtcggg ggctgctcag gggcctgtgg ccgctgcaca tcgtcctgtg gacgcgtatc      60
gccagcacga tcccaccgca cgttcagaag tcggttaata cgacatgat agtcactgac      120 aacaacggtg cagtcaagtt tccacaactg tgtaaatttt gtgatgtgag attttccacc      180
tgtgacaacc agaaatcctg catgagcaac tgcagcatca cctccatctg tgagaagcca      240
caggaagtct gtgtggctgt atggagaaag aatgacgaga acataacact agagacagtt      300
tgccatgacc ccaagctccc ctaccatgac tttattctgg aagatgctgc ttctccaaag      360
tgcattatga aggaaaaaaa aaagcctggt gagactttct tcatgtgttc ctgtagctct      420
gatgagtgca atgacaacat catcttctca gaagaatata caccagcaa tcctgacttg      480 ttgctagtca tatttcaagt gacaggcatc agcctcctgc caccactggg agttgccata      540
tctgtcatca tcatcttcta ctgctaccgc gttaaccggc agcagaagct gagttcaacc      600
tgggaaaccg gcaagacgcg gaagctcatg gagttcagcg agcactgtgc catcatcctg      660
gaagatgacc gctctgacat cagctccacg tgtgccaaca acatcaacca caacacagag      720
ctgctgccca ttgagctgga caccctggtg gggaaaggtc gctttgctga ggtctataag      780
gccaagctga gcagaacac ttcagagcag tttgagacag tggcagtcaa gatctttccc      840
tatgaggagt atgcctcttg gaagacagag aaggacatct tctcagacat caatctgaag      900
catgagaaca tactccagtt cctgacggct gaggagcgga gacggagtt ggggaaacaa      960 tactggctga tcaccgcctt ccacgccaag ggcaacctac aggagtacct gacgcggcat      1020
gtcatcagct gggaggacct gcgcaagctg ggcagctccc tcgcccgggg gattgctcac      1080

```
ctccacagtg atcacactcc atgtgggagg cccaagatgc ccatcgtgca cagggacctc      1140
aagagctcca atatcctcgt gaagaacgac ctaacctgct gcctgtgtga ctttgggctt      1200
tccctgcgtc tggaccctac tctgtctgtg atgaccctgg ctaacagtgg gcaggtggga      1260
actgcaagat acatggctcc agaagtccta gaatccagga tgaatttgga gaatgttgag      1320
tccttcaagc agaccgatgt ctactccatg gctctggtgc tctgggaaat gacatctcgc      1380
tgtaatgcag tgggagaagt aaaagattat gagcctccat ttggttccaa ggtgcgggag      1440 caccccctgtg tcgaaagcat gaaggacaac gtgttgagag atcgagggcg accagaaatt      1500
cccagcttct ggctcaacca ccagggcatc cagatggtgt gtgagacgtt gactgagtgc      1560
tgggaccacg acccagaggc ccgtctcaca gcccagtgtg tggcagaacg cttcagtgag      1620
ctggagcatc tggacaggct ctcggggagg agctgctcgg aggagaagat tcctgaagac      1680
ggctccctaa acactaccaa a                                                1701

<210> SEQ ID NO 197
<211> LENGTH: 432
<212> TYPE: DNA
<213> ORGANISM: Homo sapiens

<400> SEQUENCE: 197
acgatcccac cgcacgttca gaagtcggtt aataacgaca tgatagtcac tgacaacaac        60
ggtgcagtca agtttccaca actgtgtaaa ttttgtgatg tgagattttc cacctgtgac       120
aaccagaaat cctgcatgag caactgcagc atcacctcca tctgtgagaa gccacaggaa       180
gtctgtgtgg ctgtatggag aaagaatgac gagaacataa cactagagac agtttgccat       240
gaccccaagc tcccctacca tgactttatt ctggaagatg ctgcttctcc aaagtgcatt       300
atgaaggaaa aaaaaaagcc tggtgagact ttcttcatgt gttcctgtag ctctgatgag       360
tgcaatgaca acatcatctt ctcagaagaa tataacacca gcaatcctga cttgttgcta       420
gtcatatttc aa                                                          432

<210> SEQ ID NO 198
<211> LENGTH: 592
<212> TYPE: PRT
<213> ORGANISM: Homo sapiens

<400> SEQUENCE: 198

Met Gly Arg Gly Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
```

-continued

```
            130                 135                 140
Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Val Ile Phe Gln Val
                180                 185                 190

Thr Gly Ile Ser Leu Leu Pro Pro Leu Gly Val Ala Ile Ser Val Ile
                195                 200                 205

Ile Ile Phe Tyr Cys Tyr Arg Val Asn Arg Gln Gln Lys Leu Ser Ser
210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
                275                 280                 285

Lys Gln Asn Thr Ser Glu Gln Phe Glu Thr Val Ala Val Lys Ile Phe
290                 295                 300

Pro Tyr Glu Glu Tyr Ala Ser Trp Lys Thr Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
                340                 345                 350

His Ala Lys Gly Asn Leu Gln Glu Tyr Leu Thr Arg His Val Ile Ser
                355                 360                 365

Trp Glu Asp Leu Arg Lys Leu Gly Ser Ser Leu Ala Arg Gly Ile Ala
                370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
                420                 425                 430

Leu Ser Val Asp Asp Leu Ala Asn Ser Gly Gln Val Gly Thr Ala Arg
                435                 440                 445

Tyr Met Ala Pro Glu Val Leu Glu Ser Arg Met Asn Leu Glu Asn Val
                450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
                500                 505                 510

Lys Asp Asn Val Leu Arg Asp Arg Gly Arg Pro Glu Ile Pro Ser Phe
                515                 520                 525

Trp Leu Asn His Gln Gly Ile Gln Met Val Cys Glu Thr Leu Thr Glu
                530                 535                 540

Cys Trp Asp His Asp Pro Glu Ala Arg Leu Thr Ala Gln Cys Val Ala
545                 550                 555                 560
```

Glu Arg Phe Ser Glu Leu Glu His Leu Asp Arg Leu Ser Gly Arg Ser
            565                 570                 575

Cys Ser Glu Glu Lys Ile Pro Glu Asp Gly Ser Leu Asn Thr Thr Lys
        580                 585                 590

<210> SEQ ID NO 199
<211> LENGTH: 169
<212> TYPE: PRT
<213> ORGANISM: Homo sapiens

<400> SEQUENCE: 199

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
                165

<210> SEQ ID NO 200

<400> SEQUENCE: 200

000

<210> SEQ ID NO 201

<400> SEQUENCE: 201

000

<210> SEQ ID NO 202
<211> LENGTH: 1776
<212> TYPE: DNA
<213> ORGANISM: Homo sapiens

<400> SEQUENCE: 202
atgggtcggg ggctgctcag ggcctgtgg ccgctgcaca tcgtcctgtg gacgcgtatc      60
gccagcacga tcccaccgca cgttcagaag tcggatgtgg aaatggaggc cagaaagat    120 gaaatcatct gccccagctg taataggact gccatccac tgagacatat taataacgac    180
atgatagtca ctgacaacaa cggtgcagtc aagtttccac aactgtgtaa attttgtgat    240
gtgagatttt ccacctgtga caaccagaaa tcctgcatga gcaactgcag catcacctcc    300

```
atctgtgaga agccacagga agtctgtgtg gctgtatgga gaaagaatga cgagaacata    360
acactagaga cagtttgcca tgaccccaag ctcccctacc atgactttat tctggaagat    420
gctgcttctc caaagtgcat tatgaaggaa aaaaaaaagc ctggtgagac tttcttcatg    480
tgttcctgta gctctgatga gtgcaatgac aacatcatct tctcagaaga atataacacc    540
agcaatcctg acttgttgct agtcatattt caagtgacag gcatcagcct cctgccacca    600
ctgggagttg ccatatctgt catcatcatc ttctactgct accgcgttaa ccggcagcag    660
aagctgagtt caacctggga accggcaag acgcggaagc tcatggagtt cagcgagcac    720
tgtgccatca tcctggaaga tgaccgctct gacatcagct ccacgtgtgc caacaacatc    780
aaccacaaca cagagctgct gcccattgag ctggacaccc tggtggggaa aggtcgcttt    840
gctgaggtct ataaggccaa gctgaagcag aacacttcag agcagtttga cagtggca     900 gtcaagatct ttccctatga ggagtatgcc tcttggaaga cagagaagga catcttctca    960
gacatcaatc tgaagcatga gaacatactc cagttcctga cggctgagga gcggaagacg   1020
gagttgggga acaatactg gctgatcacc gccttccacg ccaagggcaa cctacaggag    1080
tacctgacgc ggcatgtcat cagctgggag gacctgcgca agctgggcag ctccctcgcc   1140
cgggggattg ctcacctcca cagtgatcac actccatgtg ggaggcccaa gatgcccatc   1200
gtgcacaggg acctcaagag ctccaatatc tcgtgaaga cgacctaac ctgctgcctg    1260 tgtgactttg gcttccccct gcgtctggac cctactctgt ctgtggatga cctggctaac   1320
agtgggcagg tgggaactgc aagatacatg gctccagaag tcctagaatc caggatgaat   1380
ttggagaatg ttgagtcctt caagcagacc gatgtctact ccatggctct ggtgctctgg   1440
gaaatgacat ctcgctgtaa tgcagtggga gaagtaaaag attatgagcc tccatttggt   1500
tccaaggtgc gggagcaccc ctgtgtcgaa agcatgaagg acaacgtgtt gagagatcga   1560
gggcgaccag aaattcccag cttctggctc aaccaccagg gcatccagat ggtgtgtgag   1620
acgttgactg agtgctggga ccacgaccca gaggcccgtc tcacagccca gtgtgtggca   1680
gaacgcttca gtgagctgga gcatctggac aggctctcgg ggaggagctg ctcggaggag   1740
aagattcctg aagacggctc cctaaacact accaaa                             1776

<210> SEQ ID NO 203
<211> LENGTH: 507
<212> TYPE: DNA
<213> ORGANISM: Homo sapiens

<400> SEQUENCE: 203
acgatcccac cgcacgttca gaagtcggat gtggaaatgg aggcccagaa agatgaaatc     60
atctgcccca gctgtaatag gactgcccat ccactgagac atattaataa cgacatgata    120
gtcactgaca acaacggtgc agtcaagttt ccacaactgt gtaaattttg tgatgtgaga    180
ttttccacct gtgacaacca gaaatcctgc atgagcaact gcagcatcac ctccatctgt    240
gagaagccac aggaagtctg tgtggctgta tggagaaaga atgacgagaa cataacacta    300
gagacagttt gccatgaccc caagctcccc taccatgact ttattctgga agatgctgct    360
tctccaaagt gcattatgaa ggaaaaaaaa aagcctggtg agactttctt catgtgttcc    420
tgtagctctg atgagtgcaa tgacaacatc atcttctcag aagaatataa caccagcaat    480
cctgacttgt tgctagtcat atttcaa                                         507

<210> SEQ ID NO 204
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gly Arg Cys Lys Ile Arg His Ile Gly Ser Asn Asn Arg Leu Gln Arg
1               5                   10                  15

Ser Thr Cys Gln Asn Thr Gly Trp Glu Ser Ala His Val Met Lys Thr
            20                  25                  30

Pro Gly Phe Arg
        35

<210> SEQ ID NO 205
<211> LENGTH: 3114
<212> TYPE: DNA
<213> ORGANISM: Homo sapiens

<400> SEQUENCE: 205
```

| | | | | |
|---|---|---|---|---|
| atgacttcct | cgctgcagcg | gccctggcgg | gtgccctggc | taccatggac catcctgctg | 60 |
| gtcagcactg | cggctgcttc | gcagaatcaa | gaacggctat | gtgcgtttaa agatccgtat | 120 |
| cagcaagacc | ttgggatagg | tgagagtaga | atctctcatg | aaaatgggac aatattatgc | 180 |
| tcgaaaggta | gcacctgcta | tggcctttgg | gagaaatcaa | aggggacat aaatcttgta | 240 |
| aaacaaggat | gttggtctca | cattggagat | ccccaagagt | gtcactatga gaatgtgta | 300 |
| gtaactacca | ctcctcc ctc | aattcagaat | ggaacatacc | gtttctgctg ttgtagcaca | 360 |
| gatttatgta | atgtcaactt | tactgagaat | tttccacctc | tgacacaac accactcagt | 420 |
| ccacctcatt | catttaaccg | agatgagaca | ataatcattg | ctttggcatc agtctctgta | 480 |
| ttagctgttt | tgatagttgc | cttatgcttt | ggatacagaa | tgttgacagg agaccgtaaa | 540 |
| caaggtcttc | acagtatgaa | catgatggag | gcagcagcat | ccgaaccctc tcttgatcta | 600 |
| gataatctga | aactgttgga | gctgattggc | cgaggtcgat | atggagcagt atataaaggc | 660 |
| tccttggatg | agcgtccagt | tgctgtaaaa | gtgttttcct | ttgcaaaccg tcagaatttt | 720 |
| atcaacgaaa | agaacattta | cagagtgcct | ttgatggaac | atgacaacat tgcccgcttt | 780 |
| atagttggag | atgagagagt | cactgcagat | ggacgcatgg | aatatttgct tgtgatggag | 840 |
| tactatccca | atggatcttt | atgcaagtat | ttaagtctcc | acacaagtga ctgggtaagc | 900 |
| tcttgccgtc | ttgctcattc | tgttactaga | ggactggctt | atcttcacac agaattacca | 960 |
| cgaggagatc | attataaacc | tgcaatttcc | catcgagatt | taaacagcag aaatgtccta | 1020 |
| gtgaaaaatg | atggaacctg | tgttattagt | gactttggac | tgtccatgag ctgactgga | 1080 |
| aatagactgg | tgcgcccagg | ggaggaagat | aatgcagcca | taagcgaggt tggcactatc | 1140 |
| agatatatgg | caccagaagt | gctagaagga | gctgtgaact | tgagggactg tgaatcagct | 1200 |
| ttgaaacaag | tagacatgta | tgctcttgga | ctaatctatt | gggagatatt tatgagatgt | 1260 |
| acagacctct | tcccagggga | atccgtacca | gagtaccaga | tggcttttca gacagaggtt | 1320 |
| ggaaaccatc | ccacttttga | ggatatgcag | gttctcgtgt | ctaggaaaaa acagagaccc | 1380 |
| aagttcccag | aagcctggaa | agaaaatagc | ctggcagtga | ggtcactcaa ggagacaatc | 1440 |
| gaagactgtt | gggaccagga | tgcagaggct | cggcttactg | cacagtgtgc tgaggaaagg | 1500 |
| atggctgaac | ttatgatgat | ttgggaaaga | aacaaatctg | tgagcccaac agtcaatcca | 1560 |
| atgtctactg | ctatgcagaa | tgaacgcaac | ctgtcacata | taggcgtgt gccaaaaatt | 1620 |

```
ggtccttatc cagattattc ttcctcctca tacattgaag actctatcca tcatactgac    1680
agcatcgtga agaatatttc ctctgagcat tctatgtcca gcacacctttt gactataggg    1740 gaaaaaaacc gaaattcaat taactatgaa cgacagcaag cacaagctcg aatccccagc    1800
cctgaaacaa gtgtcaccag cctctccacc aacacaacaa ccacaaacac cacaggactc    1860
acgccaagta ctggcatgac tactatatct gagatgccat acccagatga aacaaatctg    1920
cataccacaa atgttgcaca gtcaattggg ccaaccctg tctgcttaca gctgacagaa    1980
gaagacttgg aaaccaacaa gctagaccca aagaagttg ataagaacct caaggaaagc    2040
tctgatgaga atctcatgga gcactctctt aaacagttca gtggcccaga cccactgagc    2100
agtactagtt ctagcttgct ttacccactc ataaaacttg cagtagaagc aactggacag    2160
caggacttca cacagactgc aaatggccaa gcatgtttga ttcctgatgt tctgcctact    2220
cagatctatc ctctccccaa gcagcagaac cttcccaaga gacctactag tttgccttgg    2280
aacaccaaaa attcaacaaa agagcccgg ctaaaatttg gcagcaagca caaatcaaac    2340
ttgaaacaag tcgaaactgg agttgccaag atgaatacaa tcaatgcagc agaacctcat    2400
gtggtgacag tcaccatgaa tggtgtggca ggtagaaacc acagtgttaa ctcccatgct    2460
gccacaaccc aatatgccaa tgggacagta ctatctggcc aaacaaccaa catagtgaca    2520 catgggccc aagaaatgtt gcagaatcag tttattggtg aggacacccg gctgaatatt    2580
aattccagtc ctgatgagca tgagccttta ctgagacgag agcaacaagc tggccatgat    2640
gaaggtgttc tggatcgtct tgtggacagg agggaacggc cactagaagg tggccgaact    2700
aattccaata caacaacag caatccatgt tcagaacaag atgttcttgc acagggtgtt    2760
ccaagcacag cagcagatcc tgggccatca agcccagaa gagcacagag gcctaattct    2820
ctggatcttt cagccacaaa tgtcctggat ggcagcagta tacagatagg tgagtcaaca    2880
caagatggca atcaggatc aggtgaaaag atcaagaaac gtgtgaaaac tccctattct    2940
cttaagcggt ggcgcccctc cacctgggtc atctccactg aatcgctgga ctgtgaagtc    3000
aacaataatg gcagtaacag ggcagttcat tccaaatcca gcactgctgt ttaccttgca    3060
gaaggaggca ctgctacaac catggtgtct aaagatatag gaatgaactg tctg          3114

<210> SEQ ID NO 206
<211> LENGTH: 372
<212> TYPE: DNA
<213> ORGANISM: Homo sapiens

<400> SEQUENCE: 206
tcgcagaatc aagaacggct atgtgcgttt aaagatccgt atcagcaaga ccttgggata     60
ggtgagagta gaatctctca tgaaaatggg acaatattat gctcgaaagg tagcacctgc    120
tatggccttt gggagaaatc aaaagggac ataaatcttg taaaacaagg atgttggtct    180
cacattggag atccccaaga gtgtcactat gaagaatgtg tagtaactac cactcctccc    240
tcaattcaga atggaacata ccgtttctgc tgttgtagca cagatttatg taatgtcaac    300
tttactgaga attttccacc tcctgacaca acaccactca gtccacctca ttcatttaac    360
cgagatgaga ca                                                         372

<210> SEQ ID NO 207
<211> LENGTH: 1590
<212> TYPE: DNA
<213> ORGANISM: Homo sapiens
```

<400> SEQUENCE: 207

```
atgacttcct cgctgcagcg gccctggcgg gtgccctggc taccatggac catcctgctg    60
gtcagcactg cggctgcttc gcagaatcaa gaacggctat gtgcgtttaa agatccgtat   120
cagcaagacc ttgggatagg tgagagtaga atctctcatg aaaatgggac aatattatgc   180
tcgaaaggta gcacctgcta tggcctttgg gagaaatcaa aaggggacat aaatcttgta   240
aaacaaggat gttggtctca cattggagat ccccaagagt gtcactatga agaatgtgta   300
gtaactacca ctcctccctc aattcagaat ggaacatacc gtttctgctg ttgtagcaca   360
gatttatgta atgtcaactt tactgagaat tttccacctc ctgacacaac accactcagt   420
ccacctcatt catttaaccg agatgagaca ataatcattg ctttggcatc agtctctgta   480
ttagctgttt tgatagttgc cttatgcttt ggatacagaa tgttgacagg agaccgtaaa   540
caaggtcttc acagtatgaa catgatggag gcagcagcat ccgaaccctc tcttgatcta   600
gataatctga aactgttgga gctgattggc cgaggtcgat atggagcagt atataaaggc   660
tccttggatg agcgtccagt tgctgtaaaa gtgttttcct ttgcaaaccg tcagaatttt   720
atcaacgaaa agaacattta cagagtgcct ttgatggaac atgacaacat tgcccgcttt   780
atagttggag atgagagagt cactgcagat ggacgcatgg aatatttgct tgtgatggag   840
tactatccca tggatctttt atgcaagtat ttaagtctcc acacaagtga ctgggtaagc   900
tcttgccgtc ttgctcattc tgttactaga ggactggctt atcttcacac agaattacca   960
cgaggagatc attataaacc tgcaatttcc catcgagatt taaacagcag aaatgtccta  1020
gtgaaaaatg atggaacctg tgttattagt gactttggac tgtccatgag ctgactggaa  1080
aatagactgg tgcgcccagg ggaggaagat aatgcagcca taagcgaggt tggcactatc  1140
agatatatgg caccagaagt gctagaagga gctgtgaact tgagggactg tgaatcagct  1200
ttgaaacaag tagacatgta tgctcttgga ctaatctatt gggagatatt tatgagatgt  1260
acagacctct tcccagggga atccgtacca gagtaccaga tggctttttca gacagaggtt  1320
ggaaaccatc ccacttttga ggatatgcag gttctcgtgt ctagggaaaa acagagaccc  1380
aagttcccag aagcctggaa agaaaatagc ctggcagtga ggtcactcaa ggagacaatc  1440
gaagactgtt gggaccagga tgcagaggct cggcttactg cacagtgtgc tgaggaaagg  1500
atggctgaac ttatgatgat ttgggaaaga aacaaatctg tgagcccaac agtcaatcca  1560
atgtctactg ctatgcagaa tgaacgtagg                                   1590
```

<210> SEQ ID NO 208
<211> LENGTH: 372
<212> TYPE: DNA
<213> ORGANISM: Homo sapiens

<400> SEQUENCE: 208

```
tcgcagaatc aagaacggct atgtgcgttt aaagatccgt atcagcaaga ccttgggata    60
ggtgagagta gaatctctca tgaaaatggg acaatattat gctcgaaagg tagcacctgc   120
tatggccttt gggagaaatc aaaaggggac ataaatcttg taaaacaagg atgttggtct   180
cacattggag atccccaaga gtgtcactat gaagaatgtg tagtaactac cactcctccc   240
tcaattcaga atggaacata ccgtttctgc tgttgtagca cagatttatg taatgtcaac   300
tttactgaga attttccacc tcctgacaca acaccactca gtccacctca ttcatttaac   360
cgagatgaga ca                                                       372
```

<210> SEQ ID NO 209
<211> LENGTH: 1719
<212> TYPE: DNA
<213> ORGANISM: Homo sapiens

<400> SEQUENCE: 209

| | | | | | |
|---|---|---|---|---|---|
| atgctagggt | ctttggggct | ttgggcatta | cttcccacag | ctgtggaagc | acccccaaac | 60 |
| aggcgaacct | gtgtgttctt | tgaggcccct | ggagtgcggg | gaagcacaaa | gacactggga | 120 |
| gagctgctag | atacaggcac | agagctcccc | agagctatcc | gctgcctcta | cagccgctgc | 180 |
| tgctttggga | tctggaacct | gacccaagac | cgggcacagg | tggaaatgca | aggatgccga | 240 |
| gacagtgatg | agccaggctg | tgagtccctc | cactgtgacc | caagtccccg | agcccacccc | 300 |
| agccctggct | ccactctctt | cacctgctcc | tgtggcactg | acttctgcaa | tgccaattac | 360 |
| agccatctgc | ctcctccagg | gagccctggg | actcctggct | cccagggtcc | ccaggctgcc | 420 |
| ccaggtgagt | ccatctggat | ggcactggtg | ctgctggggc | tgttcctcct | cctcctgctg | 480 |
| ctgctgggca | gcatcatctt | ggccctgcta | cagcgaaaga | actacagagt | gcgaggtgag | 540 |
| ccagtgccag | agccaaggcc | agactcaggc | agggactgga | gtgtggagct | gcaggagctg | 600 |
| cctgagctgt | gtttctccca | ggtaatccgg | gaaggaggtc | atgcagtggt | ttgggccggg | 660 |
| cagctgcaag | gaaaactggt | tgccatcaag | gccttccac | cgaggtctgt | ggctcagttc | 720 |
| caagctgaga | gagcattgta | cgaacttcca | ggcctacagc | acgaccacat | tgtccgattt | 780 |
| atcactgcca | gccggggggg | tcctggccgc | ctgctctctg | ggcccctgct | ggtactggaa | 840 |
| ctgcatccca | agggctccct | gtgccactac | ttgacccagt | acaccagtga | ctggggaagt | 900 |
| tccctgcgga | tggcactgtc | cctggcccag | ggcctggcat | ttctccatga | ggagcgctgg | 960 |
| cagaatggcc | aatataaacc | aggtattgcc | caccgagatc | tgagcagcca | gaatgtgctc | 1020 |
| attcgggaag | atggatcgtg | tgccattgga | gacctgggcc | ttgccttggt | gctccctggc | 1080 |
| ctcactcagc | ccctgcctg | gacccctact | caaccacaag | gcccagctgc | catcatggaa | 1140 |
| gctggcaccc | agaggtacat | ggcaccagag | ctcttggaca | agactctgga | cctacaggat | 1200 |
| tgggcatgg | ccctccgacg | agctgatatt | tactcttgg | ctctgctcct | gtgggagata | 1260 |
| ctgagccgct | gcccagattt | gaggcctgac | agcagtccac | cacccttcca | actggcctat | 1320 |
| gaggcagaac | tggcaatac | ccctacctct | gatgagctat | gggccttggc | agtgcaggag | 1380 |
| aggaggcgtc | cctacatccc | atccacctgg | cgctgctttg | ccacagaccc | tgatgggctg | 1440 |
| agggagctcc | tagaagactg | ttgggatgca | gacccagaag | cacggctgac | agctgagtgt | 1500 |
| gtacagcagc | gcctggctgc | cttggcccat | cctcaagaga | gccacccctt | ccagagagc | 1560 |
| tgtccacgtg | gctgcccacc | tctctgccca | gaagactgta | cttcaattcc | tgcccctacc | 1620 |
| atcctcccct | gtaggcctca | gcggagtgcc | tgccacttca | gcgttcagca | aggcccttgt | 1680 |
| tccaggaatc | ctcagcctgc | ctgtaccctt | tctcctgtg | | | 1719 |

<210> SEQ ID NO 210
<211> LENGTH: 396
<212> TYPE: DNA
<213> ORGANISM: Homo sapiens

<400> SEQUENCE: 210

| | | | | | |
|---|---|---|---|---|---|
| cccccaaaca | ggcgaacctg | tgtgttcttt | gaggcccctg | gagtgcgggg | aagcacaaag | 60 |
| acactgggag | agctgctaga | tacaggcaca | gagctcccca | gagctatccg | ctgcctctac | 120 |
| agccgctgct | gctttgggat | ctggaacctg | acccaagacc | gggcacaggt | ggaaatgcaa | 180 |

```
ggatgccgag acagtgatga gccaggctgt gagtccctcc actgtgaccc aagtccccga    240
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg gcactg                              396
```

<210> SEQ ID NO 211
<211> LENGTH: 1434
<212> TYPE: DNA
<213> ORGANISM: Homo sapiens

<400> SEQUENCE: 211

```
atgctagggt ctttggggct ttgggcatta cttcccacag ctgtggaagc accccccaaac   60 aggcgaacct gtgtgttctt tgaggcccct ggagtgcggg aagcacaaa gacactggga    120 gagctgctag atacaggcac agagctcccc agagctatcc gctgcctcta cagccgctgc   180
tgctttggga tctggaacct gacccaagac cgggcacagg tggaaatgca aggatgccga   240
gacagtgatg agccaggctg tgagtccctc cactgtgacc caagtcccg agcccacccc   300 agccctggct ccactctctt cacctgctcc tgtggcactg acttctgcaa tgccaattac   360
agccatctgc ctcctccagg gagccctggg actcctggct cccagggtcc ccaggctgcc   420
ccaggtgagt ccatctggat ggcactggtg ctgctgggc tgttcctcct cctcctgctg   480
ctgctgggca gcatcatctt ggccctgcta cagcgaaaga actacagagt gcgaggtgag   540
ccagtgccag agccaaggcc agactcaggc agggactgga gtgtggagct gcaggagctg   600
cctgagctgt gtttctccca ggtaatccgg gaaggaggtc atgcagtggt ttgggccggg   660
cagctgcaag gaaaactggt tgccatcaag gccttcccac cgaggtctgt ggctcagttc   720
caagctgaga gagcattgta cgaacttcca ggcctacagc acgaccacat tgtccgattt   780
atcactgcca gccgggggg tcctggccgc ctgctctctg gcccctgct ggtactggaa   840 ctgcatccca agggctccct gtgccactac ttgacccagt acaccagtga ctggggaagt   900
tccctgcgga tggcactgtc cctggcccag gcctggcat ttctccatga ggagcgctgg   960
cagaatggcc aatataaacc aggtattgcc caccgagatc tgagcagcca gaatgtgctc   1020
attcgggaag atgatcgtg tgccattgga gacctgggcc ttgccttggt gctccctggc   1080
ctcactcagc cccctgcctg gacccctact caaccacaag gcccagctgc catcatggaa   1140
gctggcaccc agaggtacat ggaccagag ctcttggaca gactctgga cctacaggat   1200 tggggcatgg ccctccgacg agctgatatt tactctttgg ctctgctcct gtgggagata   1260
ctgagccgct gcccagattt gaggcctgca gtccaccacc cttccaactg gcctatgagg   1320
cagaactggg caatacccct acctctgatg agctatgggc cttggcagtg caggagagga   1380
ggcgtcccta catcccatcc acctggcgct gctttgccac agaccctgat gggc         1434
```

<210> SEQ ID NO 212
<211> LENGTH: 396
<212> TYPE: DNA
<213> ORGANISM: Homo sapiens

<400> SEQUENCE: 212

```
cccccaaaca ggcgaacctg tgtgttcttt gaggcccctg gagtgcgggg aagcacaaag    60
acactgggag agctgctaga tacaggcaca gagctcccca gagctatccg ctgcctctac   120
agccgctgct gctttgggat ctggaacctg acccaagacc gggcacaggt ggaaatgcaa   180
ggatgccgag acagtgatga gccaggctgt gagtccctcc actgtgaccc aagtccccga   240
```

```
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg gcactg                              396
```

<210> SEQ ID NO 213
<211> LENGTH: 1434
<212> TYPE: DNA
<213> ORGANISM: Homo sapiens

<400> SEQUENCE: 213

```
atgctagggt cttttggggct ttgggcatta cttcccacag ctgtggaagc accccccaaac    60 aggcgaacct gtgtgttctt tgaggcccct ggagtgcggg aagcacaaa gacactggga    120 gagctgctag atacaggcac agagctcccc gagctatcc gctgcctcta cagccgctgc    180
tgctttggga tctggaacct gacccaagac cgggcacagg tggaaatgca aggatgccga    240
gacagtgatg agccaggctg tgagtccctc cactgtgacc caagtcccg agcccacccc    300 agccctggct ccactctctt cacctgctcc tgtggcactg acttctgcaa tgccaattac    360
agccatctgc ctcctccagg gagccctggg actcctggct cccagggtcc ccaggctgcc    420
ccaggtgagt ccatctggat ggcactggtg ctgctgggc tgttcctcct cctcctgctg    480
ctgctgggca gcatcatctt ggccctgcta cagcgaaaga actacagagt gcgaggtgag    540
ccagtgccag agccaaggcc agactcaggc agggactgga gtgtggagct gcaggagctg    600
cctgagctgt gtttctccca ggtaatccgg aaggaggtc atgcagtggt ttgggccggg    660
cagctgcaag gaaaactggt tgccatcaag gccttccac cgaggtctgt ggctcagttc    720
caagctgaga gagcattgta cgaacttcca ggcctacagc acgaccacat tgtccgattt    780
atcactgcca gccggggggg tcctggccgc ctgctctctg ggcccctgct ggtactggaa    840
ctgcatccca agggctccct gtgccactac ttgacccagt acaccagtga ctggggaagt    900
tccctgcgga tggcactgtc cctggcccag ggcctggcat ttctccatga ggagcgctgg    960
cagaatggcc aatataaacc aggtattgcc caccgagatc tgagcagcca gaatgtgctc   1020
attcgggaag atgatcgtg tgccattgga gacctgggcc ttgccttggt gctccctggc   1080
ctcactcagc ccctgcctg gacccctact caaccacaag gcccagctgc catcatggaa   1140
gaccctgatg ggctgaggga gctcctagaa gactgttggg atgcagaccc agaagcacgg   1200
ctgacagctg agtgtgtaca gcagcgcctg gctgccttgg cccatcctca agagagccac   1260 cccttttccag agagctgtcc acgtggctgc ccacctctct gccagaaga ctgtacttca   1320 attcctgccc ctaccatcct cccctgtagg cctcagcgga gtgcctgcca cttcagcgtt   1380
cagcaaggcc cttgttccag gaatcctcag cctgcctgta ccctttctcc tgtg         1434
```

<210> SEQ ID NO 214
<211> LENGTH: 396
<212> TYPE: DNA
<213> ORGANISM: Homo sapiens

<400> SEQUENCE: 214

```
cccccaaaca ggcgaacctg tgtgttcttt gaggcccctg gagtgcgggg aagcacaaag    60
acactgggag agctgctaga tacaggcaca gagctcccca gagctatccg ctgcctctac   120
agccgctgct gctttgggat ctggaacctg acccaagacc gggcacaggt ggaaatgcaa   180
ggatgccgag acagtgatga gccaggctgt gagtccctcc actgtgaccc aagtcccga   240
```

```
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg gcactg                              396

<210> SEQ ID NO 215
<211> LENGTH: 1509
<212> TYPE: DNA
<213> ORGANISM: Homo sapiens

<400> SEQUENCE: 215
atgaccttgg gctcccccag gaaaggcctt ctgatgctgc tgatggcctt ggtgacccag     60
ggagaccctg tgaagccgtc tcggggcccg ctggtgacct gcacgtgtga gagcccacat    120 tgcaagggc ctacctgccg gggggcctgg tgcacagtag tgctggtgcg ggaggagggg     180
aggcaccccc aggaacatcg gggctgcggg aacttgcaca gggagctctg caggggcgc    240 cccaccgagt tcgtcaacca ctactgctgc gacagccacc tctgcaacca caacgtgtcc    300
ctggtgctgg aggccaccca acctccttcg gagcagccgg aacagatgg ccagctggcc     360 ctgatcctgg gccccgtgct ggccttgctg gccctggtgg ccctgggtgt cctgggcctg    420
tggcatgtcc gacggaggca ggagaagcag cgtggcctgc acagcgagct gggagagtcc    480
agtctcatcc tgaaagcatc tgagcagggc gacagcatgt tggggaccct cctggacagt    540
gactgcacca caggggagtgg ctcagggctc cccttcctgg tgcagaggac agtggcacgg    600
caggttgcct tggtggagtg tgtgggaaaa ggccgctatg gcgaagtgtg gcggggcttg    660
tggcacggtg agagtgtggc cgtcaagatc ttctcctcga gggatgaaca gtcctggttc    720
cgggagactg agatctataa cacagtgttg ctcagacacg acaacatcct aggcttcatc    780
gcctcagaca tgacctcccg caactcgagc acgcagctgt ggctcatcac gcactaccac    840
gagcacggct ccctctacga ctttctgcag agacagacgc tggagcccca tctggctctg    900
aggctagctg tgtccgcggc atgcggcctg gcgcacctgc acgtggagat cttcggtaca    960
cagggcaaac cagccattgc ccaccgcgac ttcaagagcc gcaatgtgct ggtcaagagc    1020
aacctgcagt gttgcatcgc cgacctgggc ctggctgtga tgcactcaca gggcagcgat   1080
tacctggaca tcggcaacaa cccgagagtg gcaccaagc ggtacatggc acccgaggtg   1140
ctggacgagc agatccgcac ggactgcttt gagtcctaca gtggactga catctgggcc    1200 tttggcctgg tgctgtggga gattgcccgc ggaccatcg tgaatggcat cgtggaggac    1260
tatagaccac ccttctatga tgtggtgccc aatgacccca gctttgagga catgaagaag    1320
gtggtgtgtg tggatcagca gacccccacc atccctaacc ggctggctgc agacccggtc    1380
ctctcaggcc tagctcagat gatgcgggag tgctggtacc caaaccctc tgcccgactc    1440 accgcgctgc ggatcaagaa gacactacaa aaaattagca acagtccaga gaagcctaaa    1500
gtgattcaa                                                           1509

<210> SEQ ID NO 216
<211> LENGTH: 291
<212> TYPE: DNA
<213> ORGANISM: Homo sapiens

<400> SEQUENCE: 216
gaccctgtga agccgtctcg gggcccgctg gtgacctgca cgtgtgagag cccacattgc     60
aaggggccta cctgccgggg ggcctggtgc acagtagtgc tggtgcggga ggaggggagg    120 caccccagg aacatcgggg ctgcgggaac ttgcagggg agctctgcag gggcgcccc      180
```

```
accgagttcg tcaaccacta ctgctgcgac agccacctct gcaaccacaa cgtgtccctg    240
gtgctggagg ccacccaacc tccttcggag cagccgggaa cagatggcca g             291

<210> SEQ ID NO 217
<211> LENGTH: 1527
<212> TYPE: DNA
<213> ORGANISM: Homo sapiens

<400> SEQUENCE: 217
atggtagatg gagtgatgat tcttcctgtg cttatcatga ttgctctccc ctcccctagt     60
atggaagatg agaagcccaa ggtcaacccc aaactctaca tgtgtgtgtg tgaaggtctc    120
tcctgcggta atgaggacca ctgtgaaggc cagcagtgct tttcctcact gagcatcaac    180
gatggcttcc acgtctacca gaaaggctgc ttccaggttt atgagcaggg aaagatgacc    240
tgtaagaccc cgccgtcccc tggccaagcc gtggagtgct gccaagggga ctggtgtaac    300
aggaacatca cggcccagct gcccactaaa ggaaaatcct tccctggaac acagaatttc    360
cacttggagg ttggcctcat tattctctct gtagtgttcg cagtatgtct tttagcctgc    420
ctgctgggag ttgctctccg aaaatttaaa aggcgcaacc aagaacgcct caatccccga    480
gacgtggagt atggcactat cgaagggctc atcaccacca atgttggaga cagcacttta    540
gcagatttat tggatcattc gtgtacatca ggaagtggcc tggtcttcc ttttctggta     600 caaagaacag tggctcgcca gattacactg ttggagtgtg tcgggaaagg caggtatggt    660
gaggtgtgga ggggcagctg gcaaggggag aatgttgccg tgaagatctt ctcctcccgt    720
gatgagaagt catggttcag ggaaacggaa ttgtacaaca ctgtgatgct gaggcatgaa    780
aatatcttag gtttcattgc ttcagacatg acatcaagac actccagtac ccagctgtgg    840
ttaattacac attatcatga aatgggatcg ttgtacgact atcttcagct tactactctg    900
gatacagtta gctgccttcg aatagtgctg tccatagcta gtggtcttgc acatttgcac    960
atagagatat ttgggaccca agggaaacca gccattgccc atcgagattt aaagagcaaa   1020
aatattctgg ttaagaagaa tggacagtgt gcatagcag atttgggcct ggcagtcatg   1080
cattcccaga gcaccaatca gcttgatgtg gggaacaatc ccgtgtggg caccaagcgc   1140 tacatggccc ccgaagttct agatgaaacc atccaggtgg attgtttcga ttcttataaa   1200
agggtcgata tttgggcctt tggacttgtt ttgtgggaag tggccaggcg gatggtgagc   1260
aatggtatag tggaggatta caagccaccg ttctacgatg tggttcccaa tgacccaagt   1320
tttgaagata tgaggaaggt agtctgtgtg gatcaacaaa ggccaaacat acccaacaga   1380
tggttctcag acccgacatt aacctctctg gccaagctaa tgaaagaatg ctggtatcaa   1440
aatccatccg caagactcac agcactgcgt atcaaaaaga cttgaccaa aattgataat    1500 tccctcgaca aattgaaaac tgactgt                                         1527

<210> SEQ ID NO 218
<211> LENGTH: 309
<212> TYPE: DNA
<213> ORGANISM: Homo sapiens

<400> SEQUENCE: 218
atggaagatg agaagcccaa ggtcaacccc aaactctaca tgtgtgtgtg tgaaggtctc     60
tcctgcggta atgaggacca ctgtgaaggc cagcagtgct tttcctcact gagcatcaac    120
gatggcttcc acgtctacca gaaaggctgc ttccaggttt atgagcaggg aaagatgacc    180
```

| | |
|---|---|
| tgtaagaccc cgccgtcccc tggccaagcc gtggagtgct gccaagggga ctggtgtaac | 240 |
| aggaacatca cggcccagct gcccactaaa ggaaaatcct tccctggaac acagaatttc | 300 |
| cacttggag | 309 |

<210> SEQ ID NO 219
<211> LENGTH: 1596
<212> TYPE: DNA
<213> ORGANISM: Homo sapiens

<400> SEQUENCE: 219

| | |
|---|---|
| atgcctcagc tatacattta catcagatta ttgggagcct atttgttcat catttctcgt | 60 |
| gttcaaggac agaatctgga tagtatgctt catggcactg ggatgaaatc agactccgac | 120 |
| cagaaaaagt cagaaaatgg agtaacctta gcaccagagg ataccttgcc tttttttaaag | 180 |
| tgctattgct cagggcactg tccagatgat gctattaata acacatgcat aactaatgga | 240 |
| cattgctttg ccatcataga agaagatgac cagggagaaa ccacattagc ttcagggtgt | 300 |
| atgaaatatg aaggatctga ttttcagtgc aaagattctc aaaagcccca gctacgccgg | 360 |
| acaatagaat gttgtcggac caatttatgt aaccagtatt gcaacccac actgcccct | 420 |
| gttgtcatag gtccgttttt tgatggcagc attcgatggc tggttttgct catttctatg | 480 |
| gctgtctgca taattgctat gatcatcttc tccagctgct tttgttacaa acattattgc | 540 |
| aagagcatct caagcagacg tcgttacaat cgtgatttgg aacaggatga agcatttatt | 600 |
| ccagttggag aatcactaaa agaccttatt gaccagtcac aaagttctgg tagtgggtct | 660 |
| ggactacctt tattggttca gcgaactatt gccaaacaga ttcagatggt ccggcaagtt | 720 |
| ggtaaaggcc gatatggaga agtatggatg gcaaatggc gtggcgaaaa agtggcggtg | 780 |
| aaagtattct ttaccactga agaagccagc tggtttcgag aaacagaaat ctaccaaact | 840 |
| gtgctaatgc gccatgaaaa catacttggt ttcatagcgg cagacattaa aggtacaggt | 900 |
| tcctggactc agctctatt gattactgat taccatgaaa atggatctct ctatgacttc | 960 |
| ctgaaatgtg ctacactgga caccagagcc ctgcttaaat tggcttattc agctgcctgt | 1020 |
| ggtctgtgcc acctgcacac agaaattat ggcacccaag aaagcccgc aattgctcat | 1080 |
| cgagacctaa agagcaaaaa catcctcatc aagaaaaatg ggagttgctg cattgctgac | 1140 |
| ctgggccttg ctgttaaatt caacagtgac acaaatgaag ttgatgtgcc cttgaatacc | 1200 |
| agggtgggca ccaaacgcta catggctccc gaagtgctgg acgaaagcct gaacaaaaac | 1260 |
| cacttccagc cctacatcat ggctgacatc tacagcttcg gcctaatcat ttgggagatg | 1320 |
| gctcgtcgtt gtatcacagg agggatcgtg aagaatacc aattgccata ttacaacatg | 1380 |
| gtaccgagtg atccgtcata cgaagatatg cgtgaggttg tgtgtgtcaa acgtttgcgg | 1440 |
| ccaattgtgt ctaatcggtg aacagtgat gaatgtctac gagcagtttt gaagctaatg | 1500 |
| tcagaatgct gggcccacaa tccagcctcc agactcacag cattgagaat taagaagacg | 1560 |
| cttgccaaga tggttgaatc ccaagatgta aaaatc | 1596 |

<210> SEQ ID NO 220
<211> LENGTH: 387
<212> TYPE: DNA
<213> ORGANISM: Homo sapiens

<400> SEQUENCE: 220

| | |
|---|---|
| cagaatctgg atagtatgct tcatggcact gggatgaaat cagactccga ccagaaaaag | 60 |
| tcagaaaatg gagtaacctt agcaccagag gataccttgc ctttttttaaa gtgctattgc | 120 |

```
tcagggcact gtccagatga tgctattaat aacacatgca taactaatgg acattgcttt      180
gccatcatag aagaagatga ccagggagaa accacattag cttcagggtg tatgaaatat      240
gaaggatctg attttcagtg caaagattct ccaaaagccc agctacgccg acaatagaa       300 tgttgtcgga ccaatttatg taaccagtat ttgcaaccca cactgccccc tgttgtcata      360
ggtccgtttt tgatggcag cattcga                                           387
```

<210> SEQ ID NO 221
<211> LENGTH: 1515
<212> TYPE: DNA
<213> ORGANISM: Homo sapiens

<400> SEQUENCE: 221

```
atggcggagt cggccggagc ctcctccttc ttcccccttg ttgtcctcct gctcgccggc       60
agcggcgggt ccgggccccg gggggtccag gctctgctgt gtgcgtgcac cagctgcctc     120
caggccaact acacgtgtga gacagatggg gcctgcatgg tttccatttt caatctggat     180
gggatggagc accatgtgcg cacctgcatc cccaaagtgg agctggtccc tgccgggaag     240
cccttctact gcctgagctc ggaggacctg cgcaacaccc actgctgcta cactgactac     300
tgcaacagga tcgacttgag ggtgcccagt ggtcacctca aggagcctga gcacccgtcc     360
atgtggggcc cggtggagct ggtaggcatc atcgccggcc cggtgttcct cctgttcctc     420
atcatcatca ttgtttttcct tgtcattaac tatcatcagc gtgtctatca aaccgccag     480 agactggaca tggaagatcc ctcatgtgag atgtgtctct ccaaagacaa gacgctccag     540
gatcttgtct acgatctctc cacctcaggg tctggctcag ggttacccct ctttgtccag     600
cgcacagtgg cccgaaccat cgttttacaa gagattattg caagggtcg gtttggggaa     660 gtatggcggg gccgctggag gggtggtgat gtggctgtga aaatattctc ttctcgtgaa     720
gaacggtctt ggttcaggga agcagagata taccagacgg tcatgctgcg ccatgaaaac     780
atccttggat ttattgctgc tgacaataaa gataatggca cctggacaca gctgtggctt     840
gtttctgact atcatgagca cgggtccctg tttgattatc tgaaccggta cacagtgaca     900
attgagggga tgattaagct ggccttgtct gctgctagtg ggctggcaca cctgcacatg     960
gagatcgtgg gcacccaagg gaagcctgga attgctcatc gagacttaaa gtcaaagaac    1020
attctggtga agaaaatgg catgtgtgcc atagcagacc tgggcctggc tgtccgtcat    1080
gatgcagtca ctgacaccat tgacattgcc ccgaatcaga gggtggggac caaacgatac    1140
atggcccctg aagtacttga tgaaaccatt aatatgaaac actttgactc ctttaaatgt    1200
gctgatattt atgccctcgg gcttgtatat tgggagattg ctcgaagatg caattctgga    1260
ggagtccatg aagaatatca gctgccatat tacgacttag tgccctctga cccttccatt    1320
gaggaaatgc gaaaggttgt atgtgatcag aagctgcgtc caacatccc caactggtgg    1380 cagagttatg aggcactgcg ggtgatgggg aagatgatgc gagagtgttg gtatgccaac    1440
ggcgcagccc gcctgacggc cctgcgcatc aagaagaccc tctcccagct cagcgtgcag    1500
gaagacgtga agatc                                                     1515
```

<210> SEQ ID NO 222
<211> LENGTH: 309
<212> TYPE: DNA
<213> ORGANISM: Homo sapiens

<400> SEQUENCE: 222

```
tccgggcccc gggggtcca ggctctgctg tgtgcgtgca ccagctgcct ccaggccaac      60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180
tgcctgagct cggaggacct cgcaacaccc actgctgct acactgacta ctgcaacagg     240
atcgacttga gggtgcccag tggtcacctc aaggagcctg agcaccgtc catgtggggc     300 ccggtggag                                                            309
```

\<210\> SEQ ID NO 223
\<211\> LENGTH: 1638
\<212\> TYPE: DNA
\<213\> ORGANISM: Homo sapiens

\<400\> SEQUENCE: 223

```
atggcggagt cggccggagc ctcctccttc ttccccttg ttgtcctcct gctcgccggc      60
agcggcgggt ccgggccccg gggggtccag gctctgctgt gtgcgtgcac cagctgcctc    120
caggccaact acacgtgtga gacagatggg gcctgcatgg tttccatttt caatctggat    180
gggatggagc accatgtgcg cacctgcatc cccaaagtgg agctggtccc tgccgggaag    240
cccttctact gcctgagctc ggaggacctg cgcaacaccc actgctgcta cactgactac    300
tgcaacagga tcgacttgag ggtgcccagt ggtcacctca aggagcctga gcaccgtcc    360 atgtggggcc cggtggagct ggtaggcatc atcgccggcc cggtgttcct cctgttcctc    420
atcatcatca ttgttttcct tgtcattaac tatcatcagc gtgtctatca aaccgccag     480 agactggaca tggaagatcc ctcatgtgag atgtgtctct ccaaagacaa gacgctccag    540
gatcttgtct acgatctctc cacctcaggg tctggctcag ggttacccct ctttgtccag    600
cgcacagtgg cccgaaccat cgttttacaa gagattattg caagggtcg gtttggggaa    660 gtatggcggg ccgctggag gggtggtgat gtggctgtga aaatattctc ttctcgtgaa    720
gaacggtctt ggttcaggga agcagagata taccagacgg tcatgctgcg ccatgaaaac    780
atccttggat ttattgctgc tgacaataaa gcagactgct cattcctcac attgccatgg    840
gaagttgtaa tggtctctgc tgcccccaag ctgaggagcc ttagactcca atacaaggga    900 ggaagggaa gagcaagatt tttattccca ctgaataatg gcacctggac acagctgtgg    960
cttgtttctg actatcatga gcacgggtcc ctgtttgatt atctgaaccg gtacacagtg   1020
acaattgagg ggatgattaa gctggccttg tctgctgcta gtgggctggc acacctgcac   1080
atggagatcg tgggcaccca agggaagcct ggaattgctc atcgagactt aaagtcaaag   1140
aacattctgg tgaagaaaaa tggcatgtgt gccatagcag acctgggcct ggctgtccgt   1200
catgatgcag tcactgacac cattgacatt gccccgaatc agagggtggg gaccaaacga   1260
tacatggccc ctgaagtact tgatgaaacc attaatatga acactttga ctccttaaa    1320 tgtgctgata tttatgccct cgggcttgta tattgggaga ttgctcgaag atgcaattct   1380
ggaggagtcc atgaagaata tcagctgcca tattacgact agtgccctc tgacccttcc    1440 attgaggaaa tgcgaaaggt tgtatgtgat cagaagctgc gtcccaacat ccccaactgg   1500
tggcagagtt atgaggcact gcgggtgatg gggaagatga tgcgagagtg ttggtatgcc   1560 aacgcgcag cccgcctgac ggccctgcgc atcaagaaga ccctctccca gctcagcgtg   1620
caggaagacg tgaagatc                                                 1638
```

\<210\> SEQ ID NO 224
\<211\> LENGTH: 309

```
<212> TYPE: DNA
<213> ORGANISM: Homo sapiens

<400> SEQUENCE: 224
tccgggcccc gggggtcca ggctctgctg tgtgcgtgca ccagctgcct ccaggccaac      60
tacacgtgtg agacagatgg ggcctgcatg gtttccattt tcaatctgga tgggatggag     120
caccatgtgc gcacctgcat ccccaaagtg gagctggtcc ctgccgggaa gcccttctac    180
tgcctgagct cggaggacct cgcaacacc cactgctgct acactgacta ctgcaacagg     240
atcgacttga gggtgcccag tggtcacctc aaggagcctg agcacccgtc catgtggggc    300
ccggtggag                                                             309

<210> SEQ ID NO 225
<211> LENGTH: 1509
<212> TYPE: DNA
<213> ORGANISM: Homo sapiens

<400> SEQUENCE: 225
atggaggcgg cggtcgctgc tccgcgtccc cggctgctcc tcctcgtgct ggcggcggcg      60 gcggcggcg cggcggcgct gctcccgggg gcgacggcgt acagtgtttt ctgccacctc     120
tgtacaaaag acaattttac ttgtgtgaca gatgggctct gctttgtctc tgtcacagag    180
accacagaca aagttataca caacagcatg tgtatagctg aaattgactt aattcctcga    240
gataggccgt ttgtatgtgc accctcttca aaaactgggt ctgtgactac aacatattgc    300
tgcaatcagg accattgcaa taaaatagaa cttccaacta ctgtaaagtc atcacctggc    360
cttggtcctg tggaactggc agctgtcatt gctggaccag tgtgcttcgt ctgcatctca    420
ctcatgttga tggtctatat ctgccacaac cgcactgtca ttcaccatcg agtgccaaat    480
gaagaggacc cttcattaga tcgccctttt atttcagagg gtactacgtt gaaagactta    540
atttatgata tgcaacgtc aggttctggc tcaggtttac cattgcttgt tcagagaaca    600
attgcgagaa ctattgtgtt acaagaaagc attggcaaag gtcgatttgg agaagtttgg    660
agaggaaagt ggcggggaga agaagttgct gttaagatat ctcctctcag aagaacgt     720 tcgtggttcc gtgaggcaga gatttatcaa actgtaatgt tacgtcatga aaacatcctg    780 ggattttatag cagcagacaa taagacaat ggtacttgga ctcagctctg gttggtgtca    840
gattatcatg agcatggatc cctttttgat tacttaaaca gatacacagt tactgtggaa    900
ggaatgataa aacttgctct gtccacggcg agcggtcttg cccatcttca catggagatt    960
gttggtaccc aaggaaagcc agccattgct catagagatt tgaaatcaaa gaatatcttg   1020
gtaaagaaga atggaacttg ctgtattgca gacttaggac tggcagtaag acatgattca   1080
gccacagata ccattgatat tgctccaaac cacagagtgg gaacaaaaag gtacatggcc   1140
cctgaagttc tcgatgattc cataaatatg aaacattttg aatccttcaa acgtgctgac   1200
atctatgcaa tgggcttagt attctgggaa attgctcgac gatgttccat tggtggaatt   1260
catgaagatt accaactgcc ttattatgat cttgtaccct ctgacccatc agttgaagaa   1320
atgagaaaag ttgtttgtga acagaagtta aggccaaata tcccaaacag atggcagagc   1380
tgtgaagcct tgagagtaat ggctaaaatt atgagagaat gttggtatgc caatgagca    1440 gctaggctta cagcattgcg gattaagaaa acattatcgc aactcagtca acaggaaggc   1500
atcaaaatg                                                           1509

<210> SEQ ID NO 226
```

```
<211> LENGTH: 306
<212> TYPE: DNA
<213> ORGANISM: Homo sapiens

<400> SEQUENCE: 226
gcggcgctgc tcccgggggc gacggcgtta cagtgtttct gccacctctg tacaaaagac      60
aattttactt gtgtgacaga tgggctctgc tttgtctctg tcacagagac cacagacaaa     120
gttatacaca acagcatgtg tatagctgaa attgacttaa ttcctcgaga taggccgttt     180
gtatgtgcac cctcttcaaa aactgggtct gtgactacaa catattgctg caatcaggac     240
cattgcaata aaatagaact tccaactact gtaaagtcat cacctggcct tggtcctgtg     300
gaactg                                                                306

<210> SEQ ID NO 227
<211> LENGTH: 1521
<212> TYPE: DNA
<213> ORGANISM: Homo sapiens

<400> SEQUENCE: 227
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca agttatacac aacagcatgt gtatagctg aaattgactt aattcctcga     240
gataggccgt ttgtatgtgc accctcttca aaaactgggt ctgtgactac aacatattgc     300
tgcaatcagg accattgcaa taaaatagaa cttccaacta ctggcccttt ttcagtaaag     360
tcatcacctg gccttggtcc tgtggaactg gcagctgtca ttgctggacc agtgtgcttc     420
gtctgcatct cactcatgtt gatggtctat atctgccaca accgcactgt cattcaccat     480
cgagtgccaa atgaagagga ccctttcatta gatcgccctt ttatttcaga gggtactacg     540
ttgaaagact taatttatga tatgacaacg tcaggttctg gctcaggttt accattgctt     600
gttcagagaa caattgcgag aactattgtg ttacaagaaa gcattggcaa aggtcgattt     660
ggagaagttt ggagaggaaa gtggcgggga aagaagttg ctgttaagat attctcctct     720
agagaagaac gttcgtggtt ccgtgaggca gagatttatc aaactgtaat gttacgtcat     780
gaaaacatcc tgggatttat agcagcagac aataaagaca tggtacttg gactcagctc     840 tggttggtgt cagattatca tgagcatgga tccctttttg attacttaaa cagatacaca     900
gttactgtgg aaggaatgat aaaacttgct ctgtccacgg cgagcggtct tgcccatctt     960
cacatggaga ttgttggtac ccaaggaaag ccagccattg ctcatagaga tttgaaatca    1020
aagaatatct tggtaaagaa gaatggaact tgctgtattg cagacttagg actggcagta    1080
agacatgatt cagccacaga taccattgat attgctccaa accacagagt gggaacaaaa    1140
aggtacatgg cccctgaagt tctcgatgat tccataaata tgaaacattt tgaatccttc    1200
aaacgtgctg acatctatgc aatgggctta gtattctggg aaattgctcg acgatgttcc    1260
attggtggaa ttcatgaaga ttaccaactg ccttattatg atcttgtacc ttctgaccca    1320
tcagttgaag aaatgagaaa agttgtttgt gaacagaagt taaggccaaa tatcccaaac    1380
agatggcaga gctgtgaagc cttgagagta atggctaaaa ttatgagaga atgttggtat    1440
gccaatggag cagctaggct tacagcattg cggattaaga aacattatc gcaactcagt    1500 caacaggaag gcatcaaaat g                                              1521
```

```
<210> SEQ ID NO 228
<211> LENGTH: 318
<212> TYPE: DNA
<213> ORGANISM: Homo sapiens

<400> SEQUENCE: 228
gcggcgctgc tcccgggggc gacggcgtta cagtgtttct gccacctctg tacaaaagac      60
aattttactt gtgtgacaga tgggctctgc tttgtctctg tcacagagac cacagacaaa     120
gttatacaca acagcatgtg tatagctgaa attgacttaa ttcctcgaga taggccgttt     180
gtatgtgcac cctcttcaaa aactgggtct gtgactacaa catattgctg caatcaggac     240
cattgcaata aaatagaact tccaactact ggcccttttt cagtaaagtc atcacctggc     300
cttggtcctg tggaactg                                                   318

<210> SEQ ID NO 229
<211> LENGTH: 1506
<212> TYPE: DNA
<213> ORGANISM: Homo sapiens

<400> SEQUENCE: 229
atgcttttgc gaagtgcagg aaaattaaat gtgggcacca agaaagagga tggtgagagt      60
acagccccca cccccgtcc aaaggtcttg cgttgtaaat gccaccacca ttgtccagaa     120
gactcagtca acaatatttg cagcacagac ggatattgtt tcacgatgat agaagaggat     180
gactctgggt tgcctgtggt cacttctggt tgcctaggac tagaaggctc agattttcag     240
tgtcgggaca ctcccattcc tcatcaaaga agatcaattg aatgctgcac agaaaggaac     300
gaatgtaata aagacctaca ccctacactg cctccattga aaaacagaga ttttgttgat     360
ggacctatac accacagggc tttacttata tctgtgactg tctgtagttt gctcttggtc     420
cttatcatat tattttgtta cttccggtat aaaagacaag aaaccagacc tcgatacagc     480
attgggttag aacaggatga aacttacatt cctcctggag aatccctgag agacttaatt     540
gagcagtctc agagctcagg aagtggatca ggcctccctc tgctggtcca aaggactata     600
gctaagcaga ttcagatggt gaaacagatt ggaaaaggtc gctatgggga agtttggatg     660
ggaaagtggc gtggcgaaaa ggtagctgtg aaagtgttct tcaccacaga ggaagccagc     720
tggttcagag agacagaaat atatcagaca gtgttgatga ggcatgaaaa catttttggt     780
ttcattgctg cagatatcaa agggacaggg tcctggaccc agttgtacct aatcacagac     840
tatcatgaaa atggttccct ttatgattat ctgaagtcca ccaccctaga cgctaaatca     900
atgctgaagt tagcctactc ttctgtcagt ggcttatgtc atttacacac agaaatcttt     960
agtactcaag gcaaaccagc aattgcccat cgagatctga aaagtaaaaa cattctggtg    1020
aagaaaaatg gaacttgctg tattgctgac ctgggcctgg ctgttaaatt tattagtgat    1080
acaaatgaag ttgacatacc acctaacact cgagttggca ccaaacgcta tatgcctcca    1140
gaagtgtttg acgagagctt gaacagaaat cacttccagt cttacatcat ggctgacatg    1200
tatagttttg gcctcatcct ttgggaggtt gctaggagat gtgtatcagg aggtatagtg    1260
gaagaatacc agcttcctta tcatgaccta gtgcccagtg accctctta tgaggacatg    1320 agggagattg tgtgcatcaa gaagttacgc ccctcattcc caaacggtg gagcagtgat    1380 gagtgtctaa ggcagatggg aaaactcatg acagaatgct gggctcacaa tcctgcatca    1440
aggctgacag ccctgcgggt taagaaaaca cttgccaaaa tgtcagagtc ccaggacatt    1500
aaactc                                                              1506
```

```
<210> SEQ ID NO 230
<211> LENGTH: 339
<212> TYPE: DNA
<213> ORGANISM: Homo sapiens

<400> SEQUENCE: 230
aagaaagagg atggtgagag tacagccccc accccccgtc caaaggtctt gcgttgtaaa    60
tgccaccacc attgtccaga agactcagtc aacaatattt gcagcacaga cggatattgt   120
ttcacgatga tagaagagga tgactctggg ttgcctgtgg tcacttctgg ttgcctagga   180
ctagaaggct cagattttca gtgtcgggac actcccattc ctcatcaaag aagatcaatt   240
gaatgctgca cagaaaggaa cgaatgtaat aaagacctac ccctacact gcctccattg    300
aaaaacagag attttgttga tggacctata caccacagg                          339

<210> SEQ ID NO 231
<211> LENGTH: 1596
<212> TYPE: DNA
<213> ORGANISM: Homo sapiens

<400> SEQUENCE: 231
atgggttggc tggaagaact aaactggcag cttcacattt tcttgctcat tcttctctct    60
atgcacacaa gggcaaactt ccttgataac atgcttttgc gaagtgcagg aaaattaaat   120
gtgggcacca agaagaggga tggtgagagt acagccccca ccccccgtcc aaaggtcttg   180
cgttgtaaat gccaccacca ttgtccagaa gactcagtca acaatatttg cagcacagac   240
ggatattgtt tcacgatgat agaaggat gactctgggt tgcctgtggt cacttctggt    300
tgcctaggac tagaaggctc agattttcag tgtcgggaca ctcccattcc tcatcaaaga   360
agatcaattg aatgctgcac agaaaggaac gaatgtaata aagacctaca ccctacactg   420
cctccattga aaaacagaga ttttgttgat ggacctatac cacagggc tttacttata   480
tctgtgactg tctgtagttt gctcttggtc cttatcatat tattttgtta cttccggtat   540
aaaagacaag aaaccagacc tcgatacagc attgggttag aacaggatga aacttacatt   600
cctcctggag aatccctgag agacttaatt gagcagtctc agagctcagg aagtggatca   660
ggcctccctc tgctggtcca aggactata gctaagcaga ttcagatggt gaaacagatt   720
ggaaaaggtc gctatgggga agtttggatg ggaaagtggc gtggcgaaaa ggtagctgtg   780
aaagtgttct tcaccacaga ggaagccagc tggttcagag acagaaat atatcagaca    840
gtgttgatga ggcatgaaaa catttttggt tcattgctg cagatatcaa agggacaggg   900
tcctggaccc agttgtacct aatcacagac tatcatgaaa atggttccct ttatgattat   960
ctgaagtcca ccaccctaga cgctaaatca atgctgaagt tagcctactc ttctgtcagt  1020
ggcttatgtc atttacacac agaaatcttt agtactcaag gcaaaccagc aattgcccat  1080
cgagatctga aaagtaaaaa cattctggtg aagaaaatg gaacttgctg tattgctgac  1140
ctgggcctgg ctgttaaatt tattagtgat acaaatgaag ttgacatacc acctaacact  1200
cgagttggca ccaaacgcta tatgcctcca gaagtgttgg acgagagctt gaacagaaat  1260
cacttccagt cttacatcat ggctgacatg tatagttttg gcctcatcct ttgggaggtt  1320
gctaggagat gtgtatcagg aggtatagtg gaagaatacc agcttcctta tcatgaccta  1380
gtgcccagtg acccctctta tgaggacatg agggagattg tgtgcatcaa gaagttacgc  1440
ccctcattcc caaccggtg gagcagtgat gagtgtctaa ggcagatggg aaaactcatg  1500
acagaatgct gggctcacaa tcctgcatca aggctgacag ccctgcgggt taagaaaaca  1560
```
cttgccaaaa tgtcagagtc ccaggacatt aaactc 1596

```
<210> SEQ ID NO 232
<211> LENGTH: 393
<212> TYPE: DNA
<213> ORGANISM: Homo sapiens

<400> SEQUENCE: 232
```
aacttccttg ataacatgct tttgcgaagt gcaggaaaat taaatgtggg caccaagaaa 60
gaggatggtg agagtacagc ccccaccccc cgtccaaagg tcttgcgttg taaatgccac 120
caccattgtc cagaagactc agtcaacaat atttgcagca cagacggata ttgtttcacg 180
atgatagaag aggatgactc tgggttgcct gtggtcactt ctggttgcct aggactagaa 240
ggctcagatt tcagtgtcg ggacactccc attcctcatc aaagaagatc aattgaatgc 300
tgcacagaaa ggaacgaatg taataaagac ctacacccta cactgcctcc attgaaaaac 360
agagattttg ttgatggacc tatacaccac agg 393

```
<210> SEQ ID NO 233
<211> LENGTH: 1479
<212> TYPE: DNA
<213> ORGANISM: Homo sapiens

<400> SEQUENCE: 233
```
atgacccggg cgctctgctc agcgctccgc caggctctcc tgctgctcgc agcggccgcc 60
gagctctcgc caggactgaa gtgtgtatgt cttttgtgtg attcttcaaa ctttacctgc 120
caaacagaag gagcatgttg ggcatcagtc atgctaacca atggaaaaga gcaggtgatc 180
aaatcctgtg tctcccttcc agaactgaat gctcaagtct tctgtcatag ttccaacaat 240
gttaccaaaa ccgaatgctg cttcacagat ttttgcaaca cataacact gcaccttcca 300 acagcatcac caaatgcccc aaaacttgga cccatggagc tggccatcat tattactgtg 360
cctgtttgcc tcctgtccat agctgcgatg ctgacagtat gggcatgcca gggtcgacag 420
tgctcctaca ggaagaaaaa gagaccaaat gtggaggaac cactctctga gtgcaatctg 480
gtaaatgctg gaaaaactct gaaagatctg atttatgatg tgaccgcctc tggatctggc 540
tctggtctac ctctgttggt tcaaaggaca attgcaagga cgattgtgct tcaggaaata 600
gtaggaaaag gtagatttgg tgaggtgtgg catggaagat ggtgtgggga agatgtggct 660
gtgaaaatat tctcctccag agatgaaaga tcttggtttc gtgaggcaga aatttaccag 720
acggtcatgc tgcgacatga aaacatcctt ggtttcattg ctgctgacaa caaagataat 780
ggaacttgga ctcaactttg gctggtatct gaatatcatg aacagggctc cttatatgac 840
tatttgaata gaaatatagt gaccgtggct ggaatgatca agctggcgct ctcaattgct 900
agtggtctgg cacaccttca tatggagatt gttggtacac aaggtaaacc tgctattgct 960
catcgagaca taaatcaaa gaatatctta gtgaaaagt gtgaaacttg tgccatagcg 1020
gacttagggt tggctgtgaa gcatgattca atactgaaca ctatcgacat acctcagaat 1080
cctaaagtgg gaaccaagag gtatatggct cctgaaatgc ttgatgatac aatgaatgtg 1140
aatatctttg agtccttcaa acgagctgac atcattctg ttggtctggt ttactgggaa 1200
atagcccgga ggtgttcagt cggaggaatt gttgaggagt accaattgcc ttattatgac 1260
atggtgcctt cagatccctc gatagaggaa atgagaaagg ttgtttgtga ccagaagttt 1320
cgaccaagta tcccaaacca gtggcaaagt tgtgaagcac tccgagtcat ggggagaata 1380

```
atgcgtgagt gttggtatgc caacggagcg gcccgcctaa ctgctcttcg tattaagaag    1440
actatatctc aactttgtgt caaagaagac tgcaaagcc                            1479

<210> SEQ ID NO 234
<211> LENGTH: 279
<212> TYPE: DNA
<213> ORGANISM: Homo sapiens

<400> SEQUENCE: 234
gagctctcgc caggactgaa gtgtgtatgt cttttgtgtg attcttcaaa ctttacctgc      60
caaacagaag gagcatgttg ggcatcagtc atgctaacca atggaaaaga gcaggtgatc     120
aaatcctgtg tctcccttcc agaactgaat gctcaagtct tctgtcatag ttccaacaat    180
gttaccaaaa ccgaatgctg cttcacagat ttttgcaaca acataacact gcaccttcca    240
acagcatcac caaatgcccc aaaacttgga cccatggag                           279

<210> SEQ ID NO 235
<211> LENGTH: 1329
<212> TYPE: DNA
<213> ORGANISM: Homo sapiens

<400> SEQUENCE: 235
atgctaacca atggaaaaga gcaggtgatc aaatcctgtg tctcccttcc agaactgaat     60
gctcaagtct tctgtcatag ttccaacaat gttaccaaaa ccgaatgctg cttcacagat    120
ttttgcaaca acataacact gcaccttcca acagcatcac caaatgcccc aaaacttgga    180
cccatggagc tggccatcat tattactgtg cctgtttgcc tcctgtccat agctgcgatg    240
ctgacagtat gggcatgcca gggtcgacag tgctcctaca ggaagaaaaa gagaccaaat    300
gtggaggaac cactctctga gtgcaatctg gtaaatgctg gaaaaactct gaaagatctg    360
atttatgatg tgaccgcctc tggatctggc tctggtctac ctctgttggt tcaaaggaca    420
attgcaagga cgattgtgct tcaggaaata gtaggaaaag gtagatttgg tgaggtgtgg    480
catggaagat ggtgtgggga agatgtggct gtgaaaatat tctcctccag agatgaaaga    540
tcttggtttc gtgaggcaga aatttaccag acggtcatgc tgcgacatga aaacatcctt    600
ggtttcattg ctgctgacaa caaagataat ggaacttgga ctcaactttg gctggtatct    660
gaatatcatg aacagggctc cttatatgac tatttgaata gaaatatagt gaccgtggct    720
ggaatgatca agctggcgct ctcaattgct agtggtctgg cacaccttca tatggagatt    780
gttggtacac aaggtaaacc tgctattgct catcgagaca taaaatcaaa gaatatctta    840
gtgaaaaagt gtgaaacttg tgccatagcg gacttagggt tggctgtgaa gcatgattca    900
atactgaaca ctatcgacat acctcagaat cctaaagtgg gaaccaagag gtatatggct    960
cctgaaatgc ttgatgatac aatgaatgtg aatatctttg agtccttcaa acgagctgac   1020
atctattctg ttggtctggt ttactgggaa atagcccgga ggtgttcagt cggaggaatt   1080
gttgaggagt accaattgcc ttattatgac atggtgcctt cagatccctc gatagaggaa   1140
atgagaaagg ttgtttgtga ccagaagttt cgaccaagta tcccaaacca gtggcaaagt   1200
tgtgaagcac tccgagtcat ggggagaata atgcgtgagt gttggtatgc caacggagcg   1260
gcccgcctaa ctgctcttcg tattaagaag actatatctc aactttgtgt caaagaagac   1320
tgcaaagcc                                                             1329

<210> SEQ ID NO 236
<211> LENGTH: 189
```

```
<212> TYPE: DNA
<213> ORGANISM: Homo sapiens

<400> SEQUENCE: 236
atgctaacca atggaaaaga gcaggtgatc aaatcctgtg tctcccttcc agaactgaat      60
gctcaagtct tctgtcatag ttccaacaat gttaccaaaa ccgaatgctg cttcacagat     120
ttttgcaaca acataacact gcaccttcca acagcatcac caaatgcccc aaaacttgga    180
cccatggag                                                              189

<210> SEQ ID NO 237
<211> LENGTH: 1239
<212> TYPE: DNA
<213> ORGANISM: Homo sapiens

<400> SEQUENCE: 237
atgacccggg cgctctgctc agcgctccgc caggctctcc tgctgctcgc agcggccgcc      60
gagctctcgc caggactgaa gtgtgtatgt cttttgtgtg attcttcaaa ctttacctgc     120
caaacagaag gagcatgttg ggcatcagtc atgctaacca atggaaaaga gcaggtgatc    180
aaatcctgtg tctcccttcc agaactgaat gctcaagtct tctgtcatag ttccaacaat    240
gttaccaaaa ccgaatgctg cttcacagat ttttgcaaca acataacact gcaccttcca    300
acaggtctac ctctgttggt tcaaaggaca attgcaagga cgattgtgct tcaggaaata    360
gtaggaaaag gtagatttgg tgaggtgtgg catggaagat ggtgtgggga agatgtggct    420
gtgaaaatat ctcctccag agatgaaaga tcttggtttc gtgaggcaga aatttaccag    480
acggtcatgc tgcgacatga aaacatcctt ggtttcattg ctgctgacaa caaagataat    540
ggaacttgga ctcaactttg gctggtatct gaatatcatg aacagggctc cttatatgac    600
tatttgaata gaaatatagt gaccgtggct ggaatgatca agctggcgct ctcaattgct    660
agtggtctgg cacaccttca tatggagatt gttggtacac aagtaaaacc tgctattgct    720
catcgagaca taaaatcaaa gaatatctta gtgaaaaagt gtgaaacttg tgccatagcg    780
gacttagggt tggctgtgaa gcatgattca atactgaaca ctatcgacat acctcagaat    840
cctaaagtgg gaaccaagag gtatatggct cctgaaatgc ttgatgatac aatgaatgtg    900
aatatctttg agtccttcaa acgagctgac atctattctg ttggtctggt ttactgggaa    960
atagcccgga ggtgttcagt cggaggaatt gttgaggagt accaattgcc ttattatgac   1020
atggtgcctt cagatccctc gatagaggaa atgagaaagg ttgtttgtga ccagaagttt   1080
cgaccaagta tcccaaacca gtggcaaagt tgtgaagcac tccgagtcat ggggagaata   1140
atgcgtgagt gttggtatgc caacggagcg gcccgcctaa ctgctcttcg tattaagaag   1200
actatatctc aactttgtgt caaagaagac tgcaaagcc                           1239

<210> SEQ ID NO 238
<211> LENGTH: 1179
<212> TYPE: DNA
<213> ORGANISM: Homo sapiens

<400> SEQUENCE: 238
gagctctcgc caggactgaa gtgtgtatgt cttttgtgtg attcttcaaa ctttacctgc      60
caaacagaag gagcatgttg ggcatcagtc atgctaacca atggaaaaga gcaggtgatc     120
aaatcctgtg tctcccttcc agaactgaat gctcaagtct tctgtcatag ttccaacaat    180
gttaccaaaa ccgaatgctg cttcacagat ttttgcaaca acataacact gcaccttcca    240
```

```
acaggtctac ctctgttggt tcaaaggaca attgcaagga cgattgtgct tcaggaaata      300
gtaggaaaag gtagatttgg tgaggtgtgg catggaagat ggtgtgggga agatgtggct      360
gtgaaaatat tctcctccag agatgaaaga tcttggtttc gtgaggcaga aatttaccag      420
acggtcatgc tgcgacatga aaacatcctt ggtttcattg ctgctgacaa caaagataat      480
ggaacttgga ctcaactttg gctggtatct gaatatcatg aacagggctc cttatatgac      540
tatttgaata gaaatatagt gaccgtggct ggaatgatca agctggcgct ctcaattgct      600
agtggtctgg cacaccttca tatggagatt gttggtacac aaggtaaacc tgctattgct      660
catcgagaca taaaatcaaa gaatatctta gtgaaaaagt gtgaaacttg gccatagcg       720 gacttagggt tggctgtgaa gcatgattca atactgaaca ctatcgacat acctcagaat      780
cctaaagtgg gaaccaagag gtatatggct cctgaaatgc ttgatgatac aatgaatgtg      840
aatatctttg agtccttcaa acgagctgac atctattctg ttggtctggt ttactgggaa      900
atagcccgga ggtgttcagt cggaggaatt gttgaggagt accaattgcc ttattatgac      960
atggtgcctt cagatccctc gatagaggaa atgagaaagg ttgtttgtga ccagaagttt     1020
cgaccaagta tcccaaacca gtggcaaagt tgtgaagcac tccgagtcat ggggagaata     1080
atgcgtgagt gttggtatgc caacggagcg gcccgcctaa ctgctcttcg tattaagaag     1140
actatatctc aactttgtgt caaagaagac tgcaaagcc                            1179
```

<210> SEQ ID NO 239
<211> LENGTH: 1011
<212> TYPE: DNA
<213> ORGANISM: Homo sapiens

<400> SEQUENCE: 239

```
atgacccggg cgctctgctc agcgctccgc caggctctcc tgctgctcgc agcggccgcc       60
gagctctcgc aggactgaa gtgtgtatgt cttttgtgtg attcttcaaa ctttacctgc       120
caaacagaag gagcatgttg ggcatcagtc atgctaacca atggaaaaga gcaggtgatc      180
aaatcctgtg tctcccttcc agaactgaat gctcaagtct tctgtcatag ttccaacaat      240
gttaccaaaa ccgaatgctg cttcacagat ttttgcaaca acataacact gcaccttcca      300
acagataatg gaacttggac tcaactttgg ctggtatctg aatatcatga acagggctcc      360
ttatatgact atttgaatag aaatatagtg accgtggctg gaatgatcaa gctggcgctc      420
tcaattgcta gtggtctggc acaccttcat atggagattg ttggtacaca aggtaaacct      480
gctattgctc atcgagacat aaaatcaaag aatatcttag tgaaaaagtg tgaaacttgt      540
gccatagcgg acttagggtt ggctgtgaag catgattcaa tactgaacac tatcgacata      600
cctcagaatc ctaaagtggg aaccaagagg tatatggctc ctgaaatgct tgatgataca      660
atgaatgtga atatctttga gtccttcaaa cgagctgaca tctattctgt tggtctggtt      720
tactgggaaa tagcccggag gtgttcagtc ggaggaattg ttgaggagta ccaattgcct      780
tattatgaca tggtgccttc agatccctcg atagaggaaa tgagaaaggt tgtttgtgac      840
cagaagtttc gaccaagtat cccaaaccag tggcaaagtt gtgaagcact ccgagtcatg      900
gggagaataa tgcgtgagtg ttggtatgcc aacggagcgg cccgcctaac tgctcttcgt      960
attaagaaga ctatatctca actttgtgtc aaagaagact gcaaagccta a              1011
```

<210> SEQ ID NO 240
<211> LENGTH: 951
<212> TYPE: DNA
<213> ORGANISM: Homo sapiens

<400> SEQUENCE: 240

```
gagctctcgc caggactgaa gtgtgtatgt cttttgtgtg attcttcaaa ctttacctgc      60
caaacagaag gagcatgttg ggcatcagtc atgctaacca atggaaaaga gcaggtgatc     120
aaatcctgtg tctcccttcc agaactgaat gctcaagtct tctgtcatag ttccaacaat     180
gttaccaaaa ccgaatgctg cttcacagat ttttgcaaca acataacact gcaccttcca     240
acagataatg gaacttggac tcaactttgg ctggtatctg aatatcatga cagggctcc      300
ttatatgact atttgaatag aaatatagtg accgtggctg aatgatcaa gctggcgctc      360
tcaattgcta gtggtctggc acccttcat ggagattt tggtacaca aggtaaacct         420
gctattgctc atcgagacat aaaatcaaag aatatcttag tgaaaagtg tgaaacttgt      480
gccatagcgg acttagggtt ggctgtgaag catgattcaa tactgaacac tatcgacata     540
cctcagaatc ctaaagtggg aaccaagagg tatatggctc ctgaaatgct tgatgataca     600
atgaatgtga atatctttga gtccttcaaa cgagctgaca tctattctgt tggtctggtt     660
tactgggaaa tagcccggag gtgttcagtc ggaggaattg ttgaggagta ccaattgcct     720
tattatgaca tggtgccttc agatccctcg atagaggaaa tgagaaaggt tgtttgtgac     780
cagaagtttc gaccaagtat cccaaaccag tggcaaagtt gtgaagcact ccgagtcatg     840
gggagaataa tgcgtgagtg ttggtatgcc aacggagcgg cccgcctaac tgctcttcgt     900
attaagaaga ctatatctca actttgtgtc aagaagact gcaaagccta a              951
```

<210> SEQ ID NO 241
<211> LENGTH: 1539
<212> TYPE: DNA
<213> ORGANISM: Homo sapiens

<400> SEQUENCE: 241

```
atgggagctg ctgcaaagtt ggcgtttgcc gtctttctta ctcctgttc ttcaggtgct        60
atacttggta gatcagaaac tcaggagtgt cttttcttta atgctaattg ggaaaaagac     120
agaaccaatc aaactggtgt tgaaccgtgt tatggtgaca agataaacg gcggcattgt      180
tttgctacct ggaagaatat ttctggttcc attgaaatag tgaaacaagg ttgttggctg     240
gatgatatca actgctatga caggactgat tgtgtagaaa aaaagacag ccctgaagta      300
tattttttgtt gctgtgaggg caatatgtgt aatgaaaagt tttcttattt ccggagatg     360
gaagtcacac agcccacttc aaatccagtt acacctaagc caccctatta caacatcctg     420
ctctattcct tggtgccact tatgttaatt gcggggattg tcatttgtgc attttgggtg     480
tacaggcatc acaagatggc ctaccctcct gtacttgttc caactcaaga cccaggacca    540
cccccacctt ctccattact aggtttgaaa ccactgcagt tattagaagt gaagcaagg     600
ggaagatttg gttgtgtctg aaagcccag ttgcttaacg aatatgtggc tgtcaaaata      660
tttccaatac aggacaaaca gtcatggcaa aatgaatacg aagtctacag tttgcctgga     720
atgaagcatg agaacatatt acagttcatt ggtgcagaaa acgaggcac cagtgttgat    780
gtggatcttt ggctgatcac agcatttcat gaaaagggtt cactatcaga ctttcttaag     840
gctaatgtgt tctcttggaa tgaactgtgt catattgcag aaaccatggc tagaggattg     900
gcatatttac atgaggatat acctggccta aaagatggcc acaaacctgc catatctcac    960
agggacatca aaagtaaaaa tgtgctgttg aaaaacaacc tgcagcttg cattgctgac     1020
tttgggttgg ccttaaaatt tgaggctggc aagtctgcag gcgataccca tggacaggtt    1080
```

```
ggtacccgga ggtacatggc tccagaggta ttagagggtg ctataaactt ccaaagggat    1140
gcatttttga ggatagatat gtatgccatg ggattagtcc tatgggaact ggcttctcgc    1200
tgtactgctg cagatggacc tgtagatgaa tacatgttgc catttgagga ggaaattggc    1260
cagcatccat ctcttgaaga catgcaggaa gttgttgtgc ataaaaaaaa gaggcctgtt    1320
ttaagagatt attggcagaa acatgctgga atggcaatgc tctgtgaaac cattgaagaa    1380
tgttgggatc acgacgcaga agccaggtta tcagctggat gtgtaggtga aagaattacc    1440
cagatgcaga gactaacaaa tattattacc acagaggaca ttgtaacagt ggtcacaatg    1500
gtgacaaatg ttgactttcc tcccaaagaa tctagtcta                           1539

<210> SEQ ID NO 242
<211> LENGTH: 345
<212> TYPE: DNA
<213> ORGANISM: Homo sapiens

<400> SEQUENCE: 242
atacttggta gatcagaaac tcaggagtgt cttttcttta atgctaattg ggaaaaagac      60
agaaccaatc aaactggtgt tgaaccgtgt tatggtgaca agataaacg gcggcattgt     120 tttgctacct ggaagaatat ttctggttcc attgaaaatag tgaaacaagg ttgttggctg    180
gatgatatca actgctatga caggactgat tgtgtagaaa aaaagacag ccctgaagta    240 tattttgtt gctgtgaggg caatatgtgt aatgaaaagt tttcttattt tccggagatg    300
gaagtcacac agcccacttc aaatccagtt acacctaagc caccc                    345

<210> SEQ ID NO 243
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
atggatgcaa tgaagagagg gctctgctgt gtgctgctgc tgtgtggagc agtcttcgtt      60
tcgcccggcg cctccgggcc ccgggggtc caggctctg tgtgtgcgtg caccagctgc     120
ctccaggcca actacacgtg tgagacagat ggggcctgca tggtttccat tttcaatctg    180
gatgggatgg agcaccatgt gcgcacctgc atccccaaag tggagctggt ccctgccggg    240 aagccttct actgcctgag ctcggaggac ctgcgcaaca cccactgctg ctacactgac    300
tactgcaaca ggatcgactt gagggtgccc agtggtcacc tcaaggagcc tgagcacccg    360
tccatgtggg gccggtgga gaccggtggt ggaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtacaccctg    780
cccccatccc gggaggagat gaccaagaac caggtcagcc tgacctgcct ggtcaaaggc    840
ttctatccca gcgacatcgc cgtggagtgg gagagcaatg ggcagccgga gaacaactac    900
gacaccacgc ctcccgtgct ggactccgac ggctccttct tcctctatag cgacctcacc    960
```

```
gtggacaaga gcaggtggca gcaggggaac gtcttctcat gctccgtgat gcatgaggct    1020
ctgcacaacc actacacgca gaagagcctc tccctgtctc cgggt                    1065
```

<210> SEQ ID NO 244
<211> LENGTH: 1065
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 244

```
atggatgcaa tgaagagagg gctctgctgt gtgctgctgc tgtgtggagc agtcttcgtt     60
tcgcccggcg ccatggaaga tgagaagccc aaggtcaacc ccaaactcta catgtgtgtg    120
tgtgaaggtc tctcctgcgg taatgaggac cactgtgaag ccagcagtg  cttttcctca    180 ctgagcatca acgatggctt ccacgtctac cagaaaggct gcttccaggt ttatgagcag    240
ggaaagatga cctgtaagac cccgccgtcc cctggccaag ctgtggagtg ctgccaaggg    300
gactggtgta acaggaacat cacggcccag ctgcccacta aggaaaaatc cttccctgga    360
acacagaatt ccacttgga gaccggtggt ggaactcaca catgcccacc gtgcccagca    420
cctgaactcc tgggaggacc gtcagtcttc ctcttccccc caaaacccaa ggacaccctc    480
atgatctccc ggaccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtacaccctg    780
cccccatccc gggaggagat gaccaagaac caggtcagcc tgacctgcct ggtcaaaggc    840
ttctatccca gcgacatcgc cgtggagtgg gagagcaatg ggcagccgga gaacaactac    900
gacaccacgc ctcccgtgct ggactccgac ggctccttct cctctatag cgacctcacc    960 gtggacaaga gcaggtggca gcaggggaac gtcttctcat gctccgtgat gcatgaggct   1020
ctgcacaacc actacacgca gaagagcctc tccctgtctc cgggt                  1065
```

<210> SEQ ID NO 245
<211> LENGTH: 1143
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 245

```
atggatgcaa tgaagagagg gctctgctgt gtgctgctgc tgtgtggagc agtcttcgtt     60
tcgcccggcg cccagaatct ggatagtatg cttcatggca ctgggatgaa atcagactcc    120
gaccagaaaa agtcagaaaa tggagtaacc ttagcaccag aggataccttg ccttttttta    180 aagtgctatt gctcagggca ctgtccagat gatgctatta ataacacatg cataactaat    240
ggacattgct ttgccatcat agaagaagat gaccagggag aaaccacatt agcttcaggg    300
tgtatgaaat atgaaggatc tgattttcag tgcaaagatt ctccaaaagc ccagctacgc    360
cggacaatag aatgttgtcg gaccaattta tgtaaccagt atttgcaacc cacactgccc    420
cctgttgtca taggtccgtt ttttgatggc agcattcgaa ccggtggtgg aactcacaca    480
tgcccaccgt gcccagcacc tgaactcctg ggggaccgt cagtcttcct cttccccca     540
```

```
aaacccaagg acaccctcat gatctcccgg acccctgagg tcacatgcgt ggtggtggac    600
gtgagccacg aagaccctga ggtcaagttc aactggtacg tggacggcgt ggaggtgcat    660
aatgccaaga caaagccgcg ggaggagcag tacaacagca cgtaccgtgt ggtcagcgtc    720
ctcaccgtcc tgcaccagga ctggctgaat ggcaaggagt acaagtgcaa ggtctccaac    780
aaagccctcc cagcccccat cgagaaaacc atctccaaag ccaaagggca gccccgagaa    840
ccacaggtgt acaccctgcc cccatcccgg gaggagatga ccaagaacca ggtcagcctg    900
acctgcctgg tcaaaggctt ctatcccagc gacatcgccg tggagtggga gagcaatggg    960
cagccggaga acaactacga caccacgcct cccgtgctgg actccgacgg ctccttcttc   1020
ctctatagcg aacctcaccgt ggacaagagc aggtggcagc aggggaacgt cttctcatgc   1080
tccgtgatgc atgaggctct gcacaaccac tacacgcaga gagcctctc cctgtctccg     1140 ggt                                                                  1143
```

<210> SEQ ID NO 246
<211> LENGTH: 22
<212> TYPE: PRT
<213> ORGANISM: Unknown
<220> FEATURE:
<223> OTHER INFORMATION: Description of Unknown:
      Tissue plasminogen activator

<400> SEQUENCE: 246

Met Asp Ala Met Lys Arg Gly Leu Cys Cys Val Leu Leu Cys Gly
1               5                   10                  15

Ala Val Phe Val Ser Pro
            20

<210> SEQ ID NO 247
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Asp Ala Met Lys Arg Gly Leu Cys Cys Val Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu

```
            145                 150                 155                 160
Met Ile Ser Arg Thr Pro Glu Val Thr Cys Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
        275                 280                 285

Glu Trp Glu Ser Arg Gly Gln Pro Glu Asn Asn Tyr Lys Thr Thr Pro
    290                 295                 300

Pro Val Leu Asp Ser Arg Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 248
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 248
atggatgcaa tgaagagagg gctctgctgt gtgctgctgc tgtgtggagc agtcttcgtt      60
tcgcccggcg cctccgggcc ccgggggggtc caggctctgc tgtgtgcgtg caccagctgc    120
ctccaggcca actacacgtg tgagacagat ggggcctgca tggtttccat tttcaatctg    180
gatgggatgg agcaccatgt gcgcacctgc atccccaaag tggagctggt ccctgccggg    240
aagcccttct actgcctgag ctcggaggac ctgcgcaaca cccactgctg ctacactgac    300
tactgcaaca ggatcgactt gagggtgccc agtggtcacc tcaaggagcc tgagcacccg    360
tccatgtggg gccggtggac accggtggtg gaactcaca catgcccacc gtgcccagca    420
cctgaactcc tggggggacc gtcagtcttc ctcttccccc caaaacccaa ggacaccctc    480
atgatctccc ggaccctga ggtcacatgc gtggtggtgg acgtgagcca cgaagaccct     540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtgcaccctg    780
cccccatccc gggaggagat gaccaagaac caggtcagcc tgtcctgcgc cgtcaaaggc    840
```

```
ttctatccca gcgacatcgc cgtggagtgg gagagccgcg ggcagccgga gaacaactac    900
aagaccacgc ctcccgtgct ggactcccgc ggctccttct tcctcgtgag caagctcacc    960
gtggacaaga gcaggtggca gcaggggaac gtcttctcat gctccgtgat gcatgaggct   1020
ctgcacaacc actacacgca gaagagcctc tccctgtctc cgggtaaa               1068
```

<210> SEQ ID NO 249
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255

Phe Tyr Pro Ser Asp Ile Ala Val Glu Trp Glu Ser Arg Gly Gln Pro
            260                 265                 270

Glu Asn Asn Tyr Lys Thr Thr Pro Pro Val Leu Asp Ser Arg Gly Ser
        275                 280                 285

Phe Phe Leu Val Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320
```

Tyr Thr Gln Lys Ser Leu Ser Leu Ser Pro Gly Lys
            325                 330

<210> SEQ ID NO 250
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 250

| tccgggcccc | gggggtcca | ggctctgctg | tgtgcgtgca | ccagctgcct | ccaggccaac | 60 |
| tacacgtgtg | agacagatgg | ggcctgcatg | gtttccattt | caatctgga | tgggatggag | 120 |
| caccatgtgc | gcacctgcat | ccccaaagtg | gagctggtcc | ctgccgggaa | gcccttctac | 180 |
| tgcctgagct | cggaggacct | gcgcaacacc | cactgctgct | acactgacta | ctgcaacagg | 240 |
| atcgacttga | gggtgcccag | tggtcacctc | aaggagcctg | agcacccgtc | catgtggggc | 300 |
| ccggtggaga | ccggtggtgg | aactcacaca | tgcccaccgt | gcccagcacc | tgaactcctg | 360 |
| gggggaccgt | cagtcttcct | cttccccca | aacccaagg | acaccctcat | gatctcccgg | 420 |
| accccctgagg | tcacatgcgt | ggtggtggac | gtgagccacg | aagaccctga | ggtcaagttc | 480 |
| aactggtacg | tggacggcgt | ggaggtgcat | aatgccaaga | caaagccgcg | ggaggagcag | 540 |
| tacaacagca | cgtaccgtgt | ggtcagcgtc | ctcaccgtcc | tgcaccagga | ctggctgaat | 600 |
| ggcaaggagt | acaagtgcaa | ggtctccaac | aaagcccctcc | cagccccat | cgagaaaacc | 660 |
| atctccaaag | ccaaagggca | gccccgagaa | ccacaggtgt | gcaccctgcc | cccatcccgg | 720 |
| gaggagatga | ccaagaacca | ggtcagcctg | tcctgcgccg | tcaaaggctt | ctatcccagc | 780 |
| gacatcgccg | tggagtggga | gagccgcggg | cagccggaga | caactacaa | gaccacgcct | 840 |
| cccgtgctgg | actcccgcgg | ctccttcttc | ctcgtgagca | agctcaccgt | ggacaagagc | 900 |
| aggtggcagc | aggggaacgt | cttctcatgc | tccgtgatgc | atgaggctct | gcacaaccac | 960 |
| tacacgcaga | agagcctctc | cctgtctccg | ggtaaa | | | 996 |

<210> SEQ ID NO 251
<211> LENGTH: 1068
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251

| atggatgcaa | tgaagagagg | gctctgctgt | gtgctgctgc | tgtgtggagc | agtcttcgtt | 60 |
| tcgcccggcg | cctccgggcc | ccgggggggtc | caggctctgc | tgtgtgcgtg | caccagctgc | 120 |
| ctccaggcca | actacacgtg | tgagacagat | ggggcctgca | tggtttccat | ttcaatctg | 180 |
| gatgggatgg | agcaccatgt | gcgcacctgc | atccccaaag | tggagctggt | ccctgccggg | 240 |
| aagcccttct | actgcctgag | ctcggaggac | ctgcgcaaca | cccactgctg | ctacactgac | 300 |
| tactgcaaca | ggatcgactt | gagggtgccc | agtggtcacc | tcaaggagcc | tgagcacccg | 360 |
| tccatgtggg | gcccggtgga | gaccggtggt | ggaactcaca | catgcccacc | gtgcccagca | 420 |
| cctgaactcc | tggggggacc | gtcagtcttc | ctcttccccc | caaaacccaa | ggacaccctc | 480 |
| atgatctccc | ggaccccctga | ggtcacatgc | gtggtggtgg | acgtgagcca | cgaagaccct | 540 |
| gaggtcaagt | tcaactggta | cgtggacggc | gtggaggtgc | ataatgccaa | gacaaagccg | 600 |

```
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtgcaccctg    780
cccccatccc gggaggagat gaccaagaac caggtcagcc tgtcctgcgc cgtcaaaggc    840
ttctatccca gcgacatcgc cgtggagtgg gagagcaatg ggcagccgga gaacaactac    900
aagaccacgc ctcccgtgct ggactccgac ggctccttct cctcgtgag caagctcacc    960 gtggacaaga gcaggtggca gcaggggaac gtcttctcat gctccgtgat gcatgaggct   1020
ctgcacaacc actacacgca gaagagcctc tccctgtctc cgggtaaa              1068
```

<210> SEQ ID NO 252
<211> LENGTH: 996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252

```
tccgggcccc gggggtcca ggctctgctg tgtgcgtgca ccagctgcct ccaggccaac     60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180
tgcctgagct cggaggacct gcgcaacacc cactgctgct acactgacta ctgcaacagg    240
atcgacttga gggtgcccag tggtcacctc aaggagcctg agcacccgtc catgtggggc    300
ccggtggaga ccggtggtgg aactcacaca tgcccaccgt gcccagcacc tgaactcctg    360
gggggaccgt cagtcttcct cttccccca aaacccaagg acaccctcat gatctcccgg    420 accctgagg tcacatgcgt ggtggtggac gtgagccacg aagaccctga ggtcaagttc    480
aactggtacg tggacggcgt ggaggtgcat aatgccaaga caaagccgcg ggaggagcag    540
tacaacagca cgtaccgtgt ggtcagcgtc ctcaccgtcc tgcaccagga ctggctgaat    600
ggcaaggagt acaagtgcaa ggtctccaac aaagccctcc cagcccccat cgagaaaacc    660
atctccaaag ccaagggca gccccgagaa ccacaggtgt gcaccctgcc cccatcccgg    720
gaggagatga ccaagaacca ggtcagcctg tcctgcgccg tcaaaggctt ctatcccagc    780
gacatcgccg tggagtggga gagcaatggg cagccggaga caactacaa gaccacgcct    840 cccgtgctgg actccgacgg ctccttcttc tcgtgagca agctcaccgt ggacaagagc    900
aggtggcagc aggggaacgt cttctcatgc tccgtgatgc atgaggctct gcacaaccac    960
tacacgcaga gagcctctc cctgtctccg ggtaaa                               996
```

<210> SEQ ID NO 253
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 253

```
atggatgcaa tgaagagagg gctctgctgt gtgctgctgc tgtgtggagc agtcttcgtt     60
tcgcccggcg ccgcgctgct cccggggcg acggcgttac agtgtttctg ccacctctgt    120
acaaaagaca attttacttg tgtgacagat gggctctgct ttgtctctgt cacagagacc    180
```

```
acagacaaag ttatacacaa cagcatgtgt atagctgaaa ttgacttaat tcctcgagat      240
aggccgtttg tatgtgcacc ctcttcaaaa actgggtctg tgactacaac atattgctgc      300
aatcaggacc attgcaataa aatagaactt ccaactactg taaagtcatc acctggcctt      360
ggtcctgtgg aaaccggtgg tggaactcac acatgcccac cgtgcccagc acctgaactc      420 ctgggggggac cgtcagtctt cctcttcccc ccaaaaccca aggacaccct catgatctcc      480
cggacccctg aggtcacatg cgtggtggtg gacgtgagcc acgaagaccc tgaggtcaag      540
ttcaactggt acgtggacgg cgtggaggtg cataatgcca agacaaagcc gcgggaggag      600
cagtacaaca gcacgtaccg tgtggtcagc gtcctcaccg tcctgcacca ggactggctg      660
aatggcaagg agtacaagtg caaggtctcc aacaaagccc tcccagcccc catcgagaaa      720
accatctcca aagccaaagg gcagccccga gaaccacagg tgtacaccct gcccccatcc      780
cgggaggaga tgaccaagaa ccaggtcagc ctgacctgcc tggtcaaagg cttctatccc      840
agcgacatcg ccgtggagtg ggagagcaat gggcagccgg agaacaacta cgacaccacg      900
cctcccgtgc tggactccga cggctccttc ttcctctata gcgacctcac cgtggacaag      960
agcaggtggc agcaggggaa cgtcttctca tgctccgtga tgcatgaggc tctgcacaac     1020
cactacacgc agaagagcct ctccctgtct ccgggt                               1056
```

<210> SEQ ID NO 254
<211> LENGTH: 1095
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254

```
atggatgcaa tgaagagagg gctctgctgt gtgctgctgc tgtgtggagc agtcttcgtt       60
tcgcccggcg ccaagaaaga ggatggtgag agtacagccc ccaccccccg tccaaaggtc      120
ttgcgttgta aatgccacca ccattgtcca gaagactcag tcaacaatat ttgcagcaca      180
gacggatatt gtttcacgat gatagaagag gatgactctg ggttgcctgt ggtcacttct      240
ggttgcctag gactagaagg ctcagatttt cagtgtcggg acactcccat tcctcatcaa      300
agaagatcaa ttgaatgctg cacagaaagg aacgaatgta ataaagacct acaccctaca      360
ctgcctccat tgaaaaacag agattttgtt gatggaccta tacaccacag gaccggtggt      420
ggaactcaca catgcccacc gtgcccagca cctgaactcc tggggggacc gtcagtcttc      480
ctcttccccc caaaacccaa ggacaccctc atgatctccc ggacccctga ggtcacatgc      540
gtggtggtgg acgtgagcca cgaagaccct gaggtcaagt tcaactggta cgtggacggc      600
gtggaggtgc ataatgccaa gacaaagccg cgggaggagc agtacaacag cacgtaccgt      660
gtggtcagcg tcctcaccgt cctgcaccag gactggctga atggcaagga gtacaagtgc      720
aaggtctcca acaaagccct cccagccccc atcgagaaaa ccatctccaa agccaaaggg      780
cagccccgag aaccacaggt gtacaccctg cccccatccc gggaggagat gaccaagaac      840
caggtcagcc tgacctgcct ggtcaaaggc ttctatccca gcgacatcgc cgtggagtgg      900
gagagcaatg ggcagccgga gaacaactac gacaccacgc ctcccgtgct ggactccgac      960
ggctccttct tcctctatag cgacctcacc gtggacaaga gcaggtggca gcaggggaac     1020
gtcttctcat gctccgtgat gcatgaggct ctgcacaacc actacacgca gaagagcctc     1080
tccctgtctc cgggt                                                      1095
```

<210> SEQ ID NO 255
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 255

| | | | | | |
|---|---|---|---|---|---|
| atggatgcaa | tgaagagagg | gctctgctgt | gtgctgctgc | tgtgtggagc | agtcttcgtt | 60 |
| tcgcccggcg | ccggactgaa | gtgtgtatgt | cttttgtgtg | attcttcaaa | ctttacctgc | 120 |
| caaacagaag | gagcatgttg | ggcatcagtc | atgctaacca | atggaaaaga | gcaggtgatc | 180 |
| aaatcctgtg | tctcccttcc | agaactgaat | gctcaagtct | tctgtcatag | ttccaacaat | 240 |
| gttaccaaaa | ccgaatgctg | cttcacagat | ttttgcaaca | cataacact | gcaccttcca | 300 |
| acagcatcac | caaatgcccc | aaaacttgga | cccatggaga | ccggtggtgg | aactcacaca | 360 |
| tgcccaccgt | gcccagcacc | tgaactcctg | gggggaccgt | cagtcttcct | cttccccca | 420 |
| aaacccaagg | acaccctcat | gatctcccgg | acccctgagg | tcacatgcgt | ggtggtggac | 480 |
| gtgagccacg | aagaccctga | ggtcaagttc | aactggtacg | tggacggcgt | ggaggtgcat | 540 |
| aatgccaaga | caaagccgcg | ggaggagcag | tacaacagca | cgtaccgtgt | ggtcagcgtc | 600 |
| ctcaccgtcc | tgcaccagga | ctggctgaat | ggcaaggagt | acaagtgcaa | ggtctccaac | 660 |
| aaagccctcc | cagcccccat | cgagaaaacc | atctccaaag | ccaaagggca | gccccgagaa | 720 |
| ccacaggtgt | acaccctgcc | cccatcccgg | gaggagatga | ccaagaacca | ggtcagcctg | 780 |
| acctgcctgg | tcaaaggctt | ctatcccagc | gacatcgccg | tggagtggga | gagcaatggg | 840 |
| cagccggaga | acaactacga | caccacgcct | cccgtgctgg | actccgacgg | ctccttcttc | 900 |
| ctctatagcg | acctcaccgt | ggacaagagc | aggtggcagc | aggggaacgt | cttctcatgc | 960 |
| tccgtgatgc | atgaggctct | gcacaaccac | tacacgcaga | agagcctctc | cctgtctccg | 1020 |
| ggt | | | | | | 1023 |

<210> SEQ ID NO 256
<211> LENGTH: 1107
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 256

| | | | | | |
|---|---|---|---|---|---|
| atggatgcaa | tgaagagagg | gctctgctgt | gtgctgctgc | tgtgtggagc | agtcttcgtt | 60 |
| tcgcccggcg | ccgctatact | tggtagatca | gaaactcagg | agtgtctttt | ctttaatgct | 120 |
| aattgggaaa | aagacagaac | caatcaaact | ggtgttgaac | cgtgttatgg | tgacaaagat | 180 |
| aaacggcggc | attgttttgc | tacctggaag | aatatttctg | gttccattga | aatagtgaaa | 240 |
| caaggttgtt | ggctggatga | tatcaactgc | tatgacagga | ctgattgtgt | agaaaaaaaa | 300 |
| gacagccctg | aagtatattt | ctgttgctgt | gagggcaata | tgtgtaatga | aaagttttct | 360 |
| tattttccgg | agatggaagt | cacacagccc | acttcaaatc | cagttacacc | taagccaccc | 420 |
| accggtggtg | gaactcacac | atgcccaccg | tgcccagcac | ctgaactcct | gggggaccg | 480 |
| tcagtcttcc | tcttccccc | aaaacccaag | gacaccctca | tgatctcccg | gacccctgag | 540 |
| gtcacatgcg | tggtggtgga | cgtgagccac | gaagaccctg | aggtcaagtt | caactggtac | 600 |
| gtggacggcg | tggaggtgca | taatgccaag | acaaagccgc | gggaggagca | gtacaacagc | 660 |

```
acgtaccgtg tggtcagcgt cctcaccgtc ctgcaccagg actggctgaa tggcaaggag    720
tacaagtgca aggtctccaa caaagccctc ccagccccca tcgagaaaac catctccaaa    780 gccaagggc agccccgaga accacaggtg tacaccctgc ccccatcccg gaaggagatg     840
accaagaacc aggtcagcct gacctgcctg gtcaaaggct tctatcccag cgacatcgcc    900
gtggagtggg agagcaatgg gcagccggag aacaactaca agaccacgcc tcccgtgctg    960
aagtccgacg gctccttctt cctctatagc aagctcaccg tggacaagag caggtggcag    1020
caggggaacg tcttctcatg ctccgtgatg catgaggctc tgcacaacca ctacacgcag    1080
aagagcctct ccctgtctcc gggtaaa                                         1107

<210> SEQ ID NO 257
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
atggatgcaa tgaagagagg gctctgctgt gtgctgctgc tgtgtggagc agtcttcgtt     60
tcgcccggcg cctcgcagaa tcaagaacgc ctatgtgcgt ttaaagatcc gtatcagcaa    120
gaccttggga taggtgagag tagaatctct catgaaaatg gacaatatt atgctcgaaa     180 ggtagcacct gctatggcct ttgggagaaa tcaaagggg acataaatct tgtaaaacaa     240
ggatgttggt ctcacattgg agatccccaa gagtgtcact atgaagaatg tgtagtaact    300
accactcctc cctcaattca gaatggaaca taccgtttct gctgttgtag cacagattta    360
tgtaatgtca actttactga gaattttcca cctcctgaca caacaccact cagtccacct    420
cattcattta accgagatga gaccggtggt ggaactcaca catgcccacc gtgcccagca    480
cctgaactcc tggggggacc gtcagtcttc ctcttccccc caaaacccaa ggacaccctc    540
atgatctccc ggacccctga ggtcacatgc gtggtggtgg acgtgagcca cgaagaccct    600
gaggtcaagt tcaactggta cgtggacggc gtggaggtgc ataatgccaa gacaaagccg    660
cgggaggagc agtacaacag cacgtaccgt gtggtcagcg tcctcaccgt cctgcaccag    720
gactggctga atggcaagga gtacaagtgc aaggtctcca caaagccct cccagccccc     780 atcgagaaaa ccatctccaa agccaagggg cagccccgag aaccacaggt gtacaccctg    840
cccccatccc ggaaggagat gaccaagaac caggtcagcc tgacctgcct ggtcaaaggc    900
ttctatccca gcgacatcgc cgtggagtgg gagagcaatg ggcagccgga gaacaactac    960
aagaccacgc ctcccgtgct gaagtccgac ggctccttct cctctatag caagctcacc    1020 gtggacaaga gcaggtggca gcaggggaac gtcttctcat gctccgtgat gcatgaggct    1080
ctgcacaacc actacacgca gaagagcctc tccctgtctc cgggtaaa                 1128

<210> SEQ ID NO 258
<211> LENGTH: 1053
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
atggatgcaa tgaagagagg gctctgctgt gtgctgctgc tgtgtggagc agtcttcgtt     60
```

| | | |
|---|---|---|
| tcgcccggcg ccgaccctgt gaagccgtct cggggcccgc tggtgacctg cacgtgtgag | 120 | |
| agcccacatt gcaaggggcc tacctgccgg ggggcctggt gcacagtagt gctggtgcgg | 180 | |
| gaggagggga ggcaccccca ggaacatcgg ggctgcggga acttgcacag ggagctctgc | 240 | |
| aggggccgcc ccaccgagtt cgtcaaccac tactgctgcg acagccacct ctgcaaccac | 300 | |
| aacgtgtccc tggtgctgga ggccacccaa cctccttcgg agcagccggg aacagatggc | 360 | |
| cagctggcca ccggtggtgg aactcacaca tgcccaccgt gcccagcacc tgaactcctg | 420 | |
| ggggaccgt cagtcttcct cttccccca aacccaagg acaccctcat gatctcccgg | 480 | |
| acccctgagg tcacatgcgt ggtggtggac gtgagccacg aagaccctga ggtcaagttc | 540 | |
| aactggtacg tggacggcgt ggaggtgcat aatgccaaga caaagccgcg ggaggagcag | 600 | |
| tacaacagca cgtaccgtgt ggtcagcgtc ctcaccgtcc tgcaccagga ctggctgaat | 660 | |
| ggcaaggagt acaagtgcaa ggtctccaac aaagccctcc cagcccccat cgagaaaacc | 720 | |
| atctccaaag ccaaagggca gccccgagaa ccacaggtgt acaccctgcc cccatcccgg | 780 | |
| gaggagatga ccaagaacca ggtcagcctg acctgcctgg tcaaaggctt ctatcccagc | 840 | |
| gacatcgccg tggagtggga gagcaatggg cagccggaga acaactacga caccacgcct | 900 | |
| cccgtgctgg actccgacgg ctccttcttc ctctatagcg acctcaccgt ggacaagagc | 960 | |
| aggtggcagc aggggaacgt cttctcatgc tccgtgatgc atgaggctct gcacaaccac | 1020 | |
| tacacgcaga agagcctctc cctgtctccg ggt | 1053 | |

<210> SEQ ID NO 259
<211> LENGTH: 1170
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 259

| | | |
|---|---|---|
| atggatgcaa tgaagagagg gctctgctgt gtgctgctgc tgtgtggagc agtcttcgtt | 60 | |
| tcgcccggcg ccacgatccc accgcacgtt cagaagtcgg ttaataacga catgatagtc | 120 | |
| actgacaaca acggtgcagt caagtttcca caactgtgta aattttgtga tgtgagattt | 180 | |
| tccacctgtg acaaccagaa atcctgcatg agcaactgca gcatcacctc catctgtgag | 240 | |
| aagccacagg aagtctgtgt ggctgtatgg agaaagaatg acgagaacat aacactagag | 300 | |
| acagtttgcc atgaccccaa gctcccctac catgacttta ttctggaaga tgctgcttct | 360 | |
| ccaaagtgca ttatgaagga aaaaaaaaag cctggtgaga cttttcttcat gtgttcctgt | 420 | |
| agctctgatg agtgcaatga caacatcatc ttctcagaag aatataacac cagcaatcct | 480 | |
| acaccggtg tggaactca cacatgccca ccgtgcccag cacctgaact cctgggggga | 540 | |
| ccgtcagtct tcctcttccc cccaaaaccc aaggacaccc tcatgatctc ccggacccct | 600 | |
| gaggtcacat gcgtggtggt ggacgtgagc cacgaagacc ctgaggtcaa gttcaactgg | 660 | |
| tacgtggacg gcgtggaggt gcataatgcc aagacaaagc cgcgggagga gcagtacaac | 720 | |
| agcacgtacc gtgtggtcag cgtcctcacc gtcctgcacc aggactggct gaatggcaag | 780 | |
| gagtacaagt gcaaggtctc caacaaagcc ctcccagccc ccatcgagaa aaccatctcc | 840 | |
| aaagccaaag ggcagccccg agaaccacag gtgtacaccc tgcccccatc ccggaaggag | 900 | |
| atgaccaaga accaggtcag cctgacctgc ctggtcaaag gcttctatcc cagcgacatc | 960 | |
| gccgtggagt gggagagcaa tgggcagccg gagaacaact acaagaccac gcctcccgtg | 1020 | |

| | |
|---|---|
| ctgaagtccg acggctcctt cttcctctat agcaagctca ccgtggacaa gagcaggtgg | 1080 |
| cagcagggga acgtcttctc atgctccgtg atgcatgagg ctctgcacaa ccactacacg | 1140 |
| cagaagagcc tctccctgtc tccgggtaaa | 1170 |

<210> SEQ ID NO 260
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260

| | |
|---|---|
| atggatgcaa tgaagagagg gctctgctgt gtgctgctgc tgtgtggagc agtcttcgtt | 60 |
| tcgcccggcg ccacgatccc accgcacgtt cagaagtcgg atgtggaaat ggaggcccag | 120 |
| aaagatgaaa tcatctgccc cagctgtaat aggactgccc atccactgag acatattaat | 180 |
| aacgacatga tagtcactga caacaacggt gcagtcaagt ttccacaact gtgtaaattt | 240 |
| tgtgatgtga gattttccac ctgtgacaac cagaaatcct gcatgagcaa ctgcagcatc | 300 |
| acctccatct gtgagaagcc acaggaagtc tgtgtggctg tatggagaaa gaatgacgag | 360 |
| aacataacac tagagacagt ttgccatgac cccaagctcc cctaccatga ctttattctg | 420 |
| gaagatgctg cttctccaaa gtgcattatg aaggaaaaaa aaaagcctgg tgagactttc | 480 |
| ttcatgtgtt cctgtagctc tgatgagtgc aatgacaaca tcatcttctc agaagaatat | 540 |
| aacaccagca atcctgacac cggtggtgga actcacacat gcccaccgtg cccagcacct | 600 |
| gaactcctgg ggggaccgtc agtcttcctc ttccccccaa acccaaggac caccctcatg | 660 |
| atctcccgga cccctgaggt cacatgcgtg gtggtggacg tgagccacga agaccctgag | 720 |
| gtcaagttca actggtacgt ggacggcgtg gaggtgcata atgccaagac aaagccgcgg | 780 |
| gaggagcagt acaacagcac gtaccgtgtg gtcagcgtcc tcaccgtcct gcaccaggac | 840 |
| tggctgaatg gcaaggagta caagtgcaag gtctccaaca aagcccctcc cagcccccatc | 900 |
| gagaaaacca tctccaaagc caaagggcag ccccgagaac cacaggtgta caccctgccc | 960 |
| ccatcccgga aggagatgac caagaaccag gtcagcctga cctgcctggt caaaggcttc | 1020 |
| tatcccagcg acatcgccgt ggagtgggag agcaatgggc agccggagaa caactacaag | 1080 |
| accacgcctc ccgtgctgaa gtccgacggc tccttcttcc tctatagcaa gctcaccgtg | 1140 |
| gacaagagca ggtggcagca ggggaacgtc ttctcatgct ccgtgatgca tgaggctctg | 1200 |
| cacaaccact acacgcagaa gagcctctcc ctgtctccgg gtaaa | 1245 |

<210> SEQ ID NO 261
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gly Gly Gly
1

<210> SEQ ID NO 262
<211> LENGTH: 4
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 262

Gly Gly Gly Gly
1

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Thr Gly Gly Gly Gly
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Gly Gly Gly Gly
1               5

<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Thr Gly Gly Gly
1

<210> SEQ ID NO 266
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Gly Gly Gly
1

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Gly Gly Gly Ser
1               5
```

```
<210> SEQ ID NO 268
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 268

His His His His His His
1               5

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 2-10 residues

<400> SEQUENCE: 269

Gly Gly Gly Gly Gly Gly Gly Gly Gly Gly
1               5                   10

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(5)
<223> OTHER INFORMATION: This sequence may encompass 2-5 residues

<400> SEQUENCE: 270

Gly Gly Gly Gly Gly
1               5

<210> SEQ ID NO 271
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This sequence may encompass 2-4 residues

<400> SEQUENCE: 271

Gly Gly Gly Gly
1

<210> SEQ ID NO 272
<211> LENGTH: 116
<212> TYPE: PRT
<213> ORGANISM: Homo sapiens

<400> SEQUENCE: 272

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
```

```
                    20                  25                  30
Asp Lys Asp Lys Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 273
<211> LENGTH: 115
<212> TYPE: PRT
<213> ORGANISM: Homo sapiens

<400> SEQUENCE: 273

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 274
<211> LENGTH: 150
<212> TYPE: PRT
<213> ORGANISM: Rattus sp.

<400> SEQUENCE: 274

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
```

```
                100                 105                 110
Phe Thr His Leu Pro Glu Pro Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 275
<211> LENGTH: 150
<212> TYPE: PRT
<213> ORGANISM: Sus sp.

<400> SEQUENCE: 275

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser
145                 150

<210> SEQ ID NO 276
<211> LENGTH: 150
<212> TYPE: PRT
<213> ORGANISM: Mus sp.

<400> SEQUENCE: 276

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
```

```
            115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 277
<211> LENGTH: 150
<212> TYPE: PRT
<213> ORGANISM: Homo sapiens

<400> SEQUENCE: 277

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
            130                 135                 140

Pro Ile Gly Gly Leu Ser
145                 150

<210> SEQ ID NO 278
<211> LENGTH: 150
<212> TYPE: PRT
<213> ORGANISM: Bos sp.

<400> SEQUENCE: 278

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
            35                  40                  45

Cys Glu Gly Glu Arg Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
```

```
            130                 135                 140

Pro Val Gly Gly Leu Ser
145                 150

<210> SEQ ID NO 279
<211> LENGTH: 150
<212> TYPE: PRT
<213> ORGANISM: Xenopus sp.

<400> SEQUENCE: 279

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
                20                  25                  30

Tyr Asn Ala Asn Trp Glu Leu Glu Lys Thr Asn Gln Ser Gly Val Glu
            35                  40                  45

Arg Leu Val Glu Gly Lys Lys Asp Lys Arg Leu His Cys Tyr Ala Ser
        50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150

<210> SEQ ID NO 280
<211> LENGTH: 150
<212> TYPE: PRT
<213> ORGANISM: Homo sapiens

<400> SEQUENCE: 280

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
                20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
        50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125
```

```
Pro Val Thr Pro Lys Pro Pro Tyr Tyr Asn Ile Leu Leu Tyr Ser Leu
    130             135                 140

Val Pro Leu Met Leu Ile
145                 150
```

VARIANT ACTRIIB PROTEINS AND USES THEREOF

CROSS-REFERENCE TO RELATED APPLICATIONS

This application is a continuation of U.S. application Ser. No. 16/340,048, filed Apr. 5, 2019 (now allowed), which is a national stage filing under 35 U.S.C. § 371 of International Application No. PCT/US2017/055421, filed on Oct. 5, 2017 (now expired), which claims the benefit of priority from U.S. Provisional Application No. 62/404,718, filed Oct. 5, 2016. The specifications of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Mar. 7, 2022, is named 1848179-0002-119-302_Seq.txt and is 498,228 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Changes in red blood cell levels, bone, cartilage and other tissues may be achieved by agonizing or antagonizing signaling that is mediated by an appropriate TGF-beta family member. Thus, there is a need for agents that function as potent regulators of TGF-beta signaling.

SUMMARY OF THE INVENTION

In certain aspects, the present disclosure provides variant ActRIIB polypeptides, particularly variant ActRIIB homomultimer proteins and variant ActRIIB heteromultimer proteins. As demonstrated by the examples, several variant ActRIIB polypeptides have been identified that display altered binding affinity for one or more ActRIIB-binding ligands. ActRIIB variants that decrease and increase ligand-binding activities were identified. Such variants may be particularly useful for increasing or decreasing ligand selectively compared to a corresponding unmodified ActRIIB polypeptide in a variety of applications. For example, the examples further demonstrate that some of the variant ActRIIB polypeptides have various in vivo effects including, for example, the ability to increase body mass (e.g., muscle mass) as well as increasing red blood cell and hemoglobin levels. Therefore, variant ActRIIB polypeptides should be useful in a variety of therapeutic applications including, for example, those described herein.

In certain aspects, the disclosure relate to variant ActRIIB polypeptides comprising an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2, and wherein the polypeptide comprises one or more amino acid substitutions at a position of SEQ ID NO: 2 selected from the group consisting of: K55, F82, L79, A24, K74, R64, P129, P130, E37, R40, D54, R56, W78, D80, and F82 as well as heteromultimer complexes comprising one or more such ActRIIB polypeptides. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to amino acids 20-134 of SEQ ID NO: 2. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the polypeptide comprises an amino acid substitution at the amino acid position corresponding to K55 of SEQ ID NO: 2. For example, in some embodiments, the substitution is K55A. In some embodiments, the substitution is K55E. In some embodiments, the polypeptide comprises an amino acid substitution at the amino acid position corresponding to L79 of SEQ ID NO: 2. For example, in some embodiments, the substitution is L79D. In some embodiments, the substitution is L79E. In some embodiments, the substitution is L79P. In some embodiments, the substitution is L79A. In some embodiments, the polypeptide comprises an amino acid substitution at the amino acid position corresponding to F82 of SEQ ID NO: 2. For example, in some embodiments, the substitution is F82I. In some embodiments, the substitution is F82K. In some embodiments, the substitution is F82A. In some embodiments, the polypeptide comprises an amino acid substitution at the amino acid position corresponding to A24 of SEQ ID NO: 2. For example, in some embodiments, the substitution is A24N. In some embodiments, the polypeptide comprises an amino acid substitution at the amino acid position corresponding to K74 of SEQ ID NO: 2. For example, in some embodiments, the substitution is K74A. In some embodiments, the substitution is K74A. In some embodiments, the substitution is K74F. In some embodiments, the substitution is K74A. In some embodiments, the substitution is K74I. In some embodiments, the substitution is K74A. In some embodiments, the substitution is K74Y. In some embodiments, the polypeptide comprises an amino acid substitution at the amino acid position corresponding to D80 of SEQ ID NO: 2. For example, in some embodiments, the substitution is D80A. In some embodiments, the substitution is D80F. In some embodiments, the substitution is D80K. In some embodiments, the substitution is D80G. In some embodiments, the substitution is D80M. In some embodiments, the substitution is D80I. In some embodiments, the substitution is D80N. In some embodiments, the substitution is D80R. In some embodiments, the polypeptide comprises an amino acid substitution at the amino acid position corresponding to R64 of SEQ ID NO: 2. For example, in some embodiments, the substitution is R64K. In some embodiments, the substitution is R64N. In some embodiments, the polypeptide comprises an amino acid substitution at the amino acid position corresponding to P129 of SEQ ID NO: 2. For example, in some embodiments, the substitution is P129S. In some embodiments, the polypeptide comprises an amino acid substitution at the amino acid position corresponding to P130 of SEQ ID NO: 2. For example, in some embodiments, the substitution is P130A. In some embodiments, the substitution is P130R. In some embodiments, the polypeptide comprises an amino acid substitution at the amino acid position corresponding to E37 of SEQ ID NO: 2. For example, in some embodiments, the substitution is E37A. In some embodiments, the polypeptide comprises an amino acid substitution at the amino acid position corresponding to R40 of SEQ ID NO: 2. For example, in some embodiments, the substitution is R40A. In some embodiments, the polypeptide comprises an amino acid substitution at the amino acid position corresponding to D54 of SEQ ID NO: 2. For example, in some embodiments, the substitution is D54A. In some embodiments, the polypeptide comprises an amino acid substitution at the amino acid position corresponding to R56 of SEQ ID NO: 2. For example, in some embodiments, the substitution is R56A. In some embodiments, the polypeptide comprises an amino acid substitution at the amino acid position corresponding to W78 of SEQ ID NO: 2. For example, in some embodiments, the substitution is W78A.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 31. In some embodiments, the variant ActRIIB polypeptide comprises an alanine at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 33. In some embodiments, the variant ActRIIB polypeptide comprises an alanine at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 34. In some embodiments, the variant ActRIIB polypeptide comprises a glutamic acid at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 36. In some embodiments, the variant ActRIIB polypeptide comprises a glutamic acid at the position corresponding to K55 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 37. In some embodiments, the variant ActRIIB polypeptide comprises an isoleucine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 39. In some embodiments, the variant ActRIIB polypeptide comprises an isoleucine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 40. In some embodiments, the variant ActRIIB polypeptide comprises a lysine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 42. In some embodiments, the variant ActRIIB polypeptide comprises a lysine at the position corresponding to F82 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 43. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 45. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 46. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 48. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 49. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 50. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 51. In some embodiments, the variant ActRIIB polypeptide comprises a glutamic acid at the position corresponding to L79 of SEQ ID NO: 2.

In certain aspects, the disclosure relates to a variant ActRIIB polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 52. In some embodiments, the variant ActRIIB polypeptide comprises a glutamic acid at the position corresponding to L79 of SEQ ID NO: 2.

In certain aspects, variant ActRIIB polypeptide of the disclosure form homodimers. In some embodiments, variant ActRIIB polypeptides may from heterodimers through covalent interactions. In some embodiments, variant ActRIIB polypeptides may from heterodimers through non-covalent interactions. In some embodiments, variant ActRIIB polypeptides may from heterodimers through both covalent and non-covalent interactions.

In certain aspects, a variant ActRIIB polypeptide, including homomultimers thereof (e.g., homodimers), binds to one or more TGF-beta superfamily ligands. In some embodiments, variant ActRIIB polypeptide, including homomultimers thereof, binds to one or more TGF-beta superfamily ligands with a $K_D$ of at least $1 \times 10^{-7}$ M. In some embodiments, the one or more TGF-beta superfamily ligands is selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, a variant ActRIIB polypeptide, including homomultimers thereof (e.g., homodimers), inhibits one or more TGF-beta super family ligands. In some embodiments, variant ActRIIB polypeptide, including homomultimers thereof, inhibits signaling of one or more TGF-beta super family ligands. In some embodiments, variant ActRIIB polypeptide, including homomultimers thereof, inhibits Smad signaling of one or more TGF-beta super family ligands. In some embodiments, variant ActRIIB polypeptide, including homomultimers thereof, inhibits signaling of one or more TGF-beta super family ligands in a cell-based assay. In some embodiments, variant ActRIIB polypeptide, including homomultimers thereof, inhibits one or more TGF-beta super family ligands selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, the disclosure relates to heteromultimers that comprise at least one variant ActRIIB polypeptide (e.g., one or more variant ActRIIB polypeptides described herein). For example, in some embodiments, a heteromultimer protein of the disclosure comprises a first ActRIIB polypeptide and a second ActRIIB polypeptide, wherein the first ActRIIB polypeptide comprises an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2 and comprises one or more amino acid substitutions at positions corresponding to SEQ ID NO: 2 amino acids selected from the group consisting of: A24, K74, R64, P129, P130, E37, R40, D54, R56, W78, D80, and F82, wherein the second ActRIIB polypeptide comprises an amino acid sequence that is at least 75%, 80%, 85%, 90%, 91%, 92%, 93%, 94%, 95%, 96%, 97%, 98%, 99%, or 100% identical to an amino acid sequence that begins at any one of amino acid 20-29 (e.g., 20, 21, 22, 23, 24, 25, 26, 27, 28, or 29) of SEQ ID NO: 2 and ends at any one of amino acid 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 2, and wherein the first ActRIIB polypeptide comprises a different amino acid sequence compared to the second ActRIIB polypeptide. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 29-109 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to amino acids 20-134 of SEQ ID NO: 2. In some embodiments, the second polypeptide comprises an amino acid sequence that is at least 75%, 80%, 85%, 90%, 91%, 92%, 93%, 94%, 95%, 96%, 97%, 98%, 99%, or 100% identical to amino acids 25-131 of SEQ ID NO: 2. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 53. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 5. In some embodiments, the first polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the second polypeptide comprises an amino acid sequence that is at least 75%, 80%, 85%, 90%, 91%, 92%, 93%, 94%, 95%, 96%, 97%, 98%, 99%, or 100% identical to the amino acid sequence of SEQ ID NO: 12. In some embodiments, the first polypeptide comprises an amino acid substitution at the amino acid position corresponding to K55 of SEQ ID NO: 2. For example, in some embodiments, the substitution is K55A. In some embodiments, the substitution is K55E. In some embodiments, the first polypeptide comprises an amino acid substitution at the amino acid position corresponding to L79 of SEQ ID NO: 2. For example, in some embodiments, the substitution is L79D. In some embodiments, the substitution is L79E. In some embodiments, the substitution is L79P. In some embodiments, the substitution is L79A. In some embodiments, the first polypeptide comprises an amino acid substitution at the amino acid position corresponding to F82 of SEQ ID NO: 2. For example, in some embodiments, the substitution is F82I. In some embodiments, the substitution is F82K. In some embodiments, the substitution is F82A. In some embodiments, the first polypeptide comprises an amino acid substitution at the amino acid position corresponding to A24 of SEQ ID NO: 2. For example, in some embodiments, the substitution is A24N. In some embodiments, the polypeptide comprises an amino acid substitution at the amino acid position corresponding to K74 of SEQ ID NO: 2. For example, in some embodiments, the substitution is K74A. In some embodiments, the substitution is K74A. In some embodiments, the substitution is K74F. In some embodiments, the substitution is K74A. In some embodiments, the substitution is K74I. In some embodiments, the substitution is K74A. In some embodiments, the substitution is K74Y. In some embodiments, the first polypeptide comprises an amino acid substitution at the amino acid position corresponding to D80 of SEQ ID NO: 2. For example, in some embodiments, the substitution is D80A. In some embodiments, the substitution is D80F. In some embodiments, the substitution is D80K. In some embodiments, the substitution is D80G. In some embodiments, the substitution is D80M. In some embodiments, the substitution is D80I. In some embodiments, the substitution is D80N. In some embodiments, the substitution is D80R. In some embodiments, the first polypeptide comprises an amino acid substitution at the amino acid position corresponding to R64 of SEQ ID NO: 2. For example, in some embodiments, the substitution is R64K. In some embodiments, the substitution is R64N. In some embodiments, the first polypeptide comprises an amino acid substitution at the amino acid position corresponding to P129 of SEQ ID NO: 2. For example, in some embodiments, the substitution is P129S. In some embodiments, the first polypeptide comprises an amino acid substitution at the amino acid position corresponding to P130 of SEQ ID NO: 2. For example, in some embodiments, the substitution is P130A. In some embodiments, the substitution is P130R. In some embodiments, the first polypeptide comprises an amino acid substitution at the amino acid position corresponding to E37 of SEQ ID NO: 2. For example, in some embodiments, the substitution is E37A. In some embodiments, the first polypeptide comprises an amino acid substitution at the amino acid position corresponding to R40 of SEQ ID NO: 2. For example, in some embodiments, the substitution is R40A. In some embodiments, the first polypeptide comprises an amino acid substitution at the amino acid position corresponding to D54 of SEQ ID NO: 2. For example, in some embodiments, the substitution is D54A. In some embodiments, the first polypeptide comprises an amino acid substitution at the amino acid position corresponding to R56 of SEQ ID NO: 2. For example, in some embodiments, the substitution is R56A. In some embodiments, the first polypeptide comprises an amino acid substitution at the amino acid position corresponding to W78 of SEQ ID NO: 2. For example, in some embodiments, the substitution is W78A. In some embodiments, the second ActRIIB polypeptide comprises one or more amino acid substitutions at a position of SEQ ID NO: 2 selected from the group consisting of: A24, K74, R64, P129, P130, E37, R40, D54, R56, W78, D80, and F82. For example, in some embodiments, the second ActRIIB polypeptide comprises one or more amino acid substitution with respect to the amino acid sequence of SEQ ID NO: 2 selected from the group consisting of: A24N, K74A, R64K, R64N, K74A, L79A, L79D, L79E, L79P, P129S, P130A, P130R, E37A, R40A, D54A, K55A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modifications that promote heteromultimer formation. In some embodiments, the first ActRIIB polypeptide and/or the second ActRIIB polypeptide comprise one or more amino acid modifications that inhibit heteromultimer formation. In some embodiments, the first ActRIIB polypeptide and/or the second ActRIIB polypeptide comprise one or more amino acid modifications that promote heteromultimer formation and one or more amino acid modifications that inhibit heteromultimer formation. In some embodiments, heteromultimers of the disclosure are heterodimers.

In certain aspects, an ActRIIB polypeptides of the disclosure, including a variant ActRIIB polypeptide, is a fusion protein comprising an ActRIIB polypeptide domain and one or more heterologous domains. In some embodiments, an ActRIIB polypeptide is an ActRIIB-Fc fusion protein. In some embodiments, an ActRIIB-Fc fusion protein further comprises a linker domain positioned between the ActRIIB polypeptide domain and the one or more heterologous domains or Fc domain. In some embodiments, the linker domain is selected from: TGGG (SEQ ID NO: 265), TGGGG (SEQ ID NO: 263), SGGGG (SEQ ID NO: 264), GGGGS (SEQ ID NO: 267), GGG (SEQ ID NO: 261), GGGG (SEQ ID NO: 262), and SGGG (SEQ ID NO: 266).

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 13, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 13.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 14, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 14.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 15, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 15.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 16, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 16.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 17, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 17.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 18, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 19.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 19, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 18.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 20, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 21.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 21, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 20.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 22, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 25.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 25, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 24.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 26, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 27.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 27, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 26.

In certain aspects, the disclosure relates to ActRIIB heteromultimer proteins comprising a first ActRIIB-Fc fusion protein and a second ActRIIB-Fc fusion protein wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 28, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 29. In some embodiments, the first ActRIIB-Fc fusion protein Fc domain comprises a cysteine at amino acid position 132, glutamic acid at amino acid position 138, a tryptophan at amino acid position 144, and a aspartic acid at amino acid position 217. In some embodiments, the second ActRIIB-Fc fusion protein Fc domain comprises a cysteine at amino acid position 127, a serine at amino acid position 144, an alanine at position 146 an arginine at amino acid position 162, an arginine at amino acid position 179, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 28, and the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 29. In some embodiments, the second ActRIIB-Fc fusion protein Fc domain comprises a cysteine at amino acid position 132, glutamic acid at amino acid position 138, a tryptophan at amino acid position 144, and a aspartic acid at amino acid position 217. In some embodiments, the first ActRIIB-Fc fusion protein Fc domain comprises a cysteine at amino acid position 127, a serine at amino acid position 144, an alanine at position 146 an arginine at amino acid position 162, an arginine at amino acid position 179, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 30, and the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23. In some embodiments, the first ActRIIB-Fc fusion protein Fc domain comprises a cysteine at amino acid position 132, a tryptophan at amino acid position 144, and a arginine at amino acid position 435. In some embodiments, the second ActRIIB-Fc fusion protein Fc domain comprises cysteine at amino acid position 127, a serine at amino acid position 144, an alanine at amino acid position 146, and a valine at amino acid position 185.

In certain aspects, the disclosure relates to ActRIIB heteromultimer proteins comprising a first ActRIIB-Fc fusion protein and a second ActRIIB-Fc fusion protein wherein the second ActRIIB-Fc fusion protein, wherein the second ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 30, and the first ActRIIB-Fc fusion protein comprises an Fc domain that is at least 75%, 80%, 85%, 90%, 91%, 92%, 93%, 94%, 95%, 96%, 97%, 98%, 99%, or 100% identical to the amino acid sequence of SEQ ID NO: 23. In some embodiments, the second ActRIIB-Fc fusion protein Fc domain comprises a cysteine at amino acid position 132, a tryptophan at amino acid position 144, and a arginine at amino acid position 435. In some embodiments, the first ActRIIB-Fc fusion protein Fc domain comprises cysteine at amino acid position 127, a serine at amino acid position 144, an alanine at amino acid position 146, and a valine at amino acid position 185.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 33, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a alanine at the amino acid position corresponding to 55 of SEQ ID NO: 2. In some embodiments, the second ActRIIB polypeptide does not comprise a alanine at the amino acid position corresponding to 55 of SEQ ID NO: 2. In some embodiments, the second ActRIIB polypeptide comprises a lysine at the amino acid position corresponding to 55 of SEQ ID NO: 2. In some embodiments, the first ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 36, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a glutamic acid at the amino acid position corresponding to 55 of SEQ ID NO: 2. In some embodiments, the second ActRIIB polypeptide does not comprise a glutamic acid at the amino acid position corresponding to 55 of SEQ ID NO: 2. In some embodiments, the second ActRIIB polypeptide comprises a lysine at the amino acid position corresponding to 55 of SEQ ID NO: 2. In some embodiments, the first ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, L79, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 39, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, the first ActRIIB polypeptide comprises a isoleucine at the amino acid position corresponding to 82 of SEQ ID NO: 2. In some embodiments, the second ActRIIB polypeptide does not comprise a isoleucine acid at the amino acid position corresponding to 82 of SEQ ID NO: 2. In some embodiments, the second ActRIIB polypeptide comprises a phenylalanine at the amino acid position corresponding to 82 of SEQ ID NO: 2. In some embodiments, the first ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the second ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 42, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 5, wherein the first ActRIIB polypeptide does not comprise the amino acid sequence of the second ActRIIB polypeptide. In some embodiments, first ActRIIB polypeptide comprises a lysine at the amino acid position corresponding to 82 of SEQ ID NO: 2. In some embodiments, the second ActRIIB polypeptide does not comprise a lysine acid at the amino acid position corresponding to 82 of SEQ ID NO: 2. In some embodiments, the second ActRIIB polypeptide comprises a phenylalanine at the amino acid position corresponding to 82 of SEQ ID NO: 2. In some embodiments, the first ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the second ActRIIB polypeptide comprises one or more amino acid substitutions at the amino acid positions corresponding to any one of L79, A24, K74, R64, P129, P130, E37, R40, D54, R56, W78, and D80 of SEQ ID NO: 2. In some embodiments, the one or more amino acid substitutions is selected from the group consisting of: A24N, K74A, R64K, R64N, K74A, L79A, L79D, L79E, L79P, P129S, P130A, P130R, E37A, R40A, D54A, R56A, K74F, K74I, K74Y, W78A, D80A, D80F, D80G, D80I, D80K, D80M, D80M, D80N, and D80R. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 45, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 48, wherein the first ActRIIB polypeptide does not comprise the amino acid sequence of the second ActRIIB polypeptide. In some embodiments, the first ActRIIB polypeptide comprises an acidic amino acid position corresponding to 79 of SEQ ID NO: 2. In some embodiments, the acidic amino acid is an aspartic acid. In some embodiments, the acidic amino acid is a glutamic acid. In some embodiments, the second ActRIIB polypeptide does not comprise an acidic acid (e.g., aspartic acid or glutamic acid) at the amino acid position corresponding to 79 of SEQ ID NO: 2. In some embodiments, the second ActRIIB polypeptide comprises a leucine at the amino acid position corresponding to 79 of SEQ ID NO: 2. In some embodiments, the first ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the first ActRIIB polypeptide and/or the second ActRIIB polypeptide comprise one or more amino acid modification that promote heteromultimer formation. In some embodiments, the first ActRIIB polypeptide and/or the second ActRIIB polypeptide comprise one or more amino acid modification that inhibit heteromultimer formation. In some embodiments, the heteromultimer is a heterodimer.

In certain aspects, the disclosure relates to a heteromultimer comprising a first ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 50, and second ActRIIB polypeptide that is at least 75%, 80%, 85%, 90%, 91%, 92%, 93%, 94%, 95%, 96%, 97%, 98%, 99%, or 100% identical to the amino acid sequence of SEQ ID NO: 52, wherein the first ActRIIB polypeptide does not comprise the amino acid sequence of the second ActRIIB polypeptide. In some embodiments, the first ActRIIB polypeptide comprises an acidic amino acid position corresponding to 79 of SEQ ID NO: 2. In some embodiments, the acidic amino acid is an aspartic acid. In some embodiments, the acidic amino acid is a glutamic acid. In some embodiments, the second ActRIIB polypeptide does not comprise an acidic acid (e.g., aspartic acid or glutamic acid) at the amino acid position corresponding to 79 of SEQ ID NO: 2. In some embodiments, the second ActRIIB polypeptide comprises a leucine at the amino acid position corresponding to 79 of SEQ ID NO: 2. In some embodiments, the first ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, L79P, P129S, P130A, P130R, E37A, R40A, D54A, R56A, K74F, K74I, K74Y, W78A, D80A, D80F, D80G, D80I, D80K, D80M, D80M, D80N, D80R, and F82A. In some embodiments, the second ActRIIB polypeptide comprises one or more amino acid substitutions at the amino acid positions corresponding to any one of F82, A24, K74, R64, P129, P130, E37, R40, D54, R56, W78, D80, and F82 of SEQ ID NO: 2. In some embodiments, the one or more amino acid substitutions is selected from the group consisting of: A24N, K74A, R64K, R64N, K74A, P129S, P130A, P130R, E37A, R40A, D54A, R56A, K74F, K74I, K74Y, W78A, D80A, D80F, D80G, D80I, D80K, D80M, D80M, D80N, D80R, and F82A.

In certain embodiments, the disclosure provides for a heteromultimer protein comprising any of the ActRIIB polypeptides disclosed herein and a second polypeptide selected from the group consisting of: ALK1, ALK2, ALK3, ALK4, ALK5, ALK6, ALK7, ActRIIA, TGFBRII, BMPRII, and MISRII polypeptide, or functional fragments thereof. In some embodiments, the second polypeptide is an ALK1 polypeptide or a functional fragment thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 54, or functional fragments thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 60, and 61, or functional fragments thereof. In some embodiments, the second polypeptide is an ALK2 polypeptide or a functional fragment thereof. In some embodiments, the ALK2 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 64 or 65, or functional fragments thereof. In some embodiments, the ALK2 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 70, and 71, or functional fragments thereof. In some embodiments, the second polypeptide is an ALK3 polypeptide or a functional fragment thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, or functional fragments thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, 75, 76, 77, 80, or 81, or functional fragments thereof. In some embodiments, the second polypeptide is an ALK4 polypeptide or a functional fragment thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84 or 85, or functional fragments thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84, 86, 85, 87, 88, 89, 92, and 93, or functional fragments thereof. In some embodiments, the second polypeptide is an ALK5 polypeptide or a functional fragment thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96 or 97, or functional fragments thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96, 98, 97, 99, 100, 101, 104, and 105, or functional fragments thereof. In some embodiments, the second polypeptide is an ALK6 polypeptide or a functional fragment thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108 or 110, or functional fragments thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108, 109, 110, 111, 112, 113, 116, and 117, or functional fragments thereof. In some embodiments, the second polypeptide is an ALK7 polypeptide or a functional fragment thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 121, or 122, or functional fragments thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 123, 124, 125, 121, 126, 122, 127, 128, 129, 130, 133, and 134, or functional fragments thereof. In some embodiments, the second polypeptide is an ActRIIA polypeptide or a functional fragment thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, or functional fragments thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, 138, 139, 140, 141, 144, and 145, or functional fragments thereof. In some embodiments, the second polypeptide is an TGFBRII polypeptide or a functional fragment thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 204, or functional fragments thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 161, 162, 160, 163, 164, 165, 166, 167, 172, 173, 174, and 175, or functional fragments thereof. In some embodiments, the second polypeptide is an BMPRII polypeptide or a functional fragment thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148 or 149, or functional fragments thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148, 150, 149, 151, 152, 153, 156, and 157, or functional fragments thereof. In some embodiments, the second polypeptide is an MISRII polypeptide or a functional fragment thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 181, or 182, or functional fragments thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 183, 181, 184, 182, and 185, or functional fragments thereof.

In certain aspects, heteromultimers of the disclosure bind to one or more TGF-beta superfamily ligands. In some embodiments, heteromultimers of the disclosure binds to one or more TGF-beta superfamily ligands with a $K_D$ of at least $1 \times 10^{-7}$ M. In some embodiments, the one or more TGF-beta superfamily ligands is selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, heteromultimers of the disclosure inhibits one or more TGF-beta super family ligands. In some embodiments, heteromultimers of the disclosure inhibits signaling of one or more TGF-beta super family ligands. In some embodiments, heteromultimers of the disclosure inhibits Smad signaling of one or more TGF-beta super family ligands. In some embodiments, heteromultimers of the disclosure inhibits signaling of one or more TGF-beta super family ligands in a cell-based assay. In some embodiments, heteromultimers of the disclosure inhibits one or more TGF-beta super family ligands selected from the group consisting of: BMP6, BMP7, BMP9, BMP10, GDF3, GDF7, GDF8, GDF11, GDF15, activin A, activin B, activin C, activin E, activin AB, activin AC, activin AE, activin BC, and activin BE.

In certain aspects, the disclosure relates to ActRIIB polypeptides, including variant ActRIIB polypeptides as well as homomultimer and heteromultimers comprising the same, that comprises one or more amino acid modifications selected from the group consisting of: a glycosylated amino acid, a PEGylated amino acid, a farnesylated amino acid, an acetylated amino acid, a biotinylated amino acid, and an amino acid conjugated to a lipid moiety. In some embodiments, ActRIIB polypeptides of the disclosure are glycosylated and has a glycosylation pattern obtainable from of the polypeptide in a CHO cell.

In certain embodiments, the disclosure provides for a heteromultimer protein comprising any of the ActRIIB polypeptides disclosed herein and a second polypeptide selected from the group consisting of: ALK1, ALK2, ALK3, ALK4, ALK5, ALK6, ALK7, ActRIIA, TGFBRII, BMPRII, and MISRII polypeptide, or functional fragments thereof. In some embodiments, the second polypeptide is an ALK1 polypeptide or a functional fragment thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO: 54, or functional fragments thereof. In some embodiments, the ALK1 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 58, 59, 60, 61, 62, and 63, or functional fragments thereof. In some embodiments, the second polypeptide is an ALK2 polypeptide or a functional fragment thereof. In some embodiments, the ALK2 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 64 or 65, or functional fragments thereof. In some embodiments, the ALK2 polypeptide or functional fragment thereof comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 68, 69, 70, 71, 72, and 73, or functional fragments thereof. In some embodiments, the second polypeptide is an ALK3 polypeptide or a functional fragment thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, or functional fragments thereof. In some embodiments, the ALK3 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 74, 75, 76, 77, 80, or 81, or functional fragments thereof. In some embodiments, the second polypeptide is an ALK4 polypeptide or a functional fragment thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84 or 85, or functional fragments thereof. In some embodiments, the ALK4 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 84, 86, 85, 87, 88, 89, 90, 91, 92, 93, 94, and 95, or functional fragments thereof. In some embodiments, the second polypeptide is an ALK5 polypeptide or a functional fragment thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96 or 97, or functional fragments thereof. In some embodiments, the ALK5 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 96, 98, 97, 99, 100, 101, 102, 103, 104, 105, 106, and 107, or functional fragments thereof. In some embodiments, the second polypeptide is an ALK6 polypeptide or a functional fragment thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108 or 110, or functional fragments thereof. In some embodiments, the ALK6 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 108, 109, 110, 111, 112, 113, 114, 115, 116, 117, 118, and 119, or functional fragments thereof. In some embodiments, the second polypeptide is an ALK7 polypeptide or a functional fragment thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 121, or 122, or functional fragments thereof. In some embodiments, the ALK7 polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 120, 123, 124, 125, 121, 126, 122, 127, 128, 129, 130, 131, 132, 133, 134, 135, and 136, or functional fragments thereof. In some embodiments, the second polypeptide is an ActRIIA polypeptide or a functional fragment thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, or functional fragments thereof. In some embodiments, the ActRIIA polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 137, 138, 139, 140, 141, 142, 143, 144, 145, 146, and 147, or functional fragments thereof. In some embodiments, the second polypeptide is an TGFBRII polypeptide or a functional fragment thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 204, or functional fragments thereof. In some embodiments, the TGFBRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 161, 162, 160, 163, 164, 165, 166, 167, 168, 169, 170, 171, 172, 173, 174, 175, 176, 177, 178, and 179, or functional fragments thereof. In some embodiments, the second polypeptide is an BMPRII polypeptide or a functional fragment thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148 or 149, or functional fragments thereof. In some embodiments, the BMPRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 148, 150, 149, 151, 152, 153, 154, 155, 156, 157, 158, and 159, or functional fragments thereof. In some embodiments, the second polypeptide is an MISRII polypeptide or a functional fragment thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 181, or 182, or functional fragments thereof. In some embodiments, the MISRII polypeptide or functional fragment thereof comprises an amino acid sequence that is at least 70%, 75%, 80%, 85%, 90%, 95%, 97%, 98%, 99%, or 100% identical to the amino acid sequence of SEQ ID NO: 180, 183, 181, 184, 182, 185, 186, 187, 188, 189, 190, 191, 192, and 193, or functional fragments thereof.

In certain aspects, the disclosure relates to pharmaceutical preparations comprising a ActRIIB polypeptide, including variant ActRIIB polypeptides as well as homomultimer and heteromultimers comprising the same, a pharmaceutically acceptable carrier. In some embodiments, pharmaceutical preparations comprising one or more ActRIIB heteromultimers comprises less than about 10%, 9%, 8%, 7%, 6%, 5%, 4%, 3%, 2%, or less than about 1% homomultimers.

In certain aspects, the disclosure relates to isolated and/or recombinant nucleic acids comprising a coding sequence for one or more of the ActRIIB polypeptide(s) as described herein. For example, in some embodiments, the disclosure relates to an isolated and/or recombinant nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47. In some embodiments, an isolated and/or recombinant polynucleotide sequence of the disclosure comprises a promoter sequence operably linked to a coding sequence described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the disclosure relates to vectors comprising an isolated and/or recombinant nucleic acid described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the disclosure relates to a cell comprising an isolated and/or recombinant polynucleotide sequence described herein (e.g., a nucleic acid that is at least 75%, 80%, 85%, 90%, 91%, 92%, 93%, 94%, 95%, 96%, 97%, 98%, 99%, or 100% identical to the nucleic acid sequence corresponding to any one of SEQ ID Nos: 3, 10, 31, 35, 38, 41, 44, or 47). In some embodiments, the cell is a CHO cell. In some embodiments, the cell is a COS cell.

In certain aspects, the disclosure relates to methods of making ActRIIB polypeptides, including variant ActRIIB polypeptides as well as homomultimer and heteromultimers comprising the same, as described herein. Such a method may include expressing any of the nucleic acids) disclosed herein in a suitable cell (e.g., a CHO cell or COS cell). Such a method may comprise: a) culturing a cell under conditions suitable for expression of the soluble ActRIIB polypeptide, wherein said cell comprise with an ActRIIB polypeptide expression construct. In some embodiments, the method further comprises recovering the expressed ActRIIB polypeptide. ActRIIB polypeptides may be recovered as crude, partially purified or highly purified fractions using any of the well-known techniques for obtaining protein from cell cultures.

In some embodiments, the disclosure relates to methods for increasing red blood cell levels or hemoglobin levels in a patient, comprising administering a patient in need thereof an ActRIIB polypeptide, including variant ActRIIB polypeptides as well as homomultimer and heteromultimers comprising the same, as described herein.

In some embodiments, the disclosure relates to methods for treating anemia or a disorder associated with anemia (e.g., those described herein) in a patient, comprising administering a patient in need thereof an ActRIIB polypeptide, including variant ActRIIB polypeptides as well as homomultimer and heteromultimers comprising the same, as described herein.

In some embodiments, the disclosure relates to methods for increasing muscle mass and/or muscle strength in a patient, comprising administering a patient in need thereof an ActRIIB polypeptide, including variant ActRIIB polypeptides as well as homomultimer and heteromultimers comprising the same, as described herein.

In some embodiments, the disclosure relate to methods for treating a muscle-related disorder in a patient, comprising administering a patient in need thereof an ActRIIB, including variant ActRIIB polypeptides as well as homomultimer and heteromultimers comprising the same, as described herein. In some embodiments, the disorder is associated with undesirably low muscle growth and/or muscle weakness. Such disorders include muscle atrophy, muscular dystrophy, amyotrophic lateral sclerosis (ALS), and a muscle wasting disorder (e.g., cachexia, anorexia, DMD syndrome, BMD syndrome, AIDS wasting syndrome, muscular dystrophies, neuromuscular diseases, motor neuron diseases, diseases of the neuromuscular junction, and inflammatory myopathies).

In some embodiments, the disclosure relate to methods for decreasing the body fat content or reducing the rate of increase in body fat content, and for treating a disorder associated with undesirable body weight gain, such as obesity, non-insulin dependent diabetes mellitus (NIDDM), cardiovascular disease, cancer, hypertension, osteoarthritis, stroke, respiratory problems, and gall bladder disease, comprising administering a patient in need thereof an ActRIIB, including variant ActRIIB polypeptides as well as homomultimer and heteromultimers comprising the same, as described herein.

BRIEF DESCRIPTION OF THE DRAWINGS

FIG. 2 shows an alignment of extracellular domains of human ActRIIA and human ActRIIB with the residues that are deduced herein to directly contact ligand (indicated by boxes) based on composite analysis of multiple ActRIIB and ActRIIA crystal structures.

FIG. 3 shows a multiple sequence alignment of various vertebrate ActRIIB precursor proteins without their intracellular domains, human ActRIIA precursor protein without its intracellular domain, and a consensus ActRII precursor protein.

FIG. 4 shows multiple sequence alignment of Fc domains from human IgG isotypes using Clustal 2.1. Hinge regions are indicated by dotted underline. Double underline indicates examples of positions engineered in IgG1 (SEQ ID NO: 13) Fc to promote asymmetric chain pairing and the corresponding positions with respect to other isotypes IgG4 (SEQ ID NO: 17), IgG2 (SEQ ID NO: 14), and IgG3 (SEQ ID NO: 15).

FIG. 5 shows the amino acid sequence of a human ActRIIB extracellular domain polypeptide (SEQ ID NO: 1) in which numbering is based on the native human ActRIIB precursor sequence (see SEQ ID NO: 2).

FIG. 6 shows the amino acid sequence of human ActRIIB precursor protein (SEQ ID NO: 2; NCBI Reference Sequence NP_001097.2). The signal peptide is underlined, the extracellular domain is in bold (also referred to as SEQ ID NO: 1), and the potential N-linked glycosylation sites are boxed.

FIG. 7 shows a nucleic acid sequence encoding a human ActRIIB(20-134) extracellular domain polypeptide.

FIG. 8 shows a nucleic acid sequence encoding human ActRIIB precursor protein. SEQ ID NO: 4 consists of nucleotides 25-1560 of NCBI Reference Sequence NM_001106.

FIG. 9 shows values for ligand binding kinetics of homodimeric Fc-fusion proteins comprising variant or unmodified ActRIIB domains, as determined by surface plasmon resonance at 37° C. Amino acid numbering is based on SEQ ID NO: 2.

FIG. 10 shows values for ligand binding kinetics of homodimeric Fc-fusion proteins comprising variant or unmodified ActRIIB domains, as determined by surface plasmon resonance at 25° C. Amino acid numbering is based on SEQ ID NO: 2.

DETAILED DESCRIPTION

1. Overview

Figure 1A:
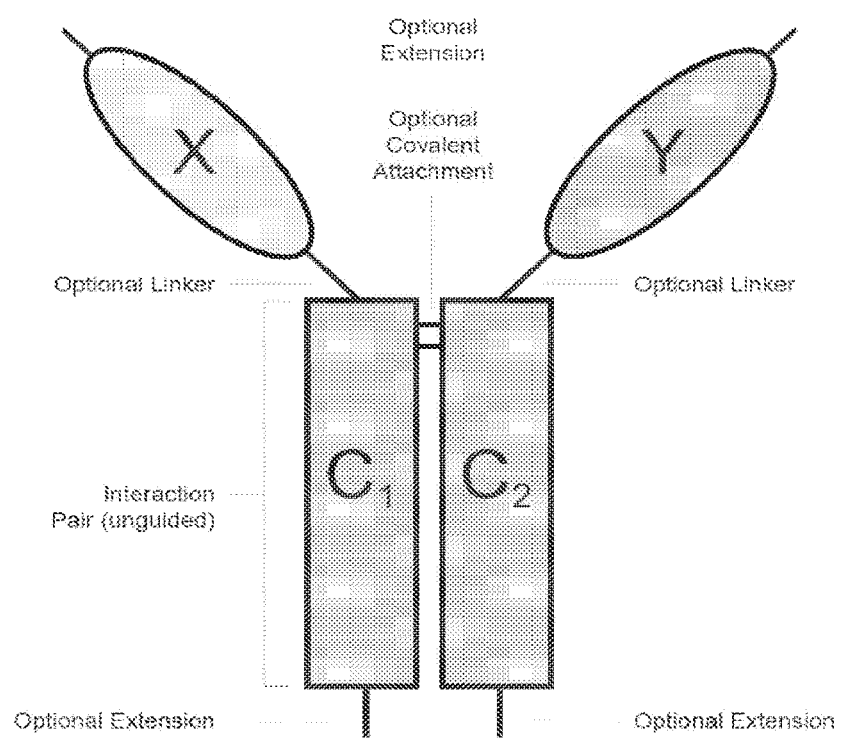
FIGS. 1A and 1B show schematic examples of heteromeric protein complexes comprising a first variant ActRIIB polypeptide (indicated as "X") and either a second variant ActRIIB polypeptide (indicated as "Y") or an unmodified ActRIIB polypeptide (indicated as "Y"). In the illustrated embodiments, the first variant ActRIIB polypeptide is part of a fusion polypeptide that comprises a first member of an interaction pair ("$C_1$"), and either a second variant ActRIIB polypeptide or an unmodified ActRIIB polypeptide is part of a fusion polypeptide that comprises a second member of an interaction pair ("$C_2$"). Suitable interaction pairs include, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the first variant ActRIIB polypeptide, second variant ActRIIB polypeptide, or unmodified ActRIIB polypeptide and the corresponding member of the interaction pair. The first and second members of the interaction pair may be unguided, meaning that the members of the pair may associate with each other or self-associate without substantial preference, and they may have the same or different amino acid sequences. See FIG. 1A. Alternatively, the interaction pair may be a guided (asymmetric) pair, meaning that the members of the pair associate preferentially with each other rather than self-associate. See FIG. 1B.

In certain aspects, the present invention relates to ActRIIB polypeptides. As used herein, the term "ActRIIB" refers to a family of activin receptor type IIB (ActRIIB) proteins and ActRIIB-related proteins, derived from any species. Members of the ActRIIB family are generally all transmembrane proteins, composed of a ligand-binding extracellular domain with cysteine-rich region, a transmembrane domain, and a cytoplasmic domain with predicted serine/threonine kinase specificity. The amino acid sequence of human ActRIIB precursor protein is shown in FIG. 6 (SEQ ID NO: 2).

The term "ActRIIB polypeptide" is used to refer to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB having a sequence at least about 80% identical to the sequence of an ActRIIB polypeptide, and preferably at least 85%, 90%, 95%, 97%, 99% or greater identity.

In a specific embodiment, the invention relates to soluble ActRIIB polypeptides. As described herein, the term "soluble ActRIIB polypeptide" generally refers to polypeptides comprising an extracellular domain of an ActRIIB protein. The term "soluble ActRIIB polypeptide," as used herein, includes any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. Examples of soluble ActRIIB polypeptides include an ActRIIB extracellular domain (SEQ ID NO: 1) shown in FIG. 5 as well as SEQ ID NO: 53. Other examples of soluble ActRIIB polypeptides comprise a signal sequence in addition to the extracellular domain of an ActRIIB protein (see Example 1). The signal sequence can be a native signal sequence of an ActRIIB, or a signal sequence from another protein, such as a tissue plasminogen activator (TPA) signal sequence or a honey bee melatin signal sequence.

TGF-β signals are mediated by heteromeric complexes of type I and type II serine/threonine kinase receptors, which phosphorylate and activate downstream Smad proteins upon ligand stimulation (Massague, 2000, Nat. Rev. Mol. Cell Biol. 1:169-178). These type I and type II receptors are all transmembrane proteins, composed of a ligand-binding extracellular domain with cysteine-rich region, a transmembrane domain, and a cytoplasmic domain with predicted serine/threonine specificity. Type I receptors are essential for signaling, and type II receptors are required for binding ligands. Type I and type II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). Applicants have found that soluble ActRIIA-Fc fusion proteins and ActRIIB-Fc fusion proteins have substantially different effects in vivo, with ActRIIA-Fc having primary effects on bone and ActRIIB-Fc having primary effects on skeletal muscle.

In certain embodiments, the present invention relates to antagonizing a ligand of ActRIIB receptors (also referred to as an ActRIIB ligand) with a subject ActRIIB polypeptide (e.g., a soluble ActRIIB polypeptide). Thus, compositions and methods of the present invention are useful for treating disorders associated with abnormal activity of one or more ligands of ActRIIB receptors. Exemplary ligands of ActRIIB receptors include some TGF-β family members, such as activin, Nodal, GDF8, GDF11, and BMP7.

Activins are dimeric polypeptide growth factors and belong to the TGF-beta superfamily. There are three activins (A, B, and AB) that are homo/heterodimers of two closely related 13 subunits ($\beta_A\beta_A$, $\beta_B\beta_B$, and $\beta_A\beta_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and differentiation factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and differentiation factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229:407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and IIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol Chem. 273:25628-36).

In certain aspects, the present invention relates to the use of certain ActRIIB polypeptides (e.g., soluble ActRIIB polypeptides) to antagonize the signaling of ActRIIB ligands generally, in any process associated with ActRIIB activity. Optionally, ActRIIB polypeptides of the invention may antagonize one or more ligands of ActRIIB receptors, such as activin, Nodal, GDF8, and GDF11, and may therefore be useful in the treatment of additional disorders.

Therefore, the present invention contemplates using ActRIIB polypeptides in treating or preventing diseases or conditions that are associated with abnormal activity of an ActRIIB or an ActRIIB ligand. ActRIIB or ActRIIB ligands are involved in the regulation of many critical biological processes. Due to their key functions in these processes, they may be desirable targets for therapeutic intervention. For example, ActRIIB polypeptides (e.g., soluble ActRIIB polypeptides) may be used to treat human or animal disorders or conditions. Example of such disorders or conditions include, but are not limited to, metabolic disorders such as type 2 diabetes, impaired glucose tolerance, metabolic syndrome (e.g., syndrome X), and insulin resistance induced by trauma (e.g., burns or nitrogen imbalance); adipose tissue disorders (e.g., obesity); muscle and neuromuscular disorders such as muscular dystrophy (including Duchenne muscular dystrophy); amyotrophic lateral sclerosis (ALS); muscle atrophy; organ atrophy; frailty; carpal tunnel syndrome; congestive obstructive pulmonary disease; and sarcopenia, cachexia and other muscle wasting syndromes. Other examples include osteoporosis, especially in the elderly and/or postmenopausal women; glucocorticoid-induced osteoporosis; osteopenia; osteoarthritis; and osteoporosis-related fractures. Yet further examples include low bone mass due to chronic glucocorticoid therapy, premature gonadal failure, androgen suppression, vitamin D deficiency, secondary hyperparathyroidism, nutritional deficiencies, and anorexia nervosa. These disorders and conditions are discussed below under "Exemplary Therapeutic Uses."

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including an unmodified (wild-type) sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%, Alternatively, and particularly in biological systems, the terms "about" and "approximately" may mean values that are within an order of magnitude, preferably <5-fold and more preferably <2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

2. ActRIIB Polypeptides

In certain aspects, the invention relates to ActRIIB variant polypeptides (e.g., soluble ActRIIB polypeptides). Optionally, the fragments, functional variants, and modified forms have similar or the same biological activities of their corresponding wild-type ActRIIB polypeptides. For example, an ActRIIB variant of the invention may bind to and inhibit function of an ActRIIB ligand (e.g., activin A, activin AB, activin B, Nodal, GDF8, GDF11 or BMP7). Optionally, an ActRIIB polypeptide modulates growth of tissues such as bone, cartilage, muscle or fat. Examples of ActRIIB polypeptides include human ActRIIB precursor polypeptide (SEQ ID NO: 2), and soluble human ActRIIB polypeptides (e.g., SEQ ID NOs: 1, 5, 6 and 12).

The disclosure identifies functionally active portions and variants of ActRIIB. Applicants have ascertained that an Fc fusion protein having the sequence disclosed by Hilden et al. (Blood. 1994 Apr. 15; 83(8):2163-70), which has an alanine at the position corresponding to amino acid 64 of SEQ ID NO: 2 (A64), has a relatively low affinity for activin and GDF11. By contrast, the same Fc fusion protein with an arginine at position 64 (R64) has an affinity for activin and GDF-11 in the low nanomolar to high picomolar range.

Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. Data disclosed in WO2008097541 show that an ActRIIB-Fc fusion protein containing amino acids 20-119 of SEQ ID NO:2, "ActRIIB(20-119)-Fc" has reduced binding to GDF11 and activin relative to an ActRIIB(20-134)-Fc, which includes the proline knot region and the complete juxtamembrane domain. However, an ActRIIB(20-129)-Fc protein retains similar but somewhat reduced activity relative to the wild type, even though the proline knot region is disrupted. Thus, ActRIIB extracellular domains that stop at amino acid 134, 133, 132, 131, 130 and 129 are all expected to be active, but constructs stopping at 134 or 133 may be most active. Similarly, mutations at any of residues 129-134 are not expected to alter ligand binding affinity by large margins. In support of this, mutations of P129 and P130 do not substantially decrease ligand binding. Therefore, an ActRIIB-Fc fusion protein may end as early as amino acid 109 (the final cysteine), however, forms ending at or between 109 and 119 are expected to have reduced ligand binding. Amino acid 119 is poorly conserved and so is readily altered or truncated. Forms ending at 128 or later retain ligand binding activity. Forms ending at or between 119 and 127 will have an intermediate binding ability. Any of these forms may be desirable to use, depending on the clinical or experimental setting.

At the N-terminus of ActRIIB, it is expected that a protein beginning at amino acid 29 or before will retain ligand binding activity. Amino acid 29 represents the initial cysteine. An alanine-to-asparagine mutation at position 24 introduces an N-linked glycosylation sequence without substantially affecting ligand binding. This confirms that mutations in the region between the signal cleavage peptide and the cysteine cross-linked region, corresponding to amino acids 20-29, are well tolerated. In particular, constructs beginning at position 20, 21, 22, 23 and 24 will retain activity, and constructs beginning at positions 25, 26, 27, 28 and 29 are also expected to retain activity. Data are shown in WO2008097541 demonstrates that, surprisingly, a construct beginning at 22, 23, 24 or 25 will have the most activity.

Taken together, an active portion of ActRIIB comprises amino acids 29-109 of SEQ ID NO:2, and constructs may, for example, begin at a residue corresponding to amino acids 20-29 and end at a position corresponding to amino acids 109-134. Other examples include constructs that begin at a position from 20-29 or 21-29 and end at a position from 119-134, 119-133 or 129-134, 129-133. Other examples include constructs that begin at a position from 20-24 (or 21-24, or 22-25) and end at a position from 109-134 (or 109-133), 119-134 (or 119-133) or 129-134 (or 129-133). Variants within these ranges are also contemplated, particularly those having at least 80%, 85%, 90%, 95% or 99% identity to the corresponding portion of SEQ ID NO:4.

The disclosure includes the results of an analysis of composite ActRIIB structures, shown in FIG. 2, demonstrating that the ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Thus, a general formula for an active ActRIIB variant protein is one that comprises amino acids 29-109, but optionally beginning at a position ranging from 20-24 or 22-25 and ending at a position ranging from 129-134, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 29-109 of SEQ ID NO: 2. Sites outside the binding pocket, at which variability may be particularly well tolerated, include the amino and carboxy termini of the extracellular domain (as noted above), and positions 42-46 and 65-73. An asparagine-to-alanine alteration at position 65 (N65A) actually improves ligand binding in the A64 background and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue such as H may be tolerated at position 64.

ActRIIB is well-conserved across nearly all vertebrates, with large stretches of the extracellular domain conserved completely. See FIG. 3. Many of the ligands that bind to ActRIIB are also highly conserved. Accordingly, comparisons of ActRIIB sequences from various vertebrate organisms provide insights into residues that may be altered. Therefore, an active, human ActRIIB variant may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in Xenopus ActRIIB, and so this position may be altered, and optionally may be altered to another hydrophobic residue, such as V, I or F, or a non-polar residue such as A. E52 is a K in Xenopus, indicating that this site may be tolerant of a wide variety of changes, including polar residues, such as E, D, K, R, H, S, T, P, G, Y and probably A. T93 is a K in Xenopus, indicating that a wide structural variation is tolerated at this position, with polar residues favored, such as S, K, R, E, D, H, G, P, G and Y. F108 is a Y in Xenopus, and therefore Y or other hydrophobic group, such as I, V or L should be tolerated. E111 is K in Xenopus, indicating that charged residues will be tolerated at this position, including D, R, K and H, as well as Q and N. R112 is K in Xenopus, indicating that basic residues are tolerated at this position, including R and H. A at position 119 is relatively poorly conserved, and appears as P in rodents and V in Xenopus, thus essentially any amino acid should be tolerated at this position.

Data disclosed in WO2008097541 demonstrate that the addition of a further N-linked glycosylation site (N-X-S/T) does not affect the activity of an ActRIIB-Fc fusion protein, relative to the ActRIIB(R64)-Fc form. Other NX(T/S) sequences are found at 42-44 (NQS) and 65-67 (NSS), although the latter may not be efficiently glycosylated with the R at position 64. N-X-S/T sequences may be generally introduced at positions outside the ligand binding pocket defined in FIG. 2. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are contemplated. Likewise, in an A24N variant, an S26T alteration may be used. Accordingly, an ActRIIB variant may include one or more additional, non-endogenous N-linked glycosylation consensus sequences.

Position L79 may be altered to confer altered activin-myostatin (GDF-11) binding properties. L79A or L79P reduces GDF-11 binding to a greater extent than activin binding. L79E or L79D retains GDF-11 binding. Remarkably, the L79E and L79D variants have greatly reduced activin binding. In vivo experiments indicate that these non-activin receptors retain significant ability to increase muscle mass but show decreased effects on other tissues. These data demonstrate the desirability and feasibility for obtaining polypeptides with reduced effects on activin.

The variations described may be combined in various ways. Additionally, the results of mutagenesis program described herein indicate that there are amino acid positions in ActRIIB that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in each of the variants disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K).

In certain embodiments, isolated fragments of the ActRIIB polypeptides can be obtained by screening polypeptides recombinantly produced from the corresponding fragment of the nucleic acid encoding an ActRIIB polypeptide (e.g., SEQ ID NOs: 3 and 4). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRIIB protein or an ActRIIB ligand.

In certain embodiments, a functional variant of the ActRIIB polypeptides has an amino acid sequence that is at least 75% identical to an amino acid sequence selected from SEQ ID NOs: 1, 2, and 53. In certain cases, the functional variant has an amino acid sequence at least 80%, 85%, 90%, 95%, 97%, 98%, 99% or 100% identical to an amino acid sequence selected from SEQ ID NOs: 1, 2, and 53.

In certain embodiments, the present invention contemplates making functional variants by modifying the structure of an ActRIIB polypeptide for such purposes as enhancing therapeutic efficacy, or stability (e.g., ex vivo shelf life and resistance to proteolytic degradation in vivo). Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide, or to bind to one or more ligands, such as activin, GDF11, or GDF8, in a fashion similar to wild type.

In certain specific embodiments, the present invention contemplates making mutations in the extracellular domain (also referred to as ligand-binding domain) of an ActRIIB polypeptide such that the variant (or mutant) ActRIIB polypeptide has altered ligand-binding activities (e.g., binding affinity or binding selectivity). In certain cases, such variant ActRIIB polypeptides have altered (elevated or reduced) binding affinity for a specific ligand. In other cases, the variant ActRIIB polypeptides have altered binding selectivity for their ligands.

In certain embodiments, the present invention contemplates specific mutations of the ActRIIB polypeptides so as to alter the glycosylation of the polypeptide. Exemplary glycosylation sites in ActRIIB polypeptides are illustrated in FIG. 6 Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (0 the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an ActRIIB polypeptide, including, optionally, truncation variants; pools of combinatorial mutants are especially useful for identifying functional variant sequences. The purpose of screening such combinatorial libraries may be to generate, for example, ActRIIB polypeptide variants which have altered properties, such as altered pharmacokinetics, or altered ligand binding. A variety of screening assays are provided below, and such assays may be used to evaluate variants. For example, an ActRIIB polypeptide variant may be screened for ability to bind to an ActRIIB polypeptide, to prevent binding of an ActRIIB ligand to an ActRIIB polypeptide.

The activity of an ActRIIB polypeptide or its variants may also be tested in a cell-based or in vivo assay. For example, the effect of an ActRIIB polypeptide variant on the expression of genes involved in bone production in an osteoblast or precursor may be assessed. This may, as needed, be performed in the presence of one or more recombinant ActRIIB ligand protein (e.g., BMP7), and cells may be transfected so as to produce an ActRIIB polypeptide and/or variants thereof, and optionally, an ActRIIB ligand. Likewise, an ActRIIB polypeptide may be administered to a mouse or other animal, and one or more bone properties, such as density or volume may be assessed. The healing rate for bone fractures may also be evaluated. Similarly, the activity of an ActRIIB polypeptide or its variants may be tested in muscle cells, adipocytes, and neuronal cells for any effect on growth of these cells, for example, by the assays as described below. Such assays are well known and routine in the art. A SMAD-responsive reporter gene may be used in such cell lines to monitor effects on downstream signaling.

Combinatorially-derived variants can be generated which have a selective potency relative to a naturally occurring ActRIIB polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRIIB polypeptide. For example, the altered protein can be rendered either more stable or less stable to proteolytic degradation or other processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and, when part of an inducible expression system, can allow tighter control of recombinant ActRIIB polypeptide levels within the cell. In certain embodiments, the ActRIIB polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of a ActRIIB polypeptide may be tested as described herein for other ActRIIB polypeptide variants. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

Figure 1B:
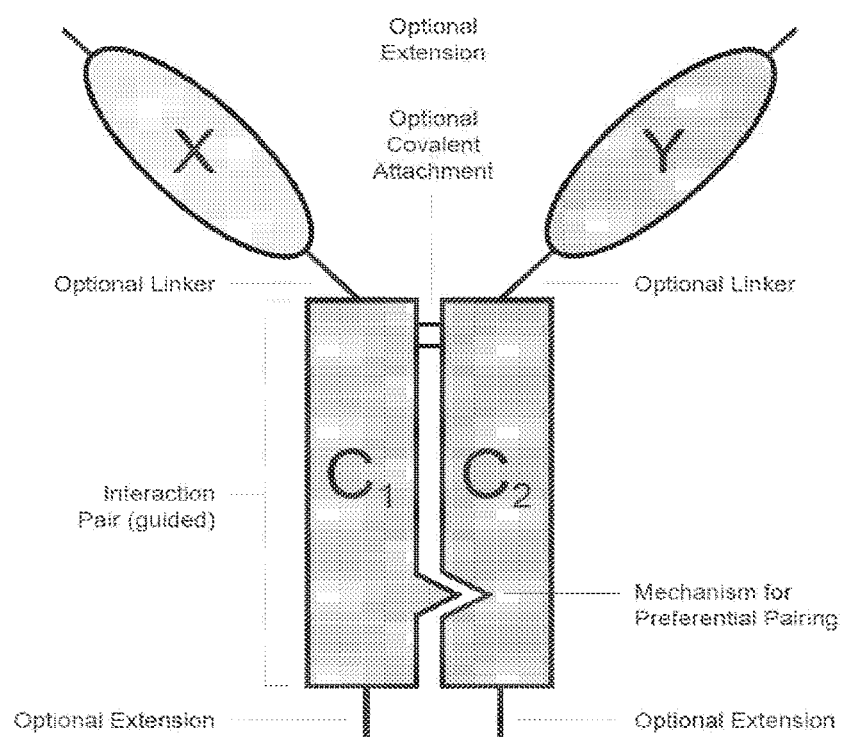

In certain aspects the polypeptides disclosed herein may form homomeric variant ActRIIB polypeptides, meaning that each fusion polypeptide chain in the protein complex comprises the same ActRIIB variant as any other such chain in the complex. In certain aspects, the polypeptides disclosed herein may form heteromultimers comprising at least one variant ActRIIB polypeptide associated, covalently or non-covalently, with at least one unmodified ActRIIB polypeptide or at least one variant ActRIIB polypeptide different from the first ActRIIB variant. In certain aspects, the polypeptides disclosed herein may form heteromultimers comprising at least one variant ActRIIB polypeptide associated, covalently or non-covalently, with at least one TGF-beta superfamily type I serine/threonine kinase receptor polypeptide (e.g., an ALK1, ALK2, ALK3, ALK4, ALK5, ALK6, and ALK7 polypeptide), including fragments and variants thereof. In certain aspects, the polypeptides disclosed herein may form heteromultimers comprising at least one variant ActRIIB polypeptide associated, covalently or non-covalently, with at least one TGF-beta superfamily type II serine/threonine kinase receptor polypeptide (e.g., ActRIIA, TGFBRII, BMPRII, and MISRII), including fragments and variants thereof. Preferably, heteromeric polypeptides disclosed herein form heterodimers, although higher order heteromultimers are also included such as, but not limited to, heterotrimers, heterotetramers, and further oligomeric structures. In some embodiments, variant ActRIIB polypeptides of the present disclosure comprise at least one multimerization domain. As disclosed herein, the term "multimerization domain" refers to an amino acid or sequence of amino acids that promote covalent or non-covalent interaction between at least a first polypeptide and at least a second polypeptide. Variant ActRIIB polypeptides disclosed herein may be joined covalently or non-covalently to a multimerization domain. Preferably, a multimerization domain promotes interaction between a first polypeptide (e.g., variant ActRIIB polypeptide) and a second polypeptide (e.g., an unmodified ActRIIB polypeptide or a variant ActRIIB polypeptide different from that present in the first polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 1).

In certain embodiments, the disclosure relates to a heteromultimer comprising at least one ALK1-Fc fusion protein and at least one ActRIIB-Fc fusion protein. In some embodiments, an ALK1-Fc:ActRIIB-Fc heteromultimers binds to one or more TGF-beta superfamily ligands such as those described herein. In some embodiments, an ALK1-Fc:ActRIIB-Fc heteromultimers inhibit signaling of one or more TGF-beta superfamily ligands such as those described herein. In some embodiments, an ALK1-Fc:ActRIIB-Fc heteromultimers is a heterodimer.

In certain embodiments, the disclosure relates to a heteromultimer comprising at least one ALK2-Fc fusion protein and at least one ActRIIB-Fc fusion protein. In some embodiments, an ALK2-Fc:ActRIIB-Fc heteromultimers binds to one or more TGF-beta superfamily ligands such as those described herein. In some embodiments, an ALK2-Fc:ActRIIB-Fc heteromultimers inhibit signaling of one or more TGF-beta superfamily ligands such as those described herein. In some embodiments, an ALK2-Fc:ActRIIB-Fc heteromultimers is a heterodimer.

In certain embodiments, the disclosure relates to a heteromultimer comprising at least one ALK3-Fc fusion protein and at least one ActRIIB-Fc fusion protein. In some embodiments, an ALK3-Fc:ActRIIB-Fc heteromultimers binds to one or more TGF-beta superfamily ligands such as those described herein. In some embodiments, an ALK3-Fc:ActRIIB-Fc heteromultimers inhibit signaling of one or more TGF-beta superfamily ligands such as those described herein. In some embodiments, an ALK3-Fc:ActRIIB-Fc heteromultimers is a heterodimer.

In certain embodiments, the disclosure relates to a heteromultimer comprising at least one ALK4-Fc fusion protein and at least one ActRIIB-Fc fusion protein. In some embodiments, an ALK4-Fc:ActRIIB-Fc heteromultimers binds to one or more TGF-beta superfamily ligands such as those described herein. In some embodiments, an ALK4-Fc:ActRIIB-Fc heteromultimers inhibit signaling of one or more TGF-beta superfamily ligands such as those described herein. In some embodiments, an ALK4-Fc:ActRIIB-Fc heteromultimers is a heterodimer.

In certain embodiments, the disclosure relates to a heteromultimer comprising at least one ALK5-Fc fusion protein and at least one ActRIIB-Fc fusion protein. In some embodiments, an ALK5-Fc:ActRIIB-Fc heteromultimers binds to one or more TGF-beta superfamily ligands such as those described herein. In some embodiments, an ALK5-Fc:ActRIIB-Fc heteromultimers inhibit signaling of one or more TGF-beta superfamily ligands such as those described herein. In some embodiments, an ALK5-Fc:ActRIIB-Fc heteromultimers is a heterodimer.

In certain embodiments, the disclosure relates to a heteromultimer comprising at least one ALK6-Fc fusion protein and at least one ActRIIB-Fc fusion protein. In some embodiments, an ALK6-Fc:ActRIIB-Fc heteromultimers binds to one or more TGF-beta superfamily ligands such as those described herein. In some embodiments, an ALK6-Fc:ActRIIB-Fc heteromultimers inhibit signaling of one or more TGF-beta superfamily ligands such as those described herein. In some embodiments, an ALK6-Fc:ActRIIB-Fc heteromultimers is a heterodimer.

In certain embodiments, the disclosure relates to a heteromultimer comprising at least one ALK7-Fc fusion protein and at least one ActRIIB-Fc fusion protein. In some embodiments, an ALK7-Fc:ActRIIB-Fc heteromultimers binds to one or more TGF-beta superfamily ligands such as those described herein. In some embodiments, an ALK7-Fc:ActRIIB-Fc heteromultimers inhibit signaling of one or more TGF-beta superfamily ligands such as those described herein. In some embodiments, an ALK7-Fc:ActRIIB-Fc heteromultimers is a heterodimer.

In certain embodiments, the disclosure relates to a heteromultimer comprising at least one ActRIIB-Fc fusion protein and at least one ActRIIA-Fc fusion protein. In some embodiments, an ActRIIB-Fc:ActRIIA-Fc heteromultimers binds to one or more TGF-beta superfamily ligands such as those described herein. In some embodiments, an ActRIIB-Fc:ActRIIA-Fc heteromultimers inhibit signaling of one or more TGF-beta superfamily ligands such as those described herein. In some embodiments, an ActRIIB-Fc:ActRIIA-Fc heteromultimers is a heterodimer.

In certain embodiments, the disclosure relates to a heteromultimer comprising at least one ActRIIB-Fc fusion protein and at least one BMPRII-Fc fusion protein. In some embodiments, an ActRIIB-Fc:BMPRII-Fc heteromultimers binds to one or more TGF-beta superfamily ligands such as those described herein. In some embodiments, an ActRIIB-Fc:BMPRII-Fc heteromultimers inhibit signaling of one or more TGF-beta superfamily ligands such as those described herein. In some embodiments, an ActRIIB-Fc:BMPRII-Fc heteromultimers is a heterodimer.

In certain embodiments, the disclosure relates to a heteromultimer comprising at least one ActRIIB-Fc fusion protein and at least one TGFBRII-Fc fusion protein. In some embodiments, an ActRIIB-Fc:TGFBRII-Fc heteromultimers binds to one or more TGF-beta superfamily ligands such as those described herein. In some embodiments, an ActRIIB-Fc:TGFBRII-Fc heteromultimers inhibit signaling of one or more TGF-beta superfamily ligands such as those described herein. In some embodiments, an ActRIIB-Fc:TGFBRII-Fc heteromultimers is a heterodimer.

In certain embodiments, the disclosure relates to a heteromultimer comprising at least one ActRIIB-Fc fusion protein and at least one MISRII-Fc fusion protein. In some embodiments, an ActRIIB-Fc:MISRII-Fc heteromultimers binds to one or more TGF-beta superfamily ligands such as those described herein. In some embodiments, an ActRIIB-Fc:MISRII-Fc heteromultimers inhibit signaling of one or more TGF-beta superfamily ligands such as those described herein. In some embodiments, an ActRIIB-Fc:MISRII-Fc heteromultimers is a heterodimer.

In certain aspects, the disclosure relates to a heteromultimer that comprises an ALK1-Fc fusion protein. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids of 22-34 (e.g., amino acid residues 22, 23, 24, 25, 26, 27, 28, 29, 30, 31, 32, 33, and 34) SEQ ID NO: 54, ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 22-118 of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-95 of SEQ ID NO: 54. In some embodiments, the ALK1-Fc fusion protein comprises an ALK1 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 54, 55, 56, 57, 58, 59, 60, 61, 62, and 63.

A representative ALK1-Fc fusion polypeptide (SEQ ID NO: 60) is as follows:

```
                                                          (SEQ ID NO: 60)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The leader sequence and linker sequence are underlined. The mature ALK1-Fc fusion protein sequence (SEQ ID NO: 61) is as follows and may optionally be provided with the lysine removed from the C-terminus.

```
                                                          (SEQ ID NO: 61)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVC TLPPSREEMT KNQVSLSCAV

251 KGFYPSDIAV EWESNGQPEN NYKTTPPVLD SDGSFFLVSK LTVDKSRWQQ

301 GNVFSCSVMH EALHNHYTQK SLSLSPGK
```

In some embodiments, the ALK1-Fc fusion polypeptide (SEQ ID NO: 56) is as follows:

```
                                                          (SEQ ID NO: 56)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP
```

```
151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 G
```

The leader sequence and linker sequence are underlined. To guide heterodimer formation with certain Fc fusion polypeptides disclosed herein, two amino acid substitutions (replacing lysines with aspartic acids) can be introduced into the Fc domain of the ALK1-Fc fusion polypeptide as indicated by double underline above. The amino acid sequence of SEQ ID NO: 56 may optionally be provided with a lysine added at the C-terminus.

This ALK1-Fc fusion protein is encoded by the following nucleic acid (SEQ ID NO: 258):

```
(SEQ ID NO: 258)
   1 ATGGATGCAA TGAAGAGAGG GCTCTGCTGT GTGCTGCTGC TGTGTGGAGC

51 AGTCTTCGTT TCGCCCGGCG CCGACCCTGT GAAGCCGTCT CGGGGCCCGC

101 TGGTGACCTG CACGTGTGAG AGCCCACATT GCAAGGGGCC TACCTGCCGG

151 GGGGCCTGGT GCACAGTAGT GCTGGTGCGG GAGGAGGGGA GGCACCCCCA

201 GGAACATCGG GGCTGCGGGA ACTTGCACAG GGAGCTCTGC AGGGGCCGCC

251 CCACCGAGTT CGTCAACCAC TACTGCTGCG ACAGCCACCT CTGCAACCAC

301 AACGTGTCCC TGGTGCTGGA GGCCACCCAA CCTCCTTCGG AGCAGCCGGG

351 AACAGATGGC CAGCTGGCCA CCGGTGGTGG AACTCACACA TGCCCACCGT

401 GCCCAGCACC TGAACTCCTG GGGGGACCGT CAGTCTTCCT CTTCCCCCCA

451 AAACCCAAGG ACACCCTCAT GATCTCCCGG ACCCCTGAGG TCACATGCGT

501 GGTGGTGGAC GTGAGCCACG AAGACCCTGA GGTCAAGTTC AACTGGTACG

551 TGGACGGCGT GGAGGTGCAT AATGCCAAGA CAAAGCCGCG GGAGGAGCAG

601 TACAACAGCA CGTACCGTGT GGTCAGCGTC CTCACCGTCC TGCACCAGGA

651 CTGGCTGAAT GGCAAGGAGT ACAAGTGCAA GGTCTCCAAC AAAGCCCTCC

701 CAGCCCCCAT CGAGAAAACC ATCTCCAAAG CCAAAGGGCA GCCCCGAGAA

751 CCACAGGTGT ACACCCTGCC CCCATCCCGG GAGGAGATGA CCAAGAACCA

801 GGTCAGCCTG ACCTGCCTGG TCAAAGGCTT CTATCCCAGC GACATCGCCG

851 TGGAGTGGGA GAGCAATGGG CAGCCGGAGA ACAACTACGA CACCACGCCT

901 CCCGTGCTGG ACTCCGACGG CTCCTTCTTC CTCTATAGCG ACCTCACCGT

951 GGACAAGAGC AGGTGGCAGC AGGGGAACGT CTTCTCATGC TCCGTGATGC

1001 ATGAGGCTCT GCACAACCAC TACACGCAGA AGAGCCTCTC CCTGTCTCCG

1051 GGT
```

The mature ALK1-Fc fusion protein sequence (SEQ ID NO: 57) is as follows and may optionally be provided with a lysine added at the C-terminus.

```
                                                                 (SEQ ID NO: 57)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVY TLPPSREEMT KNQVSLTCLV

251 KGFYPSDIAV EWESNGQPEN NYDTTPPVLD SDGSFFLYSD LTVDKSRWQQ

301 GNVFSCSVMH EALHNHYTQK SLSLSPG
```

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity.

A human ALK2 precursor protein sequence (NCBI Ref Seq NP_001096.1) is as follows:

```
                                                                 (SEQ ID NO: 64)
  1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC
```

The signal peptide is indicated by a single underline and the extracellular domain is indicated in bold font.

A processed extracellular ALK2 polypeptide sequence is as follows:

(SEQ ID NO: 65)
MEDEKPKVNPKLYMCVCEGLSCGNEDHCEGQQCFSSLSINDGFHVYQKGC

FQVYEQGKMTCKTPPSPGQAVECCQGDWCNRNITAQLPTKGKSFPGTQNF

HLE

A nucleic acid sequence encoding human ALK2 precursor protein is shown in SEQ ID NO: 217, corresponding to nucleotides 431-1957 of Genbank Reference Sequence NM 001105.4. A nucleic acid sequence encoding the extracellular ALK2 polypeptide is as in SEQ ID NO: 218.

In certain embodiments, the disclosure relates to heteromultimers that comprise at least one ALK2 polypeptide, which includes fragments, functional variants, and modified forms thereof. Preferably, ALK2 polypeptides for use in accordance with inventions of the disclosure (e.g., heteromultimers comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK2 polypeptide that is at least 70%, 75%, 80%, 85%, 90%, 95%, 97%, 98%, 99%, or 100% identical to the amino acid sequence of SEQ ID NO: 64 or 65. In some embodiments, heteromultimer complexes of the disclosure consist or consist essentially of at least one ALK2 polypeptide that is at least 70%, 75%, 80%, 85%, 90%, 95%, 97%, 98%, 99%, or 100% identical to the amino acid sequence of SEQ ID NO: 64 or 65.

In certain aspects, the disclosure relates to a heteromultimer that comprises an ALK2-Fc fusion protein. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-35 (e.g., amino acid residues 21, 22, 23, 24, 25, 26, 27, 28, 29, 30, 31, 32, 33, 34, and 35) SEQ ID NO: 64, and ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 35-99 of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-123 of SEQ ID NO: 64. In some embodiments, the ALK2-Fc fusion protein comprises an ALK2 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID Nos: 64, 65, 66, 67, 68, 69, 70, 71, 72, and 73.

In some embodiments, the ALK2-Fc fusion protein employs the TPA leader and is as follows (SEQ ID NO: 66):

(SEQ ID NO: 66)
```
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The signal sequence and linker sequence are underlined. To promote formation of the a heterodimer with certain other Fc fusions disclosed herein, two amino acid substitutions (replacing lysines with aspartic acids) can be introduced into the Fc domain of the fusion protein as indicated by double underline above. The amino acid sequence of SEQ ID NO: 66 may optionally be provided with a lysine added at the C-terminus.

This ALK2-Fc fusion protein is encoded by the following nucleic acid (SEQ ID NO: 244):

(SEQ ID NO: 244)
```
  1 ATGGATGCAA TGAAGAGAGG GCTCTGCTGT GTGCTGCTGC TGTGTGGAGC

51 AGTCTTCGTT TCGCCCGGCG CCATGGAAGA TGAAGAGCCC AAGGTCAACC

101 CCAAACTCTA CATGTGTGTG TGTGAAGGTC TCTCCTGCGG TAATGAGGAC

151 CACTGTGAAG GCCAGCAGTG CTTTTCCTCA CTGAGCATCA ACGATGGCTT
```

```
 201 CCACGTCTAC CAGAAAGGCT GCTTCCAGGT TTATGAGCAG GGAAAGATGA

251 CCTGTAAGAC CCCGCCGTCC CCTGGCCAAG CTGTGGAGTG CTGCCAAGGG

301 GACTGGTGTA ACAGGAACAT CACGGCCCAG CTGCCCACTA AAGGAAAATC

351 CTTCCCTGGA ACACAGAATT TCCACTTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAGGG

751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GGCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK2-Fc fusion protein sequence (SEQ ID NO: 67) is as follows and may optionally be provided with a lysine added at the C-terminus.

```
                                                   (SEQ ID NO: 67)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

In another approach to promoting the formation of heteromultimer complexes using asymmetric Fc fusion proteins, the Fc domains are altered to introduce complementary hydrophobic interactions and an additional intermolecular disulfide bond.

In some embodiments, the ALK2-Fc fusion polypeptide (SEQ ID NO: 70) is as follows:

```
                               (SEQ ID NO: 70)
  1 MDAMKRGLCC VLLLCGAVFV SPGAMEDEKP

KVNPKLYMCV CEGLSCGNED

51 HCEGQQCFSS LSINDGFHVY QKGCFQVYEQ

GKMTCKTPPS PGQAVECCQG

101 DWCNRNITAQ LPTKGKSFPG TQNFHLETGG

GTHTCPPCPA PELLGGPSVF

151 LFPPKPKDTL MISRTPEVTC VVVDVSHEDP

EVKFNWYVDG VEVHNAKTKP

201 REEQYNSTYR VVSVLTVLHQ DWLNGKEYKC

KVSNKALPAP IEKTISKAKG

251 QPREPQVCTL PPSREEMTKN QVSLSCAVKG

FYPSDIAVEW ESNGQPENNY
```

```
301 KTTPPVLDSD GSFFLVSKLT VDKSRWQQGN

VFSCSVMHEA LHNHYTQKSL

351 SLSPGK
```

The leader sequence and linker sequence are underlined. To guide heterodimer formation with certain Fc fusion polypeptides disclosed herein, four amino acid substitutions can be introduced into the Fc domain of the ALK2 fusion polypeptide as indicated by double underline above. Furthermore, the C-terminal lysine residue of the Fc domain can be deleted. The amino acid sequence of SEQ ID NO: 70 may optionally be provided with the lysine removed from the C-terminus.

The mature ALK2-Fc fusion protein sequence (SEQ ID NO: 71) is as follows and may optionally be provided with the lysine removed from the C-terminus.

```
                                              (SEQ ID NO: 71)
  1 MEDEKPKVNP KLYMCVCEGL SCGNEDHCEG

QQCFSSLSIN DGFHVYQKGC

51 FQVYEQGKMT CKTPPSPGQA VECCQGDWCN

RNITAQLPTK GKSFPGTQNF

101 HLETGGGTHT CPPCPAPELL GGPSVFLFPP

KPKDTLMISR TPEVTCVVVD

151 VSHEDPEVKF NWYVDGVEVH NAKTKPREEQ

YNSTYRVVSV LTVLHQDWLN

201 GKEYKCKVSN KALPAPIEKT ISKAKGQPRE

PQVCTLPPSR EEMTKNQVSL

251 SCAVKGFYPS DIAVEWESNG QPENNYKTTP

PVLDSDGSFF LVSKLTVDKS

301 RWQQGNVFSC SVMHEALHNH YTQKSLSLSP

GK
```

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity.

A representative human ALK2 precursor protein sequence (NCBI Ref Seq NP_001096.1) is as follows:

```
                                              (SEQ ID NO: 64)
  1 MVDGVMILPV LIMIALPSPS MEDEKPKVNP

KLYMCVCEGL SCGNEDHCEG

51 QQCFSSLSIN DGFHVYQKGC FQVYEQGKMT

CKTPPSPGQA VECCQGDWCN

101 RNITAQLPTK GKSFPGTQNF HLEVGLIILS

VVFAVCLLAC LLGVALRKFK

151 RRNQERLNPR DVEYGTIEGL ITTNVGDSTL

ADLLDHSCTS GSGSGLPFLV

201 QRTVARQITL LECVGKGRYG EVWRGSWQGE

NVAVKIFSSR DEKSWFRETE

251 LYNTVMLRHE NILGFIASDM TSRHSSTQLW

LITHYHEMGS LYDYLQLTTL

301 DTVSCLRIVL SIASGLAHLH IEIFGTQGKP

AIAHRDLKSK NILVKKNGQC

351 CIADLGLAVM HSQSTNQLDV GNNPRVGTKR

YMAPEVLDET IQVDCFDSYK

401 RVDIWAFGLV LWEVARRMVS NGIVEDYKPP

FYDVVPNDPS FEDMRKVVCV

451 DQQRPNIPNR WFSDPTLTSL AKLMKECWYQ

NPSARLTALR IKKTLTKIDN

501 SLDKLKTDC
```

The signal peptide is indicated by a single underline and the extracellular domain is indicated in bold font.

A processed extracellular ALK2 polypeptide sequence is as follows:

```
                                       (SEQ ID NO: 65)
MEDEKPKVNPKLYMCVCEGLSCGNEDHCEGQQCFSS

LSINDGFHVYQKGCFQVYEQGKMTCKTPPSPGQAVE

CCQGDWCNRNITAQLPTKGKSFPGTQNFHLE
```

A nucleic acid sequence encoding human ALK2 precursor protein is shown in SEQ ID NO: 217, corresponding to nucleotides 431-1957 of Genbank Reference Sequence NM_001105.4. A nucleic acid sequence encoding the extracellular ALK2 polypeptide is as in SEQ ID NO: 218.

In certain embodiments, the disclosure relates to heteromultimers that comprise at least one ALK2 polypeptide, which includes fragments, functional variants, and modified forms thereof. Preferably, ALK2 polypeptides for use in accordance with inventions of the disclosure (e.g., heteromultimers comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK2 polypeptide that is at least 70%, 75%, 80%, 85%, 90%, 95%, 97%, 98%, 99%, or 100% identical to the amino acid sequence of SEQ ID NO: 64 or 65. In some embodiments, heteromultimer complexes of the disclosure consist or consist essentially of at least one ALK2 polypeptide that is at least 70%, 75%, 80%, 85%, 90%, 95%, 97%, 98%, 99%, or 100% identical to the amino acid sequence of SEQ ID NO: 64 or 65.

In certain aspects, the present disclosure relates to protein complexes that comprise an ALK3 polypeptide. As used herein, the term "ALK3" refers to a family of activin receptor-like kinase-3 proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity.

A human ALK3 precursor protein sequence (NCBI Ref Seq NP_004320.2) is as follows:

```
                                            (SEQ ID NO: 74)
  1 MPQLYIYIRL LGAYLFIISR VQG QNLDSML

HGTGMKSDSD QKKSENGVTL APEDTLPFLK

61 CYCSGHCPDD AINNTCITNG HCFAIIEEDD

QGETTLASGC MKYEGSDFQC KDSPKAQLRR

121 TIECCRTNLC NQYLQPTLPP VVIGPFFDGS

IRWLVLLISM AVCIIAMIIF SSCFCYKHYC

181 KSISSRRRYN RDLEQDEAFI PVGESLKDLI

DQSQSSGSGS GLPLLVQRTI AKQIQMVRQV

241 GKGRYGEVWM GKWRGEKVAV KVFFTTEEAS

WFRETEIYQT VLMRHENILG FIAADIKGTG

301 SWTQLYLITD YHENGSLYDF LKCATLDTRA

LLKLAYSAAC GLCHLHTEIY GTQGKPAIAH

361 RDLKSKNILI KKNGSCCIAD LGLAVKFNSD

TNEVDVPLNT RVGTKRYMAP EVLDESLNKN

421 HFQPYIMADI YSFGLIIWEM ARRCITGGIV

EEYQLPYYNM VPSDPSYEDM REVVCVKRLR

481 PIVSNRWNSD ECLRAVLKLM SECWAHNPAS

RLTALRIKKT LAKMVESQDV KI
```

The signal peptide is indicated by a single underline and the extracellular domain is indicated in bold font.

A processed extracellular ALK3 polypeptide sequence is as follows:

```
                                            (SEQ ID NO: 75)
  1 QNLDSMLHGT GMKSDSDQKK SENGVTLAPE

DTLPFLKCYC SGHCPDDAIN NTCITNGHCF

61 AIIEEDDQGE TTLASGCMKY EGSDFQCKDS

PKAQLRRTIE CCRTNLCNQY LQPTLPPVVI

121 GPFFDGSIR
```

A nucleic acid sequence encoding human ALK3 precursor protein is shown in SEQ ID NO: 219, corresponding to nucleotides 549-2144 of Genbank Reference Sequence NM_004329.2. The signal sequence is underlined and the extracellular domain is indicated in bold font. A nucleic acid sequence encoding the extracellular human ALK3 polypeptide is shown in SEQ ID NO: 220.

A general formula for an active (e.g., ligand binding) ALK3 polypeptide is one that comprises a polypeptide that begins at any amino acid position 25-31 (i.e., position 25, 26, 27, 28, 29, 30, or 31) of SEQ ID NO: 74 and ends at any amino acid position 140-152 of SEQ ID NO: 74 (i.e., 140, 141, 142, 143, 144, 145, 146, 147, 148, 149, 150, 151, or 152). See U.S. Pat. No. 8,338,377, the teachings of which are incorporated herein by reference in their entirety.

In certain embodiments, the disclosure relates to heteromultimers that comprise at least one ALK3 polypeptide, which includes fragments, functional variants, and modified forms thereof. Preferably, ALK3 polypeptides for use in accordance with inventions of the disclosure (e.g., heteromultimers comprising an ALK3 polypeptide and uses thereof) are soluble (e.g., an extracellular domain of ALK3). In other preferred embodiments, ALK3 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK3 polypeptide that comprises an amino acid beginning at any amino acid position 25-31 (i.e., position 25, 26, 27, 28, 29, 30, or 31) of SEQ ID NO: 74 and ending at any amino acid position 140-153 of SEQ ID NO: 74 (i.e., 140, 141, 142, 143, 144, 145, 146, 147, 148, 149, 150, 151, or 152) of SEQ ID NO: 74. In some embodiments, heteromultimer complexes of the disclosure comprise at least one ALK3 polypeptide that is at least 70%, 75%, 80%, 85%, 90%, 95%, 97%, 98%, 99%, or 100% identical to the amino acid sequence of SEQ ID NO: 74, 75, 76, 77, 80, or 81. In some embodiments, heteromultimer complexes of the disclosure consist or consist essentially of at least one ALK3 polypeptide that is at least 70%, 75%, 80%, 85%, 90%, 95%, 97%, 98%, or 99% identical to the amino acid sequence of SEQ ID NO: 74, 75, 76, 77, 80, or 81.

In certain aspects, the disclosure relates to a heteromultimer that comprises an ALK3-Fc fusion protein. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 74, and ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 61-130 of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-152 of SEQ ID NO: 74. In some embodiments, the ALK3-Fc fusion protein comprises an ALK3 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 74, 75, 76, 77, 78, 79, 80, 81, 82, and 83.

In some embodiments, the ALK3-Fc fusion protein employs the TPA leader and is as follows:

```
                                    (SEQ ID NO: 76)
  1 MDAMKRGLCC VLLLCGAVFV SPGAQNLDSM
    LHGTGMKSDS DQKKSENGVT
 51 LAPEDTLPFL KCYCSGHCPD DAINNTCITN
    GHCFAIIEED DQGETTLASG
101 CMKYEGSDFQ CKDSPKAQLR RTIECCRTNL
    CNQYLQPTLP PVVIGPFFDG
151 SIRTGGGTHT CPPCPAPELL GGPSVFLFPP
    KPKDTLMISR TPEVTCVVVD
201 VSHEDPEVKF NWYVDGVEVH NAKTKPREEQ
    YNSTYRVVSV LTVLHQDWLN
251 GKEYKCKVSN KALPAPIEKT ISKAKGQPRE
    PQVYTLPPSR EEMTKNQVSL
301 TCLVKGFYPS DIAVEWESNG QPENNYDTTP
    PVLDSDGSFF LYSDLTVDKS
351 RWQQGNVFSC SVMHEALHNH YTQKSLSLSP
    G
```

The leader and linker sequences are underlined. To promote formation of the ActRIIB-Fc:ALK3-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 76 may optionally be provided with a lysine added at the C-terminus.

This ALK3-Fc fusion protein is encoded by the following nucleic acid (SEQ ID NO: 245).

```
                               (SEQ ID NO: 245)
   1 ATGGATGCAA TGAAGAGAGG GCTCTGCTGT
     GTGCTGCTGC TGTGTGGAGC
  51 AGTCTTCGTT TCGCCCGGCG CCCAGAATCT
     GGATAGTATG CTTCATGGCA
 101 CTGGGATGAA ATCAGACTCC GACCAGAAAA
     AGTCAGAAAA TGGAGTAACC
 151 TTAGCACCAG AGGATACCTT GCCTTTTTTA
     AAGTGCTATT GCTCAGGGCA
 201 CTGTCCAGAT GATGCTATTA ATAACACATG
     CATAACTAAT GGACATTGCT
 251 TTGCCATCAT AGAAGAAGAT GACCAGGGAG
     AAACCACATT AGCTTCAGGG
 301 TGTATGAAAT ATGAAGGATC TGATTTTCAG
     TGCAAAGATT CTCCAAAAGC
 351 CCAGCTACGC CGGACAATAG AATGTTGTCG
     GACCAATTTA TGTAACCAGT
 401 ATTTGCAACC CACACTGCCC CCTGTTGTCA
     TAGGTCCGTT TTTTGATGGC
 451 AGCATTCGAA CCGGTGGTGG AACTCACACA
     TGCCCACCGT GCCCAGCACC
 501 TGAACTCCTG GGGGGACCGT CAGTCTTCCT
     CTTCCCCCCA AAACCCAAGG
 551 ACACCCTCAT GATCTCCCGG ACCCCTGAGG
     TCACATGCGT GGTGGTGGAC
 601 GTGAGCCACG AAGACCCTGA GGTCAAGTTC
     AACTGGTACG TGGACGGCGT
 651 GGAGGTGCAT AATGCCAAGA CAAAGCCGCG
     GGAGGAGCAG TACAACAGCA
 701 CGTACCGTGT GGTCAGCGTC CTCACCGTCC
     TGCACCAGGA CTGGCTGAAT
 751 GGCAAGGAGT ACAAGTGCAA GGTCTCCAAC
     AAAGCCCTCC CAGCCCCCAT
 801 CGAGAAAACC ATCTCCAAAG CCAAAGGGCA
     GCCCCGAGAA CCACAGGTGT
 851 ACACCCTGCC CCCATCCCGG GAGGAGATGA
     CCAAGAACCA GGTCAGCCTG
 901 ACCTGCCTGG TCAAAGGCTT CTATCCCAGC
     GACATCGCCG TGGAGTGGGA
 951 GAGCAATGGG CAGCCGGAGA ACAACTACGA
     CACCACGCCT CCCGTGCTGG
1001 ACTCCGACGG CTCCTTCTTC CTCTATAGCG
     ACCTCACCGT GGACAAGAGC
1051 AGGTGGCAGC AGGGGAACGT CTTCTCATGC
     TCCGTGATGC ATGAGGCTCT
```

```
             1101 GCACAACCAC TACACGCAGA AGAGCCTCTC

CCTGTCTCCG GGT
```

The mature ALK3-Fc fusion protein sequence is as follows (SEQ ID NO: 77) and may optionally be provided with a lysine added at the C-terminus.

```
                                          (SEQ ID NO: 77)
   1 GAQNLDSMLH GTGMKSDSDQ KKSENGVTLA

PEDTLPFLKC YCSGHCPDDA

51 INNTCITNGH CFAIIEEDDQ GETTLASGCM

KYEGSDFQCK DSPKAQLRRT

101 IECCRTNLCN QYLQPTLPPV VIGPFFDGSI

RTGGGTHTCP PCPAPELLGG

151 PSVFLFPPKP KDTLMISRTP EVTCVVVDVS

HEDPEVKFNW YVDGVEVHNA

201 KTKPREEQYN STYRVVSVLT VLHQDWLNGK

EYKCKVSNKA LPAPIEKTIS

251 KAKGQPREPQ VYTLPPSREE MTKNQVSLTC

LVKGFYPSDI AVEWESNGQP

301 ENNYDTTPPV LDSDGSFFLY SDLTVDKSRW

QQGNVFSCSV MHEALHNHYT

351 QKSLSLSPG
```

The complementary form of ALK3-Fc fusion polypeptide (SEQ ID NO: 80) is as follows:

```
                                          (SEQ ID NO: 80)
   1 MDAMKRGLCC VLLLCGAVFV SPGAQNLDSM
     ──────────────────── ────

LHGTGMKSDS DQKKSENGVT

51 LAPEDTLPFL KCYCSGHCPD DAINNTCITN

GHCFAIIEED DQGETTLASG

101 CMKYEGSDFQ CKDSPKAQLR RTIECCRTNL

CNQYLQPTLP PVVIGPFFDG

151 SIRTGGGTHT CPPCPAPELL GGPSVFLFPP
        ═

KPKDTLMISR TPEVTCVVVD

201 VSHEDPEVKF NWYVDGVEVH NAKTKPREEQ
                  ═

YNSTYRVVSV LTVLHQDWLN

251 GKEYKCKVSN KALPAPIEKT ISKAKGQPRE

PQVCTLPPSR EEMTKNQVSL
        ═

301 SCAVKGFYPS DIAVEWESNG QPENNYKTTP
     ═ ═

PVLDSDGSFF LVSKLTVDKS
                 ═

351 RWQQGNVFSC SVMHEALHNH YTQKSLSLSP

GK
```

The leader sequence and linker are underlined. To guide heterodimer formation with certain Fc fusion polypeptides disclosed herein, four amino acid substitutions can be introduced into the Fc domain of the ALK3 fusion polypeptide as indicated by double underline above. The amino acid sequence of SEQ ID NO: 80 may optionally be provided with the lysine removed from the C-terminus.

The mature ALK3-Fc fusion protein sequence (SEQ ID NO: 81) is as follows and may optionally be provided with the lysine (K) removed from the C-terminus.

```
                                          (SEQ ID NO: 81)
   1 GAQNLDSMLH GTGMKSDSDQ KKSENGVTLA

PEDTLPFLKC YCSGHCPDDA

51 INNTCITNGH CFAIIEEDDQ GETTLASGCM

KYEGSDFQCK DSPKAQLRRT

101 IECCRTNLCN QYLQPTLPPV VIGPFFDGSI

RTGGGTHTCP PCPAPELLGG

151 PSVFLFPPKP KDTLMISRTP EVTCVVVDVS

HEDPEVKFNW YVDGVEVHNA

201 KTKPREEQYN STYRVVSVLT VLHQDWLNGK

EYKCKVSNKA LPAPIEKTIS

251 KAKGQPREPQ VCTLPPSREE MTKNQVSLSC

AVKGFYPSDI AVEWESNGQP

301 ENNYKTTPPV LDSDGSFFLV SKLTVDKSRW

QQGNVFSCSV MHEALHNHYT

351 QKSLSLSPGK
```

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity.

A human ALK4 precursor protein sequence (NCBI Ref Seq NP_004293) is as follows:

```
                                          (SEQ ID NO: 84)
   1 MAESAGASSF FPLVVLLLAG SGGSGPRGVQ

ALLCACTSCL QANYTCETDG ACMVSIFNLD

61 GMEHHVRTCI PKVELVPAGK PFYCLSSEDL

RNTHCCYTDY CNRIDLRVPS GHLKEPEHPS

121 MWGPVELVGI IAGPVFLLFL IIIIVFLVIN

YHQRVYHNRQ RLDMEDPSCE MCLSKDKTLQ
```

-continued

```
181 DLVYDLSTSG SGSGLPLFVQ RTVARTIVLQ

EIIGKGRFGE VWRGRWRGGD VAVKIFSSRE

241 ERSWFREAEI YQTVMLRHEN ILGFIAADNK

DNGTWTQLWL VSDYHEHGSL FDYLNRYTVT

301 IEGMIKLALS AASGLAHLHM EIVGTQGKPG

IAHRDLKSKN ILVKKNGMCA IADLGLAVRH

361 DAVTDTIDIA PNQRVGTKRY MAPEVLDETI

NMKHFDSFKC ADIYALGLVY WEIARRCNSG

421 GVHEEYQLPY YDLVPSDPSI EEMRKVVCDQ

KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

A processed extracellular human ALK4 polypeptide sequence is as follows: SGPRGVQALL-CACTSCLQANYTCETDGACMVSIFNLDGMEHHVRT-CIPKVELVPAGKPFYCL SSEDLRNTHCCYTDYCN-RIDLRVPSGHLKEPEHPSMWGPVE (SEQ ID NO: 86)

A nucleic acid sequence encoding an ALK4 precursor protein is shown in SEQ ID NO: 221), corresponding to nucleotides 78-1592 of Genbank Reference Sequence NM_004302.4. A nucleic acid sequence encoding the extracellular ALK4 polypeptide is shown in SEQ ID NO: 222.

An alternative isoform of human ALK4 precursor protein sequence, isoform C (NCBI Ref Seq NP_064733.3), is as follows:

```
                                    (SEQ ID NO: 85)
  1 MAESAGASSF FPLVVLLLAG SGGSGPRGVQ

ALLCACTSCL QANYTCETDG ACMVSIFNLD

61 GMEHHVRTCI PKVELVPAGK PFYCLSSEDL

RNTHCCYTDY CNRIDLRVPS GHLKEPEHPS

121 MWGPVELVGI IAGPVFLLFL IIIIVFLVIN

YHQRVYHNRQ RLDMEDPSCE MCLSKDKTLQ

181 DLVYDLSTSG SGSGLPLFVQ RTVARTIVLQ

EIIGKGRFGE VWRGRWRGGD VAVKIFSSRE

241 ERSWFREAEI YQTVMLRHEN ILGFIAADNK

ADCSFLTLPW EVVMVSAAPK LRSLRLQYKG

301 GRGRARFLFP LNNGTWTQLW LVSDYHEHGS

LFDYLNRYTV TIEGMIKLAL SAASGLAHLH

361 MEIVGTQGKP GIAHRDLKSK NILVKKNGMC

AIADLGLAVR HDAVTDTIDI APNQRVGTKR

421 YMAPEVLDET INMKHFDSFK CADIYALGLV

YWEIARRCNS GGVHEEYQLP YYDLVPSDPS

481 IEEMRKVVCD QKLRPNIPNW WQSYEALRVM

GKMMRECWYA NGAARLTALR IKKTLSQLSV

541 QEDVKI
```

The signal peptide is indicated by a single underline and the extracellular domain is indicated in bold font.

A processed extracellular ALK4 polypeptide sequence (isoform C) is as follows:

```
                                    (SEQ ID NO: 87)
SGPRGVQALLCACTSCLQANYTCETDGACMVSIFN

LDGMEHHVRTCIPKVELVPAGKPFYCLSSEDLRNT

HCCYTDYCNRIDLRVPSGHLKEPEHPSMWGPVE
```

A nucleic acid sequence encoding an ALK4 precursor protein (isoform C) is shown in SEQ ID NO: 223, corresponding to nucleotides 78-1715 of Genbank Reference Sequence NM_020328.3. A nucleic acid sequence encoding the extracellular ALK4 polypeptide (isoform C) is shown in SEQ ID NO: 224.

In certain embodiments, the disclosure relates to heteromultimers that comprise at least one ALK4 polypeptide, which includes fragments, functional variants, and modified forms thereof. Preferably, ALK4 polypeptides for use in accordance with inventions of the disclosure (e.g., heteromultimers comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK4 polypeptide that is at least 70%, 75%, 80%, 85%, 90%, 95%, 97%, 98%, 99%, or 100% identical to the amino acid sequence of SEQ ID NO: 84, 86, 85, 87, 88, 89, 92, or 93. In some embodiments, heteromultimers of the disclosure consist or consist essentially of at least one ALK4 polypeptide that is at least 70%, 75%, 80%, 85%, 90%, 95%, 97%, 98%, 99%, or 100% identical to the amino acid sequence of SEQ ID NO: 84, 86, 85, 87, 88, 89, 92, or 93.

In certain aspects, the disclosure relates to a heteromultimer that comprises an ALK4-Fc fusion protein. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-34 (e.g., amino acid residues 23, 24, 25, 26, 27, 28, 29, 30, 31, 32, 33, 34) SEQ ID NO: 84 or 85, and ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 84 or 85. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-101 of SEQ ID NOs: 84 or 85. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-126 of SEQ ID Nos: 84 or 85. In some embodiments, the ALK4-Fc fusion protein comprises an ALK4 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 84, 86, 85, 87, 88, 89, 90, 91, 92, 93, 94, and 95.

In certain embodiments, the polypeptide comprises an ALK4-Fc fusion polypeptide (SEQ ID NO: 88) as follows:

```
                                          (SEQ ID NO: 88)
  1 MDAMKRGLCC VLLLCGAVFV SPGASGPRGV

QALLCACTSC LQANYTCETD

51 GACMVSIFNL DGMEHHVRTC IPKVELVPAG

KPFYCLSSED LRNTHCCYTD

101 YCNRIDLRVP SGHLKEPEHP SMWGPVETGG

GTHTCPPCPA PELLGGPSVF

151 LFPPKPKDTL MISRTPEVTC VVVDVSHEDP

EVKFNWYVDG VEVHNAKTKP

201 REEQYNSTYR VVSVLTVLHQ DWLNGKEYKC

KVSNKALPAP IEKTISKAKG

251 QPREPQVYTL PPSREEMTKN QVSLTCLVKG

FYPSDIAVEW ESNGQPENNY

301 DTTPPVLDSD GSFFLYSDLT VDKSRWQQGN

VFSCSVMHEA LHNHYTQKSL

351 SLSPG
```

The leader sequence and linker sequence are underlined. To guide heterodimer formation with certain Fc fusion polypeptides of the disclosure, two amino acid substitutions (replacing lysines with aspartic acids) can be introduced into the Fc domain of the ALK4-Fc fusion polypeptide as indicated by double underline above. The amino acid sequence of SEQ ID NO: 88 may optionally be provided with lysine added at the C-terminus.

This ALK4-Fc fusion protein is encoded by the following nucleic acid (SEQ ID NO: 243):

```
                                         (SEQ ID NO: 243)
  1 ATGGATGCAA TGAAGAGAGG GCTCTGCTGT

GTGCTGCTGC TGTGTGGAGC

51 AGTCTTCGTT TCGCCCGGCG CCTCCGGGCC

CCGGGGGGTC CAGGCTCTGC

101 TGTGTGCGTG CACCAGCTGC CTCCAGGCCA

ACTACACGTG TGAGACAGAT

151 GGGGCCTGCA TGGTTTCCAT TTTCAATCTG

GATGGGATGG AGCACCATGT

201 GCGCACCTGC ATCCCCAAAG TGGAGCTGGT

CCCTGCCGGG AAGCCCTTCT

251 ACTGCCTGAG CTCGGAGGAC CTGCGCAACA

CCCACTGCTG CTACACTGAC

301 TACTGCAACA GGATCGACTT GAGGGTGCCC

AGTGGTCACC TCAAGGAGCC

351 TGAGCACCCG TCCATGTGGG GCCCGGTGGA

GACCGGTGGT GGAACTCACA

401 CATGCCCACC GTGCCCAGCA CCTGAACTCC

TGGGGGGACC GTCAGTCTTC

451 CTCTTCCCCC CAAAACCCAA GGACACCCTC

ATGATCTCCC GGACCCCTGA

501 GGTCACATGC GTGGTGGTGG ACGTGAGCCA

CGAAGACCCT GAGGTCAAGT

551 TCAACTGGTA CGTGGACGGC GTGGAGGTGC

ATAATGCCAA GACAAAGCCG

601 CGGGAGGAGC AGTACAACAG CACGTACCGT

GTGGTCAGCG TCCTCACCGT

651 CCTGCACCAG GACTGGCTGA ATGGCAAGGA

GTACAAGTGC AAGGTCTCCA

701 ACAAAGCCCT CCCAGCCCCC ATCGAGAAAA

CCATCTCCAA AGCCAAGGG

751 CAGCCCCGAG AACCACAGGT GTACACCCTG

CCCCCATCCC GGGAGGAGAT

801 GACCAAGAAC CAGGTCAGCC TGACCTGCCT

GGTCAAAGGC TTCTATCCCA

851 GCGACATCGC CGTGGAGTGG GAGAGCAATG

GGCAGCCGGA GAACAACTAC

901 GACACCACGC CTCCCGTGCT GGACTCCGAC

GGCTCCTTCT TCCTCTATAG

951 CGACCTCACC GTGGACAAGA GCAGGTGGCA

GCAGGGGAAC GTCTTCTCAT

1001 GCTCCGTGAT GCATGAGGCT CTGCACAACC

ACTACACGCA GAAGAGCCTC

1051 TCCCTGTCTC CGGGT
```

The mature ALK4-Fc fusion protein sequence (SEQ ID NO: 89) is as follows and may optionally be provided with lysine added at the C-terminus.

```
                                          (SEQ ID NO: 89)
  1 SGPRGVQALL CACTSCLQAN YTCETDGACM

VSIFNLDGME HHVRTCIPKV

51 ELVPAGKPFY CLSSEDLRNT HCCYTDYCNR

IDLRVPSGHL KEPEHPSMWG

101 PVETGGGTHT CPPCPAPELL GGPSVFLFPP

KPKDTLMISR TPEVTCVVVD

151 VSHEDPEVKF NWYVDGVEVH NAKTKPREEQ

YNSTYRVVSV LTVLHQDWLN
```

```
201 GKEYKCKVSN KALPAPIEKT ISKAKGQPRE

PQVYTLPPSR EEMTKNQVSL

251 TCLVKGFYPS DIAVEWESNG QPENNYDTTP

PVLDSDGSFF LYSDLTVDKS

301 RWQQGNVFSC SVMHEALHNH YTQKSLSLSP

G
```

In some embodiments, the ALK4-Fc fusion polypeptide (or any Fc fusion polypeptide disclosed herein) employs the tissue plasminogen activator (TPA) leader:

```
                                    (SEQ ID NO: 246)
    MDAMKRGLCCVLLLCGAVFVSP.
```

In some embodiments, the ALK4-Fc fusion polypeptide (SEQ ID NO: 92) is as follows and may optionally be provided with lysine removed from the C-terminus.

```
                                    (SEQ ID NO: 92)
  1 MDAMKRGLCC VLLLCGAVFV SPGASGPRGV

QALLCACTSC LQANYTCETD

51 GACMVSIFNL DGMEHHVRTC IPKVELVPAG

KPFYCLSSED LRNTHCCYTD

101 YCNRIDLRVP SGHLKEPEHP SMWGPVETGG

GTHTCPPCPA PELLGGPSVF

151 LFPPKPKDTL MISRTPEVTC VVVDVSHEDP

EVKFNWYVDG VEVHNAKTKP

201 REEQYNSTYR VVSVLTVLHQ DWLNGKEYKC

KVSNKALPAP IEKTISKAKG

251 QPREPQVCTL PPSREEMTKN QVSLSCAVKG

FYPSDIAVEW ESNGQPENNY

301 KTTPPVLDSD GSFFLVSKLT VDKSRWQQGN

VFSCSVMHEA LHNHYTQKSL

351 SLSPGK
```

The leader sequence and the linker are underlined. To guide heterodimer formation with certain Fc fusion polypeptides disclosed herein, four amino acid substitutions can be introduced into the Fc domain of the ALK4 fusion polypeptide as indicated by double underline above. The amino acid sequence of SEQ ID NO: 92 may optionally be provided with lysine removed from the C-terminus.

The mature ALK4-Fc fusion protein sequence is as follows and may optionally be provided with lysine removed from the C-terminus.

```
                                    (SEQ ID NO: 93)
  1 SGPRGVQALL CACTSCLQAN YTCETDGACM

VSIFNLDGME HHVRTCIPKV

51 ELVPAGKPFY CLSSEDLRNT HCCYTDYCNR

IDLRVPSGHL KEPEHPSMWG

101 PVETGGGTHT CPPCPAPELL GGPSVFLFPP

KPKDTLMISR TPEVTCVVVD

151 VSHEDPEVKF NWYVDGVEVH NAKTKPREEQ

YNSTYRVVSV LTVLHQDWLN

201 GKEYKCKVSN KALPAPIEKT ISKAKGQPRE

PQVCTLPPSR EEMTKNQVSL

251 SCAVKGFYPS DIAVEWESNG QPENNYKTTP

PVLDSDGSFF LVSKLTVDKS

301 RWQQGNVFSC SVMHEALHNH YTQKSLSLSP

GK
```

Purification of various ActRIIB-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In some embodiments, the ALK4-Fc fusion polypeptide (SEQ ID NO: 247) is as follows and may optionally be provided with lysine removed from the C-terminus.

```
                                    (SEQ ID NO: 247)
  1 MDAMKRGLCC VLLLCGAVFV SPGASGPRGV

QALLCACTSC LQANYTCETD

51 GACMVSIFNL DGMEHHVRTC IPKVELVPAG

KPFYCLSSED LRNTHCCYTD

101 YCNRIDLRVP SGHLKEPEHP SMWGPVETGG

GTHTCPPCPA PELLGGPSVF

151 LFPPKPKDTL MISRTPEVTC VVVDVSHEDP

EVKFNWYVDG VEVHNAKTKP

201 REEQYNSTYR VVSVLTVLHQ DWLNGKEYKC

KVSNKALPAP IEKTISKAKG

251 QPREPQVCTL PPSREEMTKN QVSLSCAVKG

FYPSDIAVEW ESRGQPENNY

301 KTTPPVLDSR GSFFLVSKLT VDKSRWQQGN

VFSCSVMHEA LHNHYTQKSL

351 SLSPGK
```

The leader sequence and the linker are underlined. To guide heterodimer formation with certain Fc fusion polypeptides disclosed herein, four amino acid substitutions (replacing a tyrosine with a cysteine, a threonine with a serine, a leucine with an alanine, and a tyrosine with a valine) can be introduced into the Fc domain of the ALK4 fusion polypeptide as indicated by double underline above. To facilitate purification of the ALK4-Fc:ActRIIB-Fc heterodimer, two amino acid substitutions (replacing an asparagine with an arginine and an aspartate with an arginine) can also be introduced into the Fc domain of the ALK4-Fc fusion polypeptide as indicated by double underline above. The amino acid sequence of SEQ ID NO: 247 may optionally be provided with lysine removed from the C-terminus.

This ALK4-Fc fusion polypeptide is encoded by the following nucleic acid (SEQ ID NO: 248):

```
                                        (SEQ ID NO: 248)
   1 ATGGATGCAA TGAAGAGAGG GCTCTGCTGT
     GTGCTGCTGC TGTGTGGAGC
  51 AGTCTTCGTT TCGCCCGGCG CCTCCGGGCC
     CCGGGGGGTC CAGGCTCTGC
 101 TGTGTGCGTG CACCAGCTGC CTCCAGGCCA
     ACTACACGTG TGAGACAGAT
 151 GGGGCCTGCA TGGTTTCCAT TTTCAATCTG
     GATGGGATGG AGCACCATGT
 201 GCGCACCTGC ATCCCCAAAG TGGAGCTGGT
     CCCTGCCGGG AAGCCCTTCT
 251 ACTGCCTGAG CTCGGAGGAC CTGCGCAACA
     CCCACTGCTG CTACACTGAC
 301 TACTGCAACA GGATCGACTT GAGGGTGCCC
     AGTGGTCACC TCAAGGAGCC
 351 TGAGCACCCG TCCATGTGGG GCCCGGTGGA
     GACCGGTGGT GGAACTCACA
 401 CATGCCCACC GTGCCCAGCA CCTGAACTCC
     TGGGGGGACC GTCAGTCTTC
 451 CTCTTCCCCC CAAAACCCAA GGACACCCTC
     ATGATCTCCC GGACCCCTGA
 501 GGTCACATGC GTGGTGGTGG ACGTGAGCCA
     CGAAGACCCT GAGGTCAAGT
 551 TCAACTGGTA CGTGGACGGC GTGGAGGTGC
     ATAATGCCAA GACAAAGCCG
 601 CGGGAGGAGC AGTACAACAG CACGTACCGT
     GTGGTCAGCG TCCTCACCGT
 651 CCTGCACCAG GACTGGCTGA ATGGCAAGGA
     GTACAAGTGC AAGGTCTCCA
 701 ACAAAGCCCT CCCAGCCCCC ATCGAGAAAA
     CCATCTCCAA AGCCAAAGGG
 751 CAGCCCCGAG AACCACAGGT GTGCACCCTG
     CCCCCATCCC GGGAGGAGAT
 801 GACCAAGAAC CAGGTCAGCC TGTCCTGCGC
     CGTCAAAGGC TTCTATCCCA
 851 GCGACATCGC CGTGGAGTGG GAGAGCCGCG
     GGCAGCCGGA GAACAACTAC
 901 AAGACCACGC CTCCCGTGCT GGACTCCCGC
     GGCTCCTTCT TCCTCGTGAG
 951 CAAGCTCACC GTGGACAAGA GCAGGTGGCA
     GCAGGGGAAC GTCTTCTCAT
1001 GCTCCGTGAT GCATGAGGCT CTGCACAACC
     ACTACACGCA GAAGAGCCTC
1051 TCCCTGTCTC CGGGTAAA
```

The mature ALK4-Fc fusion polypeptide sequence is as follows (SEQ ID NO: 249) and may optionally be provided with lysine removed from the C-terminus.

```
                                        (SEQ ID NO: 249)
   1 SGPRGVQALL CACTSCLQAN YTCETDGACM
     VSIFNLDGME HHVRTCIPKV
  51 ELVPAGKPFY CLSSEDLRNT HCCYTDYCNR
     IDLRVPSGHL KEPEHPSMWG
 101 PVETGGTHT CPPCPAPELL GGPSVFLFPP
     KPKDTLMISR TPEVTCVVVD
 151 VSHEDPEVKF NWYVDGVEVH NAKTKPREEQ
     YNSTYRVVSV LTVLHQDWLN
 201 GKEYKCKVSN KALPAPIEKT ISKAKGQPRE
     PQVCTLPPSR EEMTKNQVSL
 251 SCAVKGFYPS DIAVEWESRG QPENNYKTTP
     PVLDSRGSFF LVSKLTVDKS
 301 RWQQGNVFSC SVMHEALHNH YTQKSLSLSP
     GK
```

This ALK4-Fc fusion polypeptide is encoded by the following nucleic acid (SEQ ID NO: 250):

```
                                        (SEQ ID NO: 250)
   1 TCCGGGCCCC GGGGGGTCCA GGCTCTGCTG
     TGTGCGTGCA CCAGCTGCCT
  51 CCAGGCCAAC TACACGTGTG AGACAGATGG
     GGCCTGCATG GTTTCCATTT
 101 TCAATCTGGA TGGGATGGAG CACCATGTGC
     GCACCTGCAT CCCCAAAGTG
 151 GAGCTGGTCC CTGCCGGGAA GCCCTTCTAC
     TGCCTGAGCT CGGAGGACCT
 201 GCGCAACACC CACTGCTGCT ACACTGACTA
     CTGCAACAGG ATCGACTTGA
 251 GGGTGCCCAG TGGTCACCTC AAGGAGCCTG
     AGCACCCGTC CATGTGGGGC
```

```
301 CCGGTGGAGA CCGGTGGTGG AACTCACACA
    TGCCCACCGT GCCCAGCACC
351 TGAACTCCTG GGGGGACCGT CAGTCTTCCT
    CTTCCCCCCA AAACCCAAGG
401 ACACCCTCAT GATCTCCCGG ACCCCTGAGG
    TCACATGCGT GGTGGTGGAC
451 GTGAGCCACG AAGACCCTGA GGTCAAGTTC
    AACTGGTACG TGGACGGCGT
501 GGAGGTGCAT AATGCCAAGA CAAAGCCGCG
    GGAGGAGCAG TACAACAGCA
551 CGTACCGTGT GGTCAGCGTC CTCACCGTCC
    TGCACCAGGA CTGGCTGAAT
601 GGCAAGGAGT ACAAGTGCAA GGTCTCCAAC
    AAAGCCCTCC CAGCCCCCAT
651 CGAGAAAACC ATCTCCAAAG CCAAAGGGCA
    GCCCCGAGAA CCACAGGTGT
701 GCACCCTGCC CCCATCCCGG GAGGAGATGA
    CCAAGAACCA GGTCAGCCTG
751 TCCTGCGCCG TCAAAGGCTT CTATCCCAGC
    GACATCGCCG TGGAGTGGGA
801 GAGCCGCGGG CAGCCGGAGA ACAACTACAA
    GACCACGCCT CCCGTGCTGG
851 ACTCCCGCGG CTCCTTCTTC CTCGTGAGCA
    AGCTCACCGT GGACAAGAGC
901 AGGTGGCAGC AGGGGAACGT CTTCTCATGC
    TCCGTGATGC ATGAGGCTCT
951 GCACAACCAC TACACGCAGA AGAGCCTCTC
    CCTGTCTCCG GGTAAA
```

In certain embodiments, the ALK4-Fc fusion polypeptide is SEQ ID NO: 92 (shown above), which contains four amino acid substitutions to guide heterodimer formation certain Fc fusion polypeptides disclosed herein, and may optionally be provided with lysine removed from the C-terminus.

This ALK4-Fc fusion polypeptide is encoded by the following nucleic acid (SEQ ID NO: 251):

```
                                    (SEQ ID NO: 251)
  1 ATGGATGCAA TGAAGAGAGG GCTCTGCTGT
    GTGCTGCTGC TGTGTGGAGC
 51 AGTCTTCGTT TCGCCCGGCG CCTCCGGGCC
    CCGGGGGGTC CAGGCTCTGC
101 TGTGTGCGTG CACCAGCTGC CTCCAGGCCA
    ACTACACGTG TGAGACAGAT
151 GGGGCCTGCA TGGTTTCCAT TTTCAATCTG
    GATGGGATGG AGCACCATGT
201 GCGCACCTGC ATCCCCAAAG TGGAGCTGGT
    CCCTGCCGGG AAGCCCTTCT
251 ACTGCCTGAG CTCGGAGGAC CTGCGCAACA
    CCCACTGCTG CTACACTGAC
301 TACTGCAACA GGATCGACTT GAGGGTGCCC
    AGTGGTCACC TCAAGGAGCC
351 TGAGCACCCG TCCATGTGGG GCCCGGTGGA
    GACCGGTGGT GGAACTCACA
401 CATGCCCACC GTGCCCAGCA CCTGAACTCC
    TGGGGGGACC GTCAGTCTTC
451 CTCTTCCCCC CAAAACCCAA GGACACCCTC
    ATGATCTCCC GGACCCCTGA
501 GGTCACATGC GTGGTGGTGG ACGTGAGCCA
    CGAAGACCCT GAGGTCAAGT
551 TCAACTGGTA CGTGGACGGC GTGGAGGTGC
    ATAATGCCAA GACAAAGCCG
601 CGGGAGGAGC AGTACAACAG CACGTACCGT
    GTGGTCAGCG TCCTCACCGT
651 CCTGCACCAG GACTGGCTGA ATGGCAAGGA
    GTACAAGTGC AAGGTCTCCA
701 ACAAAGCCCT CCCAGCCCCC ATCGAGAAAA
    CCATCTCCAA AGCCAAAGGG
751 CAGCCCCGAG AACCACAGGT GTGCACCCTG
    CCCCCATCCC GGGAGGAGAT
801 GACCAAGAAC CAGGTCAGCC TGTCCTGCGC
    CGTCAAAGGC TTCTATCCCA
851 GCGACATCGC CGTGGAGTGG GAGAGCAATG
    GGCAGCCGGA GAACAACTAC
901 AAGACCACGC CTCCCGTGCT GGACTCCGAC
    GGCTCCTTCT TCCTCGTGAG
951 CAAGCTCACC GTGGACAAGA GCAGGTGGCA
    GCAGGGGAAC GTCTTCTCAT
1001 GCTCCGTGAT GCATGAGGCT CTGCACAACC
     ACTACACGCA GAAGAGCCTC
1051 TCCCTGTCTC CGGGTAAA
```

The mature ALK4-Fc fusion polypeptide sequence is SEQ ID NO: 93 (shown above) and may optionally be provided with lysine removed from the C-terminus.

This ALK4-Fc fusion polypeptide is encoded by the following nucleic acid (SEQ ID NO: 252):

```
                                        (SEQ ID NO: 252)
  1 TCCGGGCCCC GGGGGGTCCA GGCTCTGCTG
    TGTGCGTGCA CCAGCTGCCT
 51 CCAGGCCAAC TACACGTGTG AGACAGATGG
    GGCCTGCATG GTTTCCATTT
101 TCAATCTGGA TGGGATGGAG CACCATGTGC
    GCACCTGCAT CCCCAAAGTG
151 GAGCTGGTCC CTGCCGGGAA GCCCTTCTAC
    TGCCTGAGCT CGGAGGACCT
201 GCGCAACACC CACTGCTGCT ACACTGACTA
    CTGCAACAGG ATCGACTTGA
251 GGGTGCCCAG TGGTCACCTC AAGGAGCCTG
    AGCACCCGTC CATGTGGGC
301 CCGGTGGAGA CCGGTGGTGG AACTCACACA
    TGCCCACCGT GCCCAGCACC
351 TGAACTCCTG GGGGGACCGT CAGTCTTCCT
    CTTCCCCCCA AAACCCAAGG
401 ACACCCTCAT GATCTCCCGG ACCCCTGAGG
    TCACATGCGT GGTGGTGGAC
451 GTGAGCCACG AAGACCCTGA GGTCAAGTTC
    AACTGGTACG TGGACGGCGT
501 GGAGGTGCAT AATGCCAAGA CAAAGCCGCG
    GGAGGAGCAG TACAACAGCA
551 CGTACCGTGT GGTCAGCGTC CTCACCGTCC
    TGCACCAGGA CTGGCTGAAT
601 GGCAAGGAGT ACAAGTGCAA GGTCTCCAAC
    AAAGCCCTCC CAGCCCCCAT
651 CGAGAAAACC ATCTCCAAAG CCAAAGGGCA
    GCCCCGAGAA CCACAGGTGT
701 GCACCCTGCC CCCATCCCGG GAGGAGATGA
    CCAAGAACCA GGTCAGCCTG
751 TCCTGCGCCG TCAAAGGCTT CTATCCCAGC
    GACATCGCCG TGGAGTGGGA
801 GAGCAATGGG CAGCCGGAGA ACAACTACAA
    GACCACGCCT CCCGTGCTGG
851 ACTCCGACGG CTCCTTCTTC CTCGTGAGCA
    AGCTCACCGT GGACAAGAGC
901 AGGTGGCAGC AGGGGAACGT CTTCTCATGC
    TCCGTGATGC ATGAGGCTCT
```

-continued
```
951 GCACAACCAC TACACGCAGA AGAGCCTCTC
    CCTGTCTCCG GGTAAA
```

Purification of various ALK4-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography and epitope-based affinity chromatography (e.g., with an antibody or functionally equivalent ligand directed against an epitope on ALK4 or ActRIIB), and multimodal chromatography (e.g., with resin containing both electrostatic and hydrophobic ligands). The purification could be completed with viral filtration and buffer exchange.

In certain aspects, the present disclosure relates to protein complexes that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity.

A human ALK5 precursor protein sequence (NCBI Ref Seq NP_004603.1) is as follows:

```
                                        (SEQ ID NO: 96)
  1 MEAAVAAPRP RLLLLVLAAA AAAAALLPG
    ATALQCFCHL CTKDNFTCVT DGLCFVSVME
 61 TTDKVIHNSM CIAEIDLIPR DRPFVCAPSS
    KTGSVTTTYC CNQDHCNKIE LPTTVKSSPG
121 LGPVELAAVI AGPVCFVCIS LMLMVYICHN
    RTVIHHRVPN EEDPSLDRPF ISEGTTLKDL
181 IYDMTTSGSG SGLPLLVQRT IARTIVLQES
    IGKGRFGEVW RGKWRGEEVA VKIFSSREER
241 SWFREAEIYQ TVMLRHENIL GFIAADNKDN
    GTWTQLWLVS DYHEHGSLFD YLNRYTVTVE
301 GMIKLALSTA SGLAHLHMEI VGTQGKPAIA
    HRDLKSKNIL VKKNGTCCIA DLGLAVRHDS
361 ATDTIDIAPN HRVGTKRYMA PEVLDDSINM
    KHFESFKRAD IYAMGLVFWE IARRCSIGGI
421 HEDYQLPYYD LVPSDPSVEE MRKVVCEQKL
    RPNIPNRWQS CEALRVMAKI MRECWYANGA
481 ARLTALRIKK TLSQLSQQEG IKM
```

The signal peptide is indicated by a single underline and the extracellular domain is indicated in bold font.

A processed extracellular ALK5 polypeptide sequence is as follows: AALLPGATALQCFCHLCTKDNFTCVTDG-LCFVSVTETTDKVIHNSMCIAEIDLIP-RDRPFVCAPSSKTGSVTTTY CCNQDHCNKIELPTTVKSSPGLGPVEL (SEQ ID NO: 98)

A nucleic acid sequence encoding the ALK5 precursor protein is shown in SEQ ID NO: 225, corresponding to nucleotides 77-1585 of Genbank Reference Sequence NM_004612.2. A nucleic acid sequence encoding an extracellular human ALK5 polypeptide is shown in SEQ ID NO: 226.

An alternative isoform of the human ALK5 precursor protein sequence, isoform 2 (NCBI Ref Seq XP 005252207.1), is as follows:

```
                                          (SEQ ID NO: 97)
  1  MEAAVAAPRP RLLLLVLAAA AAAAAALLPG

ATALQCFCHL CTKDNFTCVT DGLCFVSVME

61  TTDKVIHNSM CIAEIDLIPR DRPFVCAPSS

KTGSVTTTYC CNQDHCNKIE LPTTGPFSVK

121  SSPGLGPVEL AAVIAGPVCF VCISLMLMVY

ICHNRTVIHH RVPNEEDPSL DRPFISEGTT

181  LKDLIYDMTT SGSGSGLPLL VQRTIARTIV

LQESIGKGRF GEVWRGKWRG EEVAVKIFSS

241  REERSWFREA EIYQTVMLRH ENILGFIAAD

NKDNGTWTQL WLVSDYHEHG SLFDYLNRYT

301  VTVEGMIKLA LSTASGLAHL HMEIVGTQGK

PAIAHRDLKS KNILVKKNGT CCIADLGLAV

361  RHDSATDTID LAPNHRVGTK RYMAPEVLDD

SINMKHFESF KRADIYAMGL VFWEIARRCS

421  IGGIHEDYQL PYYDLVPSDP SVEEMRKVVC

EQKLRPNIPN RWQSCEALRV MAKIMRECWY

481  ANGAARLTAL RIKKTLSQLS QQEGIKM
```

The signal peptide is indicated by a single underline and the extracellular domain is indicated in bold font.

A processed extracellular ALK5 polypeptide sequence (isoform 2) is as follows:

```
                                         (SEQ ID NO: 99)
AALLPGATALQCFCHLCTKDNFTCVTDGLCFVSVTE

TTDKVIHNSMCIAEIDLIPRDRPFVCAPSSKTGSVT

TTYCCNQDHCNKIELPTTGPFSVKSSPGLGPVEL
```

A nucleic acid sequence encoding human ALK5 precursor protein (isoform 2) is shown in SEQ ID NO: 227, corresponding to nucleotides 77-1597 of Genbank Reference Sequence XM_005252150.1. A nucleic acid sequence encoding a processed extracellular ALK5 polypeptide is shown in SEQ ID NO: 228.

In certain embodiments, the disclosure relates to heteromultimers that comprise at least one ALK5 polypeptide, which includes fragments, functional variants, and modified forms thereof. Preferably, ALK5 polypeptides for use in accordance with inventions of the disclosure (e.g., heteromultimers comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK5 polypeptide that is at least 70%, 75%, 80%, 85%, 90%, 95%, 97%, 98%, 99%, or 100% identical to the amino acid sequence of SEQ ID NO: 96, 98, 97, or 99. In some embodiments, heteromultimer complexes of the disclosure consist or consist essentially of at least one ALK5 polypeptide that is at least 70%, 75%, 80%, 85%, 90%, 95%, 97%, 98%, 99%, or 100% identical to the amino acid sequence of SEQ ID NO: 96, 98, 97, or 99.

In certain aspects, the disclosure relates to a heteromultimer that comprises an ALK5-Fc fusion protein. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 25-36 (e.g., amino acid residues 25, 26, 27, 28, 29, 30, 31, 32, 33, 34, 35, and 36) SEQ ID NO: 96 or 97, and ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 36-106 of SEQ ID NOs: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 25-126 of SEQ ID NOs: 96 or 97. In some embodiments, the ALK5-Fc fusion protein comprises an ALK5 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 96, 98, 97, 99, 100, 101, 102, 103, 104, 105, 106, and 107.

The complementary ALK5-Fc fusion protein employs the TPA leader and is as follows (SEQ ID NO: 100):

```
                                         (SEQ ID NO: 100)
  1  MDAMKRGLCC VLLLCGAVFV SPGAALLPGA

TALQCFCHLC TKDNFTCVTD

51  GLCFVSVTET TDKVIHNSMC IAEIDLIPRD

RPFVCAPSSK TGSVTTTYCC

101  NQDHCNKIEL PTTVKSSPGL GPVETGGGTH

TCPPCPAPEL LGGPSVFLFP

151  PKPKDTLMIS RTPEVTCVVV DVSHEDPEVK

FNWYVDGVEV HNAKTKPREE
```

```
201 QYNSTYRVVS VLTVLHQDWL NGKEYKCKVS
    NKALPAPIEK TISKAKGQPR
251 EPQVYTLPPS REEMTKNQVS LTCLVKGFYP
    SDIAVEWESN GQPENNYDTT
301 PPVLDSDGSF FLYSDLTVDK SRWQQGNVFS
    CSVMHEALHN HYTQKSLSLS
351 PG
```

The signal sequence and linker sequence are underlined. To promote formation of the ActRIIB-Fc:ALK5-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 100 may optionally be provided with a lysine added at the C-terminus.

This ALK5-Fc fusion protein is encoded by the following nucleic acid (SEQ ID NO: 253):

```
                                    (SEQ ID NO: 253)
  1 ATGGATGCAA TGAAGAGAGG GCTCTGCTGT
    GTGCTGCTGC TGTGTGGAGC
 51 AGTCTTCGTT TCGCCCGGCG CCGCGCTGCT
    CCCGGGGGCG ACGGCGTTAC
101 AGTGTTTCTG CCACCTCTGT ACAAAAGACA
    ATTTTACTTG TGTGACAGAT
151 GGGCTCTGCT TTGTCTCTGT CACAGAGACC
    ACAGACAAAG TTATACACAA
201 CAGCATGTGT ATAGCTGAAA TTGACTTAAT
    TCCTCGAGAT AGGCCGTTTG
251 TATGTGCACC CTCTTCAAAA ACTGGGTCTG
    TGACTACAAC ATATTGCTGC
301 AATCAGGACC ATTGCAATAA AATAGAACTT
    CCAACTACTG TAAAGTCATC
351 ACCTGGCCTT GGTCCTGTGG AAACCGGTGG
    TGGAACTCAC ACATGCCCAC
401 CGTGCCCAGC ACCTGAACTC CTGGGGGGAC
    CGTCAGTCTT CCTCTTCCCC
451 CCAAAACCCA AGGACACCCT CATGATCTCC
    CGGACCCCTG AGGTCACATG
501 CGTGGTGGTG GACGTGAGCC ACGAAGACCC
    TGAGGTCAAG TTCAACTGGT
551 ACGTGGACGG CGTGGAGGTG CATAATGCCA
    AGACAAAGCC GCGGGAGGAG
601 CAGTACAACA GCACGTACCG TGTGGTCAGC
    GTCCTCACCG TCCTGCACCA
651 GGACTGGCTG AATGGCAAGG AGTACAAGTG
    CAAGGTCTCC AACAAAGCCC
701 TCCCAGCCCC CATCGAGAAA ACCATCTCCA
    AAGCCAAAGG GCAGCCCCGA
751 GAACCACAGG TGTACACCCT GCCCCCATCC
    CGGGAGGAGA TGACCAAGAA
801 CCAGGTCAGC CTGACCTGCC TGGTCAAAGG
    CTTCTATCCC AGCGACATCG
851 CCGTGGAGTG GGAGAGCAAT GGGCAGCCGG
    AGAACAACTA CGACACCACG
901 CCTCCCGTGC TGGACTCCGA CGGCTCCTTC
    TTCCTCTATA GCGACCTCAC
951 CGTGGACAAG AGCAGGTGGC AGCAGGGGAA
    CGTCTTCTCA TGCTCCGTGA
1001 TGCATGAGGC TCTGCACAAC CACTACACGC
     AGAAGAGCCT CTCCCTGTCT
1051 CCGGGT
```

The mature ALK5-Fc fusion protein sequence (SEQ ID NO: 101) is as follows and may optionally be provided with a lysine added at the C-terminus.

```
                                    (SEQ ID NO: 101)
  1 ALLPGATALQ CFCHLCTKDN FTCVTDGLCF
    VSVTETTDKV IHNSMCIAEI
 51 DLIPRDRPPV CAPSSKTGSV TTTYCCNQDH
    CNKIELPTTV KSSPGLGPVE
101 TGGGTHTCPP CPAPELLGGP SVFLFPPKPK
    DTLMISRTPE VTCVVVDVSH
151 EDPEVKFNWY VDGVEVHNAK TKPREEQYNS
    TYRVVSVLTV LHQDWLNGKE
201 YKCKVSNKAL PAPIEKTISK AKGQPREPQV
    YTLPPSREEM TKNQVSLTCL
251 VKGFYPSDIA VEWESNGQPE NNYDTTPPVL
    DSDGSFFLYS DLTVDKSRWQ
301 QGNVFSCSVM HEALHNHYTQ KSLSLSPG
```

In another approach to promoting the formation of heteromultimer complexes using asymmetric Fc fusion proteins, the Fc domains are altered to introduce complementary hydrophobic interactions and an additional intermolecular disulfide bond.

In some embodiments, the ALK5-Fc fusion polypeptide (SEQ ID NO: 104) is as follows:

```
                                            (SEQ ID NO: 104)
  1 MDAMKRGLCC VLLLCGAVFV SPGAALLPGA

TALQCFCHLC TKDNFTCVTD

51 GLCFVSVTET TDKVIHNSMC IAEIDLIPRD

RPFVCAPSSK TGSVTTTYCC

101 NQDHCNKIEL PTTVKSSPGL GPVETGGGTH

TCPPCPAPEL LGGPSVFLFP

151 PKPKDTLMIS RTPEVTCVVV DVSHEDPEVK

FNWYVDGVEV HNAKTKPREE

201 QYNSTYRVVS VLTVLHQDWL NGKEYKCKVS

NKALPAPIEK TISKAKGQPR

251 EPQVCTLPPS REEMTKNQVS LSCAVKGFYP

SDIAVEWESN GQPENNYKTT

301 PPVLDSDGSF FLVSKLTVDK SRWQQGNVFS

CSVMHEALHN HYTQKSLSLS

351 PGK
```

The leader sequence and linker sequence are underlined. To guide heterodimer formation with certain Fc fusion polypeptides disclosed herein, four amino acid substitutions can be introduced into the Fc domain of the ALK5 fusion polypeptide as indicated by double underline above. Furthermore, the C-terminal lysine residue of the Fc domain can be deleted. The amino acid sequence of SEQ ID NO: 104 may optionally be provided with the lysine removed from the C-terminus.

The mature ALK5-Fc fusion protein sequence (SEQ ID NO: 105) is as follows and may optionally be provided with the lysine removed from the C-terminus.

```
                                            (SEQ ID NO: 105)
  1 ALLPGATALQ CFCHLCTKDN FTCVTDGLCF

VSVTETTDKV IHNSMCIAEI

51 DLIPRDRPPV CAPSSKTGSV TTTYCCNQDH

CNKIELPTTV KSSPGLGPVE

101 TGGGTHTCPP CPAPELLGGP SVFLFPPKPK

DTLMISRTPE VTCVVVDVSH

151 EDPEVKFNWY VDGVEVHNAK TKPREEQYNS

TYRVVSVLTV LHQDWLNGKE

201 YKCKVSNKAL PAPIEKTISK AKGQPREPQV

CTLPPSREEM TKNQVSLSCA

251 VKGFYPSDIA VEWESNGQPE NNYKTTPPVL

DSDGSFFLVS KLTVDKSRWQ

301 QGNVFSCSVM HEALHNHYTQ KSLSLSPGK
```

In certain aspects, the present disclosure relates to protein complexes that comprise an ALK6 polypeptide. As used herein, the term "ALK6" refers to a family of activin receptor-like kinase-6 proteins from any species and variants derived from such ALK6 proteins by mutagenesis or other modification. Reference to ALK6 herein is understood to be a reference to any one of the currently identified forms. Members of the ALK6 family are generally transmembrane proteins, composed of a ligand-binding extracellular domain with a cysteine-rich region, a transmembrane domain, and a cytoplasmic domain with predicted serine/threonine kinase activity.

The term "ALK6 polypeptide" includes polypeptides comprising any naturally occurring polypeptide of an ALK6 family member as well as any variants thereof (including mutants, fragments, fusions, and peptidomimetic forms) that retain a useful activity.

A human ALK6 precursor protein sequence (NCBI Ref Seq NP_001194.1) is as follows:

```
                                            (SEQ ID NO: 108)
  1 MLLRSAGKLN VGTKKEDGES TAPTPRPKVL

RCKCHHHCPE DSVNNICSTD GYCFTMIEED

61 DSGLPVVTSG CLGLEGSDFQ CRDTPIPHQR

RSIECCTERN ECNKDLHPTL PPLKNRDFVD

121 GPIHHRALLI SVTVCSLLLV LIILFCYFRY

KRQETRPRYS IGLEQDETYI PPGESLRDLI

181 EQSQSSGSGS GLPLLVQRTI AKQIQMVKQI

GKGRYGEVWM GKWRGEKVAV KVFFTTEEAS

241 WFRETEIYQT VLMRHENILG FIAADIKGTG

SWTQLYLITD YHENGSLYDY LKSTTLDAKS

301 MLKLAYSSVS GLCHLHTEIF STQGKPAIAH

RDLKSKNILV KKNGTCCIAD LGLAVKFISD

361 TNEVDIPPNT RVGTKRYMPP EVLDESLNRN

HFQSYIMADM YSFGLILWEV ARRCVSGGIV

421 EEYQLPYHDL VPSDPSYEDM REIVCIKKLR

PSFPNRWSSD ECLRQMGKLM TECWAHNPAS

481 RLTALRVKKT LAKMSESQDI KL
```

The signal peptide is indicated by a single underline and the extracellular domain is indicated in bold font.

The processed extracellular ALK6 polypeptide sequence is as follows:

```
                                            (SEQ ID NO: 109)
    KKEDGESTAPTPRPKVLRCKCHHHCPEDSVNNICSTDG

YCFTMIEEDDSGLPVVTSGCLGLEGSDFQCRDTPIPHQ

RRSIECCTERNECNKDLHPTLPPLKNRDFVDGPIHHR
```

A nucleic acid sequence encoding the ALK6 precursor protein is shown in SEQ ID NO: 229, corresponding to nucleotides 275-1780 of Genbank Reference Sequence NM_001203.2. A nucleic acid sequence encoding processed extracellular ALK6 polypeptide is shown in SEQ ID NO: 230.

An alternative isoform of human ALK6 precursor protein sequence, isoform 2 (NCBI Ref Seq NP_001243722.1) is as follows:

```
                                         (SEQ ID NO: 110)
  1 MGWLEELNWQ LHIFLLILLS MHTRANFLDN

MLLRSAGKLN VGTKKEDGES TAPTPRPKVL

61 RCKCHHHCPE DSVNNICSTD GYCFTMIEED

DSGLPVVTSG CLGLEGSDFQ CRDTPIPHQR

121 RSIECCTERN ECNKDLHPTL PPLKNRDFVD

GPIHHRALLI SVTVCSLLLV LIILFCYFRY

181 KRQETRPRYS IGLEQDETYI PPGESLRDLI

EQSQSSGSGS GLPLLVQRTI AKQIQMVKQI

241 GKGRYGEVWM GKWRGEKVAV KVFFTTEEAS

WFRETEIYQT VLMRHENILG FIAADIKGTG

301 SWTQLYLITD YHENGSLYDY LKSTTLDAKS

MLKLAYSSVS GLCHLHTEIF STQGKPAIAH

361 RDLKSKNILV KKNGTCCIAD LGLAVKFISD

TNEVDIPPNT RVGTKRYMPP EVLDESLNRN

421 HFQSYIMADM YSFGLILWEV ARRCVSGGIV

EEYQLPYHDL VPSDPSYEDM REIVCIKKLR

481 PSFPNRWSSD ECLRQMGKLM TECWAHNPAS

RLTALRVKKT LAKMSESQDI KL
```

The signal peptide is indicated by a single underline and the extracellular domain is indicated in bold font.

A processed extracellular ALK6 polypeptide sequence (isoform 2) is as follows:

```
                                         (SEQ ID NO: 111)
NFLDNMLLRSAGKLNVGTKKEDGESTAPTPRPKVLRCK

CHHHCPEDSVNNICSTDGYCFTMIEEDDSGLPVVTSGC

LGLEGSDFQCRDTPIPHQRRSIECCTERNECNKDLHPT

LPPLKNRDFVDGPIHHR
```

A nucleic acid sequence encoding human ALK6 precursor protein (isoform 2) is shown in SEQ ID NO: 231, corresponding to nucleotides 22-1617 of Genbank Reference Sequence NM_001256793.1. A nucleic acid sequence encoding a processed extracellular ALK6 polypeptide is shown in SEQ ID NO: 232.

In certain embodiments, the disclosure relates to heteromultimers that comprise at least one ALK6 polypeptide, which includes fragments, functional variants, and modified forms thereof. Preferably, ALK6 polypeptides for use in accordance with inventions of the disclosure (e.g., heteromultimers comprising an ALK6 polypeptide and uses thereof) are soluble (e.g., an extracellular domain of ALK6). In other preferred embodiments, ALK6 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK6 polypeptide that is at least 70%, 75%, 80%, 85%, 90%, 95%, 97%, 98%, 99%, or 100% identical to the amino acid sequence of SEQ ID NO: 108, 109, 110, or 111. In some embodiments, heteromultimers of the disclosure consist or consist essentially of at least one ALK6 polypeptide that is at least 70%, 75%, 80%, 85%, 90%, 95%, 97%, 98%, 99%, or 100% identical to the amino acid sequence of SEQ ID NO: 108, 109, 110, or 111.

In certain aspects, the disclosure relates to a heteromultimer that comprises an ALK6-Fc fusion protein. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 14-32 (e.g., amino acid residues 14, 15, 16, 17, 18, 19, 20, 21, 22, 23, 24, 25, 26, 27, 28, 29, 30, 31, and 32) SEQ ID NO: 108, and ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 32-102 of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 14-126 of SEQ ID NO: 108. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 108, 109, 110, 111, 112, 113, 114, 115, 116, 117, 118, and 119.

In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, and 62) SEQ ID NO: 110, and ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 110. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 62-132 of SEQ ID NO: 110. In some embodiments, the ALK6-Fc fusion protein comprises an ALK6 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 26-156 of SEQ ID NO: 110.

The complementary ALK6-Fc fusion protein employs the TPA leader and is as follows (SEQ ID NO: 112):

```
                                         (SEQ ID NO: 112)
  1 MDAMKRGLCC VLLLCGAVFV SPGAKKEDGE

STAPTPRPKV LRCKCHHHCP
```

```
 51 EDSVNNICST DGYCFTMIEE DDSGLPVVTS
    GCLGLEGSDF QCRDTPIPHQ
101 RRSIECCTER NECNKDLHPT LPPLKNRDFV
    DGPIHHRTGG GTHTCPPCPA
151 PELLGGPSVF LFPPKPKDTL MISRTPEVTC
    VVVDVSHEDP EVKFNWYVDG
201 VEVHNAKTKP REEQYNSTYR VVSVLTVLHQ
    DWLNGKEYKC KVSNKALPAP
251 IEKTISKAKG QPREPQVYTL PPSREEMTKN
    QVSLTCLVKG FYPSDIAVEW
301 ESNGQPENNY DTTPPVLDSD GSFFLYSDLT
    VDKSRWQQGN VFSCSVMHEA
351 LHNHYTQKSL SLSPG
```

The signal sequence and linker sequence are underlined. To promote formation of the ActRIIB-Fc:ALK6-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 112 may optionally be provided with a lysine added at the C-terminus.

This ALK6-Fc fusion protein is encoded by the following nucleic acid (SEQ ID NO: 254):

```
                                      (SEQ ID NO: 254)
   1 ATGGATGCAA TGAAGAGAGG GCTCTGCTGT
     GTGCTGCTGC TGTGTGGAGC
  51 AGTCTTCGTT TCGCCCGGCG CCAAGAAAGA
     GGATGGTGAG AGTACAGCCC
 101 CCACCCCCCG TCCAAAGGTC TTGCGTTGTA
     AATGCCACCA CCATTGTCCA
 151 GAAGACTCAG TCAACAATAT TTGCAGCACA
     GACGGATATT GTTTCACGAT
 201 GATAGAAGAG GATGACTCTG GGTTGCCTGT
     GGTCACTTCT GGTTGCCTAG
 251 GACTAGAAGG CTCAGATTTT CAGTGTCGGG
     ACACTCCCAT TCCTCATCAA
 301 AGAAGATCAA TTGAATGCTG CACAGAAAGG
     AACGAATGTA ATAAAGACCT
 351 ACACCCTACA CTGCCTCCAT TGAAAAACAG
     AGATTTTGTT GATGGACCTA
 401 TACACCACAG GACCGGTGGT GGAACTCACA
     CATGCCCACC GTGCCCAGCA
 451 CCTGAACTCC TGGGGGGACC GTCAGTCTTC
     CTCTTCCCCC CAAAACCCAA
 501 GGACACCCTC ATGATCTCCC GGACCCCTGA
     GGTCACATGC GTGGTGGTGG
 551 ACGTGAGCCA CGAAGACCCT GAGGTCAAGT
     TCAACTGGTA CGTGGACGGC
 601 GTGGAGGTGC ATAATGCCAA GACAAAGCCG
     CGGGAGGAGC AGTACAACAG
 651 CACGTACCGT GTGGTCAGCG TCCTCACCGT
     CCTGCACCAG GACTGGCTGA
 701 ATGGCAAGGA GTACAAGTGC AAGGTCTCCA
     ACAAAGCCCT CCCAGCCCCC
 751 ATCGAGAAAA CCATCTCCAA AGCCAAAGGG
     CAGCCCCGAG AACCACAGGT
 801 GTACACCCTG CCCCCATCCC GGGAGGAGAT
     GACCAAGAAC CAGGTCAGCC
 851 TGACCTGCCT GGTCAAAGGC TTCTATCCCA
     GCGACATCGC CGTGGAGTGG
 901 GAGAGCAATG GGCAGCCGGA GAACAACTAC
     GACACCACGC CTCCCGTGCT
 951 GGACTCCGAC GGCTCCTTCT TCCTCTATAG
     CGACCTCACC GTGGACAAGA
1001 GCAGGTGGCA GCAGGGGAAC GTCTTCTCAT
     GCTCCGTGAT GCATGAGGCT
1051 CTGCACAACC ACTACACGCA GAAGAGCCTC
     TCCCTGTCTC CGGGT
```

The mature ALK6-Fc fusion protein sequence (SEQ ID NO: 113) is as follows and may optionally be provided with a lysine added at the C-terminus.

```
                                      (SEQ ID NO: 113)
   1 KKEDGESTAP TPRPKVLRCK CHHHCPEDSV
     NNICSTDGYC FTMIEEDDSG
  51 LPVVTSGCLG LEGSDFQCRD TPIPHQRRSI
     ECCTERNECN KDLHPTLPPL
 101 KNRDFVDGPI HHRTGGGTHT CPPCPAPELL
     GGPSVFLFPP KPKDTLMISR
 151 TPEVTCVVVD VSHEDPEVKF NWYVDGVEVH
     NAKTKPREEQ YNSTYRVVSV
 201 LTVLHQDWLN GKEYKCKVSN KALPAPIEKT
     ISKAKGQPRE PQVYTLPPSR
```

```
251 EEMTKNQVSL TCLVKGFYPS DIAVEWESNG
    QPENNYDTTP PVLDSDGSFF
301 LYSDLTVDKS RWQQGNVFSC SVMHEALHNH
    YTQKSLSLSP G
```

In another approach to promoting the formation of heteromultimer complexes using asymmetric Fc fusion proteins, the Fc domains can be altered to introduce complementary hydrophobic interactions and an additional intermolecular disulfide bond.

The complementary form of ALK6-Fc fusion polypeptide (SEQ ID NO: 116) is as follows:

```
                                        (SEQ ID NO: 116)
  1 MDAMKRGLCC VLLLCGAVFV SPGAKKEDGE
    STAPTPRPKV LRCKCHHHCP
 51 EDSVNNICST DGYCFTMIEE DDSGLPVVTS
    GCLGLEGSDF QCRDTPIPHQ
101 RRSIECCTER NECNKDLHPT LPPLKNRDFV
    DGPIHHRTGG GTHTCPPCPA
151 PELLGGPSVF LFPPKPKDTL MISRTPEVTC
    VVVDVSHEDP EVKFNWYVDG
201 VEVHNAKTKP REEQYNSTYR VVSVLTVLHQ
    DWLNGKEYKC KVSNKALPAP
251 IEKTISKAKG QPREPQVCTL PPSREEMTKN
    QVSLSCAVKG FYPSDIAVEW
301 ESNGQPENNY KTTPPVLDSD GSFFLVSKLT
    VDKSRWQQGN VFSCSVMHEA
351 LHNHYTQKSL SLSPGK
```

The leader sequence and linker sequence are underlined. To guide heterodimer formation with certain Fc fusion polypeptides disclosed herein, four amino acid substitutions can be introduced into the Fc domain of the ALK6 fusion polypeptide as indicated by double underline above. Furthermore, the C-terminal lysine residue of the Fc domain can be deleted. The amino acid sequence of SEQ ID NO: 116 may optionally be provided with the lysine removed from the C-terminus.

The mature ALK6-Fc fusion protein sequence (SEQ ID NO: 117) can be as follows and may optionally be provided with the lysine removed from the C-terminus.

```
                                        (SEQ ID NO: 117)
  1 KKEDGESTAP TPRPKVLRCK CHHHCPEDSV
    NNICSTDGYC FTMIEEDDSG
 51 LPVVTSGCLG LEGSDFQCRD TPIPHQRRSI
    ECCTERNECN KDLHPTLPPL
101 KNRDFVDGPI HHRTGGGTHT CPPCPAPELL
    GGPSVFLFPP KPKDTLMISR
151 TPEVTCVVVD VSHEDPEVKF NWYVDGVEVH
    NAKTKPREEQ YNSTYRVVSV
201 LTVLHQDWLN GKEYKCKVSN KALPAPIEKT
    ISKAKGQPRE PQVCTLPPSR
251 EEMTKNQVSL SCAVKGFYPS DIAVEWESNG
    QPENNYKTTP PVLDSDGSFF
301 LVSKLTVDKS RWQQGNVFSC SVMHEALHNH
    YTQKSLSLSP GK
```

In certain aspects, the present disclosure relates to protein complexes that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity.

Four naturally occurring isoforms of human ALK7 have been described. The sequence of human ALK7 isoform 1 precursor protein (NCBI Ref Seq NP_660302.2) is as follows:

```
                                        (SEQ ID NO: 120)
  1 MTRALCSALR QALLLLAAAA ELSPGLKCVC
    LLCDSSNFTC QTEGACWASV MLTNGKEQVI
 61 KSCVSLPELN AQVFCHSSNN VTKTECCFTD
    FCNNITLHLP TASPNAPKLG PMELAIIITV
121 PVCLLSIAAM LTVWACQGRQ CSYRKKKRPN
    VEEPLSECNL VNAGKTLKDL IYDVTASGSG
181 SGLPLLVQRT IARTIVLQEI VGKGRFGEVW
    HGRWCGEDVA VKIFSSRDER SWFREAEIYQ
241 TVMLRHENIL GFIAADNKDN GTWTQLWLVS
    EYHEQGSLYD YLNRNIVTVA GMIKLALSIA
301 SGLAHLHMEI VGTQGKPAIA HRDIKSKNIL
    VKKCETCAIA DLGLAVKHDS ILNTIDIPQN
361 PKVGTKRYMA PEMLDDTMNV NIFESFKRAD
    IYSVGLVYWE IARRCSVGGI VEEYQLPYYD
421 MVPSDPSIEE MRKVVCDQKF RPSIPNQWQS
    CEALRVMGRI MRECWYANGA ARLTALRIKK
481 TISQLCVKED CKA
```

The signal peptide is indicated by a single underline and the extracellular domain is indicated in bold font.

A processed extracellular ALK7 isoform 1 polypeptide sequence is as follows:

```
                                       (SEQ ID NO: 123)
    ELSPGLKCVCLLCDSSNFTCQTEGACWASVMLTNGK

EQVIKSCVSLPELNAQVFCHSSNNVTKTECCFTDFC

NNITLHLPTASPNAPKLGPME
```

A nucleic acid sequence encoding human ALK7 isoform 1 precursor protein is shown below in SEQ ID NO: 233, corresponding to nucleotides 244-1722 of Genbank Reference Sequence NM_145259.2. A nucleic acid sequence encoding the processed extracellular ALK7 polypeptide (isoform 1) is show in in SEQ ID NO: 234.

An amino acid sequence of an alternative isoform of human ALK7, isoform 2 (NCBI Ref Seq NP_001104501.1), is shown in its processed form as follows (SEQ ID NO: 124), where the extracellular domain is indicated in bold font.

```
                                       (SEQ ID NO: 124)
  1  MLTNGKEQVI KSCVSLPELN AQVFCHSSNN VTKTECCFTD
     FCNNITLHLP TASPNAPKLG

61  PMELAIIITV PVCLLSIAAM LTVWACQGRQ CSYRKKKRPN
     VEEPLSECNL VNAGKTLKDL

121  IYDVTASGSG SGLPLLVQRT IARTIVLQEI VGKGRFGEVW
     HGRWCGEDVA VKIFSSRDER

181  SWFREAEIYQ TVMLRHENIL GFIAADNKDN GTWTQLWLVS
     EYHEQGSLYD YLNRNIVTVA

241  GMIKLALSIA SGLAHLHMEI VGTQGKPAIA HRDIKSKNIL
     VKKCETCAIA DLGLAVKHDS

301  ILNTIDIPQN PKVGTKRYMA PEMLDDTMNV NIFESFKRAD
     IYSVGLVYWE IARRCSVGGI

361  VEEYQLPYYD MVPSDPSIEE MRKVVCDQKF RPSIPNQWQS
     CEALRVMGRI MRECWYANGA

421  ARLTALRIKK TISQLCVKED CKA
```

An amino acid sequence of the extracellular ALK7 polypeptide (isoform 2) is as follows:

```
                                       (SEQ ID NO: 125)
MLTNGKEQVIKSCVSLPELNAQVFCHSSNNVTKTECCFTDFCNNITLHLP

TASPNAPKLGPME.
```

A nucleic acid sequence encoding the processed ALK7 polypeptide (isoform 2) is shown below in SEQ ID NO: 235, corresponding to nucleotides 279-1607 of NCBI Reference Sequence NM_001111031.1.

A nucleic acid sequence encoding an extracellular ALK7 polypeptide (isoform 2) is shown in SEQ ID NO: 236.

An amino acid sequence of an alternative human ALK7 precursor protein, isoform 3 (NCBI Ref Seq NP_001104502.1), is shown as follows (SEQ ID NO: 121), where the signal peptide is indicated by a single underline.

```
                                       (SEQ ID NO: 121)
  1  MTRALCSALR QALLLLAAAA ELSPGLKCVC LLCDSSNFTC
     QTEGACWASV MLTNGKEQVI

61  KSCVSLPELN AQVFCHSSNN VTKTECCFTD FCNNITLHLP
     TGLPLLVQRT IARTIVLQEI

121  VGKGRFGEVW HGRWCGEDVA VKIFSSRDER SWFREAEIYQ
     TVMLRHENIL GFIAADNKDN

181  GTWTQLWLVS EYHEQGSLYD YLNRNIVTVA GMIKLALSIA
     SGLAHLHMEI VGTQGKPAIA

241  HRDIKSKNIL VKKCETCAIA DLGLAVKHDS ILNTIDIPQN
     PKVGTKRYMA PEMLDDTMNV

301  NIFESFKRAD IYSVGLVYWE IARRCSVGGI VEEYQLPYYD
     MVPSDPSIEE MRKVVCDQKF

361  RPSIPNQWQS CEALRVMGRI MRECWYANGA ARLTALRIKK
     TISQLCVKED CKA
```

The amino acid sequence of a processed ALK7 polypeptide (isoform 3) is as follows (SEQ ID NO: 126). This isoform lacks a transmembrane domain and is therefore proposed to be soluble in its entirety (Roberts et al., 2003, Biol Reprod 68:1719-1726). N-terminal variants of SEQ ID NO: 126 are predicted as described below.

```
                                       (SEQ ID NO: 126)
  1  ELSPGLKCVC LLCDSSNFTC QTEGACWASV MLTNGKEQVI
     KSCVSLPELN AQVFCHSSNN

61  VTKTECCFTD FCNNITLHLP TGLPLLVQRT IARTIVLQEI
     VGKGRFGEVW HGRWCGEDVA

121  VKIFSSRDER SWFREAEIYQ TVMLRHENIL GFIAADNKDN
     GTWTQLWLVS EYHEQGSLYD

181  YLNRNIVTVA GMIKLALSIA SGLAHLHMEI VGTQGKPAIA
     HRDIKSKNIL VKKCETCAIA

241  DLGLAVKHDS ILNTIDIPQN PKVGTKRYMA PEMLDDTMNV
     NIFESFKRAD IYSVGLVYWE

301  IARRCSVGGI VEEYQLPYYD MVPSDPSIEE MRKVVCDQKF
     RPSIPNQWQS CEALRVMGRI

361  MRECWYANGA ARLTALRIKK TISQLCVKED CKA
```

A nucleic acid sequence encoding an unprocessed ALK7 polypeptide precursor protein (isoform 3) is shown in SEQ ID NO: 237, corresponding to nucleotides 244-1482 of NCBI Reference Sequence NM_001111032.1. A nucleic acid sequence encoding a processed ALK7 polypeptide (isoform 3) is shown in SEQ ID NO: 238.

An amino acid sequence of an alternative human ALK7 precursor protein, isoform 4 (NCBI Ref Seq NP_001104503.1), is shown as follows (SEQ ID NO: 122), where the signal peptide is indicated by a single underline.

```
                                       (SEQ ID NO: 122)
  1  MTRALCSALR QALLLLAAAA ELSPGLKCVC LLCDSSNFTC
     QTEGACWASV MLTNGKEQVI

61  KSCVSLPELN AQVFCHSSNN VTKTECCFTD FCNNITLHLP
     TDNGTWTQLW LVSEYHEQGS

121  LYDYLNRNIV TVAGMIKLAL SIASGLAHLH MEIVGTQGKP
     AIAHRDIKSK NILVKKCETC

181  AIADLGLAVK HDSILNTIDI PQNPKVGTKR YMAPEMLDDT
     MNVNIFESFK RADIYSVGLV

241  YWEIARRCSV GGIVEEYQLP YYDMVPSDPS IEEMRKVVCD
     QKFRPSIPNQ WQSCEALRVM

301  GRIMRECWYA NGAARLTALR IKKTISQLCV KEDCKA
```

An amino acid sequence of a processed ALK7 polypeptide (isoform 4) is as follows (SEQ ID NO: 127). Like ALK7 isoform 3, isoform 4 lacks a transmembrane domain and is therefore proposed to be soluble in its entirety (Roberts et al., 2003, Biol Reprod 68:1719-1726). N-terminal variants of SEQ ID NO: 127 are predicted as described below.

```
                                                  (SEQ ID NO: 127)
  1   ELSPGLKCVC LLCDSSNFTC QTEGACWASV MLTNGKEQVI
      KSCVSLPELN AQVFCHSSNN

61   VTKTECCFTD FCNNITLHLP TDNGTWTQLW LVSEYHEQGS
      LYDYLNRNIV TVAGMIKLAL

121   SIASGLAHLH MEIVGTQGKP AIAHRDIKSK NILVKKCETC
      AIADLGLAVK HDSILNTIDI

181   PQNPKVGTKR YMAPEMLDDT MNVNIFESFK RADIYSVGLV
      YWEIARRCSV GGIVEEYQLP

240   YYDMVPSDPS IEEMRKVVCD QKFRPSIPNQ WQSCEALRVM
      GRIMRECWYA NGAARLTALR

301   IKKTISQLCV KEDCKA
```

A nucleic acid sequence encoding the unprocessed ALK7 polypeptide precursor protein (isoform 4) is shown in SEQ ID NO: 239, corresponding to nucleotides 244-1244 of NCBI Reference Sequence NM_001111033.1. A nucleic acid sequence encoding the processed ALK7 polypeptide (isoform 4) is shown in SEQ ID NO: 240.

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is as follows (SEQ ID NO: 128).

```
                                                  (SEQ ID NO: 128)
  1   LKCVCLLCDS SNFTCQTEGA CWASVMLTNG KEQVIKSCVS
      LPELNAQVFC HSSNNVTKTE

61   CCFTDFCNNI TLHLPTASPN APKLGPME
```

Active variants of processed ALK7 isoform 1 are predicted in which SEQ ID NO: 123 is truncated by 1, 2, 3, 4, 5, 6, or 7 amino acids at the N-terminus and SEQ ID NO: 128 is truncated by 1 or 2 amino acids at the N-terminus. Consistent with SEQ ID NO: 128, it is further expected that leucine is the N-terminal amino acid in the processed forms of human ALK7 isoform 3 (SEQ ID NO: 126) and human ALK7 isoform 4 (SEQ ID NO: 127).

In certain embodiments, the disclosure relates to heteromultimers that comprise at least one ALK7 polypeptide, which includes fragments, functional variants, and modified forms thereof. Preferably, ALK7 polypeptides for use in accordance with inventions of the disclosure (e.g., heteromultimers comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ALK7 polypeptide that is at least 70%, 75%, 80%, 85%, 90%, 95%, 97%, 98%, 99%, or 100% identical to the amino acid sequence of SEQ ID NO: 120, 123, 129, 130, 124, 125, 121, 126, 122, 127, 128, 133, or 134. In some embodiments, heteromultimers of the disclosure consist or consist essentially of at least one ALK7 polypeptide that is at least 70%, 75%, 80%, 85%, 90%, 95%, 97%, 98%, 99%, or 100% identical to the amino acid sequence of SEQ ID NO: 120, 123, 129, 130, 124, 125, 121, 126, 122, 127, 128, 133, or 134.

In certain aspects, the disclosure relates to a heteromultimer that comprises an ALK7-Fc fusion protein. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-28 (e.g., amino acid residues 21, 22, 23, 24, 25, 26, 27, and 28) SEQ ID NO: 120, 121, or 122, and ends at any one of amino acids 92-113 (e.g., amino acid residues 92, 93, 94, 95, 96, 97, 98, 99, 100, 101, 102, 103, 104, 105, 106, 107, 108, 109, 110, 111, 112, and 113) of SEQ ID NO: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 28-92 of SEQ ID NOs: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-113 of SEQ ID NOs: 120, 121, or 122. In some embodiments, the ALK7-Fc fusion protein comprises an ALK7 domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 120, 123, 124, 125, 121, 126, 122, 127, 128, 129, 130, 131, 132, 133, 134, 135, and 136.

In some embodiments, the ALK7-Fc fusion protein employs the TPA leader and is as follows (SEQ ID NO: 129):

```
                                                  (SEQ ID NO: 129)
  1   MDAMKRGLCC VLLLCGAVFV SPGAGLKCVC LLCDSSNFTC
      QTEGACWASV

51   MLTNGKEQVI KSCVSLPELN AQVFCHSSNN VTKTECCFTD
      FCNNITLHLP

101   TASPNAPKLG PMETGGGTHT CPPCPAPELL GGPSVFLFPP
      KPKDTLMISR

151   TPEVTCVVVD VSHEDPEVKF NWYVDGVEVH NAKTKPREEQ
      YNSTYRVVSV

201   LTVLHQDWLN GKEYKCKVSN KALPAPIEKT ISKAKGQPRE
      PQVYTLPPSR

251   EEMTKNQVSL TCLVKGFYPS DIAVEWESNG QPENNYDTTP
      PVLDSDGSFF

301   LYSDLTVDKS RWQQGNVFSC SVMHEALHNH YTQKSLSLSP G
```

The signal sequence and linker sequence are underlined. To promote formation of the ActRIIB-Fc:ALK7-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 129 may optionally be provided with a lysine added at the C-terminus.

This ALK7-Fc fusion protein is encoded by the following nucleic acid (SEQ ID NO: 255):

```
                                            (SEQ ID NO: 255)
   1 ATGGATGCAA TGAAGAGAGG GCTCTGCTGT GTGCTGCTGC
     TGTGTGGAGC

51 AGTCTTCGTT TCGCCCGGCG CCGGACTGAA GTGTGTATGT
     CTTTTGTGTG

101 ATTCTTCAAA CTTTACCTGC CAAACAGAAG GAGCATGTTG
     GGCATCAGTC

151 ATGCTAACCA ATGGAAAAGA GCAGGTGATC AAATCCTGTG
     TCTCCCTTCC

201 AGAACTGAAT GCTCAAGTCT TCTGTCATAG TTCCAACAAT
     GTTACCAAAA

251 CCGAATGCTG CTTCACAGAT TTTTGCAACA ACATAACACT
     GCACCTTCCA

301 ACAGCATCAC CAAATGCCCC AAAACTTGGA CCCATGGAGA
     CCGGTGGTGG

351 AACTCACACA TGCCCACCGT GCCCAGCACC TGAACTCCTG
     GGGGGACCGT

401 CAGTCTTCCT CTTCCCCCCA AAACCCAAGG ACACCCTCAT
     GATCTCCCGG

451 ACCCCTGAGG TCACATGCGT GGTGGTGGAC GTGAGCCACG
     AAGACCCTGA

501 GGTCAAGTTC AACTGGTACG TGGACGGCGT GGAGGTGCAT
     AATGCCAAGA

551 CAAAGCCGCG GGAGGAGCAG TACAACAGCA CGTACCGTGT
     GGTCAGCGTC

601 CTCACCGTCC TGCACCAGGA CTGGCTGAAT GGCAAGGAGT
     ACAAGTGCAA

651 GGTCTCCAAC AAAGCCCTCC CAGCCCCCAT CGAGAAAACC
     ATCTCCAAAG

701 CCAAAGGGCA GCCCCGAGAA CCACAGGTGT ACACCCTGCC
     CCCATCCCGG

751 GAGGAGATGA CCAAGAACCA GGTCAGCCTG ACCTGCCTGG
     TCAAAGGCTT

801 CTATCCCAGC GACATCGCCG TGGAGTGGGA GAGCAATGGG
     CAGCCGGAGA

851 ACAACTACGA CACCACGCCT CCCGTGCTGG ACTCCGACGG
     CTCCTTCTTC

901 CTCTATAGCG ACCTCACCGT GGACAAGAGC AGGTGGCAGC
     AGGGGAACGT

951 CTTCTCATGC TCCGTGATGC ATGAGGCTCT GCACAACCAC
     TACACGCAGA

1001 AGAGCCTCTC CCTGTCTCCG GGT
```

The mature ALK7-Fc fusion protein sequence (SEQ ID NO: 130) is expected to be as follows and may optionally be provided with a lysine added at the C-terminus.

```
                                         (SEQ ID NO: 130)
  1 GLKCVCLLCD SSNFTCQTEG ACWASVMLTN GKEQVIKSCV
    SLPELNAQVF

51 CHSSNNVTKT ECCFTDFCNN ITLHLPTASP NAPKLGPMET
    GGGTHTCPPC

101 PAPELLGGPS VFLFPPKPKD TLMISRTPEV TCVVVDVSHE
    DPEVKFNWYV

151 DGVEVHNAKT KPREEQYNST YRVVSVLTVL HQDWLNGKEY
    KCKVSNKALP

201 APIEKTISKA KGQPREPQVY TLPPSREEMT KNQVSLTCLV
    KGFYPSDIAV

251 EWESNGQPEN NYDTTPPVLD SDGSFFLYSD LTVDKSRWQQ
    GNVFSCSVMH

301 EALHNHYTQK SLSLSPG
```

The complementary form of ALK7-Fc fusion polypeptide (SEQ ID NO: 133) is as follows:

```
                                         (SEQ ID NO: 133)
  1 MDAMKRGLCC VLLLCGAVFV SPGAGLKCVC LLCDSSNFTC
    QTEGACWASV

51 MLTNGKEQVI KSCVSLPELN AQVFCHSSNN VTKTECCFTD
    FCNNITLHLP

101 TASPNAPKLG PMETGGGTHT CPPCPAPELL GGPSVFLFPP
    KPKDTLMISR

151 TPEVTCVVVD VSHEDPEVKF NWYVDGVEVH NAKTKPREEQ
    YNSTYRVVSV

201 LTVLHQDWLN GKEYKCKVSN KALPAPIEKT ISKAKGQPRE
    PQVCTLPPSR

251 EEMTKNQVSL SCAVKGFYPS DIAVEWESNG QPENNYKTTP
    PVLDSDGSFF

301 LVSKLTVDKS RWQQGNVFSC SVMHEALHNH YTQKSLSLSP GK
```

The leader sequence and linker sequence are underlined. To guide heterodimer formation with certain Fc fusion polypeptides disclosed herein, four amino acid substitutions can be introduced into the Fc domain of the ALK7 fusion polypeptide as indicated by double underline above. Furthermore, the C-terminal lysine residue of the Fc domain can be deleted. The amino acid sequence of SEQ ID NO: 133 may optionally be provided with the lysine removed from the C-terminus.

The mature ALK7-Fc fusion protein sequence (SEQ ID NO: 134) is expected to be as follows and may optionally be provided with the lysine removed from the C-terminus.

```
                                         (SEQ ID NO: 134)
  1 GLKCVCLLCD SSNFTCQTEG ACWASVMLTN GKEQVIKSCV
    SLPELNAQVF

51 CHSSNNVTKT ECCFTDFCNN ITLHLPTASP NAPKLGPMET
    GGGTHTCPPC

101 PAPELLGGPS VFLFPPKPKD TLMISRTPEV TCVVVDVSHE
    DPEVKFNWYV

151 DGVEVHNAKT KPREEQYNST YRVVSVLTVL HQDWLNGKEY
    KCKVSNKALP

201 APIEKTISKA KGQPREPQVC TLPPSREEMT KNQVSLSCAV
    KGFYPSDIAV

251 EWESNGQPEN NYKTTPPVLD SDGSFFLVSK LTVDKSRWQQ
    GNVFSCSVMH

301 EALHNHYTQK SLSLSPGK
```

In certain embodiments, the present disclosure relates to a protein complex comprising an ActRIIA polypeptide. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety.

The human ActRIIA precursor protein sequence is as follows:

```
                                            (SEQ ID NO: 137)
  1 MGAAAKLAFA VFLISCSSGA ILGRSETQEC LFFNANWEKD
    RTNQTGVEPC

51 YGDKDKRRHC FATWKNISGS IEIVKQGCWL DDINCYDRTD
    CVEKKDSPEV

101 YFCCCEGNMC NEKFSYFPEM EVTQPTSNPV TPKPPYYNIL
    LYSLVPLMLI

151 AGIVICAFWV YRHHKMAYPP VLVPTQDPGP PPPSPLLGLK
    PLQLLEVKAR

201 GRFGCVWKAQ LLNEYVAVKI FPIQDKQSWQ NEYEVYSLPG
    MKHENILQFI

251 GAEKRGTSVD VDLWLITAFH EKGSLSDFLK ANVVSWNELC
    HIAETMARGL

301 AYLHEDIPGL KDGHKPAISH RDIKSKNVLL KNNLTACIAD
    FGLALKFEAG

351 KSAGDTHGQV GTRRYMAPEV LEGAINFQRD AFLRIDMYAM
    GLVLWELASR

401 CTAADGPVDE YMLPFEEEIG QHPSLEDMQE VVVHKKKRPV
    LRDYWQKHAG

451 MAMLCETIEE CWDHDAEARL SAGCVGERIT QMQRLTNIIT
    TEDIVIVVIM

501 VTNVDFPPKE SSL
```

The signal peptide is indicated by a single underline; the extracellular domain is indicated in bold font; and the potential, endogenous N-linked glycosylation sites are indicated by a double underline.

The processed extracellular human ActRIIA polypeptide sequence is as follows:

```
                                            (SEQ ID NO: 138)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP
```

The C-terminal "tail" of the extracellular domain is indicated by a single underline. The sequence with the "tail" deleted (a Δ15 sequence) is as follows:

```
                                            (SEQ ID NO: 139)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM
```

A nucleic acid sequence encoding the human ActRIIA precursor protein is shown in SEQ ID NO: 241, corresponding to nucleotides 159-1700 of Genbank Reference Sequence NM_001616.4. A nucleic acid sequence encoding a processed extracellular ActRIIA polypeptide is as shown in SEQ ID NO: 242.

A general formula for an active (e.g., ligand binding) ActRIIA polypeptide is one that comprises a polypeptide that starts at amino acid 30 and ends at amino acid 110 of SEQ ID NO: 137. Accordingly, ActRIIA polypeptides of the present disclosure may comprise a polypeptide that is at least 80%, 85%, 90%, 95%, 96%, 97%, 98%, 99%, or 100% identical to amino acids 30-110 of SEQ ID NO: 137. Optionally, ActRIIA polypeptides of the present disclosure comprise a polypeptide that is at least 80%, 85%, 90%, 95%, 96%, 97%, 98%, 99%, or 100% identical to amino acids amino acids 12-82 of SEQ ID NO: 137 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 137.

In certain embodiments, the disclosure relates to heteromultimers that comprise at least one ActRIIA polypeptide, which includes fragments, functional variants, and modified forms thereof. Preferably, ActRIIA polypeptides for use in accordance with inventions of the disclosure (e.g., heteromultimers comprising an ActRIIA polypeptide and uses thereof) are soluble (e.g., an extracellular domain of ActRIIA). In other preferred embodiments, ActRIIA polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 137, 138, 139, 140, 141, 144, or 145. In some embodiments, heteromultimers of the disclosure comprise at least one ActRIIA polypeptide that is at least 70%, 75%, 80%, 85%, 90%, 95%, 97%, 98%, 99%, or 100% identical to the amino acid sequence of any one of SEQ ID NOs: 137, 138, 139, 140, 141, 144, or 145.

In certain aspects, the disclosure relates to a heteromultimer that comprises an ActRIIA-Fc fusion protein. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21-30 (e.g., amino acid residues 21, 22, 23, 24, 25, 26, 27, 28, 29, or 30) SEQ ID NO: 137, and ends at any one of amino acids 110-135 (e.g., 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 21-135 of SEQ ID NO: 137. In some embodiments, the ActRIIA-Fc fusion protein comprises an ActRIIA domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 137, 138, 139, 140, 141, 142, 143, 144, 145, 146, and 147.

The ActRIIA-Fc polypeptide sequence (SEQ ID NO: 140) is shown below:

```
                                         (SEQ ID NO: 140)
  1  MDAMKRGLCC VLLLCGAVFV SPGAAILGRS ETQECLFFNA
     NWEKDRTNQT

51  GVEPCYGDKD KRRHCFATWK NISGSIEIVK QGCWLDDINC
     YDRTDCVEKK

101  DSPEVYFCCC EGNMCNEKFS YFPEMEVTQP TSNPVTPKPP
     TGGGTHTCPP

151  CPAPELLGGP SVFLFPPKPK DTLMISRTPE VTCVVVDVSH
     EDPEVKFNWY

201  VDGVEVHNAK TKPREEQYNS TYRVVSVLTV LHQDWLNGKE
     YKCKVSNKAL

251  PAPIEKTISK AKGQPREPQV YTLPPSRKEM TKNQVSLTCL
     VKGFYPSDIA

301  VEWESNGQPE NNYKTTPPVL KSDGSFFLYS KLTVDKSRWQ
     QGNVFSCSVM

351  HEALHNHYTQ KSLSLSPGK
```

The leader sequence and linker sequence are underlined. To promote formation of the ActRIIA-Fc:ActRIIB-Fc heterodimer rather than either of the possible homodimeric complexes, two amino acid substitutions (replacing acidic amino acids with lysine) can be introduced into the Fc domain of the ActRIIA fusion protein as indicated by double underline above. The amino acid sequence of SEQ ID NO: 140 may optionally be provided with the lysine removed from the C-terminus.

This ActRIIA-Fc fusion protein is encoded by the following nucleic acid sequence (SEQ ID NO: 256):

```
                                          (SEQ ID NO: 256)
   1  ATGGATGCAA TGAAGAGAGG GCTCTGCTGT GTGCTGCTGC
      TGTGTGGAGC

51  AGTCTTCGTT TCGCCCGGCG CCGCTATACT TGGTAGATCA
      GAAACTCAGG

101  AGTGTCTTTT CTTTAATGCT AATTGGGAAA AAGACAGAAC
      CAATCAAACT

151  GGTGTTGAAC CGTGTTATGG TGACAAAGAT AAACGGCGGC
      ATTGTTTTGC

201  TACCTGGAAG AATATTTCTG GTTCCATTGA AATAGTGAAA
      CAAGGTTGTT

251  GGCTGGATGA TATCAACTGC TATGACAGGA CTGATTGTGT
      AGAAAAAAAA
```

```
 301  GACAGCCCTG AAGTATATTT CTGTTGCTGT GAGGGCAATA
      TGTGTAATGA

351  AAAGTTTTCT TATTTTCCGG AGATGGAAGT CACACAGCCC
      ACTTCAAATC

401  CAGTTACACC TAAGCCACCC ACCGGTGGTG GAACTCACAC
      ATGCCCACCG

451  TGCCCAGCAC CTGAACTCCT GGGGGGACCG TCAGTCTTCC
      TCTTCCCCCC

501  AAAACCCAAG GACACCCTCA TGATCTCCCG GACCCCTGAG
      GTCACATGCG

551  TGGTGGTGGA CGTGAGCCAC GAAGACCCTG AGGTCAAGTT
      CAACTGGTAC

601  GTGGACGGCG TGGAGGTGCA TAATGCCAAG ACAAAGCCGC
      GGGAGGAGCA

651  GTACAACAGC ACGTACCGTG TGGTCAGCGT CCTCACCGTC
      CTGCACCAGG

701  ACTGGCTGAA TGGCAAGGAG TACAAGTGCA AGGTCTCCAA
      CAAAGCCCTC

751  CCAGCCCCCA TCGAGAAAAC CATCTCCAAA GCCAAAGGGC
      AGCCCCGAGA

801  ACCACAGGTG TACACCCTGC CCCCATCCCG GAAGGAGATG
      ACCAAGAACC

851  AGGTCAGCCT GACCTGCCTG GTCAAAGGCT TCTATCCCAG
      CGACATCGCC

901  GTGGAGTGGG AGAGCAATGG GCAGCCGGAG AACAACTACA
      AGACCACGCC

951  TCCCGTGCTG AAGTCCGACG GCTCCTTCTT CCTCTATAGC
      AAGCTCACCG

1001  TGGACAAGAG CAGGTGGCA CAGGGGAACG TCTTCTCATG
      CTCCGTGATG

1051  CATGAGGCTC TGCACAACCA CTACACGCAG AAGAGCCTCT
      CCCTGTCTCC

1101  GGGTAAA
```

The mature ActRIIA-Fc fusion polypeptide (SEQ ID NO: 141) is as follows and may optionally be provided with the lysine removed from the C-terminus.

```
                                        (SEQ ID NO: 141)
  1  ILGRSETQEC LFFNANWEKD RTNQTGVEPC YGDKDKRRHC
     FATWKNISGS

51  IEIVKQGCWL DDINCYDRTD CVEKKDSPEV YFCCCEGNMC
     NEKFSYFPEM

101  EVTQPTSNPV TPKPPTGGGT HTCPPCPAPE LLGGPSVFLF
     PPKPKDTLMI

151  SRTPEVTCVV VDVSHEDPEV KFNWYVDGVE VHNAKTKPRE
     EQYNSTYRVV

201  SVLTVLHQDW LNGKEYKCKV SNKALPAPIE KTISKAKGQP
     REPQVYTLPP

251  SRKEMTKNQV SLTCLVKGFY PSDIAVEWES NGQPENNYKT
     TPPVLKSDGS

301  FFLYSKLTVD KSRWQQGNVF SCSVMHEALH NHYTQKSLSL
     SPGK
```

The ActRIIA-Fc polypeptide sequence (SEQ ID NO: 144) is shown below:

```
                                        (SEQ ID NO: 144)
  1  MDAMKRGLCC VLLLCGAVFV SPGAAILGRS ETQECLFFNA
     NWEKDRTNQT

51  GVEPCYGDKD KRRHCFATWK NISGSIEIVK QGCWLDDINC
     YDRTDCVEKK

101  DSPEVYFCCC EGNMCNEKFS YFPEMEVTQP TSNPVTPKPP
     TGGGTHTCPP

151  CPAPELLGGP SVFLFPPKPK DTLMISRTPE VTCVVVDVSH
     EDPEVKFNWY

201  VDGVEVHNAK TKPREEQYNS TYRVVSVLTV LHQDWLNGKE
     YKCKVSNKAL

251  PAPIEKTISK AKGQPREPQV YTLPPCREEM TKNQVSLWCL
     VKGFYPSDIA

301  VEWESNGQPE NNYKTTPPVL DSDGSFFLYS KLTVDKSRWQ
     QGNVFSCSVM

351  HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 144 may optionally be provided with the lysine removed from the C-terminus.

The mature ActRIIA-Fc fusion polypeptide (SEQ ID NO: 145) is as follows and may optionally be provided with the lysine removed from the C-terminus.

```
                                        (SEQ ID NO: 145)
  1  ILGRSETQEC LFFNANWEKD RTNQTGVEPC YGDKDKRRHC
     FATWKNISGS

51  IEIVKQGCWL DDINCYDRTD CVEKKDSPEV YFCCCEGNMC
     NEKFSYFPEM

101  EVTQPTSNPV TPKPPTGGGT HTCPPCPAPE LLGGPSVFLF
     PPKPKDTLMI

151  SRTPEVTCVV VDVSHEDPEV KFNWYVDGVE VHNAKTKPRE
     EQYNSTYRVV

201  SVLTVLHQDW LNGKEYKCKV SNKALPAPIE KTISKAKGQP
     REPQVYTLPP

251  CREEMTKNQV SLWCLVKGFY PSDIAVEWES NGQPENNYKT
     TPPVLDSDGS

301  FFLYSKLTVD KSRWQQGNVF SCSVMHEALH NHYTQKSLSL
     SPGK
```

In certain aspects, the present disclosure relates to protein complexes that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, composed of a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity.

A human BMPRII precursor protein sequence (NCBI Ref Seq NP_001195.2) is as follows:

```
                                        (SEQ ID NO: 148)
   1  MTSSLQRPWR VPWLPWTILL VSTAAASQNQ ERLCAFKDPY
      QQDLGIGESR

51  ISHENGTILC SKGSTCYGLW EKSKGDINLV KQGCWSHIGD
      PQECHYEECV

101  VTTTPPSIQN GTYRFCCCST DLCNVNFTEN FPPPDTTPLS
      PPHSFNRDET

151  IIIALASVSV LAVLIVALCF GYRMLTGDRK QGLHSMNMME
      AAASEPSLDL

201  DNLKLLELIG RGRYGAVYKG SLDERPVAVK VFSFANRQNF
      INEKNIYRVP

251  LMEHDNIARF IVGDERVTAD GRMEYLLVME YYPNGSLCKY
      LSLHTSDWVS

301  SCRLAHSVTR GLAYLHTELP RGDHYKPAIS HRDLNSRNVL
      VKNDGTCVIS

351  DFGLSMRLTG NRLVRPGEED NAAISEVGTI RYMAPEVLEG
      AVNLRDCESA

401  LKQVDMYALG LIYWEIFMRC TDLFPGESVP EYQMAFQTEV
      GNHPTFEDMQ

451  VLVSREKQRP KFPEAWKENS LAVRSLKETI EDCWDQDAEA
      RLTAQCAEER

501  MAELMMIWER NKSVSPTVNP MSTAMQNERN LSHNRRVPKI
      GPYPDYSSSS

551  YIEDSIHHTD SIVKNISSEH SMSSTPLTIG EKNRNSINYE
      RQQAQARIPS

601  PETSVTSLST NTTTTNTTGL TPSTGMTTIS EMPYPDETNL
      HTTNVAQSIG

651  PTPVCLQLTE EDLETNKLDP KEVDKNLKES SDENLMEHSL
      KQFSGPDPLS

701  STSSSLLYPL IKLAVEATGQ QDFTQTANGQ ACLIPDVLPT
      QIYPLPKQQN

751  LPKRPTSLPL NTKNSTKEPR LKFGSKHKSN LKQVETGVAK
      MNTINAAEPH

801  VVTVTMNGVA GRNHSVNSHA ATTQYANGTV LSGQTTNIVT
      HRAQEMLQNQ

851  FIGEDTRLNI NSSPDEHEPL LRREQQAGHD EGVLDRLVDR
      RERPLEGGRT

901  NSNNNNSNPC SEQDVLAQGV PSTAADPGPS KPRRAQRPNS
      LDLSATNVLD

951  GSSIQIGEST QDGKSGSGEK IKKRVKTPYS LKRWRPSTWV
      ISTESLDCEV

1001  NNNGSNRAVH SKSSTAVYLA EGGTATTMVS KDIGMNCL
```

The signal peptide is indicated by a single underline and an extracellular domain is indicated in bold font.

A processed extracellular BMPRII polypeptide sequence is as follows:

(SEQ ID NO: 150)
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET

A nucleic acid sequence encoding BMPRII precursor protein is shown in SEQ ID NO: 205, as follows nucleotides 1149-4262 of Genbank Reference Sequence NM_001204.6. A nucleic acid sequence encoding an extracellular BMPRII polypeptide is shown in SEQ ID NO: 206.

An alternative isoform of BMPRII, isoform 2 (GenBank: AAA86519.1) is as follows:

```
                                              (SEQ ID NO: 149)
  1  MTSSLQRPWR VPWLPWTILL VSTAAASQNQ ERLCAFKDPY
     QQDLGIGESR

51  ISHENGTILC SKGSTCYGLW EKSKGDINLV KQGCWSHIGD
     PQECHYEECV

101  VTTTPPSIQN GTYRFCCCST DLCNVNFTEN FPPPDTTPLS
     PPHSFNRDET

151  IIIALASVSV LAVLIVALCF GYRMLTGDRK QGLHSMNMME
     AAASEPSLDL

201  DNLKLLELIG RGRYGAVYKG SLDERPVAVK VFSFANRQNF
     INEKNIYRVP

251  LMEHDNIARF IVGDERVTAD GRMEYLLVME YYPNGSLCKY
     LSLHTSDWVS

301  SCRLAHSVTR GLAYLHTELP RGDHYKPAIS HRDLNSRNVL
     VKNDGTCVIS

351  DFGLSMRLTG NRLVRPGEED NAAISEVGTI RYMAPEVLEG
     AVNLRDCESA

401  LKQVDMYALG LIYWEIFMRC TDLFPGESVP EYQMAFQTEV
     GNHPTFEDMQ

451  VLVSREKQRP KFPEAWKENS LAVRSLKETI EDCWDQDAEA
     RLTAQCAEER

501  MAELMMIWER NKSVSPTVNP MSTAMQNERR
```

The signal peptide is indicated by a single underline and the extracellular domain is indicated in bold font.

A processed extracellular BMPRII polypeptide sequence (isoform 2) is as follows:

(SEQ ID NO: 151)
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET

A nucleic acid sequence encoding human BMPRII precursor protein (isoform 2) is shown in SEQ ID NO: 207, corresponding to nucleotides 163-1752 of Genbank Reference Sequence U25110.1. The signal sequence is underlined. A nucleic acid sequence encoding an extracellular BMPRII polypeptide (isoform 2) is shown in SEQ ID NO: 208.

In certain embodiments, the disclosure relates to heteromultimers that comprise at least one BMPRII polypeptide, which includes fragments, functional variants, and modified forms thereof. Preferably, BMPRII polypeptides for use in accordance with inventions of the disclosure (e.g., heteromultimers comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one BMPRII polypeptide that is at least 70%, 75%, 80%, 85%, 90%, 95%, 97%, 98%, 99%, or 100% identical to the amino acid sequence of SEQ ID NO: 148, 150, 149, 151, 152, 153, 156, or 157. In some embodiments, heteromultimer complexes of the disclosure consist or consist essentially of at least one BMPRII polypeptide that is at least 70%, 75%, 80%, 85%, 90%, 95%, 97%, 98%, 99%, or 100% identical to the amino acid sequence of SEQ ID NO: 148, 150, 149, 151, 152, 153, 156, or 157.

In certain aspects, the disclosure relates to a heteromultimer that comprises an BMPRII-Fc fusion protein. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 27-34 (e.g., amino acid residues 27, 28, 29, 30, 31, 32, 33, and 34) SEQ ID NO: 148 or 149, and ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, and 150) of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 34-123 of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 27-150 of SEQ ID NO: 148 or 149. In some embodiments, the BMPRII-Fc fusion protein comprises an BMPRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 148, 150, 149, 151, 152, 153, 154, 155, 156, 157, 158, and 159.

The BMPRII-Fc polypeptide sequence (SEQ ID NO: 152) is shown below:

```
                                              (SEQ ID NO: 152)
  1  MDAMKRGLCC VLLLCGAVFV SPGASQNQER LCAFKDPYQQ
     DLGIGESRIS

51  HENGTILCSK GSTCYGLWEK SKGDINLVKQ GCWSHIGDPQ
     ECHYEECVVT

101  TTPPSIQNGT YRFCCCSTDL CNVNFTENFP PPDTTPLSPP
     HSFNRDETGG

151  GTHTCPPCPA PELLGGPSVF LFPPKPKDTL MISRTPEVTC
     VVVDVSHEDP

201  EVKFNWYVDG VEVHNAKTKP REEQYNSTYR VVSVLTVLHQ
     DWLNGKEYKC
```

-continued

```
251  KVSNKALPAP IEKTISKAKG QPREPQVYTL PPSRKEMTKN
     QVSLTCLVKG

301  FYPSDIAVEW ESNGQPENNY KTTPPVLKSD GSFFLYSKLT
     VDKSRWQQGN

351  VFSCSVMHEA LHNHYTQKSL SLSPGK
```

The leader sequence and linker sequence are underlined. To promote formation of the BMPRII-Fc:ActRIIB-Fc heterodimer rather than either of the possible homodimeric complexes, two amino acid substitutions (replacing acidic amino acids with lysine) can be introduced into the Fc domain of the BMPRII-Fc fusion protein as indicated by double underline above. The amino acid sequence of SEQ ID NO: 152 may optionally be provided with the lysine removed from the C-terminus.

This BMPRII-Fc fusion protein is encoded by the following nucleic acid sequence (SEQ ID NO: 257):

```
                                        (SEQ ID NO: 257)
  1  ATGGATGCAA TGAAGAGAGG GCTCTGCTGT GTGCTGCTGC
     TGTGTGGAGC

51  AGTCTTCGTT TCGCCCGGCG CCTCGCAGAA TCAAGAACGC
     CTATGTGCGT

101  TTAAAGATCC GTATCAGCAA GACCTTGGGA TAGGTGAGAG
     TAGAATCTCT

151  CATGAAAATG GGACAATATT ATGCTCGAAA GGTAGCACCT
     GCTATGGCCT

201  TTGGGAGAAA TCAAAGGGG ACATAAATCT TGTAAAACAA
     GGATGTTGGT

251  CTCACATTGG AGATCCCCAA GAGTGTCACT ATGAAGAATG
     TGTAGTAACT

301  ACCACTCCTC CCTCAATTCA GAATGGAACA TACCGTTTCT
     GCTGTTGTAG

351  CACAGATTTA TGTAATGTCA ACTTTACTGA GAATTTTCCA
     CCTCCTGACA

401  CAACACCACT CAGTCCACCT CATTCATTTA ACCGAGATGA
     GACCGGTGGT

451  GGAACTCACA CATGCCCACC GTGCCCAGCA CCTGAACTCC
     TGGGGGGACC

501  GTCAGTCTTC CTCTTCCCCC CAAAACCCAA GGACACCCTC
     ATGATCTCCC

551  GGACCCCTGA GGTCACATGC GTGGTGGTGG ACGTGAGCCA
     CGAAGACCCT

601  GAGGTCAAGT TCAACTGGTA CGTGGACGGC GTGGAGGTGC
     ATAATGCCAA

651  GACAAAGCCG CGGGAGGAGC AGTACAACAG CACGTACCGT
     GTGGTCAGCG

701  TCCTCACCGT CCTGCACCAG GACTGGCTGA ATGGCAAGGA
     GTACAAGTGC

751  AAGGTCTCCA ACAAAGCCCT CCCAGCCCCC ATCGAGAAAA
     CCATCTCCAA

801  AGCCAAAGGG CAGCCCCGAG AACCACAGGT GTACACCCTG
     CCCCCATCCC

851  GGAAGGAGAT GACCAAGAAC CAGGTCAGCC TGACCTGCCT
     GGTCAAAGGC

901  TTCTATCCCA GCGACATCGC CGTGGAGTGG GAGAGCAATG
     GGCAGCCGGA

951  GAACAACTAC AAGACCACGC CTCCCGTGCT GAAGTCCGAC
     GGCTCCTTCT

1001 TCCTCTATAG CAAGCTCACC GTGGACAAGA GCAGGTGGCA
     GCAGGGGAAC

1051 GTCTTCTCAT GCTCCGTGAT GCATGAGGCT CTGCACAACC
     ACTACACGCA

1101 GAAGAGCCTC TCCCTGTCTC CGGGTAAA
```

The mature BMPRII-Fc fusion polypeptide (SEQ ID NO: 153) is as follows and may optionally be provided with the lysine removed from the C-terminus.

```
                                        (SEQ ID NO: 153)
  1  SQNQERLCAF KDPYQQDLGI GESRISHENG TILCSKGSTC
     YGLWEKSKGD

51  INLVKQGCWS HIGDPQECHY EECVVTTTPP SIQNGTYRFC
     CCSTDLCNVN

101  FTENFPPPDT TPLSPPHSFN RDETGGGTHT CPPCPAPELL
     GGPSVFLFPP

151  KPKDTLMISR TPEVTCVVVD VSHEDPEVKF NWYVDGVEVH
     NAKTKPREEQ

201  YNSTYRVVSV LTVLHQDWLN GKEYKCKVSN KALPAPIEKT
     ISKAKGQPRE

251  PQVYTLPPSR KEMTKNQVSL TCLVKGFYPS DIAVEWESNG
     QPENNYKTTP

301  PVLKSDGSFF LYSKLTVDKS RWQQGNVFSC SVMHEALHNH
     YTQKSLSLSP

351  GK
```

The BMPRII-Fc polypeptide sequence (SEQ ID NO: 156) is shown below:

```
                                        (SEQ ID NO: 156)
  1  MDAMKRGLCC VLLLCGAVFV SPGASQNQER LCAFKDPYQQ
     DLGIGESRIS

51  HENGTILCSK GSTCYGLWEK SKGDINLVKQ GCWSHIGDPQ
     ECHYEECVVT

101  TTPPSIQNGT YRFCCCSTDL CNVNFTENFP PPDTTPLSPP
     HSFNRDETGG

151  GTHTCPPCPA PELLGGPSVF LFPPKPKDTL MISRTPEVTC
     VVVDVSHEDP

201  EVKFNWYVDG VEVHNAKTKP REEQYNSTYR VVSVLTVLHQ
     DWLNGKEYKC

251  KVSNKALPAP IEKTISKAKG QPREPQVYTL PPCREEMTKN
     QVSLWCLVKG

301  FYPSDIAVEW ESNGQPENNY KTTPPVLDSD GSFFLYSKLT
     VDKSRWQQGN

351  VFSCSVMHEA LHNHYTQKSL SLSPGK
```

The leader sequence and linker sequence are underlined. To promote formation of the BMPRII-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 156 may optionally be provided with the lysine removed from the C-terminus.

The mature BMPRII-Fc fusion polypeptide (SEQ ID NO: 157) is as follows and may optionally be provided with the lysine (K) removed from the C-terminus.

```
                                              (SEQ ID NO: 157)
  1  SQNQERLCAF KDPYQQDLGI GESRISHENG TILCSKGSTC
     YGLWEKSKGD

51  INLVKQGCWS HIGDPQECHY EECVVTTTPP SIQNGTYRFC
     CCSTDLCNVN

101  FTENFPPPDT TPLSPPHSFN RDETGGGTHT CPPCPAPELL
     GGPSVFLFPP

151  KPKDTLMISR TPEVTCVVVD VSHEDPEVKF NWYVDGVEVH
     NAKTKPREEQ

201  YNSTYRVVSV LTVLHQDWLN GKEYKCKVSN KALPAPIEKT
     ISKAKGQPRE

251  PQVYTLPPCR EEMTKNQVSL WCLVKGFYPS DIAVEWESNG
     QPENNYKTTP

301  PVLDSDGSFF LYSKLTVDKS RWQQGNVFSC SVMHEALHNH
     YTQKSLSLSP

351  GK
```

In certain aspects, the present disclosure relates to protein complexes that comprise a TGFBRII polypeptide. As used herein, the term "TGFBRII" refers to a family of transforming growth factor-beta receptor II (TGFBRII) proteins from any species and variants derived from such proteins by mutagenesis or other modification. Reference to TGFBRII herein is understood to be a reference to any one of the currently identified forms. Members of the TGFBRII family are generally transmembrane proteins, composed of a ligand-binding extracellular domain with a cysteine-rich region, a transmembrane domain, and a cytoplasmic domain with predicted serine/threonine kinase activity.

The term "TGFBRII polypeptide" includes polypeptides comprising any naturally occurring polypeptide of a TGFBRII family member as well as any variants thereof (including mutants, fragments, fusions, and peptidomimetic forms) that retain a useful activity.

A human TGFBRII precursor protein sequence (NCBI Ref Seq NP_003233.4) is as follows:

```
                                              (SEQ ID NO: 194)
  1  MGRGLLRGLW PLHIVLWTRI ASTIPPHVQK SVNNDMIVTD
     NNGAVKFPQL

51  CKFCDVRFST CDNQKSCMSN CSITSICEKP QEVCVAVWRK
     NDENITLETV

101  CHDPKLPYHD FILEDAASPK CIMKEKKKPG ETFFMCSCSS
     DECNDNIIFS

151  EEYNTSNPDL LLVIFQVTGI SLLPPLGVAI SVIIIFYCYR
     VNRQQKLSST

201  WEIGKIRKLM EFSEHCAIIL EDDRSDISST CANNINHNTE
     LLPIELDTLV

251  GKGRFAEVYK AKLKQNTSEQ FETVAVKIFP YEEYASWKTE
     KDIFSDINLK

301  HENILQFLTA EERKTELGKQ YWLITAFHAK GNLQEYLTRH
     VISWEDLRKL

351  GSSLARGIAH LHSDHTPCGR PKMPIVHRDL KSSNILVKND
     LTCCLCDFGL

401  SLRLDPTLSV DDLANSGQVG TARYMAPEVL ESRMNLENVE
     SFKQTDVYSM

451  ALVLWEMTSR CNAVGEVKDY EPPFGSKVRE HPCVESMKDN
     VLRDRGRPEI

501  PSFWLNHQGI QMVCETLTEC WDHDPEARLT AQCVAERFSE
     LEHLDRLSGR

551  SCSEEKIPED GSLNTTK
```

The signal peptide is indicated by a single underline and the extracellular domain is indicated in bold font.

A processed extracellular TGFBRII polypeptide sequence is as follows:

```
                                              (SEQ ID NO: 195)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ
```

A nucleic acid sequence encoding TGFBRII precursor protein is shown in SEQ ID NO:196, corresponding to nucleotides 383-2083 of Genbank Reference Sequence NM_003242.5. A nucleic acid sequence encoding a processed extracellular TGFBRII polypeptide is shown in SEQ ID NO: 197.

An alternative isoform of TGFBRII, isoform A (NP_001020018.1), is as follows:

```
                                              (SEQ ID NO: 198)
  1  MGRGLLRGLW PLHIVLWTRI ASTIPPHVQK SDVEMEAQKD EIICPSCNRT

51  AHPLRHINND MIVTDNNGAV KFPQLCKFCD VRFSTCDNQK SCMSNCSITS

101  ICEKPQEVCV AVWRKNDENI TLETVCHDPK LPYHDFILED AASPKCIMKE

151  KKKPGETFFM CSCSSDECND NIIFSEEYNT SNPDLLLVIF QVTGISLLPP

201  LGVAISVIII FYCYRVNRQQ KLSSTWETGK TRKLMEFSEH CAIILEDDRS

251  DISSTCANNI NHNTELLPIE LDTLVGKGRF AEVYKAKLKQ NTSEQFETVA

301  VKIFPYEEYA SWTEKDIFS DINLKHENIL QFLTAEERKT ELGKQYWLIT

351  AFHAKGNLQE YLTRHVISWE DLRKLGSSLA RGIAHLHSDH TPCGRPKMPI
```

```
401 VHRDLKSSNI LVKNDLTCCL CDFGLSLRLD PTLSVDDLAN SGQVGTARYM

451 APEVLESRMN LENVESFKQT DVYSMALVLW EMTSRCNAVG EVKDYEPPFG

501 SKVREHPCVE SMKDNVLRDR GRPEIPSFWL NHQGIQMVCE TLTECWDHDP

551 EARLTAQCVA ERFSELEHLD RLSGRSCSEE KIPEDGSLNT TK
```

The signal peptide is indicated by a single underline and the extracellular domain is indicated in bold font.

A processed extracellular TGFBRII polypeptide sequence (isoform A) is as follows:

```
                                              (SEQ ID NO: 199)
TIPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENITL

ETVCHDPKLPYHDFILEDAASPKCIMKEKKKPGETFFMCSCSSDECNDNI

IFSEEYNTSNPDLLLVIFQ
```

A nucleic acid sequence encoding the TGFBRII precursor protein (isoform A) is shown in SEQ ID NO: 202, corresponding to nucleotides 383-2158 of Genbank Reference Sequence NM_001024847.2. A nucleic acid sequence encoding the processed extracellular TGFBRII polypeptide (isoform A) is shown in SEQ ID NO: 203.

Either of the foregoing TGFβRII isoforms (SEQ ID NOs: 194, 195, 198, and 199) could incorporate an insertion of 36 amino acids (SEQ ID NO: 204) between the pair of glutamate residues (positions 151 and 152 of SEQ ID NO: 194; positions 129 and 130 of SEQ ID NO: 195; positions 176 and 177 of SEQ ID NO: 198; or positions 154 and 155 of SEQ ID NO: 199) located near the C-terminus of the TGFβRII ECD, as occurs naturally in the TGFβRII isoform C (Konrad et al., BMC Genomics 8:318, 2007).

```
                                              (SEQ ID NO: 204)
GRCKIRHIGS NNRLQRSTCQ NTGWESAHVM KTPGFR
```

In certain embodiments, the disclosure relates to heteromultimers that comprise at least one TGFBRII polypeptide, which includes fragments, functional variants, and modified forms thereof. Preferably, TGFBRII polypeptides for use in accordance with inventions of the disclosure (e.g., heteromultimers comprising a TGFBRII polypeptide and uses thereof) are soluble (e.g., an extracellular domain of TGFBRII). In other preferred embodiments, TGFBRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one TGFBRII polypeptide that is at least 70%, 75%, 80%, 85%, 90%, 95%, 97%, 98%, 99%, or 100% identical to the amino acid sequence of SEQ ID NOs: 194, 195, 198, or 199, with or without insertion of SEQ ID NO: 204 as described above. In some embodiments, heteromultimer complexes of the disclosure consist or consist essentially of at least one TGFBRII polypeptide that is at least 70%, 75%, 80%, 85%, 90%, 95%, 97%, 98%, 99%, or 100% identical to the amino acid sequence of SEQ ID NOs: 194, 195, 198, or 199, with or without insertion of SEQ ID NO: 204.

In certain aspects, the disclosure relates to a heteromultimer that comprises an TGFBII-Fc fusion protein. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-44 (e.g., 23, 24, 25, 26, 27, 28, 29, 30, 31, 32, 33, 34, 35, 36, 37, 38, 39, 40, 41, 42, 43 or 44) of SEQ ID NO: 160, and ends at any one of amino acids 168-191 (e.g., 168, 169, 170, 171, 172, 173, 174, 175, 176, 177, 178, 179, 180, 181, 182, 183, 184, 185, 186, 187, 188, 189, 190 or 191) of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 44-168 of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-191 of SEQ ID NO: 160. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 161, 162, 160, 163, 164, 165, 166, 167, 168, 169, 170, 171, 172, 173, 174, 175, 176, 177, 178, and 179. In some embodiments, the TGFBII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 23-51 (e.g., 23, 24, 25, 26, 27, 28, 29, 30, 31, 32, 33, 34, 35, 36, 37, 38, 39, 40, 41, 42, 43, 44, 45, 46, 47, 48, 49, 50, and 51) of SEQ ID NO: 161, and ends at any one of amino acids 143-166 (e.g., 143, 144, 145, 146, 147, 148, 149, 150, 151, 152, 153, 154, 155, 156, 157, 158, 159, 160, 161, 162, 163, 164, 165, and 166) of SEQ ID NO: 161. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 51-143 of SEQ ID NO: 161. In some embodiments, the TGFBRII-Fc fusion protein comprises an TGFBRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 23-166 of SEQ ID NO: 161.

A human TGFBRII precursor protein sequence (NCBI Ref Seq NP_003233.4) is as follows:

(SEQ ID NO: 161)

```
  1 MGRGLLRGLW PLHIVLWTRI ASTIPPHVQK SVNNDMIVTD NNGAVKFPQL

51 CKFCDVRFST CDNQKSCMSN CSITSICEKP QEVCVAVWRK NDENITLETV

101 CHDPKLPYHD FILEDAASPK CIMKEKKKPG ETFFMCSCSS DECNDNIIFS

151 EEYNTSNPDL LLVIFQVTGI SLLPPLGVAI SVIIIFYCYR VNRQQKLSST

201 WETGKTRKLM EFSEHCAIIL EDDRSDISST CANNINHNTE LLPIELDTLV

251 GKGRFAEVYK AKLKQNTSEQ FETVAVKIFP YEEYASWKTE KDIFSDINLK

301 HENILQFLTA EERKTELGKQ YWLITAFHAK GNLQEYLTRH VISWEDLRKL

351 GSSLARGIAH LHSDHTPCGR PKMPIVHRDL KSSNILVKND LTCCLCDFGL

401 SLRLDPTLSV DDLANSGQVG TARYMAPEVL ESRMNLENVE SFKQTDVYSM

451 ALVLWEMTSR CNAVGEVKDY EPPFGSKVRE HPCVESMKDN VLRDRGRPEI

501 PSFWLNHQGI QMVCETLTEC WDHDPEARLT AQCVAERFSE LEHLDRLSGR

551 SCSEEKIPED GSLNTTK
```

The signal peptide is indicated by a single underline and the extracellular domain is indicated in bold font.

A processed extracellular TGFBRII polypeptide sequence is as follows:

(SEQ ID NO: 162)

TIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDLLLVIFQ

An alternative isoform of TGFBRII, isoform A (NP_001020018.1), is as follows:

(SEQ ID NO: 160)

```
  1 MGRGLLRGLW PLHIVLWTRI ASTIPPHVQK SDVEMEAQKD EIICPSCNRT

51 AHPLRHINND MIVTDNNGAV KFPQLCKFCD VRFSTCDNQK SCMSNCSITS

101 ICEKPQEVCV AVWRKNDENI TLETVCHDPK LPYHDFILED AASPKCIMKE

151 KKKPGETFFM CSCSSDECND NIIFSEEYNT SNPDLLLVIF QVTGISLLPP

201 LGVAISVIII FYCYRVNRQQ KLSSTWETGK TRKLMEFSEH CAIILEDDRS

251 DISSTCANNI NHNTELLPIE LDTLVGKGRF AEVYKAKLKQ NTSEQFETVA

301 VKIFPYEEYA SWKTEKDIFS DINLKHENIL QFLTAEERKT ELGKQYWLIT

351 AFHAKGNLQE YLTRHVISWE DLRKLGSSLA RGIAHLHSDH TPCGRPKMPI

401 VHRDLKSSNI LVKNDLTCCL CDFGLSLRLD PTLSVDDLAN SGQVGTARYM

451 APEVLESRMN LENVESFKQT DVYSMALVLW EMTSRCNAVG EVKDYEPPFG

501 SKVREHPCVE SMKDNVLRDR GRPEIPSFWL NHQGIQMVCE TLTECWDHDP

551 EARLTAQCVA ERFSELEHLD RLSGRSCSEE KIPEDGSLNT TK
```

The signal peptide is indicated by a single underline and the extracellular domain is indicated in bold font.

A processed extracellular TGFBRII polypeptide sequence (isoform A) is as follows:

(SEQ ID NO: 163)
TIPPHVQKSDVEMEAQKDEIICPSCNRTAHPLRHINNDMIVTDNNGAVKFP

QLCKFCDVRFSTCDNQKSCMSNCSITSICEKPQEVCVAVWRKNDENITLET

VCHDPKLPYHDFILEDAASPKCIMKEKKKPGETFFMCSCSSDECNDNIIFS

EEYNTSNPDLLLVIFQ

The TGFβRII$_{SHORT}$-Fc polypeptide sequence (SEQ ID NO: 164) is shown below:

```
                                                    (SEQ ID NO: 164)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPSRKE

301 MTKNQVSLTC LVKGFYPSDI AVEWESNGQP ENNYKTTPPV LKSDGSFFLY

351 SKLTVDKSRW QQGNVFSCSV MHEALHNHYT QKSLSLSPGK
```

The leader sequence and linker sequence are underlined. To promote formation of the TGFβRII$_{SHORT}$-Fc:ActRIIB-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated by double underline above. The amino acid sequence of SEQ ID NO: 164 may optionally be provided with the lysine removed from the C-terminus.

This TGFβRII$_{SHORT}$-Fc fusion protein is encoded by the following nucleic acid sequence (SEQ ID NO: 259):

```
                                                    (SEQ ID NO: 259)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAACTCA

501 CACATGCCCA CCGTGCCCAG CACCTGAACT CCTGGGGGGA CCGTCAGTCT

551 TCCTCTTCCC CCCAAAACCC AAGGACACCC TCATGATCTC CCGGACCCCT

601 GAGGTCACAT GCGTGGTGGT GGACGTGAGC CACGAAGACC CTGAGGTCAA

651 GTTCAACTGG TACGTGGACG GCGTGGAGGT GCATAATGCC AAGACAAAGC
```

```
 701 CGCGGGAGGA GCAGTACAAC AGCACGTACC GTGTGGTCAG CGTCCTCACC

751 GTCCTGCACC AGGACTGGCT GAATGGCAAG GAGTACAAGT GCAAGGTCTC

801 CAACAAAGCC CTCCCAGCCC CCATCGAGAA AACCATCTCC AAAGCCAAAG

851 GGCAGCCCCG AGAACCACAG GTGTACACCC TGCCCCCATC CCGGAAGGAG

901 ATGACCAAGA ACCAGGTCAG CCTGACCTGC CTGGTCAAAG GCTTCTATCC

951 CAGCGACATC GCCGTGGAGT GGGAGAGCAA TGGGCAGCCG GAGAACAACT

1001 ACAAGACCAC GCCTCCCGTG CTGAAGTCCG ACGGCTCCTT CTTCCTCTAT

1051 AGCAAGCTCA CCGTGGACAA GAGCAGGTGG CAGCAGGGGA ACGTCTTCTC

1101 ATGCTCCGTG ATGCATGAGG CTCTGCACAA CCACTACACG CAGAAGAGCC

1151 TCTCCCTGTC TCCGGGTAAA
```

The mature TGFβRII$_{SHORT}$-Fc fusion polypeptide (SEQ ID NO: 165) is as follows and may optionally be provided with the lysine removed from the C-terminus.

```
                                                    (SEQ ID NO: 165)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSRKEMTKN QVSLTCLVKG FYPSDIAVEW

301 ESNGQPENNY KTTPPVLKSD GSFFLYSKLT VDKSRWQQGN VFSCSVMHEA

351 LHNHYTQKSL SLSPGK
```

The TGFβRII$_{LONG}$-Fc polypeptide sequence (SEQ ID NO: 166) is shown below:

```
                                                    (SEQ ID NO: 166)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSRKEMTKNQ VSLTCLVKGF YPSDIAVEWE

351 SNGQPENNYK TTPPVLKSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ActRIIB-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated by double underline above. The amino acid sequence of SEQ ID NO: 166 may optionally be provided with the lysine removed from the C-terminus.

This TGFβRII$_{LONG}$-Fc fusion protein is encoded by the following nucleic acid sequence (SEQ ID NO: 260):

```
                                                   (SEQ ID NO: 260)
    1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA ACTCACACAT GCCCACCGTG CCCAGCACCT

601 GAACTCCTGG GGGGACCGTC AGTCTTCCTC TTCCCCCCAA AACCCAAGGA

651 CACCCTCATG ATCTCCCGGA CCCCTGAGGT CACATGCGTG GTGGTGGACG

701 TGAGCCACGA AGACCCTGAG GTCAAGTTCA ACTGGTACGT GGACGGCGTG

751 GAGGTGCATA ATGCCAAGAC AAAGCCGCGG GAGGAGCAGT ACAACAGCAC

801 GTACCGTGTG GTCAGCGTCC TCACCGTCCT GCACCAGGAC TGGCTGAATG

851 GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA

951 CACCCTGCCC CCATCCCGGA AGGAGATGAC CAAGAACCAG GTCAGCCTGA

1001 CCTGCCTGGT CAAAGGCTTC TATCCCAGCG ACATCGCCGT GGAGTGGGAG

1051 AGCAATGGGC AGCCGGAGAA CAACTACAAG ACCACGCCTC CCGTGCTGAA

1101 GTCCGACGGC TCCTTCTTCC TCTATAGCAA GCTCACCGTG GACAAGAGCA

1151 GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAA
```

The mature TGFβRII$_{LONG}$-Fc fusion polypeptide (SEQ ID NO: 167) is as follows and may optionally be provided with the lysine removed from the C-terminus.

```
                                                   (SEQ ID NO: 167)
    1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT
```

```
201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPSRK

301 EMTKNQVSLT CLVKGFYPSD IAVEWESNGQ PENNYKTTPP VLKSDGSFFL

351 YSKLTVDKSR WQQGNVFSCS VMHEALHNHY TQKSLSLSPG K
```

In a second approach to promote the formation of heteromultimer complexes using asymmetric Fc fusion proteins, the Fc domains are altered to introduce complementary hydrophobic interactions and an additional intermolecular disulfide bond.

The TGFβRII$_{SHORT}$-Fc polypeptide sequence (SEQ ID NO: 172) is shown below:

```
                                              (SEQ ID NO: 172)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPCREE

301 MTKNQVSLWC LVKGFYPSDI AVEWESNGQP ENNYKTTPPV LDSDGSFFLY

351 SKLTVDKSRW QQGNVFSCSV MHEALHNHYT QKSLSLSPGK
```

The leader sequence and linker sequence are underlined. To promote formation of the TGFβRII$_{SHORT}$-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 172 may optionally be provided with the lysine removed from the C-terminus.

The mature TGFβRII$_{SHORT}$-Fc fusion polypeptide (SEQ ID NO: 173) is as follows and may optionally be provided with the lysine removed from the C-terminus.

```
                                              (SEQ ID NO: 173)
  1 TIPPHVQKSV NNDMIVTDNN GAVKFPQLCK FCDVRFSTCD
    NQKSCMSNCS

51 ITSICEKPQE VCVAVWRKND ENITLETVCH DPKLPYHDFI
    LEDAASPKCI

101 MKEKKKPGET FFMCSCSSDE CNDNIIFSEE YNTSNPDTGG
    GTHTCPPCPA

151 PELLGGPSVF LFPPKPKDTL MISRTPEVTC VVVDVSHEDP
    EVKFNWYVDG

201 VEVHNAKTKP REEQYNSTYR VVSVLTVLHQ DWLNGKEYKC
    KVSNKALPAP

251 IEKTISKAKG QPREPQVYTL PPCREEMTKN QVSLWCLVKG
    FYPSDIAVEW

301 ESNGQPENNY KTTPPVLDSD GSFFLYSKLT VDKSRWQQGN
    VFSCSVMHEA

351 LHNHYTQKSL SLSPGK
```

To guide heterodimer formation with the certain Fc fusion polypeptides disclosed herein, four amino acid substitutions can be introduced into the Fc domain of the ALK1 fusion polypeptide.

In some embodiments, the TGFβRII$_{LONG}$-Fc polypeptide sequence (SEQ ID NO: 174) is below:

```
                                              (SEQ ID NO: 174)
  1 MDAMKRGLCC VLLLCGAVFV SPGATIPPHV QKSDVEMEAQ
    KDEITCPSCN

51 RTAHPLRHIN NDMIVTDNNG AVKFPQLCKF CDVRFSTCDN
    QKSCMSNCSI

101 TSICEKPQEV CVAVWRKNDE NITLETVCHD PKLPYHDFIL
    EDAASPKCIM

151 KEKKKPGETF FMCSCSSDEC NDNIIFSEEY NTSNPDTGGG
    THTCPPCPAP

201 ELLGGPSVFL FPPKPKDTLM ISRTPEVTCV VVDVSHEDPE
    VKFNWYVDGV

251 EVHNAKTKPR EEQYNSTYRV VSVLTVLHQD WLNGKEYKCK
    VSNKALPAPI

301 EKTISKAKGQ PREPQVYTLP PCREEMTKNQ VSLWCLVKGF
    YPSDIAVEWE

351 SNGQPENNYK TTPPVLDSDG SFFLYSKLTV DKSRWQQGNV
    FSCSVMHEAL

401 HNHYTQKSLS LSPGK
```

The leader sequence and linker sequence are underlined. To promote formation of the TGFβRII$_{LONG}$-Fc:ActRIIB-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 174 may optionally be provided with the lysine removed from the C-terminus.

The mature TGFβRII$_{LONG}$-Fc fusion polypeptide (SEQ ID NO: 175) is as follows and may optionally be provided with the lysine removed from the C-terminus.

```
                                              (SEQ ID NO: 175)
  1 TIPPHVQKSD VEMEAQKDEI ICPSCNRTAH PLRHINNDMI
    VTDNNGAVKF

51 PQLCKFCDVR FSTCDNQKSC MSNCSITSIC EKPQEVCVAV
    WRKNDENITL

101 ETVCHDPKLP YHDFILEDAA SPKCIMKEKK KPGETFFMCS
    CSSDECNDNI

151 IFSEEYNTSN PDTGGGTHTC PPCPAPELLG GPSVFLFPPK
    PKDTLMISRT

201 PEVTCVVVDV SHEDPEVKFN WYVDGVEVHN AKTKPREEQY
    NSTYRVVSVL

251 TVLHQDWLNG KEYKCKVSNK ALPAPIEKTI SKAKGQPREP
    QVYTLPPCRE

301 EMTKNQVSLW CLVKGFYPSD IAVEWESNGQ PENNYKTTPP
    VLDSDGSFFL

351 YSKLTVDKSR WQQGNVFSCS VMHEALHNHY TQKSLSLSPG K
```

In certain aspects, the present disclosure relates to protein complexes that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MIS-RII family member as well as any variants thereof (including mutants, fragments, fusions, and peptidomimetic forms) that retain a useful activity.

A human MISRII precursor protein sequence (NCBI Ref Seq NP_065434.1) is as follows:

```
                                              (SEQ ID NO: 180)
  1 MLGSLGLWAL LPTAVEAPPN RRTCVFFEAP GVRGSTKTLG
    ELLDTGTELP

51 RAIRCLYSRC CFGIWNLTQD RAQVEMQGCR DSDEPGCESL
    HCDPSPRAHP

101 SPGSTLFTCS CGTDFCNANY SHLPPPGSPG TPGSQGPQAA
    PGESIWMALV

151 LLGLFLLLLL LLGSIILALL QRKNYRVRGE PVPEPRPDSG
    RDWSVELQEL

201 PELCFSQVIR EGGHAVVWAG QLQGKLVAIK AFPPRSVAQF
    QAERALYELP

251 GLQHDHIVRF ITASRGGPGR LLSGPLLVLE LHPKGSLCHY
    LTQYTSDWGS

301 SLRMALSLAQ GLAFLHEERW QNGQYKPGIA HRDLSSQNVL
    IREDGSCAIG

351 DLGLALVLPG LTQPPAWTPT QPQGPAAIME AGTQRYMAPE
    LLDKTLDLQD

401 WGMALRRADI YSLALLLWEI LSRCPDLRPD SSPPPFQLAY
    EAELGNTPTS

451 DELWALAVQE RRRPYIPSTW RCFATDPDGL RELLEDCWDA
    DPEARLTAEC

501 VQQRLAALAH PQESHPFPES CPRGCPPLCP EDCTSIPAPT
    ILPCRPQRSA

551 CHFSVQQGPC SRNPQPACTL SPV
```

The signal peptide is indicated by a single underline and an extracellular domain is indicated in bold font.

A processed extracellular MISRII polypeptide sequence is as follows:

```
                                              (SEQ ID NO: 183)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL
```

A nucleic acid sequence encoding the MISRII precursor protein is shown in SEQ ID NO: 209, corresponding to nucleotides 81-1799 of Genbank Reference Sequence NM_020547.2. A nucleic acid sequence encoding the extracellular human MISRII polypeptide is shown in SEQ ID NO: 210.

An alternative isoform of the human MISRII precursor protein sequence, isoform 2 (NCBI Ref Seq NP_001158162.1), is as follows:

```
                                              (SEQ ID NO: 181)
  1 MLGSLGLWAL LPTAVEAPPN RRTCVFFEAP GVRGSTKTLG
    ELLDTGTELP

51 RAIRCLYSRC CFGIWNLTQD RAQVEMQGCR DSDEPGCESL
    HCDPSPRAHP

101 SPGSTLFTCS CGTDFCNANY SHLPPPGSPG TPGSQGPQAA
    PGESIWMALV

151 LLGLFLLLLL LLGSIILALL QRKNYRVRGE PVPEPRPDSG
    RDWSVELQEL

201 PELCFSQVIR EGGHAVVWAG QLQGKLVAIK AFPPRSVAQF
    QAERALYELP

251 GLQHDHIVRF ITASRGGPGR LLSGPLLVLE LHPKGSLCHY
    LTQYTSDWGS

301 SLRMALSLAQ GLAFLHEERW QNGQYKPGIA HRDLSSQNVL
    IREDGSCAIG

351 DLGLALVLPG LTQPPAWTPT QPQGPAAIME AGTQRYMAPE
    LLDKTLDLQD

401 WGMALRRADI YSLALLLWEI LSRCPDLRPA VHHPSNWPMR
    QNWAIPLPLM

451 SYGPWQCRRG GVPTSHPPGA ALPQTLMG
```

The signal peptide is indicated by a single underline and the extracellular domain is indicated in bold font.

A processed extracellular MISRII polypeptide sequence (isoform 2) is as follows:

```
                                        (SEQ ID NO: 184)
PPNRRTCVFFEAPGVRGSTKTLGELLDTGTELPRAIRCLYSRCCFGIWN

LTQDRAQVEMQGCRDSDEPGCESLHCDPSPRAHPSPGSTLFTCSCGTDF

CNANYSHLPPPGSPGTPGSQGPQAAPGESIWMAL
```

A nucleic acid sequence encoding the MISRII precursor protein (isoform 2) is shown in SEQ ID NO: 211, corresponding to nucleotides 81-1514 of Genbank Reference Sequence NM_001164690.1. A nucleic acid sequence encoding processed soluble (extracellular) human MISRII polypeptide (isoform 2) is shown in SEQ ID NO: 212.

An alternative isoform of the human MISRII precursor protein sequence, isoform 3 (NCBI Ref Seq NP_001158163.1), is as follows:

```
                                        (SEQ ID NO: 182)
  1  MLGSLGLWAL LPTAVEAPPN RRTCVFFEAP GVRGSTKTLG
     ELLDTGTELP

51  RAIRCLYSRC CFGIWNLTQD RAQVEMQGCR DSDEPGCESL
     HCDPSPRAHP

101  SPGSTLFTCS CGTDFCNANY SHLPPPGSPG TPGSQGPQAA
     PGESIWNALV

151  LLGLFLLLLL LLGSIILALL QRKNYRVRGE PVPEPRPDSG
     RDWSVELQEL

201  PELCFSQVIR EGGHAVVWAG QLQGKLVAIK AFPPRSVAQF
     QAERALYELP

251  GLQHDHIVRF ITASRGGPGR LLSGPLLVLE LHPKGSLCHY
     LTQYTSDWGS

301  SLRMALSLAQ GLAFLHEERW QNGQYKPGIA HRDLSSQNVL
     IREDGSCAIG

351  DLGLALVLPG LTQPPAWTPT QPQGPAAIME DPDGLRELLE
     DCWDADPEAR

401  LTAECVQQRL AALAHPQESH PFPESCPRGC PPLCPEDCTS
     IPAPTILPCR

451  PQRSACHFSV QQGPCSRNPQ PACTLSPV
```

The signal peptide is indicated by a single underline and the extracellular domain is indicated in bold font.

A processed extracellular MISRII polypeptide sequence (isoform 3) is as follows:

```
                                        (SEQ ID NO: 185)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL
```

A nucleic acid sequence encoding human MISRII precursor protein (isoform 3) is shown in SEQ ID NO: 213, corresponding to nucleotides 81-1514 of Genbank Reference Sequence NM_001164691.1. A nucleic acid sequence encoding a processed soluble (extracellular) human MISRII polypeptide (isoform 3) is shown in SEQ ID NO: 214.

In certain embodiments, the disclosure relates to heteromultimers that comprise at least one MISRII polypeptide, which includes fragments, functional variants, and modified forms thereof. Preferably, MISRII polypeptides for use in accordance with inventions of the disclosure (e.g., heteromultimers comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimers of the disclosure comprise at least one MISRII polypeptide that is at least 70%, 75%, 80%, 85%, 90%, 95%, 97%, 98%, 99%, or 100% identical to the amino acid sequence of SEQ ID NOs: 180, 183, 181, 184, 182, or 185. In some embodiments, heteromultimers of the disclosure consist or consist essentially of at least one MISRII polypeptide that is at least 70%, 75%, 80%, 85%, 90%, 95%, 97%, 98%, 99%, or 100% identical to the amino acid sequence of SEQ ID NOs: 180, 183, 181, 184, 182, or 185.

In certain aspects, the disclosure relates to a heteromultimer that comprises an MISRII-Fc fusion protein. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 17-24 (e.g., amino acid residues 17, 18, 19, 20, 21, 22, 23, and 24) SEQ ID NO: 180, 181, or 182 and ends at any one of amino acids 116-149 (e.g., amino acid residues 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, and 149) of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 24-116 of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to amino acids 17-149 of SEQ ID NO: 180, 181, or 182. In some embodiments, the MISRII-Fc fusion protein comprises an MISRII domain comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID Nos: 180, 183, 181, 184, 182, 185, 186, 187, 188, 189, 190, 191, 192, and 193.

In some embodiments, the present disclosure contemplates making functional variants by modifying the structure of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty.

In some embodiments, the present disclosure contemplates making functional variants by modifying the structure of the TGF-beta superfamily type I receptor polypeptide and/or TGF-beta superfamily type II receptor polypeptide for such purposes as enhancing therapeutic efficacy or stability (e.g., increased shelf-life and/or increased resistance to proteolytic degradation).

In certain embodiments, the present disclosure contemplates specific mutations of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) receptor of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, TGF-beta superfamily type I and II receptor complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) disclosed herein, as well as truncation mutants. Pools of combinatorial mutants are especially useful for identifying functionally active (e.g., ligand binding) TGF-beta superfamily type I and/or TGF-beta superfamily type II receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta superfamily type I and II receptor complex variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of a TGF-beta superfamily heteromultimer of the disclosure also may be tested, for example in a cell-based or in vivo assay. For example, the effect of a heteromultimer complex on the expression of genes or the activity of proteins involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), and cells may be transfected so as to produce a TGF-beta superfamily type I and II receptor complex, and optionally, a TGF-beta superfamily ligand. Likewise, a heteromultimer complex of the disclosure may be administered to a mouse or other animal, and one or more measurements, such as muscle formation and strength may be assessed using art-recognized methods. Similarly, the activity of a heteromultimer, or variants thereof, may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily heteromultimer. Such variants, when expressed from recombinant DNA constructs, can be used in gene therapy protocols. Likewise, mutagenesis can give rise to variants which have intracellular half-lives dramatically different than the corresponding unmodified TGF-beta superfamily heteromultimer. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the TGF-beta superfamily heteromultimer complex including, for example, immunogenicity, half-life, and solubility.

Many methods known in the art can be used to generate heteromultimers of the disclosure. For example, non-naturally occurring disulfide bonds may be constructed by replacing on a first polypeptide (e.g., a variant ActRIIB polypeptide) a naturally occurring amino acid with a free thiol-containing residue, such as cysteine, such that the free thiol interacts with another free thiol-containing residue on a second polypeptide (e.g., an unmodified ActRIIB polypeptide or a variant ActRIIB polypeptide different from that present in the first polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S. 20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a variant ActRIIB polypeptide and the amino acid sequence of a first member of an interaction pair; and the second polypeptide comprises the amino acid sequence of an unmodified ActRIIB polypeptide, or a variant ActRIIB polypeptide different from that present in the first polypeptide, and the amino acid sequence of a second member of an interaction pair. The interaction pair may be any two polypeptide sequences that interact to form a complex, particularly a heterodimeric complex although operative embodiments may also employ an interaction pair that can form a homodimeric complex. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 1B). Alternatively, the interaction pair may be unguided, meaning that the members of the pair may associate with each other or self-associate without substantial preference and thus may have the same or different amino acid sequences (see, e.g., FIG. 1A). Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising a variant ActRIIB polypeptide or an unmodified ActRIIB polypeptide fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimers of the disclosure. Optionally, the IgG1 Fc domain of SEQ ID NO: 13 has one or more mutations at residues such as Asp-265, Lys-322, and Asn-434 (numbered in accordance with the corresponding full-length IgG1). In certain cases, the variant Fc domain having one or more of these mutations (e.g., Asp-265 mutation) has reduced ability of binding to the Fcγ receptor relative to a wildtype Fc domain. In other cases, the variant Fc domain having one or more of these mutations (e.g., Asn-434 mutation) has increased ability of binding to the MHC class I-related Fc-receptor (FcRN) relative to a wild-type Fc domain.

An example of a native amino acid sequence that may be used for the Fc portion of human IgG1 (G1Fc) is shown below (SEQ ID NO: 13). Dotted underline indicates the hinge region, and solid underline indicates positions with naturally occurring variants. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 13. Naturally occurring variants in G1Fc would include E134D and M136L according to the numbering system used in SEQ ID NO: 13 (see Uniprot P01857).

```
                                          (SEQ ID NO: 13)
  1 THTCPPCPAP ELLGGPSVFL FPPKPKDTLM

ISRTPEVTCV VVDVSHEDPE

51 VKFNWYVDGV EVHNAKTKPR EEQYNSTYRV
    VSVLTVLHQD WLNGKEYKCK

101 VSNKALPAPI EKTISKAKGQ PREPQVYTLP
    PSREEMTKNQ VSLTCLVKGF
```

```
151 YPSDIAVEWE SNGQPENNYK TTPPVLDSDG
    SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 14). Dotted underline indicates the hinge region and double underline indicates positions where there are data base conflicts in the sequence (according to UniProt P01859). In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 14.

```
                                    (SEQ ID NO: 14)
  1 VECPPCPAPP VAGPSVFLFP PKPKDTLMIS
    RTPEVTCVVV DVSHEDPEVQ

51 FNWYVDGVEV HNAKTKPREE QFNSTFRVVS
    VLTVVHQDWL NGKEYKCKVS

101 NKGLPAPIEK TISKTKGQPR EPQVYTLPPS
    REEMTKNQVS LTCLVKGFYP

151 SDIAVEWESN GQPENNYKTT PPMLDSDGSF
    FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 15) contains a short hinge region consisting of a single 15-residue segment, whereas the second G3Fc sequence (SEQ ID NO: 16) contains a full-length hinge region. In each case, dotted underline indicates the hinge region, and solid underline indicates positions with naturally occurring variants according to UniProt P01859. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NOs: 15 and 16.

```
                                    (SEQ ID NO: 15)
  1 EPKSCDTPPP CPRCPAPELL GGPSVFLFPP
    KPKDTLMISR TPEVTCVVVD

51 VSHEDPEVQF KWYVDGVEVH NAKTKPREEQ
    YNSTFRVVSV LTVLHQDWLN

101 GKEYKCKVSN KALPAPIEKT ISKTKGQPRE
    PQVYTLPPSR EEMTKNQVSL

151 TCLVKGFYPS DIAVEWESSG QPENNYNTTP
    PMLDSDGSFF LYSKLTVDKS

201 RWQQGNIFSC SVMHEALHNR FTQKSLSLSP
    GK
                                    (SEQ ID NO: 16)
  1 ELKTPLGDTT HTCPRCPEPK SCDTPPPCPR
    CPEPKSCDTP PPCPRCPEPK
```

```
 51 SCDTPPPCPR CPAPELLGGP SVFLFPPKPK
    DTLMISRTPE VTCVVVDVSH

101 EDPEVQFKWY VDGVEVHNAK TKPREEQYNS
    TFRVVSVLTV LHQDWLNGKE

151 YKCKVSNKAL PAPIEKTISK TKGQPREPQV
    YTLPPSREEM TKNQVSLTCL

201 VKGFYPSDIA VEWESSGQPE NNYNTTPPML
    DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 15, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 17). Dotted underline indicates the hinge region. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 17.

```
                                    (SEQ ID NO: 17)
  1 ESKYGPPCPS CPAPEFLGGP SVFLFPPKPK
    DTLMISRTPE VTCVVVDVSQ

51 EDPEVQFNWY VDGVEVHNAK TKPREEQFNS
    TYRVVSVLTV LHQDWLNGKE

101 YKCKVSNKGL PSSIEKTISK AKGQPREPQV
    YTLPPSQEEM TKNQVSLTCL

151 VKGFYPSDIA VEWESNGQPE NNYKTTPPVL
    DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 13), and analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 13, 14, 15, and 17. It can also be appreciated that a given amino acid position in an immunoglobulin sequence consisting of hinge, CH2, and CH3 regions (e.g., SEQ ID NOs: 13, 14, 15, 16, or 17) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 13), the human IgG1 heavy chain constant domain (Uniprot P01857), and the human IgG1 heavy chain is as follows.

| Correspondence of $C_H3$ Positions in Different Numbering Systems | | |
|---|---|---|
| G1Fc (Numbering begins at first threonine in hinge region) | IgG1 heavy chain constant domain (Numbering begins at $C_H1$) | IgG1 heavy chain (EU numbering scheme of Kabat et al., 1991*) |
| Y127 | Y232 | Y349 |
| S132 | S237 | S354 |
| E134 | E239 | E356 |
| K138 | K243 | K360 |
| T144 | T249 | T366 |
| L146 | L251 | L368 |
| N162 | N267 | N384 |
| K170 | K275 | K392 |
| D177 | D282 | D399 |
| D179 | D284 | D401 |
| Y185 | Y290 | Y407 |
| K187 | K292 | K409 |
| H213 | H318 | H435 |
| K217 | K322 | K439 |

*Kabat et al. (eds) 1991; pp. 688-696 in *Sequences of Proteins of Immunological Interest*, 5th ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain-association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605. As described herein, these methods may be used to generate heterodimers comprising a variant ActRIIB polypeptide and another, optionally different, variant ActRIIB polypeptide or an unmodified ActRIIB polypeptide.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance heteromultimer formation of the heteromultimers disclosed herein.

| Examples of Pair-Wise Charged Residue Mutations to Enhance Heterodimer Formation | | | |
|---|---|---|---|
| Position in first chain | Mutation in first chain | Interacting position in second chain | Corresponding mutation in second chain |
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to a first variant ActRIIB polypeptide, a second variant ActRIIB polypeptide, or an unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct (e.g., a variant ActRIIB-Fc heteromultimer). In this example based on electrostatic steering, SEQ ID NO: 200 [human G1Fc(E134K/D177K)] and SEQ ID NO: 201 [human G1Fc(K170D/K187D)] are examples of complementary Fc sequences in which the engineered amino acid substitutions are double underlined, and a first variant ActRIIB polypeptide, second variant ActRIIB polypeptide, or unmodified ActRIIB polypeptide of the construct can be fused to either SEQ ID NO: 18 or SEQ ID NO: 19, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 18 and 19).

```
                                                (SEQ ID NO: 18)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PSRKEMTKNQ
     VSLTCLVKGF

151  YPSDIAVEWE SNGQPENNYK TTPPVLKSDG SFFLYSKLTV
     DKSRWQQGNV

201  FSCSVMHEAL HNHYTQKSLS LSPGK
```

```
                                                (SEQ ID NO: 19)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PSREEMTKNQ
     VSLTCLVKGF

151  YPSDIAVEWE SNGQPENNYD TTPPVLDSDG SFFLYSDLTV
     DKSRWQQGNV

201  FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to a first variant ActRIIB polypeptide, a second variant ActRIIB polypeptide, or an unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct. In this example based on knobs-into-holes pairing, SEQ ID NO: 20 [human G1Fc(T144Y)] and SEQ ID NO: 21 [human G1Fc(Y185T)] are examples of complementary Fc sequences in which the engineered amino acid substitutions are double underlined, and a first variant ActRIIB polypeptide, second variant ActRIIB polypeptide, or unmodified ActRIIB polypeptide of the construct can be fused to either SEQ ID NO: 20 or SEQ ID NO: 21, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 20 and 21).

```
                                                (SEQ ID NO: 20)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PSREEMTKNQ
     VSLYCLVKGF
```

```
151  YPSDIAVEWE  SNGQPENNYK  TTPPVLDSDG  SFFLYSKLTV
     DKSRWQQGNV

201  FSCSVMHEAL  HNHYTQKSLS  LSPGK (SEQ ID NO: 21)
  1  THTCPPCPAP  ELLGGPSVFL  FPPKPKDTLM  ISRTPEVTCV
     VVDVSHEDPE

51  VKFNWYVDGV  EVHNAKTKPR  EEQYNSTYRV  VSVLTVLHQD
     WLNGKEYKCK

101  VSNKALPAPI  EKTISKAKGQ  PREPQVYTLP  PSREEMTKNQ
     VSLTCLVKGF

151  YPSDIAVEWE  SNGQPENNYK  TTPPVLDSDG  SFFLTSKLTV
     DKSRWQQGNV

201  FSCSVMHEAL  HNHYTQKSLS  LSPGK
```

An example of Fc complementarity based on knobs-into-holes pairing combined with an engineered disulfide bond is disclosed in SEQ ID NO: 22 [hG1Fc(S132C/T144W)] and SEQ ID NO: 23 [hG1Fc(Y127C/T144S/L146A/Y185V)]. The engineered amino acid substitutions in these sequences are double underlined, and a first variant ActRIIB polypeptide, second variant ActRIIB polypeptide, or unmodified ActRIIB polypeptide of the construct can be fused to either SEQ ID NO: 22 or SEQ ID NO: 23, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 22 and 23).

```
                                            (SEQ ID NO: 22)
  1  THTCPPCPAP  ELLGGPSVFL  FPPKPKDTLM  ISRTPEVTCV
     VVDVSHEDPE

51  VKFNWYVDGV  EVHNAKTKPR  EEQYNSTYRV  VSVLTVLHQD
     WLNGKEYKCK

101  VSNKALPAPI  EKTISKAKGQ  PREPQVYTLP  PCREEMTKNQ
     VSLWCLVKGF

151  YPSDIAVEWE  SNGQPENNYK  TTPPVLDSDG  SFFLYSKLTV
     DKSRWQQGNV

201  FSCSVMHEAL  HNHYTQKSLS  LSPGK (SEQ ID NO: 23)
  1  THTCPPCPAP  ELLGGPSVFL  FPPKPKDTLM  ISRTPEVTCV
     VVDVSHEDPE

51  VKFNWYVDGV  EVHNAKTKPR  EEQYNSTYRV  VSVLTVLHQD
     WLNGKEYKCK

101  VSNKALPAPI  EKTISKAKGQ  PREPQVCTLP  PSREEMTKNQ
     VSLSCAVKGF

151  YPSDIAVEWE  SNGQPENNYK  TTPPVLDSDG  SFFLVSKLTV
     DKSRWQQGNV

201  FSCSVMHEAL  HNHYTQKSLS  LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins [see, for example, Davis et al (2010) Protein Eng Design Sel 23:195-202]. One of a pair of Fc sequences with SEEDbody complementarity can be arbitrarily fused to a first variant ActRIIB polypeptide, second variant ActRIIB polypeptide, or unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence complementary to the first Fc sequence to favor generation of the desired multichain construct. In this example based on SEEDbody (Sb) pairing, SEQ ID NO: 24 [hG1Fc(SbAG)] and SEQ ID NO: 25 [hG1Fc(SbGA)] are examples of complementary IgG Fc sequences in which the engineered amino acid substitutions from IgA Fc are double underlined, and a first variant ActRIIB polypeptide, second variant ActRIIB polypeptide, or unmodified ActRIIB polypeptide of the construct can be fused to either SEQ ID NO: 24 or SEQ ID NO: 25, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 4) will generate an Fc monomer which may be used in the complementary IgG-IgA pair below (SEQ ID NOs: 24 and 25).

```
                                            (SEQ ID NO: 24)
  1  THTCPPCPAP  ELLGGPSVFL  FPPKPKDTLM  ISRTPEVTCV
     VVDVSHEDPE

51  VKFNWYVDGV  EVHNAKTKPR  EEQYNSTYRV  VSVLTVLHQD
     WLNGKEYKCK

101  VSNKALPAPI  EKTISKAKGQ  PFRPEVHLLP  PSREEMTKNQ
     VSLTCLARGF

151  YPKDIAVEWE  SNGQPENNYK  TTPSRQEPSQ  GTTTFAVTSK
     LTVDKSRWQQ

201  GNVFSCSVMH  EALHNHYTQK  TISLSPGK (SEQ ID NO: 25)
  1  THTCPPCPAP  ELLGGPSVFL  FPPKPKDTLM  ISRTPEVTCV
     VVDVSHEDPE

51  VKFNWYVDGV  EVHNAKTKPR  EEQYNSTYRV  VSVLTVLHQD
     WLNGKEYKCK

101  VSNKALPAPI  EKTISKAKGQ  PREPQVYTLP  PPSEELALNE
     LVTLTCLVKG

151  FYPSDIAVEW  ESNGQELPRE  KYLTWAPVLD  SDGSFFLYSI
     LRVAAEDWKK

201  GDTFSCSVMH  EALHNHYTQK  SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains. See, e.g., Wranik et al (2012) J Biol Chem 287:43331-43339. As disclosed herein, one of a pair of Fc sequences attached to a leucine zipper-forming strand can be arbitrarily fused to a first variant ActRIIB polypeptide, second variant ActRIIB polypeptide, or unmodified ActRIIB polypeptide of the construct, with or without an optional linker, to generate a variant ActRIIB-Fc or unmodified ActRIIB-Fc fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 26 [hG1Fc-Ap1 (acidic)] and SEQ ID NO: 27 [hG1Fc-Bp1 (basic)] are examples of complementary IgG Fc sequences in which the engineered complimentary leucine zipper sequences are underlined, and a first variant ActRIIB polypeptide, second variant ActRIIB polypeptide, or wild-type ActRIIB polypeptide of the construct can be fused to either SEQ ID NO: 26 or SEQ ID NO: 27, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 4) will generate an Fc monomer which may be used in the complementary leucine zipper-forming pair below (SEQ ID NOs: 26 and 27).

```
                                          (SEQ ID NO: 26)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PSREEMTKNQ
     VSLTCLVKGF

151  YPSDIAVEWE SNGQPENNYK TTPPVLDSDG SFFLYSKLTV
     DKSRWQQGNV

201  FSCSVMHEAL HNHYTQKSLS LSPGKGGSAQ LEKELQALEK
     ENAQLEWELQ

251  ALEKELAQGA T
```

```
                                          (SEQ ID NO: 27)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PSREEMTKNQ
     VSLTCLVKGF

151  YPSDIAVEWE SNGQPENNYK TTPPVLDSDG SFFLYSKLTV
     DKSRWQQGNV

201  FSCSVMHEAL HNHYTQKSLS LSPGKGGSAQ LKKKLQALKK
     KNAQLKWKLQ

251  ALKKKLAQGA T
```

In part, the disclosure provides desired pairing of asymmetric Fc-containing polypeptide chains by methods described above in combination with additional mutations in the Fc domain which facilitate purification of the desired heteromeric species. An example uses complementarity of Fc domains based on knobs-into-holes pairing combined with an engineered disulfide bond, as disclosed in SEQ ID NOs: 22 and 23, plus additional substitution of two negatively charged amino acids (aspartic acid or glutamic acid) in one Fc-containing polypeptide chain and two positively charged amino acids (e.g., arginine) in the complementary Fc-containing polypeptide chain (SEQ ID NOs: 28-29). These four amino acid substitutions facilitate selective purification of the desired heteromeric fusion protein from a heterogeneous polypeptide mixture based on differences in isoelectric point or net molecular charge. The engineered amino acid substitutions in these sequences are double underlined below, and a first variant ActRIIB polypeptide, second variant ActRIIB polypeptide, or unmodified ActRIIB polypeptide of the construct can be fused to either SEQ ID NO: 28 or SEQ ID NO: 29, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair below (SEQ ID NOs: 28-29).

```
                                          (SEQ ID NO: 28)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PCREEMTENQ
     VSLWCLVKGF

151  YPSDIAVEWE SNGQPENNYK TTPPVLDSDG SFFLYSKLTV
     DKSRWQQGNV

201  FSCSVMHEAL HNHYTQDSLS LSPGK
```

```
                                          (SEQ ID NO: 29)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVCTLP PSREEMTKNQ
     VSLSCAVKGF

151  YPSDIAVEWE SRGQPENNYK TTPPVLDSRG SFFLVSKLTV
     DKSRWQQGNV

201  FSCSVMHEAL HNHYTQKSLS LSPGK
```

Another example involves complementarity of Fc domains based on knobs-into-holes pairing combined with an engineered disulfide bond, as disclosed in SEQ ID NOs: 22-23, plus a histidine-to-arginine substitution at position 213 in one Fc-containing polypeptide chain (SEQ ID NO: 30). This substitution (denoted H435R in the numbering system of Kabat et al.) facilitates separation of desired heteromer from undesirable homodimer based on differences in affinity for protein A. The engineered amino acid substitution is indicated by double underline, and a first variant ActRIIB polypeptide, second variant ActRIIB polypeptide, or unmodified ActRIIB polypeptide of the construct can be fused to either SEQ ID NO: 30 or SEQ ID NO: 23, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 4) will generate complementary Fc pairs which may be used instead of the complementary hG1Fc pair of SEQ ID NO: 30 (below) and SEQ ID NO: 23.

```
                                          (SEQ ID NO: 30)
  1  THTCPPCPAP ELLGGPSVFL FPPKPKDTLM ISRTPEVTCV
     VVDVSHEDPE

51  VKFNWYVDGV EVHNAKTKPR EEQYNSTYRV VSVLTVLHQD
     WLNGKEYKCK

101  VSNKALPAPI EKTISKAKGQ PREPQVYTLP PCREEMTKNQ
     VSLWCLVKGF
```

```
151 YPSDIAVEWE SNGQPENNYK TTPPVLDSDG SFFLYSKLTV
    DKSRWQQGNV

201 FSCSVMHEAL HNRYTQKSLS LSPGK
```

A variety of engineered mutations in the Fc domain are presented above with respect to the G1Fc sequence (SEQ ID NO: 13). Analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 13, 14, 15, 16, and 17 as summarized in the following table.

Correspondence between $C_H3$ Positions for Human Fc Isotypes*

| IgG1<br>SEQ ID NO: 13<br>Numbering<br>begins<br>at THT . . . | IgG4<br>SEQ ID NO: 17<br>Numbering<br>begins<br>at ESK . . . | IgG2<br>SEQ ID NO: 14<br>Numbering<br>begins<br>at VEC . . . | IgG3<br>SEQ ID NO: 15<br>Numbering<br>begins<br>at EPK . . . |
|---|---|---|---|
| Y127 | Y131 | Y125 | Y134 |
| S132 | S136 | S130 | S139 |
| E134 | E138 | E132 | E141 |
| K138 | K142 | K136 | K145 |
| T144 | T148 | T142 | T151 |
| L146 | L150 | L144 | L153 |
| N162 | N166 | N160 | S169 |
| K170 | K174 | K168 | N177 |
| D177 | D181 | D175 | D184 |
| D179 | D183 | D177 | D186 |
| Y185 | Y189 | Y183 | Y192 |
| K187 | R191 | K185 | K194 |
| H213 | H217 | H211 | R220 |
| K217 | K221 | K215 | K224 |

*Numbering based on multiple sequence alignment shown in FIG. 4

It is understood that different elements of the fusion proteins (e.g., immunoglobulin Fc fusion proteins) may be arranged in any manner that is consistent with desired functionality. For example, an ActRIIB polypeptide domain may be placed C-terminal to a heterologous domain, or alternatively, a heterologous domain may be placed C-terminal to an ActRIIB polypeptide domain. The ActRIIB polypeptide domain and the heterologous domain need not be adjacent in a fusion protein, and additional domains or amino acid sequences may be included C- or N-terminal to either domain or between the domains.

For example, a ActRIIB polypeptide may comprise an amino acid sequence as set forth in the formula A-B-C. The B portion corresponds to an ActRIIB polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 261), GGGG (SEQ ID NO: 262), TGGGG (SEQ ID NO: 263), SGGGG (SEQ ID NO: 264), TGGG (SEQ ID NO: 265), or SGGG (SEQ ID NO: 266) singlets, or repeats. In certain embodiments, an ActRIIB fusion protein comprises an amino acid sequence as set forth in the formula A-B-C, wherein A is a leader (signal) sequence, B consists of an ActRIIB polypeptide domain, and C is a polypeptide portion that enhances one or more of in vivo stability, in vivo half-life, uptake/administration, tissue localization or distribution, formation of protein complexes, and/or purification. In certain embodiments, an ActRIIB fusion protein comprises an amino acid sequence as set forth in the formula A-B-C, wherein A is a TPA leader sequence, B consists of an ActRIIB polypeptide domain, and C is an immunoglobulin Fc domain.

In certain embodiments, the variant ActRIIB polypeptides of the present invention contain one or more modifications that are capable of stabilizing the variant ActRIIB polypeptides. For example, such modifications enhance the in vitro half life of the variant ActRIIB polypeptides, enhance circulatory half life of the variant ActRIIB polypeptides or reducing proteolytic degradation of the variant ActRIIB polypeptides. Such stabilizing modifications include, but are not limited to, fusion proteins (including, for example, fusion proteins comprising a variant ActRIIB polypeptide and a stabilizer domain), modifications of a glycosylation site (including, for example, addition of a glycosylation site to a variant ActRIIB polypeptide), and modifications of carbohydrate moiety (including, for example, removal of carbohydrate moieties from a variant ActRIIB polypeptide). In the case of fusion proteins, a variant ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the present invention makes available isolated and/or purified forms of the variant ActRIIB polypeptides, which are isolated from, or otherwise substantially free of, other proteins.

In certain embodiments, ActRIIB polypeptides (unmodified or modified) of the invention can be produced by a variety of art-known techniques. For example, such ActRIIB polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the ActRIIB polypeptides, fragments or variants thereof may be recombinantly produced using various expression systems (e.g., *E. coli*, Chinese Hamster Ovary cells, COS cells, baculovirus) as is well known in the art (also see below). In a further embodiment, the modified or unmodified ActRIIB polypeptides may be produced by digestion of naturally occurring or recombinantly produced full-length ActRIIB polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRIIB polypeptides may be produced from naturally occurring or recombinantly produced full-length ActRIIB polypeptides such as standard techniques known in the art, such as by chemical cleavage (e.g., cyanogen bromide, hydroxylamine).

3. Nucleic Acids Encoding ActRIIB Polypeptides

In certain aspects, the invention provides isolated and/or recombinant nucleic acids encoding any of the ActRIIB polypeptides (e.g., soluble ActRIIB polypeptides), including any of the variants disclosed herein. For example, SEQ ID NO: 4 encodes a naturally occurring ActRIIB precursor polypeptide, while SEQ ID NO: 3 encodes a soluble ActRIIB polypeptide. The subject nucleic acids may be single-stranded or double stranded. Such nucleic acids may be DNA or RNA molecules. These nucleic acids are may be used, for example, in methods for making ActRIIB polypeptides or as direct therapeutic agents (e.g., in a gene therapy approach).

In certain aspects, the subject nucleic acids encoding ActRIIB polypeptides are further understood to include nucleic acids that are variants of SEQ ID NO: 3. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 4.

In certain embodiments, the invention provides isolated or recombinant nucleic acid sequences that are at least 80%, 85%, 90%, 95%, 97%, 98%, 99% or 100% identical to SEQ ID NO: 3. One of ordinary skill in the art will appreciate that nucleic acid sequences complementary to SEQ ID NO: 3, and variants of SEQ ID NO: 3 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 3, complement sequence of SEQ ID NO: 3, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct.

Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIB polypeptide and operably linked to at least one regulatory sequence. Regulatory sequences are art-recognized and are selected to direct expression of the variant ActRIIB polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, CA (1990). For instance, any of a wide variety of expression control sequences that control the expression of a DNA sequence when operatively linked to it may be used in these vectors to express DNA sequences encoding a variant ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant variant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

In a preferred embodiment, a vector will be designed for production of the subject variant ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wisc.). As will be apparent, the subject gene constructs can be used to cause expression of the subject variant ActRIIB polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 4) for one or more of the subject variant ActRIIB polypeptides. The host cell may be any prokaryotic or eukaryotic cell. For example, a variant ActRIIB polypeptide of the invention may be expressed in bacterial cells such as *E. coli,* insect cells (e.g., using a baculovirus expression system), yeast, or mammalian cells. Other suitable host cells are known to those skilled in the art.

Accordingly, the present invention further pertains to methods of producing the subject variant ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB polypeptides. In a preferred embodiment, the variant ActRIIB polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant variant ActRIIB polypeptide, can allow purification of the expressed fusion protein by affinity chromatography using a Ni' metal resin. The purification leader sequence can then be subsequently removed by treatment with enterokinase to provide the purified variant ActRIIB polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Screening Assays

In certain aspects, the present invention relates to the use of the subject variant ActRIIB polypeptides (e.g., soluble ActRIIB polypeptides) to identify compounds (agents) which are agonist or antagonists of the variant ActRIIB polypeptides. Compounds identified through this screening can be tested in tissues such as bone, cartilage, muscle, fat, and/or neurons, to assess their ability to modulate tissue growth in vitro. Optionally, these compounds can further be tested in animal models to assess their ability to modulate tissue growth in vivo.

There are numerous approaches to screening for therapeutic agents for modulating tissue growth by targeting the variant ActRIIB polypeptides. In certain embodiments, high-throughput screening of compounds can be carried out to identify agents that perturb ActRIIB-mediated effects on growth of bone, cartilage, muscle, fat, and/or neurons. In certain embodiments, the assay is carried out to screen and identify compounds that specifically inhibit or reduce binding of an ActRIIB polypeptide to its binding partner, such as an ActRIIB ligand (e.g., activin, Nodal, GDF8, GDF11 or BMP7). Alternatively, the assay can be used to identify compounds that enhance binding of an ActRIIB polypeptide to its binding protein such as an ActRIIB ligand. In a further embodiment, the compounds can be identified by their ability to interact with an ActRIIB polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB polypeptide and its binding protein (e.g., an ActRIIB ligand).

Merely to illustrate, in an exemplary screening assay of the present invention, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIB polypeptide and its binding protein may be detected by a variety of techniques. For instance, modulation of the formation of complexes can be quantitated using, for example, detectably labeled proteins such as radiolabeled (e.g., $^{32}$P, $^{35}$S, $^{14}$C or $^{3}$H), fluorescently labeled (e.g., FITC), or enzymatically labeled ActRIIB polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIB polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIB polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIB polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a variant ActRIIB polypeptide of the invention. The interaction between the compound and the variant ActRIIB polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a variant ActRIIB polypeptide. This may include a solid phase or fluid phase binding event. Alternatively, the gene encoding a variant ActRIIB polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for stimulating muscle growth and increasing muscle mass, for example, by antagonizing functions of an ActRIIB polypeptide and/or an ActRIIB ligand. Therefore, any compound identified can be tested in whole cells or tissues, in vitro or in vivo, to confirm their ability to modulate muscle growth. Various methods known in the art can be utilized for this purpose. For example, methods of the invention are performed such that the signal transduction through an ActRIIB protein activated by binding to an ActRIIB ligand (e.g., GDF8) has been reduced or inhibited. It will be recognized that the growth of muscle tissue in the organism would result in an increased muscle mass in the organism as compared to the muscle mass of a corresponding organism (or population of organisms) in which the signal transduction through an ActRIIB protein had not been so effected.

For example, the effect of the variant ActRIIB polypeptides or test compounds on muscle cell growth/proliferation can be determined by measuring gene expression of Pax-3 and Myf-5 which are associated with proliferation of myogenic cells, and gene expression of MyoD which is associated with muscle differentiation (e.g., Amthor et al., Dev Biol. 2002, 251:241-57). It is known that GDF8 downregulates gene expression of Pax-3 and Myf-5, and prevents gene expression of MyoD. The variant ActRIIB polypeptides or test compounds are expected to antagonize this activity of GDF8. Another example of cell-based assays includes measuring the proliferation of myoblasts such as C(2)C(12) myoblasts in the presence of the ActRIIB polypeptides or test compounds (e.g., Thomas et al., J Biol Chem. 2000, 275:40235-43).

The present invention also contemplates in vivo assays to measure muscle mass and strength. For example, Whittemore et al. (Biochem Biophys Res Commun. 2003, 300: 965-71) discloses a method of measuring increased skeletal muscle mass and increased grip strength in mice. Optionally, this method can be used to determine therapeutic effects of test compounds (e.g., variant ActRIIB polypeptides) on muscle diseases or conditions, for example those diseases for which muscle mass is limiting.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone or cartilage growth. Various methods known in the art can be utilized for this purpose.

For example, the effect of the variant ActRIIB polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ActRIIB polypeptides and test compounds in mesenchymal progenitor and osteoblastic cells. To illustrate, recombinant adenoviruses expressing an ActRIIB polypeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

In certain aspects, the present invention provides methods and agents for controlling weight gain and obesity. At the cellular level, adipocyte proliferation and differentiation is critical in the development of obesity, which leads to the generation of additional fat cells (adipocytes). Therefore, any compound identified can be tested in whole cells or tissues, in vitro or in vivo, to confirm their ability to modulate adipogenesis by measuring adipocyte proliferation or differentiation. Various methods known in the art can be utilized for this purpose. For example, the effect of a variant ActRIIB polypeptide (e.g., a soluble ActRIIB polypeptide) or test compounds on adipogenesis can be determined by measuring differentiation of 3T3-L1 preadipocytes to mature adipocytes in cell based assays, such as, by observing the accumulation of triacylglycerol in Oil Red 0 staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of variant ActRIIB polypeptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189:1-7; Masuno et al., 2003, Toxicol Sci. 75:314-20.

It is understood that the screening assays of the present invention apply to not only the subject ActRIIB polypeptides and variants of the ActRIIB polypeptides, but also any test compounds including agonists and antagonist of the ActRIIB polypeptides. Further, these screening assays are useful for drug target verification and quality control purposes.

6. Exemplary Therapeutic Uses

In certain embodiments, compositions of the present invention (e.g., variant ActRIIB proteins in either homomeric or heteromeric forms) can be used for treating or preventing a disease or condition that is associated with abnormal activity of ActRIIB and/or an ActRIIB ligand (e.g., GDF8 or GDF11). These diseases, disorders or conditions are generally referred to herein as "ActRIIB-associated conditions." In certain embodiments, the present invention provides methods of treating or preventing an individual in need thereof through administering to the individual a therapeutically effective amount of a variant ActRIIB protein as described above. These methods are particularly aimed at therapeutic and prophylactic treatments of animals, and more particularly, humans. The terms "subject," an "individual," or a "patient" are interchangeable throughout the specification and generally refer to mammals. Mammals include, but are not limited to, domesticated animals (e.g., cows, sheep, cats, dogs, and horses), primates (e.g., humans and non-human primates such as monkeys), rabbits, and rodents (e.g., mice and rats).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

Endogenous complexes between ActRIIB and ActRIIB ligands play essential roles in tissue growth as well as early developmental processes such as the correct formation of various structures or in one or more post-developmental capacities including sexual development, pituitary hormone production, and creation of bone and cartilage. Thus, ActRIIB-associated conditions include abnormal tissue growth and developmental defects. In addition, ActRIIB-associated conditions include, but are not limited to, disorders of cell growth and differentiation such as inflammation, allergy, autoimmune diseases, infectious diseases, and tumors.

Exemplary ActRIIB-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes, and bone degenerative disease (e.g., osteoporosis). Other exemplary ActRIIB-associated conditions include anemia, musculodegenerative and neuromuscular disorders, tissue repair (e.g., wound healing), neurodegenerative diseases (e.g., amyotrophic lateral sclerosis), immunologic disorders (e.g., disorders related to abnormal proliferation or function of lymphocytes), and obesity or disorders related to abnormal proliferation of adipocytes.

In certain embodiments, compositions of the invention (e.g., variant ActRIIB proteins) are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject variant ActRIIB proteins include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD) (also known as Steinert's disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, studies demonstrate that blocking or eliminating function of GDF8 in vivo can effectively treat at least certain symptoms in DMD and BMD patients. Thus, the subject variant ActRIIB proteins may act as GDF8 inhibitors (antagonists), and constitute an alternative means of blocking the functions of GDF8 and/or ActRIIB in vivo in DMD and BMD patients.

Similarly, the subject variant ActRIIB proteins provide an effective means to increase muscle mass in other disease conditions that are in need of muscle growth. For example, ALS, also called Lou Gehrig's disease (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset.

Variant ActRIIB protein-induced increased muscle mass might also benefit those suffering from muscle wasting diseases. Gonzalez-Cadavid et al. (supra) reported that that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject variant ActRIIB proteins may further be used as a therapeutic agent for slowing or preventing the development of obesity and type 2 diabetes.

Cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process. Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of GDF8 in adult mice was found to induce profound muscle and fat loss analogous to that seen in human cachexia syndromes (Zimmers et al., supra), the subject variant ActRIIB proteins as pharmaceutical compositions can be beneficially used to prevent, treat, or alleviate the symptoms of the cachexia syndrome, where muscle growth is desired.

In other embodiments, the present invention provides methods of inducing bone and/or cartilage formation, preventing bone loss, increasing bone mineralization or preventing the demineralization of bone. For example, the subject variant ActRIIB proteins have application in treating osteoporosis and the healing of bone fractures and cartilage defects in humans and other animals. Variant ActRIIB proteins may be useful in patients that are diagnosed with subclinical low bone density, as a protective measure against the development of osteoporosis.

In one specific embodiment, methods and compositions of the present invention may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent contributes to the repair of congenital, trauma-induced, or oncologic resection induced craniofacial defects, and also is useful in cosmetic plastic surgery. Further, methods and compositions of the invention may be used in the treatment of periodontal disease, and in other tooth repair processes. In certain cases, the subject variant ActRIIB proteins may provide an environment to attract bone-forming cells, stimulate growth of bone-forming cells or induce differentiation of progenitors of bone-forming cells. Variant ActRIIB proteins of the invention may also be useful in the treatment of osteoporosis. Further, variant ActRIIB proteins may be used in cartilage defect repair and prevention/reversal of osteoarthritis.

In another specific embodiment, the invention provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See e.g., PCT Publication No. WO84/01106. Such compositions comprise a therapeutically effective amount of at least one of the variant ActRIIB proteins of the invention in admixture with a pharmaceutically acceptable vehicle, carrier or matrix.

In another specific embodiment, methods and variant ActRIIB proteins of the invention can be applied to conditions causing bone loss such as osteoporosis, hyperparathyroidism, Cushing's disease, thyrotoxicosis, chronic diarrheal state or malabsorption, renal tubular acidosis, or anorexia nervosa. Many people know that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In a condition known as Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones (which are produced by the thyroid gland) are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anticlotting medication; and cholestyramine (Questran) and colestipol (Colestid), used to treat high cholesterol. Gum disease causes bone loss because these harmful bacteria in our mouths force our bodies to defend against them. The bacteria produce toxins and enzymes under the gum-line, causing a chronic infection.

In a further embodiment, the variant ActRIIB proteins of the present invention provide methods and therapeutic agents for treating diseases or disorders associated with abnormal or unwanted bone growth. For example, patients having the disease known as fibrodysplasia ossificans progressiva (FOP) grow an abnormal "second skeleton" that prevents any movement. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In other embodiments, variant ActRIIB proteins of the present invention provide compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof a variant ActRIIB protein.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

In certain aspects, variant ActRIIB proteins can be used to increase red blood cell levels, treat or prevent an anemia, and/or treat or prevent ineffective erythropoiesis in a subject in need thereof. In certain aspects, a variant ActRIIB protein of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, a variant ActRIIB protein of the present disclosure can be used to treat or prevent an anemia in a subject in need thereof. In certain embodiments, a variant ActRIIB protein of the present disclosure can be used to treat or prevent ineffective erythropoiesis and/or the disorders associated with ineffective erythropoiesis in a subject in need thereof. In certain aspects, a variant ActRIIB protein of the present disclosure can be used in combination with conventional therapeutic approaches for treating or preventing an anemia or ineffective erythropoiesis disorder, particularly those used to treat anemias of multifactorial origin.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" as used herein includes amelioration or elimination of the condition once it has been established.

In either case, prevention or treatment may be discerned in the diagnosis provided by a physician or other health care provider and the intended result of administration of the therapeutic agent.

In general, treatment or prevention of a disease or condition as described in the present disclosure is achieved by administering one or more variant ActRIIB proteins of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, one or more variant ActRIIB proteins of the disclosure, optionally combined with an EPO receptor activator, may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with one or more variant ActRIIB proteins to increase red blood cell levels, and then blood is drawn and stored for later use in transfusions.

One or more variant ActRIIB proteins of the disclosure, optionally combined with an EPO receptor activator, may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, New York, pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or autoantibodies and/or for religious reasons (e.g., some Jehovah's Witnesses); infections (e.g., malaria and osteomyelitis); hemoglobinopathies including, for example, sickle cell disease (anemia), thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, New York, pp 628-634]. In some embodiments, one or more variant ActRIIB proteins of the disclosure could be used to treat or prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more variant ActRIIB proteins of the disclosure, optionally combined with an EPO receptor activator, could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more variant ActRIIB proteins of the disclosure, optionally combined with an EPO receptor activator, could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more variant ActRIIB proteins, optionally combined with an EPO receptor activator, could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more variant ActRIIB proteins, optionally combined with an EPO receptor activator, could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, New York, pp 628-634]. Appropriate therapy for iron-deficiency anemia depends on its cause and severity, with oral iron preparations, parenteral iron formulations, and RBC transfusion as major conventional options. In some embodiments, one or more variant ActRIIB proteins of the disclosure, optionally combined with an EPO receptor activator, could be used to treat a chronic iron-deficiency.

Myelodysplastic syndrome (MDS) is a diverse collection of hematological conditions characterized by ineffective production of myeloid blood cells and risk of transformation to acute myelogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effects due to frequency of such therapies. For example, patients who receive frequent red blood cell transfusion can exhibit tissue and organ damage from the buildup of extra iron. Accordingly, one or more variant ActRIIB proteins of the disclosure, may be used to treat patients having MDS. In certain embodiments, patients suffering from MDS may be treated using one or more variant ActRIIB proteins of the disclosure, optionally in combination with an EPO receptor activator. In other embodiments, a patient suffering from MDS may be treated using a combination of one or more variant ActRIIB proteins of the disclosure and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow [Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, a variant ActRIIB protein of the present disclosure may break the aforementioned cycle and thus alleviate not only the underlying anemia but also the associated complications of elevated erythropoietin levels, splenomegaly, bone pathology, and tissue iron overload. In some embodiments, one or more variant ActRIIB proteins can be used to treat or prevent ineffective erythropoiesis, including anemia and elevated EPO levels as well as complications such as splenomegaly, erythroblast-induced bone pathology, iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudo-tumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):S16-S19], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. In certain embodiments, one or more variant ActRIIB proteins of the disclosure, optionally combined with an EPO receptor activator, can be used to treat or prevent a thalassemia syndrome.

In some embodiments, one or more variant ActRIIB proteins of the disclosure, optionally combined with an EPO receptor activator, can be used for treating disorders of ineffective erythropoiesis besides thalassemia syndromes. Such disorders include siderblastic anemia (inherited or acquired); dyserythropoietic anemia (types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and lead poisoning.

In certain embodiments, one or more variant ActRIIB proteins of the disclosure may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more variant ActRIIB proteins of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more variant ActRIIB proteins of the disclosure may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of β-thalassemia [Gardenghi et al. (2010) J Clin Invest 120: 4466-4477].

One or more variant ActRIIB proteins of the disclosure, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more variant ActRIIB proteins of the disclosure and a EPO receptor activator. In certain embodiments, one or more variant ActRIIB proteins of the disclosure may be used in combination with EPO receptor activators to reduce the required dose of these activators in patients that are susceptible to adverse effects of EPO. These methods may be used for therapeutic and prophylactic treatments of a patient.

One or more variant ActRIIB proteins of the disclosure may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that variant ActRIIB proteins of the present disclosure act by a different mechanism than EPO, these antagonists may be useful for increasing red blood cell and hemoglobin levels in patients that do not respond well to EPO. For example, an antagonist of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more variant ActRIIB proteins of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more variant ActRIIB proteins of the disclosure may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more variant ActRIIB proteins of the disclosure, then onset of administration of the one or more variant ActRIIB proteins of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more variant ActRIIB proteins of the disclosure may be delayed until the levels have returned to a normal or acceptable level.

In certain embodiments, if one or more hematologic parameters are outside the normal range or on the high side of normal in a patient who is a candidate to be treated with one or more variant ActRIIB proteins of the disclosure, then the onset of administration may not be delayed. However, the dosage amount or frequency of dosing of the one or more variant ActRIIB proteins of the disclosure may be set at an amount that would reduce the risk of an unacceptable increase in the hematologic parameters arising upon administration of the one or more variant ActRIIB proteins of the disclosure. Alternatively, a therapeutic regimen may be developed for the patient that combines one or more variant ActRIIB proteins of the disclosure with a therapeutic agent that addresses the undesirable level of the hematologic parameter. For example, if the patient has elevated blood pressure, then a therapeutic regimen involving administration of one or more variant ActRIIB proteins of the disclosure and a blood pressure-lowering agent may be designed. For a patient having lower than desired iron stores, a therapeutic regimen of one or more variant ActRIIB proteins and iron supplementation may be developed.

In one embodiment, baseline parameter(s) for one or more hematologic parameters may be established for a patient who is a candidate to be treated with one or more variant ActRIIB proteins of the disclosure and an appropriate dosing regimen established for that patient based on the baseline value(s). Alternatively, established baseline parameters based on a patient's medical history could be used to inform an appropriate antagonist-dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more variant ActRIIB proteins of the disclosure may also be used as the relevant comparative values for monitoring any changes to the hematologic parameters during treatment with the one or more antagonists of the disclosure.

In certain embodiments, one or more hematologic parameters are measured in patients who are being treated with a one or more variant ActRIIB proteins of the disclosure. The hematologic parameters may be used to monitor the patient during treatment and permit adjustment or termination of the dosing with the one or more antagonists of the disclosure or additional dosing with another therapeutic agent. For example, if administration of one or more variant ActRIIB proteins of the disclosure results in an increase in blood pressure, red blood cell level, or hemoglobin level, or a reduction in iron stores, then the dose of the one or more variant ActRIIB proteins of the disclosure may be reduced in amount or frequency in order to decrease the effects of the one or more variant ActRIIB proteins of the disclosure on the one or more hematologic parameters. If administration of one or more variant ActRIIB proteins of the disclosure results in a change in one or more hematologic parameters that is adverse to the patient, then the dosing of the one or more variant ActRIIB proteins of the disclosure may be terminated either temporarily, until the hematologic parameter(s) return to an acceptable level, or permanently. Similarly, if one or more hematologic parameters are not brought within an acceptable range after reducing the dose or frequency of administration of the one or more variant ActRIIB proteins of the disclosure, then the dosing may be terminated. As an alternative, or in addition to, reducing or terminating the dosing with the one or more variant ActRIIB proteins of the disclosure, the patient may be dosed with an additional therapeutic agent that addresses the undesirable level in the hematologic parameter(s), such as, for example, a blood pressure-lowering agent or an iron supplement. For example, if a patient being treated with one or more variant ActRIIB proteins of the disclosure has elevated blood pressure, then dosing with the one or more variant ActRIIB proteins of the disclosure may continue at the same level and a blood pressure-lowering agent is added to the treatment regimen, dosing with the one or more variant ActRIIB proteins of the disclosure may be reduced (e.g., in amount and/or frequency) and a blood pressure-lowering agent is added to the treatment regimen, or dosing with the one or more variant ActRIIB proteins of the disclosure may be terminated and the patient may be treated with a blood pressure-lowering agent.

7 Pharmaceutical Compositions

In certain embodiments, compounds of the present invention (e.g., variant ActRIIB proteins in either homomeric or heteromeric forms) are formulated with a pharmaceutically acceptable carrier. For example, a variant ActRIIB protein can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having a tissue damage. Topical administration may be suitable for wound healing and tissue repair. Therapeutically useful agents other than the variant ActRIIB proteins which may also optionally be included in the composition as described above, may alternatively or additionally, be administered simultaneously or sequentially with the subject compounds (e.g., variant ActRIIB proteins) in the methods of the invention.

In certain embodiments, compositions of the present invention may include a matrix capable of delivering one or more therapeutic compounds (e.g., variant ActRIIB proteins) to a target tissue site, providing a structure for the developing tissue and optimally capable of being resorbed into the body. For example, the matrix may provide slow release of the variant ActRIIB proteins. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, variant ActRIIB proteins of the invention can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more variant ActRIIB proteins of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., a variant ActRIIB protein), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more variant ActRIIB proteins in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., variant ActRIIB proteins). The various factors will depend upon the disease to be treated. In the case of muscle disorders, factors may include, but are not limited to, amount of muscle mass desired to be formed, the muscles most affected by disease, the condition of the deteriorated muscle, the patient's age, sex, and diet, time of administration, and other clinical factors. The addition of other known growth factors to the final composition, may also affect the dosage. Progress can be monitored by periodic assessment of muscle growth and/or repair, for example, by strength testing, MRI assessment of muscle size and analysis of muscle biopsies.

In certain embodiments of the invention, one or more variant ActRIIB proteins can be administered, together (simultaneously) or at different times (sequentially or overlapping). In addition, variant ActRIIB proteins can be administered with another type of therapeutic agents, for example, a cartilage-inducing agent, a bone-inducing agent, a muscle-inducing agent, a fat-reducing, or a neuron-inducing agent. The two types of compounds may be administered simultaneously or at different times. It is expected that the variant ActRIIB proteins of the invention may act in concert with or perhaps synergistically with another therapeutic agent.

In a specific example, a variety of osteogenic, cartilage-inducing and bone-inducing factors have been described, particularly bisphosphonates. See e.g., European Patent Application Nos. 148,155 and 169,016. For example, other factors that can be combined with the subject variant ActRIIB proteins include various growth factors such as epidermal growth factor (EGF), platelet derived growth factor (PDGF), transforming growth factors (TGF-α and TGF-β), and insulin-like growth factor (IGF).

In certain embodiments, the present invention also provides gene therapy for the in vivo production of variant ActRIIB proteins. Such therapy would achieve its therapeutic effect by introduction of the variant ActRIIB polynucleotide sequences into cells or tissues having the disorders as listed above. Delivery of variant ActRIIB polynucleotide sequences can be achieved using a recombinant expression vector such as a chimeric virus or a colloidal dispersion system. Preferred for therapeutic delivery of variant ActRIIB polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the variant ActRIIB polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for variant ActRIIB polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ActRIIB-Fc Fusion Protein

Applicants constructed a soluble ActRIIB fusion protein that has the extracellular domain of human ActRIIB fused to a human G1Fc domain with a minimal linker (three glycine amino acids) in between. The construct is referred to as ActRIIB-G1Fc.

ActRIIB-G1Fc is shown below in SEQ ID NO: 5 (with the linker underlined) as purified from CHO cell lines:

```
                                          (SEQ ID NO: 5)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPTGGGTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSF

FLYSKLTVDKSRWQQGNVFSCSVMHEALHNHYTQKSLSLSPGK
```

The ActRIIB-G1Fc protein was expressed in CHO cell lines. Three different leader sequences were considered:

```
    (i) Honey bee mellitin (HBML):
                                          (SEQ ID NO: 7)
    MKFLVNVALVFMVVYISYIYA (ii) Tissue plasminogen activator (TPA):
                                          (SEQ ID NO: 8)
    MDAMKRGLCCVLLLCGAVFVSP (iii) Native:
                                          (SEQ ID NO: 9)
    MTAPWVALALLWGSLCAG.
```

The selected form employs the TPA leader and has the following unprocessed amino acid sequence:

```
                                          (SEQ ID NO: 6)
MDAMKRGLCCVLLLCGAVFVSPGASGRGEAETRECIYYNANWELERTNQS

GLERCEGEQDKRLHCYASWRNSSGTIELVKKGCWLDDFNCYDRQECVATE

ENPQVYFCCCEGNFCNERFTHLPEAGGPEVTYEPPPTAPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLICLVKGFYPSDIAV

EWESNGQPENNYKTTPPVLDSDGSFFLYSKLTVDKSRWQQGNVFSCSVMH

EALHNHYTQKSLSLSPGK
```

This polypeptide is encoded by the following nucleic acid sequence (SEQ ID NO: 10):

```
                                          (SEQ ID NO: 10)
A TGGATGCAAT GAAGAGAGGG CTCTGCTGTG TGCTGCTGCT

GTGTGGAGCA GTCTTCGTTT CGCCCGGCGC CTCTGGGCGT

GGGGAGGCTG AGACACGGGA GTGCATCTAC TACAACGCCA

ACTGGGAGCT GGAGCGCACC AACCAGAGCG GCCTGGAGCG

CTGCGAAGGC GAGCAGGACA AGCGGCTGCA CTGCTACGCC

TCCTGGCGCA ACAGCTCTGG CACCATCGAG CTCGTGAAGA

AGGGCTGCTG GCTAGATGAC TTCAACTGCT ACGATAGGCA

GGAGTGTGTG GCCACTGAGG AGAACCCCCA GGTGTACTTC

TGCTGCTGTG AAGGCAACTT CTGCAACGAG CGCTTCACTC

ATTTGCCAGA GGCTGGGGGC CCGGAAGTCA CGTACGAGCC

ACCCCCGACA GCCCCCACCG GTGGTGGAAC TCACACATGC

CCACCGTGCC CAGCACCTGA ACTCCTGGGG GGACCGTCAG

TCTTCCTCTT CCCCCCAAAA CCCAAGGACA CCCTCATGAT

CTCCCGGACC CCTGAGGTCA CATGCGTGGT GGTGGACGTG

AGCCACGAAG ACCCTGAGGT CAAGTTCAAC TGGTACGTGG

ACGGCGTGGA GGTGCATAAT GCCAAGACAA AGCCGCGGGA

GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG CCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

N-terminal sequencing of the CHO-cell produced material revealed a major sequence of -GRGEAE (SEQ ID NO: 11). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

The ActRIIB-Fc fusion protein was also expressed in HEK293 cells and COS cells. Although material from all cell lines and reasonable culture conditions provided protein with muscle-building activity in vivo, variability in potency was observed perhaps relating to cell line selection and/or culture conditions.

Example 2: Generation of Variant ActRIIB-Fc Proteins

Applicants generated a series of mutations (sequence variations) in the extracellular domain of ActRIIB and produced these variant polypeptides as soluble homodimeric fusion proteins comprising a variant ActRIIB extracellular domain and an Fc domain joined by an optional linker. The background ActRIIB-Fc fusion was ActRIIB-G1Fc as shown in SEQ ID NO: 5

Various substitution mutations were introduced into the background ActRIIB-Fc protein. Based on the data presented in Example 1, it is expected that these constructs, if expressed with a TPA leader, will lack the N-terminal serine.

Mutations were generated in the ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into *E. coli* DH5 alpha, colonies were picked and DNAs were isolated. For murine constructs (mFc), a murine IgG2a was substituted for the human IgG1. All mutants were sequence verified.

The amino acid sequence of unprocessed ActRIIB (K55A)-G1Fc is shown below (SEQ ID NO: 31). The signal sequence and linker sequence are indicated by solid underline, and the K55A substitution is indicated by double underline. The amino acid sequence of SEQ ID NO:31 may optionally be provided with the lysine removed from the C-terminus.

```
                                              (SEQ ID NO: 31)
  1 MDAMKRGLCC VLLLCGAVFV SPGASGRGEA ETRECIYYNA
    NWELERTNQS

51 GLERCEGEQD ARLHCYASWR NSSGTIELVK KGCWLDDFNC
    YDRQECVATE

101 ENPQVYFCCC EGNFCNERFT HLPEAGGPEV TYEPPPTAPT
    GGGTHTCPPC

151 PAPELLGGPS VFLFPPKPKD TLMISRTPEV TCVVVDVSHE
    DPEVKFNWYV

201 DGVEVHNAKT KPREEQYNST YRVVSVLTVL HQDWLNGKEY
    KCKVSNKALP

251 APIEKTISKA KGQPREPQVY TLPPSREEMT KNQVSLTCLV
    KGFYPSDIAV

301 EWESNGQPEN NYKTTPPVLD SDGSFFLYSK LTVDKSRWQQ
    GNVFSCSVMH

351 EALHNHYTQK SLSLSPGK
```

This ActRIIB(K55A)-G1Fc fusion polypeptide is encoded by the following nucleic acid sequence (SEQ ID NO: 32):

```
                                              (SEQ ID NO: 32)
  1 ATGGATGCAA TGAAGAGAGG GCTCTGCTGT GTGCTGCTGC
    TGTGTGGAGC

51 AGTCTTCGTT TCGCCCGGCG CCTCTGGGCG TGGGGAGGCT
    GAGACACGGG

101 AGTGCATCTA CTACAACGCC AACTGGGAGC TGGAGCGCAC
    CAACCAGAGC

151 GGCCTGGAGC GCTGCGAAGG CGAGCAGGAC GCCCGGCTGC
    ACTGCTACGC

201 CTCCTGGCGC AACAGCTCTG GCACCATCGA GCTCGTGAAG
    AAGGGCTGCT

251 GGCTAGATGA CTTCAACTGC TACGATAGGC AGGAGTGTGT
    GGCCACTGAG

301 GAGAACCCCC AGGTGTACTT CTGCTGCTGT GAAGGCAACT
    TCTGCAACGA

351 GCGCTTCACT CATTTGCCAG AGGCTGGGGG CCCGGAAGTC
    ACGTACGAGC

401 CACCCCCGAC AGCCCCCACC GGTGGTGGAA CTCACACATG
    CCCACCGTGC
```

```
                        -continued
451 CCAGCACCTG AACTCCTGGG GGGACCGTCA GTCTTCCTCT
    TCCCCCCAAA

501 ACCCAAGGAC ACCCTCATGA TCTCCCGGAC CCCTGAGGTC
    ACATGCGTGG

551 TGGTGGACGT GAGCCACGAA GACCCTGAGG TCAAGTTCAA
    CTGGTACGTG

601 GACGGCGTGG AGGTGCATAA TGCCAAGACA AAGCCGCGGG
    AGGAGCAGTA

651 CAACAGCACG TACCGTGTGG TCAGCGTCCT CACCGTCCTG
    CACCAGGACT

701 GGCTGAATGG CAAGGAGTAC AAGTGCAAGG TCTCCAACAA
    AGCCCTCCCA

751 GCCCCCATCG AGAAAACCAT CTCCAAAGCC AAAGGGCAGC
    CCCGAGAACC

801 ACAGGTGTAC ACCCTGCCCC CATCCCGGGA GGAGATGACC
    AAGAACCAGG

851 TCAGCCTGAC CTGCCTGGTC AAAGGCTTCT ATCCCAGCGA
    CATCGCCGTG

901 GAGTGGGAGA GCAATGGGCA GCCGGAGAAC AACTACAAGA
    CCACGCCTCC

951 CGTGCTGGAC TCCGACGGCT CCTTCTTCCT CTATAGCAAG
    CTCACCGTGG

1001 ACAAGAGCAG GTGGCAGCAG GGGAACGTCT TCTCATGCTC
     CGTGATGCAT

1051 GAGGCTCTGC ACAACCACTA CACGCAGAAG AGCCTCTCCC
     TGTCCCCGGG

1101 TAAA
```

The mature ActRIIB(K55A)-G1Fc fusion polypeptide (SEQ ID NO: 33) is as follows and may optionally be provided with the lysine removed from the C-terminus.

```
                                              (SEQ ID NO: 33)
  1 GRGEAETREC IYYNANWELE RTNQSGLERC EGEQDARLHC
    YASWRNSSGT

51 IELVKKGCWL DDFNCYDRQE CVATEENPQV YFCCCEGNFC
    NERFTHLPEA

101 GGPEVTYEPP PTAPTGGGTH TCPPCPAPEL LGGPSVFLFP
    PKPKDTLMIS

151 RTPEVTCVVV DVSHEDPEVK FNWYVDGVEV HNAKTKPREE
    QYNSTYRVVS

201 VLTVLHQDWL NGKEYKCKVS NKALPAPIEK TISKAKGQPR
    EPQVYTLPPS

251 REEMTKNQVS LTCLVKGFYP SDIAVEWESN GQPENNYKTT
    PPVLDSDGSF

301 FLYSKLTVDK SRWQQGNVFS CSVMHEALHN HYTQKSLSLS
    PGK
```

The amino acid sequence of unprocessed ActRIIB (K55E)-G1Fc is shown below (SEQ ID NO: 34). The signal sequence and linker sequence are indicated by solid underline, and the K55E substitution is indicated by double underline. The amino acid sequence of SEQ ID NO:34 may optionally be provided with the lysine removed from the C-terminus.

```
                                        (SEQ ID NO: 34)
  1  MDAMKRGLCC VLLLCGAVFV SPGASGRGEA ETRECIYYNA
     NWELERTNQS

51  GLERCEGEQD ERLHCYASWR NSSGTIELVK KGCWLDDFNC
     YDRQECVATE

101  ENPQVYFCCC EGNFCNERFT HLPEAGGPEV TYEPPPTAPT
     GGGTHTCPPC

151  PAPELLGGPS VFLFPPKPKD TLMISRTPEV TCVVVDVSHE
     DPEVKFNWYV

201  DGVEVHNAKT KPREEQYNST YRVVSVLTVL HQDWLNGKEY
     KCKVSNKALP

251  APIEKTISKA KGQPREPQVY TLPPSREEMT KNQVSLTCLV
     KGFYPSDIAV

301  EWESNGQPEN NYKTTPPVLD SDGSFFLYSK LTVDKSRWQQ
     GNVFSCSVMH

351  EALHNHYTQK SLSLSPGK
```

This ActRIIB(K55E)-G1Fc fusion polypeptide is encoded by the following nucleic acid sequence (SEQ ID NO: 35):

```
                                        (SEQ ID NO: 35)
  1  ATGGATGCAA TGAAGAGAGG GCTCTGCTGT GTGCTGCTGC
     TGTGTGGAGC

51  AGTCTTCGTT TCGCCCGGCG CCTCTGGGCG TGGGGAGGCT
     GAGACACGGG

101  AGTGCATCTA CTACAACGCC AACTGGGAGC TGGAGCGCAC
     CAACCAGAGC

151  GGCCTGGAGC GCTGCGAAGG CGAGCAGGAC GAGCGGCTGC
     ACTGCTACGC

201  CTCCTGGCGC AACAGCTCTG GCACCATCGA GCTCGTGAAG
     AAGGGCTGCT

251  GGCTAGATGA CTTCAACTGC TACGATAGGC AGGAGTGTGT
     GGCCACTGAG

301  GAGAACCCCC AGGTGTACTT CTGCTGCTGT GAAGGCAACT
     TCTGCAACGA

351  GCGCTTCACT CATTTGCCAG AGGCTGGGGG CCCGGAAGTC
     ACGTACGAGC

401  CACCCCCGAC AGCCCCCACC GGTGGTGGAA CTCACACATG
     CCCACCGTGC

451  CCAGCACCTG AACTCCTGGG GGGACCGTCA GTCTTCCTCT
     TCCCCCCAAA

501  ACCCAAGGAC ACCCTCATGA TCTCCCGGAC CCCTGAGGTC
     ACATGCGTGG

551  TGGTGGACGT GAGCCACGAA GACCCTGAGG TCAAGTTCAA
     CTGGTACGTG

601  GACGGCGTGG AGGTGCATAA TGCCAAGACA AAGCCGCGGG
     AGGAGCAGTA

651  CAACAGCACG TACCGTGTGG TCAGCGTCCT CACCGTCCTG
     CACCAGGACT

701  GGCTGAATGG CAAGGAGTAC AAGTGCAAGG TCTCCAACAA
     AGCCCTCCCA

751  GCCCCCATCG AGAAAACCAT CTCCAAAGCC AAAGGGCAGC
     CCCGAGAACC

801  ACAGGTGTAC ACCCTGCCCC CATCCCGGGA GGAGATGACC
     AAGAACCAGG

851  TCAGCCTGAC CTGCCTGGTC AAAGGCTTCT ATCCCAGCGA
     CATCGCCGTG

901  GAGTGGGAGA GCAATGGGCA GCCGGAGAAC AACTACAAGA
     CCACGCCTCC

951  CGTGCTGGAC TCCGACGGCT CCTTCTTCCT CTATAGCAAG
     CTCACCGTGG

1001 ACAAGAGCAG GTGGCAGCAG GGGAACGTCT TCTCATGCTC
     CGTGATGCAT

1051 GAGGCTCTGC ACAACCACTA CACGCAGAAG AGCCTCTCCC
     TGTCCCCGGG

1101 TAAA
```

The mature ActRIIB(K55E)-G1Fc fusion polypeptide (SEQ ID NO: 36) is as follows and may optionally be provided with the lysine removed from the C-terminus.

```
                                        (SEQ ID NO: 36)
  1  GRGEAETREC IYYNANWELE RTNQSGLERC EGEQDERLHC
     YASWRNSSGT

51  IELVKKGCWL DDFNCYDRQE CVATEENPQV YFCCCEGNFC
     NERFTHLPEA

101  GGPEVTYEPP PTAPTGGGTH TCPPCPAPEL LGGPSVFLFP
     PKPKDTLMIS

151  RTPEVTCVVV DVSHEDPEVK FNWYVDGVEV HNAKTKPREE
     QYNSTYRVVS

201  VLTVLHQDWL NGKEYKCKVS NKALPAPIEK TISKAKGQPR
     EPQVYTLPPS

251  REEMTKNQVS LTCLVKGFYP SDIAVEWESN GQPENNYKTT
     PPVLDSDGSF

301  FLYSKLTVDK SRWQQGNVFS CSVMHEALHN HYTQKSLSLS
     PGK
```

The amino acid sequence of unprocessed ActRIIB(F82I)-G1Fc is shown below (SEQ ID NO: 37). The signal sequence and linker sequence are indicated by solid underline, and the F82I substitution is indicated by double underline. The amino acid sequence of SEQ ID NO: 37 may optionally be provided with the lysine removed from the C-terminus.

```
                                        (SEQ ID NO: 37)
  1  MDAMKRGLCC VLLLCGAVFV SPGASGRGEA ETRECIYYNA
     NWELERTNQS

51  GLERCEGEQD KRLHCYASWR NSSGTIELVK KGCWLDDINC
     YDRQECVATE

101  ENPQVYFCCC EGNFCNERFT HLPEAGGPEV TYEPPPTAPT
     GGGTHTCPPC

151  PAPELLGGPS VFLFPPKPKD TLMISRTPEV TCVVVDVSHE
     DPEVKFNWYV

201  DGVEVHNAKT KPREEQYNST YRVVSVLTVL HQDWLNGKEY
     KCKVSNKALP

251  APIEKTISKA KGQPREPQVY TLPPSREEMT KNQVSLTCLV
     KGFYPSDIAV

301  EWESNGQPEN NYKTTPPVLD SDGSFFLYSK LTVDKSRWQQ
     GNVFSCSVMH

351  EALHNHYTQK SLSLSPGK
```

This ActRIIB(F82I)-G1Fc fusion polypeptide is encoded by the following nucleic acid sequence (SEQ ID NO: 38):

```
                                           (SEQ ID NO: 38)
   1 ATGGATGCAA TGAAGAGAGG GCTCTGCTGT GTGCTGCTGC
     TGTGTGGAGC

51 AGTCTTCGTT TCGCCCGGCG CCTCTGGGCG TGGGGAGGCT
     GAGACACGGG

101 AGTGCATCTA CTACAACGCC AACTGGGAGC TGGAGCGCAC
     CAACCAGAGC

151 GGCCTGGAGC GCTGCGAAGG CGAGCAGGAC AAGCGGCTGC
     ACTGCTACGC

201 CTCCTGGCGC AACAGCTCTG GCACCATCGA GCTCGTGAAG
     AAGGGCTGCT

251 GGCTAGATGA CATCAACTGC TACGATAGGC AGGAGTGTGT
     GGCCACTGAG

301 GAGAACCCCC AGGTGTACTT CTGCTGCTGT GAAGGCAACT
     TCTGCAACGA

351 GCGCTTCACT CATTTGCCAG AGGCTGGGGG CCCGGAAGTC
     ACGTACGAGC

401 CACCCCCGAC AGCCCCCACC GGTGGTGGAA CTCACACATG
     CCCACCGTGC

451 CCAGCACCTG AACTCCTGGG GGGACCGTCA GTCTTCCTCT
     TCCCCCCAAA

501 ACCCAAGGAC ACCCTCATGA TCTCCCGGAC CCCTGAGGTC
     ACATGCGTGG

551 TGGTGGACGT GAGCCACGAA GACCCTGAGG TCAAGTTCAA
     CTGGTACGTG

601 GACGGCGTGG AGGTGCATAA TGCCAAGACA AAGCCGCGGG
     AGGAGCAGTA

651 CAACAGCACG TACCGTGTGG TCAGCGTCCT CACCGTCCTG
     CACCAGGACT

701 GGCTGAATGG CAAGGAGTAC AAGTGCAAGG TCTCCAACAA
     AGCCCTCCCA

751 GCCCCCATCG AGAAAACCAT CTCCAAAGCC AAAGGGCAGC
     CCCGAGAACC

801 ACAGGTGTAC ACCCTGCCCC CATCCCGGGA GGAGATGACC
     AAGAACCAGG

851 TCAGCCTGAC CTGCCTGGTC AAAGGCTTCT ATCCCAGCGA
     CATCGCCGTG

901 GAGTGGGAGA GCAATGGGCA GCCGGAGAAC AACTACAAGA
     CCACGCCTCC

951 CGTGCTGGAC TCCGACGGCT CCTTCTTCCT CTATAGCAAG
     CTCACCGTGG

1001 ACAAGAGCAG GTGGCAGCAG GGGAACGTCT TCTCATGCTC
     CGTGATGCAT

1051 GAGGCTCTGC ACAACCACTA CACGCAGAAG AGCCTCTCCC
     TGTCTCCGGG

1101 TAAA
```

The mature ActRIIB(F82I)-G1Fc fusion polypeptide (SEQ ID NO: 39) is as follows and may optionally be provided with the lysine removed from the C-terminus.

```
                                            (SEQ ID NO: 39)
   1 GRGEAETREC IYYNANWELE RTNQSGLERC EGEQDKRLHC
     YASWRNSSGT

51 IELVKKGCWL DDINCYDRQE CVATEENPQV YFCCCEGNFC
     NERFTHLPEA

101 GGPEVTYEPP PTAPTGGGTH TCPPCPAPEL LGGPSVFLFP
     PKPKDTLMIS

151 RTPEVTCVVV DVSHEDPEVK FNWYVDGVEV HNAKTKPREE
     QYNSTYRVVS

201 VLTVLHQDWL NGKEYKCKVS NKALPAPIEK TISKAKGQPR
     EPQVYTLPPS

251 REEMTKNQVS LTCLVKGFYP SDIAVEWESN GQPENNYKTT
     PPVLDSDGSF

301 FLYSKLTVDK SRWQQGNVFS CSVMHEALHN HYTQKSLSLS
     PGK
```

The amino acid sequence of unprocessed ActRIIB (F82K)-G1Fc is shown below (SEQ ID NO: 40). The signal sequence and linker sequence are indicated by solid underline, and the F82K substitution is indicated by double underline. The amino acid sequence of SEQ ID NO: 40 may optionally be provided with the lysine removed from the C-terminus.

```
                                            (SEQ ID NO: 40)
   1 MDAMKRGLCC VLLLCGAVFV SPGASGRGEA ETRECIYYNA
     NWELERTNQS

51 GLERCEGEQD KRLHCYASWR NSSGTIELVK KGCWLDDKNC
     YDRQECVATE

101 ENPQVYFCCC EGNFCNERFT HLPEAGGPEV TYEPPPTAPT
     GGGTHTCPPC

151 PAPELLGGPS VFLFPPKPKD TLMISRTPEV TCVVVDVSHE
     DPEVKFNWYV

201 DGVEVHNAKT KPREEQYNST YRVVSVLTVL HQDWLNGKEY
     KCKVSNKALP

251 APIEKTISKA KGQPREPQVY TLPPSREEMT KNQVSLTCLV
     KGFYPSDIAV

301 EWESNGQPEN NYKTTPPVLD SDGSFFLYSK LTVDKSRWQQ
     GNVFSCSVMH

351 EALHNHYTQK SLSLSPGK
```

This ActRIIB(F82K)-G1Fc fusion polypeptide is encoded by the following nucleic acid sequence (SEQ ID NO: 41):

```
                                            (SEQ ID NO: 41)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC
```

-continued

```
 201 CTCCTGGCGC AACAGCTCTG GCACCATCGA GCTCGTGAAG AAGGGCTGCT
 251 GGCTAGATGA CAAGAACTGC TACGATAGGC AGGAGTGTGT GGCCACTGAG
 301 GAGAACCCCC AGGTGTACTT CTGCTGCTGT GAAGGCAACT TCTGCAACGA
 351 GCGCTTCACT CATTTGCCAG AGGCTGGGGG CCCGGAAGTC ACGTACGAGC
 401 CACCCCCGAC AGCCCCCACC GGTGGTGGAA CTCACACATG CCCACCGTGC
 451 CCAGCACCTG AACTCCTGGG GGGACCGTCA GTCTTCCTCT TCCCCCCAAA
 501 ACCCAAGGAC ACCCTCATGA TCTCCCGGAC CCCTGAGGTC ACATGCGTGG
 551 TGGTGGACGT GAGCCACGAA GACCCTGAGG TCAAGTTCAA CTGGTACGTG
 601 GACGGCGTGG AGGTGCATAA TGCCAAGACA AAGCCGCGGG AGGAGCAGTA
 651 CAACAGCACG TACCGTGTGG TCAGCGTCCT CACCGTCCTG CACCAGGACT
 701 GGCTGAATGG CAAGGAGTAC AAGTGCAAGG TCTCCAACAA AGCCCTCCCA
 751 GCCCCCATCG AGAAAACCAT CTCCAAAGCC AAAGGGCAGC CCCGAGAACC
 801 ACAGGTGTAC ACCCTGCCCC CATCCCGGGA GGAGATGACC AAGAACCAGG
 851 TCAGCCTGAC CTGCCTGGTC AAAGGCTTCT ATCCCAGCGA CATCGCCGTG
 901 GAGTGGGAGA GCAATGGGCA GCCGGAGAAC AACTACAAGA CCACGCCTCC
 951 CGTGCTGGAC TCCGACGGCT CCTTCTTCCT CTATAGCAAG CTCACCGTGG
1001 ACAAGAGCAG GTGGCAGCAG GGGAACGTCT TCTCATGCTC CGTGATGCAT
1051 GAGGCTCTGC ACAACCACTA CACGCAGAAG AGCCTCTCCC TGTCTCCGGG
1101 TAAA
```

The mature ActRIIB(F82K)-G1Fc fusion polypeptide (SEQ ID NO: 42) is as follows and may optionally be provided with the lysine removed from the C-terminus.

(SEQ ID NO: 42)
```
  1 GRGEAETREC IYYNANWELE RTNQSGLERC EGEQDKRLHC YASWRNSSGT

51 IELVKKGCWL DDKNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYKTT PPVLDSDGSF

301 FLYSKLTVDK SRWQQGNVFS CSVMHEALHN HYTQKSLSLS PGK
```

Constructs were expressed in COS or CHO cells and purified by filtration and protein A chromatography. In some instances, assays were performed with conditioned medium rather than purified proteins. Purity of samples for reporter gene assays was evaluated by SDS-PAGE and Western blot analysis.

Mutants were tested in binding assays and/or bioassays described below.

Alternatively, similar mutations could be introduced into an ActRIIB extracellular domain possessing an N-terminal truncation of five amino acids and a C-terminal truncation of three amino acids as shown below (SEQ ID NO: 53). This truncated ActRIIB extracellular domain is denoted ActRIIB (25-131) based on numbering in SEQ ID NO: 2.

```
                                                      (SEQ ID NO: 53)
 25 ETRECIYYNA NWELERTNQS GLERCEGEQD KRLHCYASWR NSSGTIELVK

75 KGCWLDDFNC YDRQECVATE ENPQVYFCCC EGNFCNERFT HLPEAGGPEV

125 TYEPPPT
```

The corresponding background fusion polypeptide, ActRIIB(25-131)-G1Fc, is shown below (SEQ ID NO: 12).

```
                                                      (SEQ ID NO: 12)
  1 ETRECIYYNA NWELERTNQS GLERCEGEQD KRLHCYASWR NSSGTIELVK

51 KGCWLDDFNC YDRQECVATE ENPQVYFCCC EGNFCNERFT HLPEAGGPEV

101 TYEPPPTGGG THTCPPCPAP ELLGGPSVFL FPPKPKDTLM ISRTPEVTCV

151 VVDVSHEDPE VKFNWYVDGV EVHNAKTKPR EEQYNSTYRV VSVLTVLHQD

201 WLNGKEYKCK VSNKALPAPI EKTISKAKGQ PREPQVYTLP PSREEMTKNQ

251 VSLTCLVKGF YPSDIAVEWE SNGQPENNYK TTPPVLDSDG SFFLYSKLTV

301 DKSRWQQGNV FSCSVMHEAL HNHYTQKSLS LSPGK
```

Example 3. Activity of Variant ActRIIB-Fc Proteins in a Cell-Based Assay

An A204 cell-based assay was used to compare effects among variant ActRIIB-Fc proteins on signaling by activin A, GDF11, and BMP9. In brief, this assay uses a human A204 rhabdomyosarcoma cell line (ATCC®: HTB-82™) derived from muscle and the reporter vector pGL3(CAGA) 12 (Dennler et al., 1998, EMBO 17: 3091-3100) as well as a *Renilla* reporter plasmid (pRLCMV) to control for transfection efficiency. The CAGA12 motif is present in TGF-β responsive genes (e.g., PAI-1 gene), so this vector is of general use for ligands that can signal through Smad2/3, including activin A, GDF11, and BMP9.

On day 1, A-204 cells were transferred into one or more 48-well plates. On day 2, these cells were transfected with 10 μg pGL3(CAGA)12 or pGL3(CAGA)12(10 μg)+ pRLCMV (1 μg) and Fugene. On day 3, ligands diluted in medium containing 0.1% BSA were preincubated with ActRIIB-Fc proteins for 1 hr before addition to cells. Approximately six hour later, the cells were rinsed with PBS and lysed. Cell lysates were analyzed in a luciferase assay to determine the extent of Smad activation.

This assay was used to screen variant ActRIIB-Fc proteins for inhibitory effects on cell signaling by activin A, GDF11, and BMP9. Potencies of homodimeric Fc fusion proteins incorporating amino acid substitutions in the human ActRIIB extracellular domain were compared with that of an Fc fusion protein comprising unmodified human ActRIIB extracellular domain.

| ActRIIB protein | Inhibitory Potency of Homodimeric ActRIIB-Fc Constructs $IC_{50}$ (ng/mL) | | |
|---|---|---|---|
| | Activin A | GDF11 | BMP9 |
| Wild-type | 8 | 9 | 31 |
| A24N | 128 | 99 | 409 |
| R40A | — | 591 | 1210 |
| E50K | 132 | 180 | 721 |
| E50P | 756 | 638 | ~3000 |
| E52A | 198 | 71 | 359 |
| E52K | 762 | 296 | ~10000 |
| K55A | 15 | 11 | 122 |
| K55D | 396 | 365 | 5500 |
| K55E | 19 | 14 | 290 |
| K55R | 206 | 318 | 777 |
| Y60K | — | 414 | Neg |
| Y60P | — | 544 | Neg |
| K74R | — | 45 | 165 |
| K74Y | — | Neg | Neg |
| K74A/L79P | — | Neg | Neg |
| L79K | — | 477 | Neg |
| L79P | — | Neg | Neg |
| L79R | — | 234 | Neg |
| D80A | — | Neg | Neg |
| F82I | 11 | 9 | 277 |
| F82K | 10 | 15 | ~5000 |
| F82W | — | 276 | Neg |

Inhibitory Potency of
Homodimeric ActRIIB-Fc Constructs

| ActRIIB protein | IC$_{50}$ (ng/mL) | | |
|---|---|---|---|
| | Activin A | GDF11 | BMP9 |
| F82W/N83A | — | 389 | ~40000 |
| V99E | — | Neg | Neg |
| V99K | — | Neg | — |

Neg Absence of inhibition over concentration range tested
—Not tested

As shown in the table above, single amino acid substitutions in the ActRIIB extracellular domain can alter the balance between activin A or GDF11 inhibition and BMP9 inhibition in a cell-based reporter gene assay. Compared to a fusion protein containing unmodified ActRIIB extracellular domain, the variants ActRIIB(K55A)-Fc, ActRIIB (K55E)-Fc, ActRIIB(F82I)-Fc, and ActRIIB(F82K)-Fc showed less potent inhibition of BMP9 (increased IC$_{50}$ values) while maintaining essentially undiminished inhibition of activin A and GDF11.

These results indicate that variant ActRIIB-Fc proteins such as ActRIIB(K55A)-Fc, ActRIIB(K55E)-Fc, ActRIIB (F82I)-Fc, and ActRIIB(F82K)-Fc are more selective antagonists of activin A and GDF11 compared to an Fc fusion protein comprising unmodified ActRIIB extracellular domain. Accordingly, these variants may be more useful than ActRIIB-Fc in certain applications where such selective antagonism is advantageous. Examples include therapeutic applications where it is desirable to retain antagonism of one or more of activin A, GDF8, and GDF11 while reducing antagonism of BMP9 and potentially BMP10.

Example 4. Ligand Binding Profiles of Variant ActRIIB-Fc Homodimers

A Biacore™-based binding assay was used to compare ligand binding kinetics of certain variant ActRIIB-Fc proteins screened in Example 3 as well as other variant ActRIIB-Fc proteins not evaluated previously. ActRIIB-Fc proteins to be tested were independently captured onto the system using an anti-Fc antibody. Ligands were then injected and allowed to flow over the captured receptor protein. Results of variant ActRIIB-Fc proteins analyzed at 37° C. are shown in FIG. 8. Compared to Fc-fusion protein comprising unmodified ActRIIB extracellular domain, the variant proteins ActRIIB(K55A)-Fc, ActRIIB(K55E)-Fc, ActRIIB(F82I)-Fc, and ActRIIB(F82K)-Fc exhibited greater reduction in their affinity for BMP9 than for GDF11. Results of additional variant ActRIIB-Fc proteins analyzed at 25° C. are shown in FIG. 9.

These results confirm K55A, K55E, F82I, and F82K as substitutions that reduce ActRIIB binding affinity for BMP9 more than they reduce ActRIIB affinity for activin A or GDF11. Accordingly, these variant ActRIIB-Fc proteins may be more useful than unmodified ActRIIB-Fc protein in certain applications where such selective antagonism is advantageous. Examples include therapeutic applications where it is desirable to retain antagonism of one or more of activin A, activin B, GDF8, and GDF11 while reducing antagonism of BMP9.

Example 5. Activity of Variant ActRIIB-Fc Homodimers in Mice

Selected variant ActRIIB-G1Fc homodimers were tested in mice to investigate differences in their activity profiles in vivo. Adult wild-type C57BL/6 mice were dosed at 10 mg/kg (i.p.) with ActRIIB(K55A)-Fc, ActRIIB(K55E)-Fc, ActRIIB(F82I)-Fc, ActRIIB(F82K)-Fc, unmodified ActRIIB-Fc, or vehicle twice per week for 4 weeks (n=8 mice per group). Study endpoints included: body weight, CBC, and total lean mass and total adipose mass as determined by nuclear magnetic resonance (NMR) at baseline and study completion.

Treatment of mice with unmodified ActRIIB-Fc more than tripled the gain in body weight over the course of the study compared to vehicle-treated controls. The increase in body weight caused by ActRIIB(F82I)-Fc (25%) was nearly as large as that caused by unmodified ActRIIB-Fc (29%), while the other variant ActRIIB-Fc proteins produced body weight gains in the range of 12-17% (FIG. 10). NMR analysis revealed that ActRIIB(F82I)-Fc treatment significantly increased total lean mass and reduced total fat mass compared to vehicle as shown in the table below.

| Test Article | Change in lean mass from baseline | Change in fat mass from baseline |
|---|---|---|
| Vehicle | −2.3% ± 0.6% | 17.6% ± 5.8% |
| ActRIIB-G1Fc | 3.1% ± 0.7% (P < 0.001 vs vehicle) | −40.1% ± 5.6% (P = 0.0011 vs vehicle) |
| ActRIIB(F82I)-G1Fc | 1.5% ± 0.7% (P < 0.001 vs vehicle) | −19.6% ± 6.3% (P < 0.01 vs vehicle) |

ActRIIB(F82I)-Fc produced changes in lean mass and fat mass approximately half the magnitude of those produced by ActRIIB-Fc. It should be recognized that normalized (percentage-based) changes in lean and adipose tissues differ in their correspondence to absolute changes because lean mass (typically about 70% of body weight in a mouse) is much larger than adipose mass (typically about 10% of body weight). Individual skeletal muscles examined, including the gastrocnemius, femoris, and pectoralis all increased significantly in weight over the course of treatment with ActRIIB(F82I)-Fc compared to vehicle.

Figure 11:
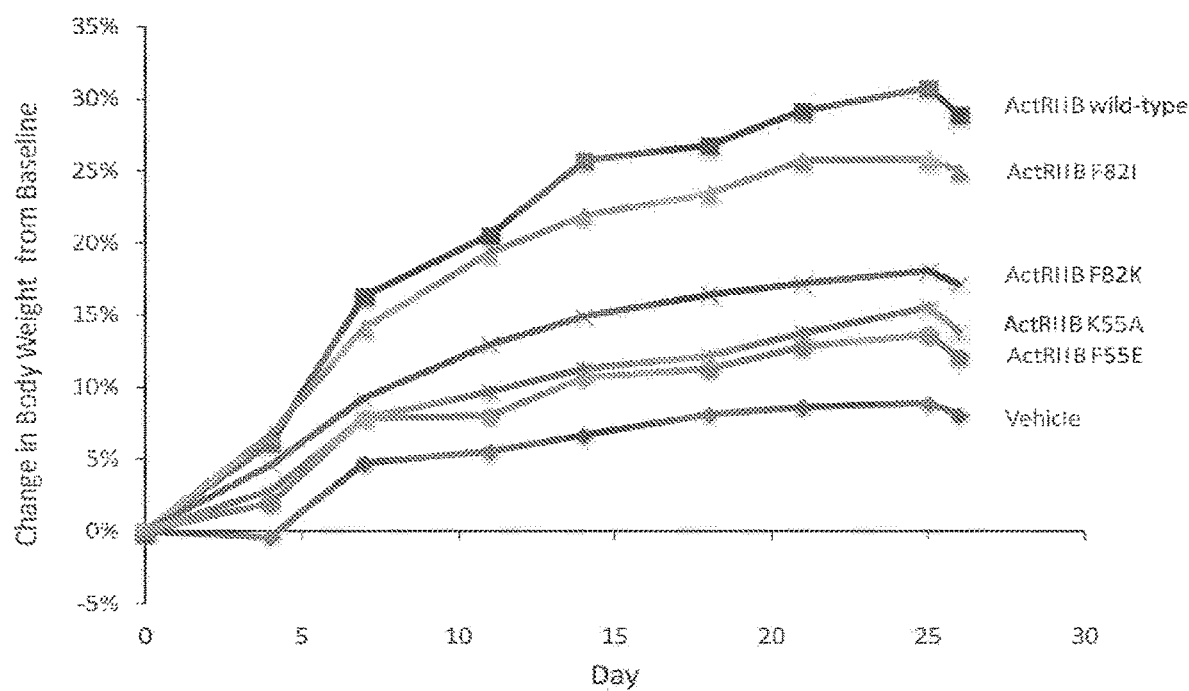
FIG. 11 shows changes in body weight from baseline for wild-type mice treated with vehicle or homodimeric Fc-fusion proteins comprising variant or unmodified ActRIIB domains.

All five of the ActRIIB-Fc fusion proteins evaluated produced significantly higher values for red blood cell parameters (RBC count, hematocrit, and hemoglobin concentration) than did vehicle, and the stimulatory effect of ActRIIB(F82I)-Fc on these parameters exceeded that of unmodified ActRIIB-Fc (FIG. 11).

Thus, homodimeric Fc-fusion proteins comprising a variant ActRIIB extracellular domain can exert beneficial anabolic effects on red blood cells and skeletal muscle as well as catabolic effects on adipose tissue similar to those of unmodified ActRIIB-Fc homodimer. However, variant ActRIIB-Fc homodimers bind with reduced affinity to BMP9 compared to unmodified ActRIIB-Fc and so will exert diminished inhibition of processes mediated by that ligand, such as angiogenesis. This novel selectivity will be useful, for example, in treating patients in need of stimulatory effects on red blood cells and muscle as well as inhibitory effects on fat, but not in need of altered angiogenesis.

Example 6. Activity of ActRIIB(F82I)-Fc Homodimer in Non-Human Primates

Figure 12:
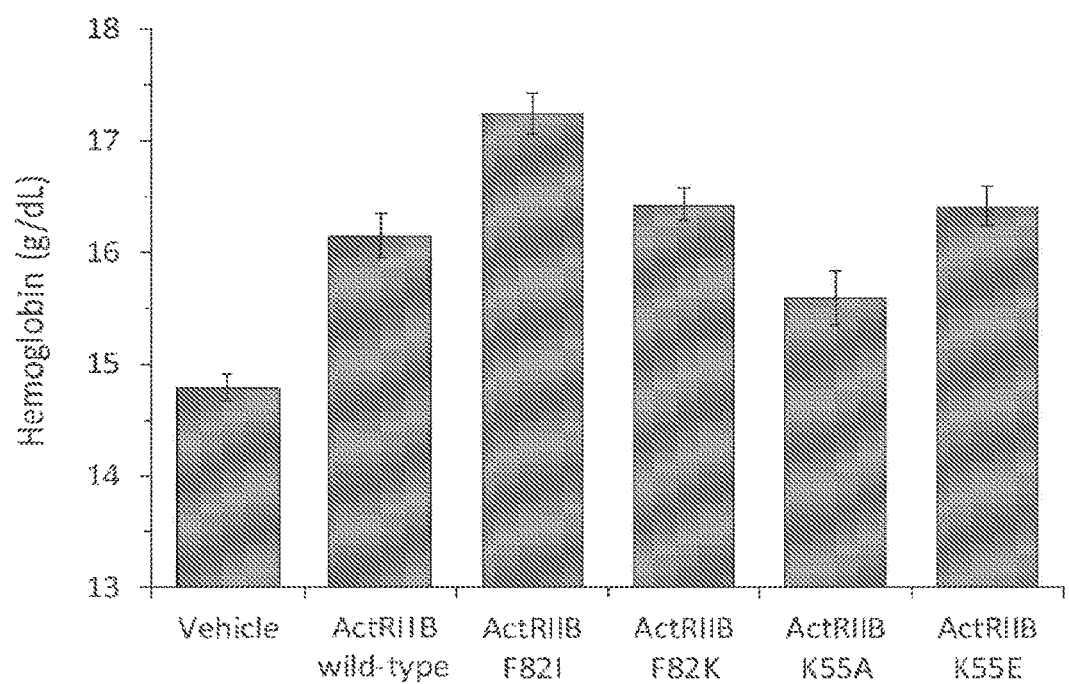
FIG. 12 shows hemoglobin concentrations in wild-type mice treated with vehicle or homodimeric Fc-fusion proteins comprising variant or unmodified ActRIIB domains.
Figure 13:
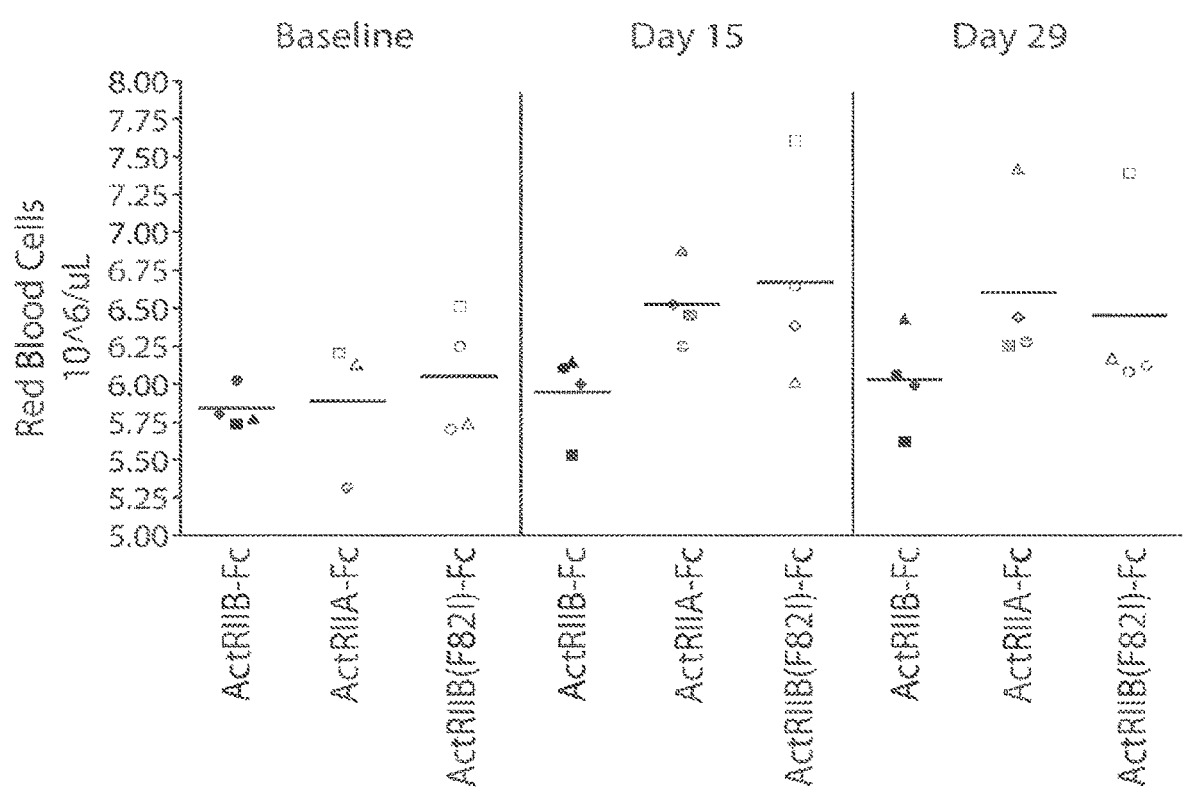
FIG. 13 shows red blood cell counts in cynomolgus monkeys treated with ActRIIB-Fc, ActRIIA-Fc, or ActRIIB (F82I)-Fc at 9 mg/kg (s.c.) on days 1 and 15. ActRIIB(F82I)-Fc treatment increased RBC counts compared to ActRIIB-Fc (negative control) by an amount similar to that of ActRIIA-Fc (positive control).

Applicants then investigated whether ActRIIB(F82I)-Fc homodimer alters RBC parameters in non-human primates. Cynomolgus monkeys (M. fascicularis) were treated with ActRIIB(F82I)-G1Fc, unmodified ActRIIB-G1Fc, or unmodified ActRIIA-G1Fc at 9 mg/kg (s.c.) on days 1 and 15 of a 29-day study (n=4 monkeys per group). As shown in FIG. 12, ActRIIB(F82I)-Fc treatment increased RBC counts compared to ActRIIB-Fc (negative control in primates) by an amount similar to that of ActRIIA-Fc (positive control). Comparable results were obtained for hemoglobin concentration and hematocrit (data not shown). These data confirm that ActRIIB(F82I)-Fc homodimer possesses activity in vivo different from that of unmodified ActRIIB-Fc homodimer.

Example 7. Generation of an ActRIIB-Fc:ActRIIB(L79E)-Fc Heterodimer

Applicants envision generation of a soluble ActRIIB-Fc:ActRIIB(L79E)-Fc heteromeric complex comprising the extracellular domains of unmodified human ActRIIB and human ActRIIB with a leucine-to-glutamate substitution at position 79, which are each separately fused to an G1Fc domain with a linker positioned between the extracellular domain and the G1Fc domain. The individual constructs are referred to as ActRIIB-Fc fusion polypeptide and ActRIIB (L79E)-Fc fusion polypeptide, respectively, and the sequences for each are provided below.

A methodology for promoting formation of ActRIIB-Fc:ActRIIB(L79E)-Fc heteromeric complexes, as opposed to the ActRIIB-Fc or ActRIIB(L79E)-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB(L79E)-Fc and ActRIIB-Fc polypeptide sequences of SEQ ID NOs: 43-45 and 46-48, respectively, one Fc domain can be altered to introduce cationic amino acids at the interaction face, while the other Fc domain can be altered to introduce anionic amino acids at the interaction face. The ActRIIB(L79E)-Fc fusion polypeptide and ActRIIB-Fc fusion polypeptide can each employ the TPA leader (SEQ ID NO: 8).

The ActRIIB(L79E)-Fc polypeptide sequence (SEQ ID NO: 43) is shown below:

```
                                                          (SEQ ID NO: 43)
  1 MDAMKRGLCC VLLLCGAVFV SPGASGRGEA ETRECIYYNA NWELERTNQS

51 GLERCEGEQD KRLHCYASWR NSSGTIELVK KGCWEDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYDTTPPVLD SDGSFFLYSD LTVDKSRWQQ GNVFSCSVMH

351 EALHNHYTQK SLSLSPG
```

The leader (signal) sequence and linker are underlined, and the L79E substitution is indicated by double underline. To promote formation of the ActRIIB-Fc:ActRIIB(L79E)-Fc heterodimer rather than either of the possible homodimeric complexes, two amino acid substitutions (replacing lysines with acidic amino acids) can be introduced into the Fc domain of the ActRIIB fusion protein as indicated by double underline above. The amino acid sequence of SEQ ID NO: 43 may optionally be provided with lysine added to the C-terminus.

This ActRIIB(L79E)-Fc fusion protein can be encoded by the following nucleic acid sequence (SEQ ID NO: 44):

```
                                                          (SEQ ID NO: 44)
  1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGGAAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA
```

```
501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGGA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACGACA CCACGCCTCC

951 CGTGCTGGAC TCCGACGGCT CCTTCTTCCT CTATAGCGAC CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 T
```

The mature ActRIIB(L79E)-Fc fusion polypeptide (SEQ ID NO: 45) is as follows, and may optionally be provided with lysine added to the C-terminus.

```
                                                     (SEQ ID NO: 45)
  1 GRGEAETREC IYYNANWELE RTNQSGLERC EGEQDKRLHC YASWRNSSGT

51 IELVKKGCWE DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYDTT PPVLDSDGSF

301 FLYSDLTVDK SRWQQGNVFS CSVMHEALHN HYTQKSLSLS PG
```

The complementary form of ActRIIB-Fc fusion polypeptide (SEQ ID NO: 46) is as follows:

```
                                                     (SEQ ID NO: 46)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSRKEMT KNQVSLTCLV KGFYPSDIAV

301 EWESNGQPEN YKTTPPVLK SDGSFFLYSK LTVDKSRWQQ GNVFSCSVMH

351 EALHNHYTQK SLSLSPGK
```

The leader sequence and linker sequence are underlined. To guide heterodimer formation with the ActRIIB(L79E)-Fc fusion polypeptide of SEQ ID NOs: 43 and 45 above, two amino acid substitutions (replacing a glutamate and an aspartate with lysines) can be introduced into the Fc domain of the ActRIIB-Fc fusion polypeptide as indicated by double underline above. The amino acid sequence of SEQ ID NO: 46 may optionally be provided with lysine removed from the C-terminus.

This ActRIIB-Fc fusion protein can be encoded by the following nucleic acid (SEQ ID NO: 47):

```
                                              (SEQ ID NO: 47)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGAA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGAAG TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB-Fc fusion protein sequence (SEQ ID NO: 48) is as follows and may optionally be provided with lysine removed from the C-terminus.

```
                                              (SEQ ID NO: 48)
   1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS
```

```
251 RKEMTKNQVS LTCLVKGFYP SDIAVEWESN GQPENNYKTT PPVLKSDGSF

301 FLYSKLTVDK SRWQQGNVFS CSVMHEALHN HYTQKSLSLS PGK
```

The ActRIIB(L79E)-Fc and ActRIIB-Fc polypeptides of SEQ ID NO: 45 and SEQ ID NO: 48, respectively, may be co-expressed and purified from a CHO cell line, to give rise to a heteromeric protein complex comprising ActRIIB-Fc: ActRIIB(L79E)-Fc.

In another approach to promote the formation of heteromultimer complexes using asymmetric Fc fusion proteins, the Fc domains can be altered to introduce complementary hydrophobic interactions and an additional intermolecular disulfide bond as illustrated in the ActRIIB(L79E)-Fc and ActRIIB-Fc polypeptide sequences of SEQ ID NOs: 49-50 and 51-52, respectively. The ActRIIB(L79E)-Fc fusion polypeptide and ActRIIB-Fc fusion polypeptide can each employ the TPA leader (SEQ ID NO: 8).

The ActRIIB(L79E)-Fc polypeptide sequence (SEQ ID NO: 49) is shown below:

```
                                                       (SEQ ID NO: 49)
  1 MDAMKRGLCC VLLLCGAVFV SPGASGRGEA ETRECIYYNA NWELERTNQS

51 GLERCEGEQD KRLHCYASWR NSSGTIELVK KGCWEDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPG
```

The signal sequence and linker sequence are underlined, and the L79E substitution is indicated by double underline. To promote formation of the ActRIIB-Fc:ActRIIB(L79E)-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 49 may optionally be provided with lysine added to the C-terminus.

The mature ActRIIB(L79E)-Fc fusion polypeptide (SEQ ID NO: 50) is as follows:

```
                                                       (SEQ ID NO: 50)
  1 GRGEAETREC IYYNANWELE RTNQSGLERC EGEQDKRLHC YASWRNSSGT

51 IELVKKGCWE DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PG
```

The complementary form of ActRIIB-Fc fusion polypeptide (SEQ ID NO: 51) is as follows and may optionally be provided with lysine removed from the C-terminus.

(SEQ ID NO: 51)
```
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVC TLPPSREEMT KNQVSLSCAV KGFYPSDIAV

301 EWESNGQPEN NYKTTPPVLD SDGSFFLVSK LTVDKSRWQQ GNVFSCSVMH

351 EALHNHYTQK SLSLSPGK
```

The leader sequence and linker are underlined. To guide heterodimer formation with the ActRIIB(L79E)-Fc fusion polypeptide of SEQ ID NOs: 49-50 above, four amino acid substitutions (replacement of tyrosine with cysteine, threonine with serine, leucine with alanine, and tyrosine with valine) can be introduced into the Fc domain of the ActRIIB-Fc fusion polypeptide as indicated by double underline above. The amino acid sequence of SEQ ID NO: 51 may optionally be provided with lysine removed from the C-terminus.

The mature ActRIIB-Fc fusion protein sequence is as follows and may optionally be provided with lysine removed from the C-terminus.

(SEQ ID NO: 52)
```
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVCTLPPS

251 REEMTKNQVS LSCAVKGFYP SDIAVEWESN GQPENNYKTT PPVLDSDGSF

301 FLVSKLTVDK SRWQQGNVFS CSVMHEALHN HYTQKSLSLS PGK
```

The ActRIIB(L79E)-Fc and ActRIIB-Fc polypeptides of SEQ ID NO: 50 and SEQ ID NO: 52, respectively, may be co-expressed and purified from a CHO cell line, to give rise to a heteromeric protein complex comprising ActRIIB-Fc:ActRIIB(L79E)-Fc.

Purification of various ActRIIB-Fc:ActRIIB(L79E)-Fc complexes can be achieved by a series of column chromatography steps, including, for example, three or more of the following, in any order: protein A chromatography, Q sepharose chromatography, phenylsepharose chromatography, size exclusion chromatography, cation exchange chromatography, multimodal chromatography (e.g., with resin containing both electrostatic and hydrophobic ligands), and epitope-based affinity chromatography (e.g., with an antibody or functionally equivalent ligand directed against an epitope of ActRIIB). The purification can be completed with viral filtration and buffer exchange.

Example 8. Ligand Binding Profile of ActRIIB-Fc:ActRIIB(L79E)-Fc Heteromer

A Biacore™-based binding assay was used to compare the ligand binding kinetics of an ActRIIB-Fc:ActRIIB (L79E)-Fc heterodimer with those of unmodified ActRIIB-Fc homodimer. Fusion proteins were captured onto the system using an anti-Fc antibody. Ligands were then injected and allowed to flow over the captured receptor protein at 37° C. Results are summarized in the table below, in which ligand off-rates ($k_d$) most indicative of effective ligand traps are denoted in bold.

Ligand binding of ActRIIB-Fc:ActRIIB(L79E)-Fc heterodimer compared to ActRII-Fc homodimer at 37° C.

| | ActRIIB-Fc homodimer | | | ActRIIB-Fc:ActRIIB(L79E)-Fc heterodimer | | |
|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) |
| Activin A | $7.4 \times 10^6$ | $1.9 \times 10^{-4}$ | 25 | $8.8 \times 10^6$ | $1.5 \times 10^{-3}$ | 170 |
| Activin B | $8.1 \times 10^6$ | $6.6 \times 10^{-5}$ | 8 | $8.3 \times 10^6$ | $2.1 \times 10^{-4}$ | 25 |
| GDF3 | $1.4 \times 10^6$ | $2.2 \times 10^{-3}$ | 1500 | $5.8 \times 10^5$ | $5.9 \times 10^{-3}$ | 10000 |
| GDF8 | $3.8 \times 10^6$ | $2.6 \times 10^{-4}$ | 70 | $3.4 \times 10^6$ | $5.0 \times 10^{-4}$ | 150 |
| GDF11 | $4.1 \times 10^7$ | $1.7 \times 10^{-4}$ | 4 | $4.0 \times 10^7$ | $3.6 \times 10^{-4}$ | 9 |

Ligand binding of ActRIIB-Fc:ActRIIB(L79E)-Fc heterodimer compared to ActRII-Fc homodimer at 37° C.

| Ligand | ActRIIB-Fc homodimer | | | ActRIIB-Fc:ActRIIB(L79E)-Fc heterodimer | | |
|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) |
| BMP6 | $1.3 \times 10^8$ | $7.4 \times 10^{-3}$ | 56 | $3.3 \times 10^8$ | $1.8 \times 10^{-2}$ | 56 |
| BMP9 | $5.0 \times 10^6$ | $1.3 \times 10^{-3}$ | 250 | Transient* | | >2800 |
| BMP10 | $5.1 \times 10^7$ | $2.0 \times 10^{-4}$ | 4 | $4.8 \times 10^7$ | $2.0 \times 10^{-3}$ | 42 |

*Indeterminate due to transient nature of interaction

In this example, a single amino acid substitution in one of two ActRIIB polypeptide chains altered ligand binding selectivity of the Fc-fusion protein relative to unmodified ActRIIB-Fc homodimer. Compared to ActRIIB-Fc homodimer, the ActRIIB(L79E)-Fc heterodimer largely retained high-affinity binding to activin B, GDF8, GDF11, and BMP6 but exhibited approximately ten-fold faster off-rates for activin A and BMP10 and an even greater reduction in the strength of binding to BMP9. Accordingly, a variant ActRIIB-Fc heteromer may be more useful than unmodified ActRIIB-Fc homodimer in certain applications where such selective antagonism is advantageous. Examples include therapeutic applications where it is desirable to retain antagonism of one or more of activin B, GDF8, GDF11, and BMP6, while reducing antagonism of activin A, BMP9, or BMP10.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

(SEQ ID NO: 196)

```
ATGGGTCGGGGGCTGCTCAGGGGCCTGTGGCCGCTGCACATCGTCCTGTGGACGCGTATCGC

CAGCACGATCCCACCGCACGTTCAGAAGTCGGTTAATAACGACATGATAGTCACTGACAACA

ACGGTGCAGTCAAGTTTCCACAACTGTGTAAATTTTGTGATGTGAGATTTTCCACCTGTGAC

AACCAGAAATCCTGCATGAGCAACTGCAGCATCACCTCCATCTGTGAGAAGCCACAGGAAGT

CTGTGTGGCTGTATGGAGAAAGAATGACGAGAACATAACACTAGAGACAGTTTGCCATGACC

CCAAGCTCCCCTACCATGACTTTATTCTGGAAGATGCTGCTTCTCCAAAGTGCATTATGAAG

GAAAAAAAAAGCCTGGTGAGACTTTCTTCATGTGTTCCTGTAGCTCTGATGAGTGCAATGA

CAACATCATCTTCTCAGAAGAATATAACACCAGCAATCCTGACTTGTTGCTAGTCATATTTC

AAGTGACAGGCATCAGCCTCCTGCCACCACTGGGAGTTGCCATATCTGTCATCATCATCTTC

TACTGCTACCGCGTTAACCGGCAGCAGAAGCTGAGTTCAACCTGGGAAACCGGCAAGACGCG

GAAGCTCATGGAGTTCAGCGAGCACTGTGCCATCATCCTGGAAGATGACCGCTCTGACATCA

GCTCCACGTGTGCCAACAACATCAACCACAACACGAGCTGCTGCCCATTGAGCTGGACACC

CTGGTGGGAAAGGTCGCTTTGCTGAGGTCTATAAGGCCAAGCTGAAGCAGAACACTTCAGA

GCAGTTTGAGACAGTGGCAGTCAAGATCTTTCCCTATGAGGAGTATGCCTCTTGGAAGACAG

AGAAGGACATCTTCTCAGACATCAATCTGAAGCATGAGAACATACTCCAGTTCCTGACGGCT

GAGGAGCGGAAGACGGAGTTGGGGAAACAATACTGGCTGATCACCGCCTTCCACGCCAAGGG

CAACCTACAGGAGTACCTGACGCGGCATGTCATCAGCTGGGAGGACCTGCGCAAGCTGGGCA

GCTCCCTCGCCCGGGGGATTGCTCACCTCCACAGTGATCACACTCCATGTGGGAGGCCCAAG

ATGCCCATCGTGCACAGGGACCTCAAGAGCTCCAATATCCTCGTGAAGAACGACCTAACCTG

CTGCCTGTGTGACTTTGGGCTTTCCCTGCGTCTGGACCCTACTCTGTCTGTGGATGACCTGG

CTAACAGTGGGCAGGTGGGAACTGCAAGATACATGGCTCCAGAAGTCCTAGAATCCAGGATG

AATTTGGAGAATGTTGAGTCCTTCAAGCAGACCGATGTCTACTCCATGGCTCTGGTGCTCTG

GGAAATGACATCTCGCTGTAATGCAGTGGGAGAAGTAAAAGATTATGAGCCTCCATTTGGTT

CCAAGGTGCGGGAGCACCCCTGTGTCGAAAGCATGAAGGACAACGTGTTGAGAGATCGAGGG

CGACCAGAAATTCCCAGCTTCTGGCTCAACCACCAGGGCATCCAGATGGTGTGTGAGACGTT

GACTGAGTGCTGGGACCACGACCCAGAGGCCCGTCTCACAGCCCAGTGTGTGGCAGAACGCT
```

-continued

TCAGTGAGCTGGAGCATCTGGACAGGCTCTCGGGGAGGAGCTGCTCGGAGGAGAAGATTCCT

GAAGACGGCTCCCTAAACACTACCAAA (SEQ ID NO: 197)

ACGATCCCACCGCACGTTCAGAAGTCGGTTAATAACGACATGATAGTCACTGACAACAACGG

TGCAGTCAAGTTTCCACAACTGTGTAAATTTTGTGATGTGAGATTTTCCACCTGTGACAACC

AGAAATCCTGCATGAGCAACTGCAGCATCACCTCCATCTGTGAGAAGCCACAGGAAGTCTGT

GTGGCTGTATGGAGAAAGAATGACGAGAACATAACACTAGAGACAGTTTGCCATGACCCCAA

GCTCCCCTACCATGACTTTATTCTGGAAGATGCTGCTTCTCCAAAGTGCATTATGAAGGAAA

AAAAAAAGCCTGGTGAGACTTTCTTCATGTGTTCCTGTAGCTCTGATGAGTGCAATGACAAC

ATCATCTTCTCAGAAGAATATAACACCAGCAATCCTGACTTGTTGCTAGTCATATTTCAA (SEQ ID NO: 202)

<u>ATGGGTCGGGGCTGCTCAGGGGCCTGTGGCCGCTGCACATCGTCCTGTGGACGCGTATCGC</u>

<u>CAGC</u>ACGATCCCACCGCACGTTCAGAAGTCGGATGTGGAAATGGAGGCCCAGAAAGATGAAA

TCATCTGCCCCAGCTGTAATAGGACTGCCCATCCACTGAGACATATTAATAACGACATGATA

GTCACTGACAACAACGGTGCAGTCAAGTTTCCACAACTGTGTAAATTTTGTGATGTGAGATT

TTCCACCTGTGACAACCAGAAATCCTGCATGAGCAACTGCAGCATCACCTCCATCTGTGAGA

AGCCACAGGAAGTCTGTGTGGCTGTATGGAGAAAGAATGACGAGAACATAACACTAGAGACA

GTTTGCCATGACCCCAAGCTCCCCTACCATGACTTTATTCTGGAAGATGCTGCTTCTCCAAA

GTGCATTATGAAGGAAAAAAAAAGCCTGGTGAGACTTTCTTCATGTGTTCCTGTAGCTCTG

ATGAGTGCAATGACAACATCATCTTCTCAGAAGAATATAACACCAGCAATCCTGACTTGTTG

CTAGTCATATTTCAAGTGACAGGCATCAGCCTCCIGCCACCACTGGGAGTTGCCATATCTGT

CATCATCATCTTCTACTGCTACCGCGTTAACCGGCAGCAGAAGCTGAGTTCAACCTGGGAAA

CCGGCAAGACGCGGAAGCTCATGGAGTTCAGCGAGCACTGTGCCATCATCCTGGAAGATGAC

CGCTCTGACATCAGCTCCACGTGTGCCAACAACATCAACCACAACACAGAGCTGCTGCCCAT

TGAGCTGGACACCCTGGTGGGAAAGGTCGCTTTGCTGAGGTCTATAAGGCCAAGCTGAAGC

AGAACACTTCAGAGCAGTTTGAGACAGTGGCAGTCAAGATCTTTCCCTATGAGGAGTATGCC

TCTTGGAAGACAGAGAAGGACATCTTCTCAGACATCAATCTGAAGCATGAGAACATACTCCA

GTTCCTGACGGCTGAGGAGCGGAAGACGGAGTTGGGGAAACAATACTGGCTGATCACCGCCT

TCCACGCCAAGGGCAACCTACAGGAGTACCTGACGCGGCATGTCATCAGCTGGGAGGACCTG

CGCAAGCTGGGCAGCTCCCTCGCCCGGGGGATTGCTCACCTCCACAGTGATCACACTCCATG

TGGGAGGCCCAAGATGCCCATCGTGCACAGGGACCTCAAGAGCTCCAATATCCTCGTGAAGA

ACGACCTAACCTGCTGCCTGTGTGACTTTGGGCTTTCCCTGCGTCTGGACCCTACTCTGTCT

GTGGATGACCTGGCTAACAGTGGGCAGGTGGGAACTGCAAGATACATGGCTCCAGAAGTCCT

AGAATCCAGGATGAATTTGGAGAATGTTGAGTCCTTCAAGCAGACCGATGTCTACTCCATGG

CTCTGGTGCTCTGGGAAATGACATCTCGCTGTAATGCAGTGGGAGAAGTAAAAGATTATGAG

CCTCCATTTGGTTCCAAGGTGCGGGAGCACCCCTGTGTCGAAAGCATGAAGGACAACGTGTT

GAGAGATCGAGGGCGACCAGAAATTCCCAGCTTCTGGCTCAACCACCAGGGCATCCAGATGG

TGTGTGAGACGTTGACTGAGTGCTGGGACCACGACCCAGAGGCCCGTCTCACAGCCCAGTGT

GTGGCAGAACGCTTCAGTGAGCTGGAGCATCTGGACAGGCTCTCGGGGAGGAGCTGCTCGGA

GGAGAAGATTCCTGAAGACGGCTCCCTAAACACTACCAAA (SEQ ID NO: 203)
ACGATCCCACCGCACGTTCAGAAGTCGGATGTGGAAATGGAGGCCCAGAAAGATGAAATCAT

CTGCCCCAGCTGTAATAGGACTGCCCATCCACTGAGACATATTAATAACGACATGATAGTCA

CTGACAACAACGGTGCAGTCAAGTTTCCACAACTGTGTAAATTTTGTGATGTGAGATTTTCC

ACCTGTGACAACCAGAAATCCTGCATGAGCAACTGCAGCATCACCTCCATCTGTGAGAAGCC

ACAGGAAGTCTGTGTGGCTGTATGGAGAAAGAATGACGAGAACATAACACTAGAGACAGTTT

GCCATGACCCCAAGCTCCCCTACCATGACTTTATTCTGGAAGATGCTGCTTCTCCAAAGTGC

ATTATGAAGGAAAAAAAAAGCCTGGTGAGACTTTCTTCATGTGTTCCTGTAGCTCTGATGA

GTGCAATGACAACATCATCTTCTCAGAAGAATATAACACCAGCAATCCTGACTTGTTGCTAG

TCATATTTCAA.

(SEQ ID NO: 205)
ATGACTTCCTCGCTGCAGCGGCCCTGGCGGGTGCCCTGGCTACCATGGACCATCCTGCTGGTCAGCACTGCGGCT

GCTTCGCAGAATCAAGAACGGCTATGTGCGTTTAAAGATCCGTATCAGCAAGACCTTGGGATAGGTGAGAGTAGA

ATCTCTCATGAAAATGGGACAATATTATGCTCGAAAGGTAGCACCTGCTATGGCCTTTGGGAGAAATCAAAAGGG

GACATAAATCTTGTAAAACAAGGATGTTGGTCTCACATTGGAGATCCCCAAGAGTGTCACTATGAAGAATGTGTA

GTAACTACCACTCCTCCCTCAATTCAGAATGGAACATACCGTTTCTGCTGTTGTAGCACAGATTTATGTAATGTC

AACTTTACTGAGAATTTTCCACCTCCTGACACAACACCACTCAGTCCACCTCATTCATTTAACCGAGATGAGACA

ATAATCATTGCTTTGGCATCAGTCTCTGTATTAGCTGTTTTGATAGTTGCCTTATGCTTTGGATACAGAATGTTG

ACAGGAGACCGTAAACAAGGTCTTCACAGTATGAACATGATGGAGGCAGCAGCATCCGAACCCTCTCTTGATCTA

GATAATCTGAAACTGTTGGAGCTGATTGGCCGAGGTCGATATGGAGCAGTATATAAAGGCTCCTTGGATGAGCGT

CCAGTTGCTGTAAAAGTGTTTTCCTTTGCAAACCGTCAGAATTTTATCAACGAAAAGAACATTTACAGAGTGCCT

TTGATGGAACATGACAACATTGCCCGCTTTATAGTTGGAGATGAGAGTCACTGCAGATGGACGCATGGAATAT

TTGCTTGTGATGGAGTACTATCCCAATGGATCTTTATGCAAGTATTTAAGTCTCCACACAAGTGACTGGGTAAGC

TCTTGCCGTCTTGCTCATTCTGTTACTAGAGGACTGGCTTATCTTCACACAGAATTACCACGAGGAGATCATTAT

AAACCTGCAATTTCCCATCGAGATTTAAACAGCAGAAATGTCCTAGTGAAAAATGATGGAACCTGTGTTATTAGT

GACTTTGGACTGTCCATGAGGCTGACTGGAAATAGACTGGTGCGCCCAGGGGAGGAAGATAATGCAGCCATAAGC

GAGGTTGGCACTATCAGATATATGGCACCAGAAGTGCTAGAAGGAGCTGTGAACTTGAGGGACTGTGAATCAGCT

TTGAAACAAGTAGACATGTATGCTCTTGGACTAATCTATTGGGAGATATTTATGAGATGTACAGACCTCTTCCCA

GGGGAATCCGTACCAGAGTACCAGATGGCTTTTCAGACAGAGGTTGGAAACCATCCCACTTTTGAGGATATGCAG

GTTCTCGTGTCTAGGGAAAAACAGAGACCCAAGTTCCCAGAAGCCTGGAAAGAAAATAGCCTGGCAGTGAGGTCA

CTCAAGGAGACAATCGAAGACTGTTGGGACCAGGATGCAGAGGCTCGGCTTACTGCACAGTGTGCTGAGGAAAGG

ATGGCTGAACTTATGATGATTTGGGAAAGAAACAAATCTGTGAGCCCAACAGTCAATCCAATGTCTACTGCTATG

CAGAATGAACGCAACCTGTCACATAATAGGCGTGTGCCAAAAATTGGTCCTTATCCAGATTATTCTTCCTCCTCA

TACATTGAAGACTCTATCCATCATACTGACAGCATCGTGAAGAATATTTCCTCTGAGCATTCTATGTCCAGCACA

CCTTTGACTATAGGGGAAAAAAACCGAAATTCAATTAACTATGAACGACAGCAAGCACAAGCTCGAATCCCCAGC

CCTGAAACAAGTGTCACCAGCCTCTCCACCAACACAACAACCACAAACACCACAGGACTCACGCCAAGTACTGGC

ATGACTACTATATCTGAGATGCCATACCCAGATGAAACAAATCTGCATACCACAAATGTTGCACAGTCAATTGGG

CCAACCCCTGTCTGCTTACAGCTGACAGAAGAAGACTTGGAAACCAACAAGCTAGACCCAAAAGAAGTTGATAAG

AACCTCAAGGAAAGCTCTGATGAGAATCTCATGGAGCACTCTCTTAAACAGTTCAGTGGCCCAGACCCACTGAGC

AGTACTAGTTCTAGCTTGCTTTACCCACTCATAAAACTTGCAGTAGAAGCAACTGGACAGCAGGACTTCACACAG

ACTGCAAATGGCCAAGCATGTTTGATTCCTGATGTTCTGCCTACTCAGATCTATCCTCTCCCCAAGCAGCAGAAC

-continued

CTTCCCAAGAGACCTACTAGTTTGCCTTTGAACACCAAAAATTCAACAAAAGAGCCCCGGCTAAAATTTGGCAGC

AAGCACAAATCAAACTTGAAACAAGTCGAAACTGGAGTTGCCAAGATGAATACAATCAATGCAGCAGAACCTCAT

GTGGTGACAGTCACCATGAATGGTGTGGCAGGTAGAAACCACAGTGTTAACTCCCATGCTGCCACAACCCAATAT

GCCAATGGGACAGTACTATCTGGCCAAACAACCAACATAGTGACACATAGGGCCCAAGAAATGTTGCAGAATCAG

TTTATTGGTGAGGACACCCGGCTGAATATTAATTCCAGTCCTGATGAGCATGAGCCTTTACTGAGACGAGAGCAA

CAAGCTGGCCATGATGAAGGTGTTCTGGATCGTCTTGTGGACAGGAGGGAACGGCCACTAGAAGGTGGCCGAACT

AATTCCAATAACAACAACAGCAATCCATGTTCAGAACAAGATGTTCTTGCACAGGGTGTTCCAAGCACAGCAGCA

GATCCTGGGCCATCAAAGCCCAGAAGAGCACAGAGGCCTAATTCTCTGGATCTTTCAGCCACAAATGTCCTGGAT

GGCAGCAGTATACAGATAGGTGAGTCAACACAAGATGGCAAATCAGGATCAGGTGAAAAGATCAAGAAACGTGTG

AAAACTCCCTATTCTCTTAAGCGGTGGCGCCCCTCCACCTGGGTCATCTCCACTGAATCGCTGGACTGTGAAGTC

AACAATAATGGCAGTAACAGGGCAGTTCATTCCAAATCCAGCACTGCTGTTTACCTTGCAGAAGGAGGCACTGCT

ACAACCATGGTGTCTAAAGATATAGGAATGAACTGTCTG (SEQ ID NO: 206)
TCGCAGAATCAAGAACGGCTATGTGCGTTTAAAGATCCGTATCAGCAAGACCTTGGGATAGGTGAGAGTAGAATC

TCTCATGAAAATGGGACAATATTATGCTCGAAAGGTAGCACCTGCTATGGCCTTTGGGAGAAATCAAAAGGGGAC

ATAAATCTTGTAAAACAAGGATGTTGGTCTCACATTGGAGATCCCCAAGAGTGTCACTATGAAGAATGTGTAGTA

ACTACCACTCCTCCCTCAATTCAGAATGGAACATACCGTTTCTGCTGTTGTAGCACAGATTTATGTAATGTCAAC

TTTACTGAGAATTTTCCACCTCCTGACACAACACCACTCAGTCCACCTCATTCATTTAACCGAGATGAGACA (SEQ ID NO: 207)
<u>ATGACTTCCTCGCTGCAGCGGCCCTGGCGGGTGCCCTGGCTACCATGGACCATCCTGCTGGT</u>

<u>CAGCACTGCGGCTGCTT</u>CGCAGAATCAAGAACGGCTATGTGCGTTTAAAGATCCGTATCAGC

AAGACCTTGGGATAGGTGAGAGTAGAATCTCTCATGAAAATGGGACAATATTATGCTCGAAA

GGTAGCACCTGCTATGGCCTTTGGGAGAAATCAAAAGGGGACATAAATCTTGTAAAACAAGG

ATGTTGGTCTCACATTGGAGATCCCCAAGAGTGTCACTATGAAGAATGTGTAGTAACTACCA

CTCCTCCCTCAATTCAGAATGGAACATACCGTTTCTGCTGTTGTAGCACAGATTTATGTAAT

GTCAACTTTACTGAGAATTTTCCACCTCCTGACACAACACCACTCAGTCCACCTCATTCATT

TAACCGAGATGAGACAATAATCATTGCTTTGGCATCAGTCTCTGTATTAGCTGTTTTGATAG

TTGCCTTATGCTTTGGATACAGAATGTTGACAGGAGACCGTAAACAAGGTCTTCACAGTATG

AACATGATGGAGGCAGCAGCATCCGAACCCTCTCTTGATCTAGATAATCTGAAACTGTTGGA

GCTGATTGGCCGAGGTCGATATGGAGCAGTATATAAAGGCTCCTTGGATGAGCGTCCAGTTG

CTGTAAAAGTGTTTTCCTTTGCAAACCGTCAGAATTTTATCAACGAAAAGAACATTTACAGA

GTGCCTTTGATGGAACATGACAACATTGCCCGCTTTATAGTTGGAGATGAGAGAGTCACTGC

AGATGGACGCATGGAATATTTGCTTGTGATGGAGTACTATCCCAATGGATCTTTATGCAAGT

ATTTAAGTCTCCACACAAGTGACTGGGTAAGCTCTTGCCGTCTTGCTCATTCTGTTACTAGA

GGACTGGCTTATCTTCACACAGAATTACCACGAGGAGATCATTATAAACCTGCAATTTCCCA

TCGAGATTTAAACAGCAGAAATGTCCTAGTGAAAAATGATGGAACCTGTGTTATTAGTGACT

TTGGACTGTCCATGAGGCTGACTGGAAATAGACTGGTGCGCCCAGGGGAGGAAGATAATGCA

GCCATAAGCGAGGTTGGCACTATCAGATATATGGCACCAGAAGTGCTAGAAGGAGCTGTGAA

CTTGAGGGACTGTGAATCAGCTTTGAAACAAGTAGACATGTATGCTCTTGGACTAATCTATT

GGGAGATATTTATGAGATGTACAGACCTCTTCCCAGGGGAATCCGTACCAGAGTACCAGATG

GCTTTTCAGACAGAGGTTGGAAACCATCCCACTTTTGAGGATATGCAGGTTCTCGTGTCTAG

GGAAAAACAGAGACCCAAGTTCCCAGAAGCCTGGAAAGAAAATAGCCTGGCAGTGAGGTCAC

```
TCAAGGAGACAATCGAAGACTGTTGGGACCAGGATGCAGAGGCTCGGCTTACTGCACAGTGT

GCTGAGGAAAGGATGGCTGAACTTATGATGATTTGGGAAAGAAACAAATCTGTGAGCCCAAC

AGTCAATCCAATGTCTACTGCTATGCAGAATGAACGTAGG
```

(SEQ ID NO: 208)
```
TCGCAGAATCAAGAACGGCTATGTGCGTTTAAAGATCCGTATCAGCAAGACCTTGGGATAGG

TGAGAGTAGAATCTCTCATGAAAATGGGACAATATTATGCTCGAAAGGTAGCACCTGCTATG

GCCTTTGGGAGAAATCAAAAGGGGACATAAATCTTGTAAAACAAGGATGTTGGTCTCACATT

GGAGATCCCCAAGAGTGTCACTATGAAGAATGTGTAGTAACTACCACTCCTCCCTCAATTCA

GAATGGAACATACCGTTTCTGCTGTTGTAGCACAGATTTATGTAATGTCAACTTTACTGAGA

ATTTTCCACCTCCTGACACAACACCACTCAGTCCACCTCATTCATTTAACCGAGATGAGACA
```

(SEQ ID NO: 209)
```
ATGCTAGGGTCTTTGGGGCTTTGGGCATTACTTCCCACAGCTGTGGAAGCACCCCCAAACAGGCGAACCTGTGTG

TTCTTTGAGGCCCCTGGAGTGCGGGGAAGCACAAAGACACTGGGAGAGCTGCTAGATACAGGCACAGAGCTCCCC

AGAGCTATCCGCTGCCTCTACAGCCGCTGCTGCTTTGGGATCTGGAACCTGACCCAAGACCGGGCACAGGTGGAA

ATGCAAGGATGCCGAGACAGTGATGAGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAATGCCAATTACAGCCATCTGCCTCCT

CCAGGGAGCCCTGGGACTCCTGGCTCCCAGGGTCCCCAGGCTGCCCCAGGTGAGTCCATCTGGATGGCACTGGTG

CTGCTGGGCTGTTCCTCCTCCTCCTGCTGCTGCTGGGCAGCATCATCTTGGCCCTGCTACAGCGAAAGAACTAC

AGAGTGCGAGGTGAGCCAGTGCCAGAGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGTTTGGGCCGGGCAGCTGCAAGGAAAA

CTGGTTGCCATCAAGGCCTTCCCACCGAGGTCTGTGGCTCAGTTCCAAGCTGAGAGAGCATTGTACGAACTTCCA

GGCCTACAGCACGACCACATTGTCCGATTTATCACTGCCAGCCGGGGGGGTCCTGGCCGCCTGCTCTCTGGGCCC

CTGCTGGTACTGGAACTGCATCCCAAGGGCTCCCTGTGCCACTACTTGACCCAGTACACCAGTGACTGGGGAAGT

TCCCTGCGGATGGCACTGTCCCTGGCCCAGGGCCTGGCATTTCTCCATGAGGAGCGCTGGCAGAATGGCCAATAT

AAACCAGGTATTGCCCACCGAGATCTGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTGGACCCCTACTCAACCACAAGGCCCA

GCTGCCATCATGGAAGCTGGCACCCAGAGGTACATGGCACCAGAGCTCTTGGACAAGACTCTGGACCTACAGGAT

TGGGGCATGGCCCTCCGACGAGCTGATATTTACTCTTTGGCTCTGCTCCTGTGGGAGATACTGAGCCGCTGCCCA

GATTTGAGGCCTGACAGCAGTCCACCACCCCTTCCAACTGGCCTATGAGGCAGAACTGGGCAATACCCCTACCTCT

GATGAGCTATGGGCCTTGGCAGTGCAGGAGAGGAGGCGTCCCTACATCCCATCCACCTGGCGCTGCTTTGCCACA

GACCCTGATGGGCTGAGGGAGCTCCTAGAAGACTGTTGGGATGCAGACCCAGAAGCACGGCTGACAGCTGAGTGT

GTACAGCAGCGCCTGGCTGCCTTGGCCCATCCTCAAGAGAGCCACCCCTTTCCAGAGAGCTGTCCACGTGGCTGC

CCACCTCTCTGCCCAGAAGACTGTACTTCAATTCCTGCCCCTACCATCCTCCCCTGTAGGCCTCAGCGGAGTGCC

TGCCACTTCAGCGTTCAGCAAGGCCCTTGTTCCAGGAATCCTCAGCCTGCCTGTACCCTTTCTCCTGTG
```

(SEQ ID NO: 210)
```
CCCCCAAACAGGCGAACCTGTGTGTTCTTTGAGGCCCCTGGAGTGCGGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG
```

(SEQ ID NO: 211)
ATGCTAGGGTCTTTGGGGCTTTGGGCATTACTTCCCACAGCTGTGGAAGCACCCCCAAACAGGCGAACCTGTGTG

TTCTTTGAGGCCCCTGGAGTGCGGGGAAGCACAAAGACACTGGGAGAGCTGCTAGATACAGGCACAGAGCTCCCC

AGAGCTATCCGCTGCCTCTACAGCCGCTGCTGCTTTGGGATCTGGAACCTGACCCAAGACCGGGCACAGGTGGAA

ATGCAAGGATGCCGAGACAGTGATGAGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAATGCCAATTACAGCCATCTGCCTCCT

CCAGGGAGCCCTGGGACTCCTGGCTCCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTTGGCCCTGCTACAGCGAAAGAACTAC

AGAGTGCGAGGTGAGCCAGTGCCAGAGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGTTTGGGCCGGGCAGCTGCAAGGAAAA

CTGGTTGCCATCAAGGCCTTCCCACCGAGGTCTGTGGCTCAGTTCCAAGCTGAGAGAGCATTGTACGAACTTCCA

GGCCTACAGCACGACCACATTGTCCGATTTATCACTGCCAGCCGGGGGGTCCTGGCCGCCTGCTCTCTGGGCCC

CTGCTGGTACTGGAACTGCATCCCAAGGGCTCCCTGTGCCACTACTTGACCCAGTACACCAGTGACTGGGGAAGT

TCCCTGCGGATGGCACTGTCCCTGGCCCAGGGCCTGGCATTTCTCCATGAGGAGCGCTGGCAGAATGGCCAATAT

AAACCAGGTATTGCCCACCGAGATCTGAGCAGCCAGAATGTGCTCATTCGGGAAGATGGATCGTGTGCCATTGGA

GACCTGGGCCTTGCCTTGGTGCTCCCTGGCCTCACTCAGCCCCTGCCTGGACCCCTACTCAACCACAAGGCCCA

GCTGCCATCATGGAAGCTGGCACCCAGAGGTACATGGCACCAGAGCTCTTGGACAAGACTCTGGACCTACAGGAT

TGGGGCATGGCCCTCCGACGAGCTGATATTTACTCTTTGGCTCTGCTCCTGTGGGAGATACTGAGCCGCTGCCCA

GATTTGAGGCCTGCAGTCCACCACCCTTCCAACTGGCCTATGAGGCAGAACTGGGCAATACCCCTACCTCTGATG

AGCTATGGGCCTTGGCAGTGCAGGAGAGGAGGCGTCCCTACATCCCATCCACCTGGCGCTGCTTTGCCACAGACC

CTGATGGGC (SEQ ID NO: 212)
CCCCCAAACAGGCGAACCTGTGTGTTCTTTGAGGCCCCTGGAGTGCGGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG (SEQ ID NO: 213)
ATGCTAGGGTCTTTGGGGCTTTGGGCATTACTTCCCACAGCTGTGGAAGCACCCCCAAACAG

GCGAACCTGTGTGTTCTTTGAGGCCCCTGGAGTGCGGGGAAGCACAAAGACACTGGGAGAGC

TGCTAGATACAGGCACAGAGCTCCCCAGAGCTATCCGCTGCCTCTACAGCCGCTGCTGCTTT

GGGATCTGGAACCTGACCCAAGACCGGGCACAGGTGGAAATGCAAGGATGCCGAGACAGTGA

TGAGCCAGGCTGTGAGTCCCTCCACTGTGACCCAAGTCCCCGAGCCCACCCCAGCCCTGGCT

CCACTCTCTTCACCTGCTCCTGTGGCACTGACTTCTGCAATGCCAATTACAGCCATCTGCCT

CCTCCAGGGAGCCCTGGGACTCCTGGCTCCCAGGGTCCCCAGGCTGCCCCAGGTGAGTCCAT

CTGGATGGCACTGGTGCTGCTGGGGCTGTTCCTCCTCCTCCTGCTGCTGCTGGGCAGCATCA

TCTTGGCCCTGCTACAGCGAAAGAACTACAGAGTGCGAGGTGAGCCAGTGCCAGAGCCAAGG

CCAGACTCAGGCAGGGACTGGAGTGTGGAGCTGCAGGAGCTGCCTGAGCTGTGTTTCTCCCA

GGTAATCCGGGAAGGAGGTCATGCAGTGGTTTGGGCCGGGCAGCTGCAAGGAAAACTGGTTG

CCATCAAGGCCTTCCCACCGAGGTCTGTGGCTCAGTTCCAAGCTGAGAGAGCATTGTACGAA

-continued

CTTCCAGGCCTACAGCACGACCACATTGTCCGATTTATCACTGCCAGCCGGGGGGTCCTGG

CCGCCTGCTCTCTGGGCCCCTGCTGGTACTGGAACTGCATCCCAAGGGCTCCCTGTGCCACT

ACTTGACCCAGTACACCAGTGACTGGGGAAGTTCCCTGCGGATGGCACTGTCCCTGGCCCAG

GGCCTGGCATTTCTCCATGAGGAGCGCTGGCAGAATGGCCAATATAAACCAGGTATTGCCCA

CCGAGATCTGAGCAGCCAGAATGTGCTCATTCGGGAAGATGGATCGTGTGCCATTGGAGACC

TGGGCCTTGCCTTGGTGCTCCCTGGCCTCACTCAGCCCCCTGCCTGGACCCCTACTCAACCA

CAAGGCCCAGCTGCCATCATGGAAGACCCTGATGGGCTGAGGGAGCTCCTAGAAGACTGTTG

GGATGCAGACCCAGAAGCACGGCTGACAGCTGAGTGTGTACAGCAGCGCCTGGCTGCCTTGG

CCCATCCTCAAGAGAGCCACCCCTTTCCAGAGAGCTGTCCACGTGGCTGCCCACCTCTCTGC

CCAGAAGACTGTACTTCAATTCCTGCCCCTACCATCCTCCCCTGTAGGCCTCAGCGGAGTGC

CTGCCACTTCAGCGTTCAGCAAGGCCCTTGTTCCAGGAATCCTCAGCCTGCCTGTACCCTTT

CTCCTGTG (SEQ ID NO: 214)

CCCCCAAACAGGCGAACCTGTGTGTTCTTTGAGGCCCCTGGAGTGCGGGGAAGCACAAAGAC

ACTGGGAGAGCTGCTAGATACAGGCACAGAGCTCCCCAGAGCTATCCGCTGCCTCTACAGCC

GCTGCTGCTTTGGGATCTGGAACCTGACCCAAGACCGGGCACAGGTGGAAATGCAAGGATGC

CGAGACAGTGATGAGCCAGGCTGTGAGTCCCTCCACTGTGACCCAAGTCCCCGAGCCCACCC

CAGCCCTGGCTCCACTCTCTTCACCTGCTCCTGTGGCACTGACTTCTGCAATGCCAATTACA

GCCATCTGCCTCCTCCAGGGAGCCCTGGGACTCCTGGCTCCCAGGGTCCCCAGGCTGCCCCA

GGTGAGTCCATCTGGATGGCACTG (SEQ ID NO: 215)

ATGACCTTGGGCTCCCCAGGAAAGGCCTTCTGATGCTGCTGATGGCCTTGGTGACCCAGGGAGACCCTGTGAAG

CCGTCTCGGGGCCCGCTGGTGACCTGCACGTGTGAGAGCCCACATTGCAAGGGGCCTACCTGCCGGGGGCCTGG

TGCACAGTAGTGCTGGTGCGGGAGGAGGGGAGGCACCCCCAGGAACATCGGGGCTGCGGGAACTTGCACAGGGAG

CTCTGCAGGGGCGCCCCACCGAGTTCGTCAACCACTACTGCTGCGACAGCCACCTCTGCAACCACAACGTGTCC

CTGGTGCTGGAGGCCACCCAACCTCCTTCGGAGCAGCCGGGAACAGATGGCCAGCTGGCCCTGATCCTGGGCCCC

GTGCTGGCCTTGCTGGCCCTGGTGGCCCTGGGTGTCCTGGGCCTGTGGCATGTCCGACGGAGGCAGGAGAAGCAG

CGTGGCCTGCACAGCGAGCTGGGAGAGTCCAGTCTCATCCTGAAAGCATCTGAGCAGGGCGACAGCATGTTGGGG

GACCTCCTGGACAGTGACTGCACCACAGGGAGTGGCTCAGGGCTCCCCTTCCTGGTGCAGAGGACAGTGGCACGG

CAGGTTGCCTTGGTGGAGTGTGTGGGAAAAGGCCGCTATGGCGAAGTGTGGCGGGGCTTGTGGCACGGTGAGAGT

GTGGCCGTCAAGATCTTCTCCTCGAGGGATGAACAGTCCTGGTTCCGGGAGACTGAGATCTATAACACAGTGTTG

CTCAGACACGACAACATCCTAGGCTTCATCGCCTCAGACATGACCTCCCGCAACTCGAGCACGCAGCTGTGGCTC

ATCACGCACTACCACGAGCACGGCTCCCTCTACGACTTTCTGCAGAGACAGACGCTGGAGCCCCATCTGGCTCTG

AGGCTAGCTGTGTCCGCGGCATGCGGCCTGGCGCACCTGCACGTGGAGATCTTCGGTACACAGGGCAAACCAGCC

ATTGCCCACCGCGACTTCAAGAGCCGCAATGTGCTGGTCAAGAGCAACCTGCAGTGTTGCATCGCCGACCTGGGC

CTGGCTGTGATGCACTCACAGGGCAGCGATTACCTGGACATCGGCAACAACCCGAGAGTGGGCACCAAGCGGTAC

ATGGCACCCGAGGTGCTGGACGAGCAGATCCGCACGGACTGCTTTGAGTCCTACAAGTGGACTGACATCTGGGCC

TTTGGCCTGGTGCTGTGGGAGATTGCCCGCCGGACCATCGTGAATGGCATCGTGGAGGACTATAGACCACCCTTC

TATGATGTGGTGCCCAATGACCCCAGCTTTGAGGACATGAAGAAGGTGGTGTGTGTGGATCAGCAGACCCCCACC

ATCCCTAACCGGCTGGCTGCAGACCCGGTCCTCTCAGGCCTAGCTCAGATGATGCGGGAGTGCTGGTACCCAAAC

CCCTCTGCCCGACTCACCGCGCTGCGGATCAAGAAGACACTACAAAAAATTAGCAACAGTCCAGAGAAGCCTAAA

GTGATTCAA (SEQ ID NO: 216)

GACCCTGTGAAGCCGTCTCGGGGCCCGCTGGTGACCTGCACGTGTGAGAGCCCACATTGCAA

GGGGCCTACCTGCCGGGGGGCCTGGTGCACAGTAGTGCTGGTGCGGGAGGAGGGGAGGCACC

CCCAGGAACATCGGGGCTGCGGGAACTTGCACAGGGAGCTCTGCAGGGGGCGCCCCACCGAG

TTCGTCAACCACTACTGCTGCGACAGCCACCTCTGCAACCACAACGTGTCCCTGGTGCTGGA

GGCCACCCAACCTCCTTCGGAGCAGCCGGGAACAGATGGCCAG (SEQ ID NO: 217)

<u>ATGGTAGATGGAGTGATGATTCTTCCTGTGCTTATCATGATTGCTCTCCCCTCCCCTAGT</u>ATGGAAGATGAGAAG

CCCAAGGTCAACCCCAAACTCTACATGTGTGTGTGTGAAGGTCTCTCCTGCGGTAATGAGGACCACTGTGAAGGC

CAGCAGTGCTTTTCCTCACTGAGCATCAACGATGGCTTCCACGTCTACCAGAAAGGCTGCTTCCAGGTTTATGAG

CAGGGAAAGATGACCTGTAAGACCCCGCCGTCCCCTGGCCAAGCCGTGGAGTGCTGCCAAGGGGACTGGTGTAAC

AGGAACATCACGGCCCAGCTGCCCACTAAAGGAAAATCCTTCCCTGGAACACAGAATTTCCACTTGGAGGTTGGC

CTCATTATTCTCTCTGTAGTGTTCGCAGTATGTCTTTTAGCCTGCCTGCTGGGAGTTGCTCTCCGAAAATTTAAA

AGGCGCAACCAAGAACGCCTCAATCCCCGAGACGTGGAGTATGGCACTATCGAAGGGCTCATCACCACCAATGTT

GGAGACAGCACTTTAGCAGATTTATTGGATCATTCGTGTACATCAGGAAGTGGCTCTGGTCTTCCTTTTCTGGTA

CAAAGAACAGTGGCTCGCCAGATTACACTGTTGGAGTGTGTCGGGAAAGGCAGGTATGGTGAGGTGTGGAGGGGC

AGCTGGCAAGGGGAGAATGTTGCCGTGAAGATCTTCTCCTCCCGTGATGAGAAGTCATGGTTCAGGGAAACGGAA

TTGTACAACACTGTGATGCTGAGGCATGAAAATATCTTAGGTTTCATTGCTTCAGACATGACATCAAGACACTCC

AGTACCCAGCTGTGGTTAATTACACATTATCATGAAATGGGATCGTTGTACGACTATCTTCAGCTTACTACTCTG

GATACAGTTAGCTGCCTTCGAATAGTGCTGTCCATAGCTAGTGGTCTTGCACATTTGCACATAGAGATATTTGGG

ACCCAAGGGAAACCAGCCATTGCCCATCGAGATTTAAAGAGCAAAAATATTCTGGTTAAGAAGAATGGACAGTGT

TGCATAGCAGATTTGGGCCTGGCAGTCATGCATTCCCAGAGCACCAATCAGCTTGATGTGGGGAACAATCCCCGT

GTGGGCACCAAGCGCTACATGGCCCCCGAAGTTCTAGATGAAACCATCCAGGTGGATTGTTTCGATTCTTATAAA

AGGGTCGATATTTGGGCCTTTGGACTTGTTTTGTGGGAAGTGGCCAGGCGGATGGTGAGCAATGGTATAGTGGAG

GATTACAAGCCACCGTTCTACGATGTGGTTCCCAATGACCCAAGTTTTGAAGATATGAGGAAGGTAGTCTGTGTG

GATCAACAAAGGCCAAACATACCCAACAGATGGTTCTCAGACCCGACATTAACCTCTCTGGCCAAGCTAATGAAA

GAATGCTGGTATCAAAATCCATCCGCAAGACTCACAGCACTGCGTATCAAAAAGACTTTGACCAAAATTGATAAT

TCCCTCGACAAATTGAAAACTGACTGT (SEQ ID NO: 218)

ATGGAAGATGAGAAGCCCAAGGTCAACCCCAAACTCTACATGTGTGTGTGTGAAGGTCTCTC

CTGCGGTAATGAGGACCACTGTGAAGGCCAGCAGTGCTTTTCCTCACTGAGCATCAACGATG

GCTTCCACGTCTACCAGAAAGGCTGCTTCCAGGTTTATGAGCAGGGAAAGATGACCTGTAAG

ACCCCGCCGTCCCCTGGCCAAGCCGTGGAGTGCTGCCAAGGGGACTGGTGTAACAGGAACAT

CACGGCCCAGCTGCCCACTAAAGGAAAATCCTTCCCTGGAACACAGAATTTCCACTTGGAG (SEQ ID NO: 219)

```
  1 ATGCCTCAGC TATACATTTA CATCAGATTA TTGGGAGCCT ATTTGTTCAT CATTTCTCGT
 61 GTTCAAGGAC AGAATCTGGA TAGTATGCTT CATGGCACTG GGATGAAATC AGACTCCGAC
121 CAGAAAAAGT CAGAAAATGG AGTAACCTTA GCACCAGAGG ATACCTTGCC TTTTTTAAAG
181 TGCTATTGCT CAGGGCACTG TCCAGATGAT GCTATTAATA ACACATGCAT AACTAATGGA
```

-continued

```
 241 CATTGCTTTG CCATCATAGA AGAAGATGAC CAGGGAGAAA CCACATTAGC TTCAGGGTGT

301 ATGAAATATG AAGGATCTGA TTTTCAGTGC AAAGATTCTC CAAAAGCCCA GCTACGCCGG

361 ACAATAGAAT GTTGTCGGAC CAATTTATGT AACCAGTATT TGCAACCCAC ACTGCCCCCT

421 GTTGTCATAG GTCCGTTTTT TGATGGCAGC ATTCGATGGC TGGTTTTGCT CATTTCTATG

481 GCTGTCTGCA TAATTGCTAT GATCATCTTC TCCAGCTGCT TTTGTTACAA ACATTATTGC

541 AAGAGCATCT CAAGCAGACG TCGTTACAAT CGTGATTTGG AACAGGATGA AGCATTTATT

601 CCAGTTGGAG AATCACTAAA AGACCTTATT GACCAGTCAC AAAGTTCTGG TAGTGGGTCT

661 GGACTACCTT TATTGGTTCA GCGAACTATT GCCAAACAGA TTCAGATGGT CCGGCAAGTT

721 GGTAAAGGCC GATATGGAGA AGTATGGATG GGCAAATGGC GTGGCGAAAA AGTGGCGGTG

781 AAAGTATTCT TTACCACTGA AGAAGCCAGC TGGTTTCGAG AAACAGAAAT CTACCAAACT

841 GTGCTAATGC GCCATGAAAA CATACTTGGT TTCATAGCGG CAGACATTAA AGGTACAGGT

901 TCCTGGACTC AGCTCTATTT GATTACTGAT TACCATGAAA ATGGATCTCT CTATGACTTC

961 CTGAAATGTG CTACACTGGA CACCAGAGCC CTGCTTAAAT TGGCTTATTC AGCTGCCTGT

1021 GGTCTGTGCC ACCTGCACAC AGAAATTTAT GGCACCCAAG GAAAGCCCGC AATTGCTCAT

1081 CGAGACCTAA AGAGCAAAAA CATCCTCATC AAGAAAAATG GGAGTTGCTG CATTGCTGAC

1141 CTGGGCCTTG CTGTTAAATT CAACAGTGAC ACAAATGAAG TTGATGTGCC CTTGAATACC

1201 AGGGTGGGCA CCAAACGCTA CATGGCTCCC GAAGTGCTGG ACGAAAGCCT GAACAAAAC

1261 CACTTCCAGC CCTACATCAT GGCTGACATC TACAGCTTCG GCCTAATCAT TTGGGAGATG

1321 GCTCGTCGTT GTATCACAGG AGGGATCGTG GAAGAATACC AATTGCCATA TTACAACATG

1381 GTACCGAGTG ATCCGTCATA CGAAGATATG CGTGAGGTTG TGTGTGTCAA ACGTTTGCGG

1441 CCAATTGTGT CTAATCGGTG GAACAGTGAT GAATGTCTAC GAGCAGTTTT GAAGCTAATG

1501 TCAGAATGCT GGGCCCACAA TCCAGCCTCC AGACTCACAG CATTGAGAAT TAAGAAGACG

1561 CTTGCCAAGA TGGTTGAATC CCAAGATGTA AAAATC
```

(SEQ ID NO: 220)

```
   1 CAGAATCTGG ATAGTATGCT TCATGGCACT GGGATGAAAT CAGACTCCGA CCAGAAAAAG

61 TCAGAAAATG GAGTAACCTT AGCACCAGAG GATACCTTGC CTTTTTTAAA GTGCTATTGC

121 TCAGGGCACT GTCCAGATGA TGCTATTAAT AACACATGCA TAACTAATGG ACATTGCTTT

181 GCCATCATAG AAGAAGATGA CCAGGGAGAA ACCACATTAG CTTCAGGGTG TATGAAATAT

241 GAAGGATCTG ATTTTCAGTG CAAAGATTCT CCAAAAGCCC AGCTACGCCG GACAATAGAA

301 TGTTGTCGGA CCAATTTATG TAACCAGTAT TTGCAACCCA CACTGCCCCC TGTTGTCATA

361 GGTCCGTTTT TTGATGGCAG CATTCGA
```

(SEQ ID NO: 221)

```
ATGGCGGAGTCGGCCGGAGCCTCCTCCTTCTTCCCCCTTGTTGTCCTCCTGCTCGC

CGGCAGCGGCGGGTCCGGGCCCCGGGGGGTCCAGGCTCTGCTGTGTGCGTG

CACCAGCTGCCTCCAGGCCAACTACACGTGTGAGACAGATGGGGCCTGCAT

GGTTTCCATTTTCAATCTGGATGGGATGGAGCACCATGTGCGCACCTGCATC

CCCAAAGTGGAGCTGGTCCCTGCCGGGAAGCCCTTCTACTGCCTGAGCTCG

GAGGACCTGCGCAACACCCACTGCTGCTACACTGACTACTGCAACAGGATC

GACTTGAGGGTGCCCAGTGGTCACCTCAAGGAGCCTGAGCACCCGTCCATG

TGGGGCCCGGTGGAGCTGGTAGGCATCATCGCCGGCCCGGTGTTCCTCCTGTTC

CTCATCATCATCATTGTTTTCCTTGTCATTAACTATCATCAGCGTGTCTATCACAA

CCGCCAGAGACTGGACATGGAAGATCCCTCATGTGAGATGTGTCTCTCCAAAGA
```

-continued

CAAGACGCTCCAGGATCTTGTCTACGATCTCTCCACCTCAGGGTCTGGCTCAGGG
TTACCCCTCTTTGTCCAGCGCACAGTGGCCCGAACCATCGTTTTACAAGAGATTA
TTGGCAAGGGTCGGTTTGGGGAAGTATGGCGGGGCCGCTGGAGGGGTGGTGATG
TGGCTGTGAAAATATTCTCTTCTCGTGAAGAACGGTCTTGGTTCAGGGAAGCAGA
GATATACCAGACGGTCATGCTGCGCCATGAAAACATCCTTGGATTTATTGCTGCT
GACAATAAAGATAATGGCACCTGGACACAGCTGTGGCTTGTTTCTGACTATCATG
AGCACGGGTCCCTGTTTGATTATCTGAACCGGTACACAGTGACAATTGAGGGGAT
GATTAAGCTGGCCTTGTCTGCTGCTAGTGGGCTGGCACACCTGCACATGGAGATC
GTGGGCACCCAAGGGAAGCCTGGAATTGCTCATCGAGACTTAAAGTCAAAGAAC
ATTCTGGTGAAGAAAAATGGCATGTGTGCCATAGCAGACCTGGGCCTGGCTGTCC
GTCATGATGCAGTCACTGACACCATTGACATTGCCCCGAATCAGAGGGTGGGGA
CCAAACGATACATGGCCCCTGAAGTACTTGATGAAACCATTAATATGAAACACTT
TGACTCCTTTAAATGTGCTGATATTTATGCCCTCGGGCTTGTATATTGGGAGATTG
CTCGAAGATGCAATTCTGGAGGAGTCCATGAAGAATATCAGCTGCCATATTACG
ACTTAGTGCCCTCTGACCCTTCCATTGAGGAAATGCGAAAGGTTGTATGTGATCA
GAAGCTGCGTCCCAACATCCCCAACTGGTGGCAGAGTTATGAGGCACTGCGGGT
GATGGGAAGATGATGCGAGAGTGTTGGTATGCCAACGGCGCAGCCCGCCTGAC
GGCCCTGCGCATCAAGAAGACCCTCTCCCAGCTCAGCGTGCAGGAAGACGTGAA
GATC (SEQ ID NO: 222)
TCCGGGCCCCGGGGGGTCCAGGCTCTGCTGTGTGCGTGCACCAGCTGCCTCCAGGCCAACTA
CACGTGTGAGACAGATGGGGCCTGCATGGTTTCCATTTTCAATCTGGATGGGATGGAGCACC
ATGTGCGCACCTGCATCCCCAAAGTGGAGCTGGTCCCTGCCGGGAAGCCCTTCTACTGCCTG
AGCTCGGAGGACCTGCGCAACACCCACTGCTGCTACACTGACTACTGCAACAGGATCGACTT
GAGGGTGCCCAGTGGTCACCTCAAGGAGCCTGAGCACCCGTCCATGTGGGGCCCGGTGGAG (SEQ ID NO: 223)
<ins>ATGGCGGAGTCGGCCGGAGCCTCCTCCTTCTTCCCCCTTGTTGTCCTCCTGCTCGCCGGCAGCGGCGGG</ins>**TCCGGG
CCCCGGGGGGTCCAGGCTCTGCTGTGTGCGTGCACCAGCTGCCTCCAGGCCAACTACACGTGTGAGACAGATGGG
GCCTGCATGGTTTCCATTTTCAATCTGGATGGGATGGAGCACCATGTGCGCACCTGCATCCCCAAAGTGGAGCTG
GTCCCTGCCGGGAAGCCCTTCTACTGCCTGAGCTCGGAGGACCTGCGCAACACCCACTGCTGCTACACTGACTAC
TGCAACAGGATCGACTTGAGGGTGCCCAGTGGTCACCTCAAGGAGCCTGAGCACCCGTCCATGTGGGGCCCGGTG
GAG**CTGGTAGGCATCATCGCCGGCCCGGTGTTCCTCCTGTTCCTCATCATCATCATTGTTTTCCTTGTCATTAAC
TATCATCAGCGTGTCTATCACAACCGCCAGAGACTGGACATGGAAGATCCCTCATGTGAGATGTGTCTCTCCAAA
GACAAGACGCTCCAGGATCTTGTCTACGATCTCTCCACCTCAGGGTCTGGCTCAGGGTTACCCCTCTTTGTCCAG
CGCACAGTGGCCCGAACCATCGTTTTACAAGAGATTATTGGCAAGGGTCGGTTTGGGGAAGTATGGCGGGGCCGC
TGGAGGGGTGGTGATGTGGCTGTGAAAATATTCTCTTCTCGTGAAGAACGGTCTTGGTTCAGGGAAGCAGAGATA
TACCAGACGGTCATGCTGCGCCATGAAAACATCCTTGGATTTATTGCTGCTGACAATAAAGCAGACTGCTCATTC
CTCACATTGCCATGGGAAGTTGTAATGGTCTCTGCTGCCCCCAAGCTGAGGAGCCTTAGACTCCAATACAAGGGA
GGAAGGGGAAGAGCAAGATTTTTATTCCCACTGAATAATGGCACCTGGACACAGCTGTGGCTTGTTTCTGACTAT
CATGAGCACGGGTCCCTGTTTGATTATCTGAACCGGTACACAGTGACAATTGAGGGGATGATTAAGCTGGCCTTG
TCTGCTGCTAGTGGGCTGGCACACCTGCACATGGAGATCGTGGGCACCCAAGGGAAGCCTGGAATTGCTCATCGA

GACTTAAAGTCAAAGAACATTCTGGTGAAGAAAAATGGCATGTGTGCCATAGCAGACCTGGGCCTGGCTGTCCGT

CATGATGCAGTCACTGACACCATTGACATTGCCCCGAATCAGAGGGTGGGGACCAAACGATACATGGCCCCTGAA

GTACTTGATGAAACCATTAATATGAAACACTTTGACTCCTTTAAATGTGCTGATATTTATGCCCTCGGGCTTGTA

TATTGGGAGATTGCTCGAAGATGCAATTCTGGAGGAGTCCATGAAGAATATCAGCTGCCATATTACGACTTAGTG

CCCTCTGACCCTTCCATTGAGGAAATGCGAAAGGTTGTATGTGATCAGAAGCTGCGTCCCAACATCCCCAACTGG

TGGCAGAGTTATGAGGCACTGCGGGTGATGGGGAAGATGATGCGAGAGTGTTGGTATGCCAACGGCGCAGCCCGC

CTGACGGCCCTGCGCATCAAGAAGACCCTCTCCCAGCTCAGCGTGCAGGAAGACGTGAAGATC (SEQ ID NO: 224)
TCCGGGCCCCGGGGGGTCCAGGCTCTGCTGTGTGCGTGCACCAGCTGCCTCCAGGCCAACTA

CACGTGTGAGACAGATGGGGCCTGCATGGTTTCCATTTTCAATCTGGATGGGATGGAGCACC

ATGTGCGCACCTGCATCCCCAAAGTGGAGCTGGTCCCTGCCGGGAAGCCCTTCTACTGCCTG

AGCTCGGAGGACCTGCGCAACACCCACTGCTGCTACACTGACTACTGCAACAGGATCGACTT

GAGGGTGCCCAGTGGTCACCTCAAGGAGCCTGAGCACCCGTCCATGTGGGGCCCGGTGGAG (SEQ ID NO: 225)
<u>ATGGAGGCGGCGGTCGCTGCTCCGCGTCCCCGGCTGCTCCTCCTCGTGCTGGCGGCGGCGGCGGCGGCG</u>GCG

GCGCTGCTCCCGGGGGCGACGGCGTTACAGTGTTTCTGCCACCTCTGTACAAAAGACAATTTTACTTGTGTGACA

GATGGGCTCTGCTTTGTCTCTGTCACAGAGACCACAGACAAAGTTATACACAACAGCATGTGTATAGCTGAAATT

GACTTAATTCCTCGAGATAGGCCGTTTGTATGTGCACCCTCTTCAAAAACTGGGTCTGTGACTACAACATATTGC

TGCAATCAGGACCATTGCAATAAAATAGAACTTCCAACTACTGTAAAGTCATCACCTGGCCTTGGTCCTGTGGAA

CTGGCAGCTGTCATTGCTGGACCAGTGTGCTTCGTCTGCATCTCACTCATGTTGATGGTCTATATCTGCCACAAC

CGCACTGTCATTCACCATCGAGTGCCAAATGAAGAGGACCCTTCATTAGATCGCCCTTTTATTTCAGAGGGTACT

ACGTTGAAAGACTTAATTTATGATATGACAACGTCAGGTTCTGGCTCAGGTTTACCATTGCTTGTTCAGAGAACA

ATTGCGAGAACTATTGTGTTACAAGAAAGCATTGGCAAAGGTCGATTGGAGAAGTTTGGAGAGGAAAGTGGCGG

GGAGAAGAAGTTGCTGTTAAGATATTCTCCTCTAGAGAAGAACGTTCGTGGTTCCGTGAGGCAGAGATTTATCAA

ACTGTAATGTTACGTCATGAAAACATCCTGGGATTTATAGCAGCAGACAATAAAGACAATGGTACTTGGACTCAG

CTCTGGTTGGTGTCAGATTATCATGAGCATGGATCCCTTTTTGATTACTTAAACAGATACACAGTTACTGTGGAA

GGAATGATAAAACTTGCTCTGTCCACGGCGAGCGGTCTTGCCCATCTTCACATGGAGATTGTTGGTACCCAAGGA

AAGCCAGCCATTGCTCATAGAGATTTGAAATCAAAGAATATCTTGGTAAAGAAGAATGGAACTTGCTGTATTGCA

GACTTAGGACTGGCAGTAAGACATGATTCAGCCACAGATACCATTGATATTGCTCCAAACCACAGAGTGGGAACA

AAAAGGTACATGGCCCCTGAAGTTCTCGATGATTCCATAAATATGAAACATTTTGAATCCTTCAAACGTGCTGAC

ATCTATGCAATGGGCTTAGTATTCTGGGAAATTGCTCGACGATGTTCCATTGGTGGAATTCATGAAGATTACCAA

CTGCCTTATTATGATCTTGTACCTTCTGACCCATCAGTTGAAGAAATGAGAAAAGTTGTTTGTGAACAGAAGTTA

AGGCCAAATATCCCAAACAGATGGCAGAGCTGTGAAGCCTTGAGAGTAATGGCTAAAATTATGAGAGAATGTTGG

TATGCCAATGGAGCAGCTAGGCTTACAGCATTGCGGATTAAGAAAACATTATCGCAACTCAGTCAACAGGAAGGC

ATCAAAATG (SEQ ID NO: 226)
GCGGCGCTGCTCCCGGGGGCGACGGCGTTACAGTGTTTCTGCCACCTCTGTACAAAAGACAA

TTTTACTTGTGTGACAGATGGGCTCTGCTTTGTCTCTGTCACAGAGACCACAGACAAAGTTA

TACACAACAGCATGTGTATAGCTGAAATTGACTTAATTCCTCGAGATAGGCCGTTTGTATGT

GCACCCTCTTCAAAAACTGGGTCTGTGACTACAACATATTGCTGCAATCAGGACCATTGCAA

TAAAATAGAACTTCCAACTACTGTAAAGTCATCACCTGGCCTTGGTCCTGTGGAACTG (SEQ ID NO: 227)

<u>ATGGAGGCGGCGGTCGCTGCTCCGCGTCCCCGGCTGCTCCTCCTCGTGCTGGCGGCGGCGGC</u>
<u>GGCGGCGGCGG</u>CGGCGCTGCTCCCGGGGGCGACGGCGTTACAGTGTTTCTGCCACCTCTGTA
CAAAAGACAATTTTACTTGTGTGACAGATGGGCTCTGCTTTGTCTCTGTCACAGAGACCACA
GACAAAGTTATACACAACAGCATGTGTATAGCTGAAATTGACTTAATTCCTCGAGATAGGCC
GTTTGTATGTGCACCCTCTTCAAAAACTGGGTCTGTGACTACAACATATTGCTGCAATCAGG
ACCATTGCAATAAAATAGAACTTCCAACTACTGGCCCTTTTTCAGTAAAGTCATCACCTGGC
CTTGGTCCTGTGGAACTGGCAGCTGTCATTGCTGGACCAGTGTGCTTCGTCTGCATCTCACT
CATGTTGATGGTCTATATCTGCCACAACCGCACTGTCATTCACCATCGAGTGCCAAATGAAG
AGGACCCTTCATTAGATCGCCCTTTTATTTCAGAGGGTACTACGTTGAAAGACTTAATTTAT
GATATGACAACGTCAGGTTCTGGCTCAGGTTTACCATTGCTTGTTCAGAGAACAATTGCGAG
AACTATTGTGTTACAAGAAAGCATTGGCAAAGGTCGATTTGGAGAAGTTTGGAGAGGAAAGT
GGCGGGGAGAAGAAGTTGCTGTTAAGATATTCTCCTCTAGAGAAGAACGTTCGTGGTTCCGT
GAGGCAGAGATTTATCAAACTGTAATGTTACGTCATGAAAACATCCTGGGATTTATAGCAGC
AGACAATAAAGACAATGGTACTTGGACTCAGCTCTGGTTGGTGTCAGATTATCATGAGCATG
GATCCCTTTTTGATTACTTAAACAGATACACAGTTACTGTGGAAGGAATGATAAAACTTGCT
CTGTCCACGGCGAGCGGTCTTGCCCATCTTCACATGGAGATTGTTGGTACCCAAGGAAAGCC
AGCCATTGCTCATAGAGATTTGAAATCAAAGAATATCTTGGTAAAGAAGAATGGAACTTGCT
GTATTGCAGACTTAGGACTGGCAGTAAGACATGATTCAGCCACAGATACCATTGATATTGCT
CCAAACCACAGAGTGGGAACAAAAAGGTACATGGCCCCTGAAGTTCTCGATGATTCCATAAA
TATGAAACATTTTGAATCCTTCAAACGTGCTGACATCTATGCAATGGGCTTAGTATTCTGGG
AAATTGCTCGACGATGTTCCATTGGTGGAATTCATGAAGATTACCAACTGCCTTATTATGAT
CTTGTACCTTCTGACCCATCAGTTGAAGAAATGAGAAAAGTTGTTTGTGAACAGAAGTTAAG
GCCAAATATCCCAAACAGATGGCAGAGCTGTGAAGCCTTGAGAGTAATGGCTAAAATTATGA
GAGAATGTTGGTATGCCAATGGAGCAGCTAGGCTTACAGCATTGCGGATTAAGAAAACATTA
TCGCAACTCAGTCAACAGGAAGGCATCAAAATG (SEQ ID NO: 228)

GCGGCGCTGCTCCCGGGGGCGACGGCGTTACAGTGTTTCTGCCACCTCTGTACAAAAGACAA
TTTTACTTGTGTGACAGATGGGCTCTGCTTTGTCTCTGTCACAGAGACCACAGACAAAGTTA
TACACAACAGCATGTGTATAGCTGAAATTGACTTAATTCCTCGAGATAGGCCGTTTGTATGT
GCACCCTCTTCAAAAACTGGGTCTGTGACTACAACATATTGCTGCAATCAGGACCATTGCAA
TAAAATAGAACTTCCAACTACTGGCCCTTTTTCAGTAAAGTCATCACCTGGCCTTGGTCCTG
TGGAACTG (SEQ ID NO: 229)

<u>ATGCTTTTGCGAAGTGCAGGAAAATTAAATGTGGGCACC</u>AAGAAAGAGGATGGTGAGAGTACAGCCCCCACCCCC
CGTCCAAAGGTCTTGCGTTGTAAATGCCACCACCATTGTCCAGAAGACTCAGTCAACATATTTGCAGCACAGAC
GGATATTGTTTCACGATGATAGAAGAGGATGACTCTGGGTTGCCTGTGGTCACTTCTGGTTGCCTAGGACTAGAA
GGCTCAGATTTTCAGTGTCGGGACACTCCCATTCCTCATCAAAGAAGATCAATTGAATGCTGCACAGAAAGGAAC
GAATGTAATAAAGACCTACACCCTACACTGCCTCCATTGAAAAACAGAGATTTTGTTGATGGACCTATACACCAC
AGGGCTTTACTTATATCTGTGACTGTCTGTAGTTTGCTCTTGGTCCTTATCATATTATTTTGTTACTTCCGGTAT
AAAAGACAAGAAACCAGACCTCGATACAGCATTGGGTTAGAACAGGATGAAACTTACATTCCTCCTGGAGAATCC
CTGAGAGACTTAATTGAGCAGTCTCAGAGCTCAGGAAGTGGATCAGGCCTCCCTCTGCTGGTCCAAAGGACTATA

-continued

GCTAAGCAGATTCAGATGGTGAAACAGATTGGAAAAGGTCGCTATGGGAAGTTTGGATGGGAAAGTGGCGTGGC

GAAAAGGTAGCTGTGAAAGTGTTCTTCACCACAGAGGAAGCCAGCTGGTTCAGAGAGACAGAAATATATCAGACA

GTGTTGATGAGGCATGAAAACATTTTGGGTTTCATTGCTGCAGATATCAAAGGGACAGGGTCCTGGACCCAGTTG

TACCTAATCACAGACTATCATGAAAATGGTTCCCTTTATGATTATCTGAAGTCCACCACCCTAGACGCTAAATCA

ATGCTGAAGTTAGCCTACTCTTCTGTCAGTGGCTTATGTCATTTACACACAGAAATCTTTAGTACTCAAGGCAAA

CCAGCAATTGCCCATCGAGATCTGAAAAGTAAAAACATTCTGGTGAAGAAAATGGAACTTGCTGTATTGCTGAC

CTGGGCCTGGCTGTTAAATTTATTAGTGATACAAATGAAGTTGACATACCACCTAACACTCGAGTTGGCACCAAA

CGCTATATGCCTCCAGAAGTGTTGGACGAGAGCTTGAACAGAAATCACTTCCAGTCTTACATCATGGCTGACATG

TATAGTTTTGGCCTCATCCTTTGGGAGGTTGCTAGGAGATGTGTATCAGGAGGTATAGTGGAAGAATACCAGCTT

CCTTATCATGACCTAGTGCCCAGTGACCCCTCTTATGAGGACATGAGGGAGATTGTGTGCATCAAGAAGTTACGC

CCCTCATTCCCAAACCGGTGGAGCAGTGATGAGTGTCTAAGGCAGATGGGAAAACTCATGACAGAATGCTGGGCT

CACAATCCTGCATCAAGGCTGACAGCCCTGCGGGTTAAGAAAACACTTGCCAAAATGTCAGAGTCCCAGGACATT

AAACTC (SEQ ID NO: 230)
AAGAAAGAGGATGGTGAGAGTACAGCCCCCACCCCCCGTCCAAAGGTCTTGCGTTGTAAATG

CCACCACCATTGTCCAGAAGACTCAGTCAACAATATTTGCAGCACAGACGGATATTGTTTCA

CGATGATAGAAGAGGATGACTCTGGGTTGCCTGTGGTCACTTCTGGTTGCCTAGGACTAGAA

GGCTCAGATTTTCAGTGTCGGGACACTCCCATTCCTCATCAAAGAAGATCAATTGAATGCTG

CACAGAAAGGAACGAATGTAATAAAGACCTACACCCTACACTGCCTCCATTGAAAAACAGAG

ATTTTGTTGATGGACCTATACACCACAGG (SEQ ID NO: 231)
ATGGGTTGGCTGGAAGAACTAAACTGGCAGCTTCACATTTTCTTGCTCATTCTTCTCTATGCACACAAGGGCA

AACTTCCTTGATAACATGCTTTTGCGAAGTGCAGGAAAATTAAATGTGGGCACCAAGAAAGAGGATGGTGAGAGT

ACAGCCCCCACCCCCCGTCCAAAGGTCTTGCGTTGTAAATGCCACCACCATTGTCCAGAAGACTCAGTCAACAAT

ATTTGCAGCACAGACGGATATTGTTTCACGATGATAGAAGAGGATGACTCTGGGTTGCCTGTGGTCACTTCTGGT

TGCCTAGGACTAGAAGGCTCAGATTTTCAGTGTCGGGACACTCCCATTCCTCATCAAAGAAGATCAATTGAATGC

TGCACAGAAAGGAACGAATGTAATAAAGACCTACACCCTACACTGCCTCCATTGAAAAACAGAGATTTTGTTGAT

GGACCTATACACCACAGGGCTTTACTTATATCTGTGACTGTCTGTAGTTTGCTCTTGGTCCTTATCATATTATTT

TGTTACTTCCGGTATAAAAGACAAGAAACCAGACCTCGATACAGCATTGGGTTAGAACAGGATGAAACTTACATT

CCTCCTGGAGAATCCCTGAGAGACTTAATTGAGCAGTCTCAGAGCTCAGGAAGTGGATCAGGCCTCCCTCTGCTG

GTCCAAAGGACTATAGCTAAGCAGATTCAGATGGTGAAACAGATTGGAAAAGGTCGCTATGGGAAGTTTGGATG

GGAAAGTGGCGTGGCGAAAAGGTAGCTGTGAAAGTGTTCTTCACCACAGAGGAAGCCAGCTGGTTCAGAGAGACA

GAAATATATCAGACAGTGTTGATGAGGCATGAAAACATTTTGGGTTTCATTGCTGCAGATATCAAAGGGACAGGG

TCCTGGACCCAGTTGTACCTAATCACAGACTATCATGAAAATGGTTCCCTTTATGATTATCTGAAGTCCACCACC

CTAGACGCTAAATCAATGCTGAAGTTAGCCTACTCTTCTGTCAGTGGCTTATGTCATTTACACACAGAAATCTTT

AGTACTCAAGGCAAACCAGCAATTGCCCATCGAGATCTGAAAAGTAAAAACATTCTGGTGAAGAAAATGGAACT

TGCTGTATTGCTGACCTGGGCCTGGCTGTTAAATTTATTAGTGATACAAATGAAGTTGACATACCACCTAACACT

CGAGTTGGCACCAAACGCTATATGCCTCCAGAAGTGTTGGACGAGAGCTTGAACAGAAATCACTTCCAGTCTTAC

ATCATGGCTGACATGTATAGTTTTGGCCTCATCCTTTGGGAGGTTGCTAGGAGATGTGTATCAGGAGGTATAGTG

GAAGAATACCAGCTTCCTTATCATGACCTAGTGCCCAGTGACCCCTCTTATGAGGACATGAGGGAGATTGTGTGC

ATCAAGAAGTTACGCCCCTCATTCCCAAACCGGTGGAGCAGTGATGAGTGTCTAAGGCAGATGGGAAAACTCATG

ACAGAATGCTGGGCTCACAATCCTGCATCAAGGCTGACAGCCCTGCGGGTTAAGAAAACACTTGCCAAAATGTCA

GAGTCCCAGGACATTAAACTC (SEQ ID NO: 232)
AACTTCCTTGATAACATGCTTTTGCGAAGTGCAGGAAAATTAAATGTGGGCACCAAGAAAGA

GGATGGTGAGAGTACAGCCCCCACCCCCCGTCCAAAGGTCTTGCGTTGTAAATGCCACCACC

ATTGTCCAGAAGACTCAGTCAACAATATTTGCAGCACAGACGGATATTGTTTCACGATGATA

GAAGAGGATGACTCTGGGTTGCCTGTGGTCACTTCTGGTTGCCTAGGACTAGAAGGCTCAGA

TTTTCAGTGTCGGGACACTCCCATTCCTCATCAAAGAAGATCAATTGAATGCTGCACAGAAA

GGAACGAATGTAATAAAGACCTACACCCTACACTGCCTCCATTGAAAAACAGAGATTTTGTT

GATGGACCTATACACCACAGG (SEQ ID NO: 233)
ATGACCCGGGCGCTCTGCTCAGCGCTCCGCCAGGCTCTCCTGCTGCTCGCAGCGGCCGCCGAGCTCTCGCCAGGA

CTGAAGTGTGTATGTCTTTTGTGTGATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCCAGAACTGAATGCTCAAGTCTTCTGT

CATAGTTCCAACAATGTTACCAAAACCGAATGCTGCTTCACAGATTTTTGCAACAACATAACACTGCACCTTCCA

ACAGCATCACCAAATGCCCCAAAACTTGGACCCATGGAGCTGGCCATCATTATTACTGTGCCTGTTTGCCTCCTG

TCCATAGCTGCGATGCTGACAGTATGGGCATGCCAGGGTCGACAGTGCTCCTACAGGAAGAAAAAGAGACCAAAT

GTGGAGGAACCACTCTCTGAGTGCAATCTGGTAAATGCTGGAAAAACTCTGAAAGATCTGATTTATGATGTGACC

GCCTCTGGATCTGGCTCTGGTCTACCTCTGTTGGTTCAAAGGACAATTGCAAGGACGATTGTGCTTCAGGAAATA

GTAGGAAAGGTAGATTTGGTGAGGTGTGGCATGGAAGATGGTGTGGGGAAGATGTGGCTGTGAAAATATTCTCC

TCCAGAGATGAAAGATCTTGGTTTCGTGAGGCAGAAATTTACCAGACGGTCATGCTGCGACATGAAAACATCCTT

GGTTTCATTGCTGCTGACAACAAAGATAATGGAACTTGGACTCAACTTTGGCTGGTATCTGAATATCATGAACAG

GGCTCCTTATATGACTATTTGAATAGAAATATAGTGACCGTGGCTGGAATGATCAAGCTGGCGCTCTCAATTGCT

AGTGGTCTGGCACACCTTCATATGGAGATTGTTGGTACACAAGGTAAACCTGCTATTGCTCATCGAGACATAAAA

TCAAAGAATATCTTAGTGAAAAAGTGTGAAACTTGTGCCATAGCGGACTTAGGGTTGGCTGTGAAGCATGATTCA

ATACTGAACACTATCGACATACCTCAGAATCCTAAAGTGGGAACCAAGAGGTATATGGCTCCTGAAATGCTTGAT

GATACAATGAATGTGAATATCTTTGAGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCCTTATTATGACATGGTGCCTTCAGAT

CCCTCGATAGAGGAAATGAGAAAGGTTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGCCAACGGAGCGGCCCGCCTAACTGCT

CTTCGTATTAAGAAGACTATATCTCAACTTTGTGTCAAAGAAGACTGCAAAGCC (SEQ ID NO: 234)
GAGCTCTCGCCAGGACTGAAGTGTGTATGTCTTTTGTGTGATTCTTCAAACTTTACCTGCCA

AACAGAAGGAGCATGTTGGGCATCAGTCATGCTAACCAATGGAAAAGAGCAGGTGATCAAAT

CCTGTGTCTCCCTTCCAGAACTGAATGCTCAAGTCTTCTGTCATAGTTCCAACAATGTTACC

AAAACCGAATGCTGCTTCACAGATTTTTGCAACAACATAACACTGCACCTTCCAACAGCATC

ACCAAATGCCCCAAAACTTGGACCCATGGAG (SEQ ID NO: 235)
ATGCTAACCAATGGAAAAGAGCAGGTGATCAAATCCTGTGTCTCCCTTCCAGAACTGAATGC

TCAAGTCTTCTGTCATAGTTCCAACAATGTTACCAAAACCGAATGCTGCTTCACAGATTTTT

GCAACAACATAACACTGCACCTTCCAAGAGCATCACCAAATGCCCCAAAACTTGGACCCATG

GAGCTGGCCATCATTATTACTGTGCCTGTTTGCCTCCTGTCCATAGCTGCGATGCTGACAGT

ATGGGCATGCCAGGGTCGACAGTGCTCCTACAGGAAGAAAAAGAGACCAAATGTGGAGGAAC

-continued

```
CACTCTCTGAGTGCAATCTGGTAAATGCTGGAAAAACTCTGAAAGATCTGATTTATGATGTG
ACCGCCTCTGGATCTGGCTCTGGTCTACCTCTGTTGGTTCAAAGGACAATTGCAAGGACGAT
TGTGCTTCAGGAAATAGTAGGAAAAGGTAGATTTGGTGAGGTGTGGCATGGAAGATGGTGTG
GGGAAGATGTGGCTGTGAAAATATTCTCCTCCAGAGATGAAAGATCTTGGTTTCGTGAGGCA
GAAATTTACCAGACGGTCATGCTGCGACATGAAAACATCCTTGGTTTCATTGCTGCTGACAA
CAAAGATAATGGAACTTGGACTCAACTTTGGCTGGTATCTGAATATCATGAACAGGGCTCCT
TATATGACTATTTGAATAGAAATATAGTGACCGTGGCTGGAATGATCAAGCTGGCGCTCTCA
ATTGCTAGTGGTCTGGCACACCTTCATATGGAGATTGTTGGTACACAAGGTAAACCTGCTAT
TGCTCATCGAGACATAAAATCAAAGAATATCTTAGTGAAAAAGTGTGAAACTTGTGCCATAG
CGGACTTAGGGTTGGCTGTGAAGCATGATTCAATACTGAACACTATCGACATACCTCAGAAT
CCTAAAGTGGGAACCAAGAGGTATATGGCTCCTGAAATGCTTGATGATACAATGAATGTGAA
TATCTTTGAGTCCTTCAAACGAGCTGACATCTATTCTGTTGGTCTGGTTTACTGGGAAATAG
CCCGGAGGTGTTCAGTCGGAGGAATTGTTGAGGAGTACCAATTGCCTTATTATGACATGGTG
CCTTCAGATCCCTCGATAGAGGAAATGAGAAAGGTTGTTTGTGACCAGAAGTTTCGACCAAG
TATCCCAAACCAGTGGCAAAGTTGTGAAGCACTCCGAGTCATGGGGAGAATAATGCGTGAGT
GTTGGTATGCCAACGGAGCGGCCCGCCTAACTGCTCTTCGTATTAAGAAGACTATATCTCAA
CTTTGTGTCAAAGAAGACTGCAAAGCC
```

(SEQ ID NO: 236)
```
ATGCTAACCAATGGAAAAGAGCAGGTGATCAAATCCTGTGTCTCCCTTCCAGAACTGAATGC
TCAAGTCTTCTGTCATAGTTCCAACAATGTTACCAAAACCGAATGCTGCTTCACAGATTTTT
GCAACAACATAACACTGCACCTTCCAACAGCATCACCAAATGCCCCAAAACTTGGACCCATG
GAG
```

(SEQ ID NO: 237)
```
ATGACCCGGGCGCTCTGCTCAGCGCTCCGCCAGGCTCTCCTGCTGCTCGCAGCGGCCGCCGA
GCTCTCGCCAGGACTGAAGTGTGTATGTCTTTTGTGTGATTCTTCAAACTTTACCTGCCAAA
CAGAAGGAGCATGTTGGGCATCAGTCATGCTAACCAATGGAAAAGAGCAGGTGATCAAATCC
TGTGTCTCCCTTCCAGAACTGAATGCTCAAGTCTTCTGTCATAGTTCCAACAATGTTACCAA
AACCGAATGCTGCTTCACAGATTTTTGCAACAACATAACACTGCACCTTCCAACAGGTCTAC
CTCTGTTGGTTCAAAGGACAATTGCAAGGACGATTGTGCTTCAGGAAATAGTAGGAAAAGGT
AGATTTGGTGAGGTGTGGCATGGAAGATGGTGTGGGGAAGATGTGGCTGTGAAAATATTCTC
CTCCAGAGATGAAAGATCTTGGTTTCGTGAGGCAGAAATTTACCAGACGGTCATGCTGCGAC
ATGAAAACATCCTTGGTTTCATTGCTGCTGACAACAAAGATAATGGAACTTGGACTCAACTT
TGGCTGGTATCTGAATATCATGAACAGGGCTCCTTATATGACTATTTGAATAGAAATATAGT
GACCGTGGCTGGAATGATCAAGCTGGCGCTCTCAATTGCTAGTGGTCTGGCACACCTTCATA
TGGAGATTGTTGGTACACAAGGTAAACCTGCTATTGCTCATCGAGACATAAAATCAAAGAAT
ATCTTAGTGAAAAAGTGTGAAACTTGTGCCATAGCGGACTTAGGGTTGGCTGTGAAGCATGA
TTCAATACTGAACACTATCGACATACCTCAGAATCCTAAAGTGGGAACCAAGAGGTATATGG
CTCCTGAAATGCTTGATGATACAATGAATGTGAATATCTTTGAGTCCTTCAAACGAGCTGAC
ATCTATTCTGTTGGTCTGGTTTACTGGGAAATAGCCCGGAGGTGTTCAGTCGGAGGAATTGT
TGAGGAGTACCAATTGCCTTATTATGACATGGTGCCTTCAGATCCCTCGATAGAGGAAATGA
GAAAGGTTGTTTGTGACCAGAAGTTTCGACCAAGTATCCCAAACCAGTGGCAAAGTTGTGAA
GCACTCCGAGTCATGGGGAGAATAATGCGTGAGTGTTGGTATGCCAACGGAGCGGCCCGCCT
```

```
AACTGCTCTTCGTATTAAGAAGACTATATCTCAACTTTGTGTCAAAGAAGACTGCAAAGCC
```
(SEQ ID NO: 238)
```
GAGCTCTCGCCAGGACTGAAGTGTGTATGTCTTTTGTGTGATTCTTCAAACTTTACCTGCCA

AACAGAAGGAGCATGTTGGGCATCAGTCATGCTAACCAATGGAAAAGAGCAGGTGATCAAAT

CCTGTGTCTCCCTTCCAGAACTGAATGCTCAAGTCTTCTGTCATAGTTCCAACAATGTTACC

AAAACCGAATGCTGCTTCACAGATTTTTGCAACAACATAACACTGCACCTTCCAACAGGTCT

ACCTCTGTTGGTTCAAAGGACAATTGCAAGGACGATTGTGCTTCAGGAAATAGTAGGAAAAG

GTAGATTTGGTGAGGTGTGGCATGGAAGATGGTGTGGGAAGATGTGGCTGTGAAAATATTC

TCCTCCAGAGATGAAAGATCTTGGTTTCGTGAGGCAGAAATTTACCAGACGGTCATGCTGCG

ACATGAAAACATCCTTGGTTTCATTGCTGCTGACAACAAAGATAATGGAACTTGGACTCAAC

TTTGGCTGGTATCTGAATATCATGAACAGGGCTCCTTATATGACTATTTGAATAGAAATATA

GTGACCGTGGCTGGAATGATCAAGCTGGCGCTCTCAATTGCTAGTGGTCTGGCACACCTTCA

TATGGAGATTGTTGGTACACAAGGTAAACCTGCTATTGCTCATCGAGACATAAAATCAAAGA

ATATCTTAGTGAAAAGTGTGAAACTTGTGCCATAGCGGACTTAGGGTTGGCTGTGAAGCAT

GATTCAATACTGAACACTATCGACATACCTCAGAATCCTAAAGTGGGAACCAAGAGGTATAT

GGCTCCTGAAATGCTTGATGATACAATGAATGTGAATATCTTTGAGTCCTTCAAACGAGCTG

ACATCTATTCTGTTGGTCTGGTTTACTGGGAAATAGCCCGGAGGTGTTCAGTCGGAGGAATT

GTTGAGGAGTACCAATTGCCTTATTATGACATGGTGCCTTCAGATCCCTCGATAGAGGAAAT

GAGAAAGGTTGTTTGTGACCAGAAGTTTCGACCAAGTATCCCAAACCAGTGGCAAAGTTGTG

AAGCACTCCGAGTCATGGGGAGAATAATGCGTGAGTGTTGGTATGCCAACGGAGCGGCCCGC

CTAACTGCTCTTCGTATTAAGAAGACTATATCTCAACTTTGTGTCAAAGAAGACTGCAAAGC

C
```
(SEQ ID NO: 239)
<u>ATGACCCGGGCGCTCTGCTCAGCGCTCCGCCAGGCTCTCCTGCTGCTCGCAGCGGCCGCCGA</u>
```
GCTCTCGCCAGGACTGAAGTGTGTATGTCTTTTGTGTGATTCTTCAAACTTTACCTGCCAAA

CAGAAGGAGCATGTTGGGCATCAGTCATGCTAACCAATGGAAAAGAGCAGGTGATCAAATCC

TGTGTCTCCCTTCCAGAACTGAATGCTCAAGTCTTCTGTCATAGTTCCAACAATGTTACCAA

AACCGAATGCTGCTTCACAGATTTTTGCAACAACATAACACTGCACCTTCCAACAGATAATG

GAACTTGGACTCAACTTTGGCTGGTATCTGAATATCATGAACAGGGCTCCTTATATGACTAT

TTGAATAGAAATATAGTGACCGTGGCTGGAATGATCAAGCTGGCGCTCTCAATTGCTAGTGG

TCTGGCACACCTTCATATGGAGATTGTTGGTACACAAGGTAAACCTGCTATTGCTCATCGAG

ACATAAAATCAAAGAATATCTTAGTGAAAAGTGTGAAACTTGTGCCATAGCGGACTTAGGG

TTGGCTGTGAAGCATGATTCAATACTGAACACTATCGACATACCTCAGAATCCTAAAGTGGG

AACCAAGAGGTATATGGCTCCTGAAATGCTTGATGATACAATGAATGTGAATATCTTTGAGT

CCTTCAAACGAGCTGACATCTATTCTGTTGGTCTGGTTTACTGGGAAATAGCCCGGAGGTGT

TCAGTCGGAGGAATTGTTGAGGAGTACCAATTGCCTTATTATGACATGGTGCCTTCAGATCC

CTCGATAGAGGAAATGAGAAAGGTTGTTTGTGACCAGAAGTTTCGACCAAGTATCCCAAACC

AGTGGCAAAGTTGTGAAGCACTCCGAGTCATGGGGAGAATAATGCGTGAGTGTTGGIATGCC

AACGGAGCGGCCCGCCTAACTGCTCTTCGTATTAAGAAGACTATATCTCAACTTTGTGTCAA

AGAAGACTGCAAAGCCTAA
```

(SEQ ID NO: 240)

```
GAGCTCTCGCCAGGACTGAAGTGTGTATGTCTTTTGTGTGATTCTTCAAACTTTACCTGCCA
AACAGAAGGAGCATGTTGGGCATCAGTCATGCTAACCAATGGAAAAGAGCAGGTGATCAAAT
CCTGTGTCTCCCTTCCAGAACTGAATGCTCAAGTCTTCTGTCATAGTTCCAACAATGTTACC
AAAACCGAATGCTGCTTCACAGATTTTTGCAACAACATAACACTGCACCTTCCAACAGATAA
TGGAACTTGGACTCAACTTTGGCTGGTATCTGAATATCATGAACAGGGCTCCTTATATGACT
ATTTGAATAGAAATATAGTGACCGTGGCTGGAATGATCAAGCTGGCGCTCTCAATTGCTAGT
GGTCTGGCACACCTTCATATGGAGATTGTTGGTACACAAGGTAAACCTGCTATTGCTCATCG
AGACATAAAATCAAAGAATATCTTAGTGAAAAAGTGTGAAACTTGTGCCATAGCGGACTTAG
GGTTGGCTGTGAAGCATGATTCAATACTGAACACTATCGACATACCTCAGAATCCTAAAGTG
GGAACCAAGAGGTATATGGCTCCTGAAATGCTTGATGATACAATGAATGTGAATATCTTTGA
GTCCTTCAAACGAGCTGACATCTATTCTGTTGGTCTGGTTTACTGGGAAATAGCCCGGAGGT
GTTCAGTCGGAGGAATTGTTGAGGAGTACCAATTGCCTTATTATGACATGGTGCCTTCAGAT
CCCTCGATAGAGGAAATGAGAAAGGTTGTTTGTGACCAGAAGTTTCGACCAAGTATCCCAAA
CCAGTGGCAAAGTTGTGAAGCACTCCGAGTCATGGGAGAATAATGCGTGAGTGTTGGTATG
CCAACGGAGCGGCCCGCCTAACTGCTCTTCGTATTAAGAAGACTATATCTCAACTTTGTGTC
AAAGAAGACTGCAAAGCCTAA
```

(SEQ ID NO: 241)

```
   1 ATGGGAGCTG CTGCAAAGTT GGCGTTTGCC GTCTTTCTTA TCTCCTGTTC
  51 TTCAGGTGCT ATACTTGGTA GATCAGAAAC TCAGGAGTGT CTTTTCTTTA
 101 ATGCTAATTG GGAAAAAGAC AGAACCAATC AAACTGGTGT TGAACCGTGT
 151 TATGGTGACA AAGATAAACG GCGGCATTGT TTTGCTACCT GGAAGAATAT
 201 TTCTGGTTCC ATTGAAATAG TGAAACAAGG TTGTTGGCTG GATGATATCA
 251 ACTGCTATGA CAGGACTGAT TGTGTAGAAA AAAAGACAG CCCTGAAGTA
 301 TATTTTTGTT GCTGTGAGGG CAATATGTGT AATGAAAAGT TTTCTTATTT
 351 TCCGGAGATG GAAGTCACAC AGCCCACTTC AAATCCAGTT ACACCTAAGC
 401 CACCCTATTA ACATCCTG CTCTATTCCT TGGTGCCACT TATGTTAATT
 451 GCGGGGATTG TCATTTGTGC ATTTTGGGTG TACAGGCATC ACAAGATGGC
 501 CTACCCTCCT GTACTTGTTC AACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA AATGAATACG
 701 AAGTCTACAG TTTGCCTGGA ATGAAGCATG AGAACATATT ACAGTTCATT
 751 GGTGCAGAAA AACGAGGCAC CAGTGTTGAT GTGGATCTTT GGCTGATCAC
 801 AGCATTTCAT GAAAAGGGTT CACTATCAGA CTTTCTTAAG GCTAATGTGG
 851 TCTCTTGGAA TGAACTGTGT CATATTGCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAAGTAAAAA TGTGCTGTTG AAAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
```

```
1201 TGTACTGCTG CAGATGGACC TGTAGATGAA TACATGTTGC CATTTGAGGA

1251 GGAAATTGGC CAGCATCCAT CTCTTGAAGA CATGCAGGAA GTTGTTGTGC

1301 ATAAAAAAAA GAGGCCTGTT TTAAGAGATT ATTGGCAGAA ACATGCTGGA

1351 ATGGCAATGC TCTGTGAAAC CATTGAAGAA TGTTGGGATC ACGACGCAGA

1401 AGCCAGGTTA TCAGCTGGAT GTGTAGGTGA AGAATTACC CAGATGCAGA

1451 GACTAACAAA TATTATTACC ACAGAGGACA TTGTAACAGT GGTCACAATG

1501 GTGACAAATG TTGACTTTCC TCCCAAAGAA TCTAGTCTA
```

(SEQ ID NO: 242)

```
  1 ATACTTGGTA GATCAGAAAC TCAGGAGTGT CTTTTCTTTA ATGCTAATTG

51 GGAAAAAGAC AGAACCAATC AAACTGGTGT TGAACCGTGT TATGGTGACA

101 AAGATAAACG GCGGCATTGT TTTGCTACCT GGAAGAATAT TTCTGGTTCC

151 ATTGAAATAG TGAAACAAGG TTGTTGGCTG GATGATATCA ACTGCTATGA

201 CAGGACTGAT TGTGTAGAAA AAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

---

We claim:

1. An ActRIIB polypeptide comprising an amino acid sequence that is at least 90% identical to amino acids 20-134 of SEQ ID NO: 2, wherein the polypeptide comprises a glutamic acid at the position corresponding to position 55 of SEQ ID NO: 2, and wherein the ActRIIB polypeptide maintains inhibition of activin A and GDF11, and demonstrates less potent inhibition of BMP9, compared to a wild type ActRIIB polypeptide.

2. The polypeptide of claim 1, wherein the ActRIIB polypeptide is a fusion protein further comprising an Fc polypeptide domain.

3. The polypeptide of claim 2, wherein the fusion protein further comprises a linker domain positioned between the ActRIIB polypeptide and the Fc polypeptide domain.

4. The polypeptide of claim 3, wherein the linker domain is selected from the group consisting of TGGG (SEQ ID NO: 265), TGGGG (SEQ ID NO: 263), SGGGG (SEQ ID NO: 264), GGGGS (SEQ ID NO: 267), GGG (SEQ ID NO: 261), GGGG (SEQ ID NO: 262, and SGGG (SEQ ID NO: 266).

5. The polypeptide of claim 3, wherein the linker domain comprises GGG.

6. The polypeptide of claim 2, wherein the fusion protein comprises an amino acid sequence that is at least 90% identical to the amino acid sequence of SEQ ID NO: 5.

7. The polypeptide of claim 2, wherein the fusion protein comprises an amino acid sequence that is at least 90% identical to the amino acid sequence of SEQ ID NO: 6.

8. The polypeptide of claim 2, wherein the fusion protein comprises an amino acid sequence that is at least 90% identical to the amino acid sequence of SEQ ID NO: 12.

9. The polypeptide of claim 2, wherein the fusion protein comprises an amino acid sequence that is at least 90% identical to the amino acid sequence of SEQ ID NO: 34.

10. The polypeptide of claim 2, wherein the fusion protein comprises an amino acid sequence that is at least 90% identical to the amino acid sequence of SEQ ID NO: 36.

11. The polypeptide of claim 2, wherein the fusion protein is encoded by a nucleic acid sequence that is at least 90% identical to the nucleic acid sequence of SEQ ID NO: 35.

12. The polypeptide of claim 1, wherein the ActRIIB polypeptide is a homodimer protein.

13. The polypeptide of claim 1, wherein the ActRIIB polypeptide is a heterodimer protein.

14. The polypeptide of claim 13, wherein the heterodimer comprises a second ActRIIB polypeptide, wherein the first ActRIIB polypeptide comprises a different amino acid sequence compared to the second ActRIIB polypeptide.

15. The polypeptide of claim 14, wherein the second ActRIIB polypeptide is a wild-type ActRIIB extracellular domain polypeptide.

16. The polypeptide of claim 1, wherein the ActRIIB polypeptide is glycosylated and has a glycosylation pattern obtainable from expression of the polypeptide in a CHO cell.

17. A pharmaceutical composition comprising the ActRIIB polypeptide of claim 1, and a pharmaceutically acceptable carrier.

18. An ActRIIB polypeptide comprising an amino acid sequence that is at least 90% identical to amino acids 29-109 of SEQ ID NO: 2, wherein the polypeptide comprises a glutamic acid at the position corresponding to position 55 of SEQ ID NO: 2, and wherein the ActRIIB polypeptide maintains inhibition of activin A and GDF11, and demonstrates less potent inhibition of BMP9, compared to a wild type ActRIIB polypeptide.

19. An ActRIIB polypeptide comprising an amino acid sequence that is at least 90% identical to amino acids 25-131 of SEQ ID NO: 2, wherein the polypeptide comprises a glutamic acid at the position corresponding to position 55 of SEQ ID NO: 2, and wherein the ActRIIB polypeptide maintains inhibition of activin A and GDF11, and demonstrates less potent inhibition of BMP9, compared to a wild type ActRIIB polypeptide.

* * * * *

UNITED STATES PATENT AND TRADEMARK OFFICE
CERTIFICATE OF CORRECTION

PATENT NO. : 12,240,887 B2
APPLICATION NO. : 17/687934
DATED : March 4, 2025
INVENTOR(S) : Ravindra Kumar, Asya Grinberg and Erik M. Vogan Page 1 of 1

It is certified that error appears in the above-identified patent and that said Letters Patent is hereby corrected as shown below:

On the Title Page

Item (63) Under Related U.S. Application Data it reads:
"(63) Continuation of application No. 16/340,048, filed as application No. PCT/US2017/055421 on Oct. 5, 2017, now Pat. No. 11,267,865."

This should be corrected to read:
--(63) Continuation of application No. 16/340,048, now Pat. No. 11,267,865 filed Apr. 05, 2019, as a national phase entry of application No. PCT/US2017/055421 filed on Oct. 5, 2017.--

Signed and Sealed this
Twenty-ninth Day of April, 2025

Coke Morgan Stewart
*Acting Director of the United States Patent and Trademark Office*